(12) United States Patent
Zheng et al.

(10) Patent No.: US 11,407,990 B2
(45) Date of Patent: Aug. 9, 2022

(54) FUSION PROTEINS AND METHODS FOR SITE-DIRECTED GENOME EDITING

(71) Applicant: The Regents of the University of California, Oakland, CA (US)

(72) Inventors: Yuxuan Zheng, Davis, CA (US); Claire Lorenzo, Davis, CA (US); Peter Beal, Davis, CA (US); Andrew Fisher, Davis, CA (US); Leanna Monteleone, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/877,020

(22) Filed: May 18, 2020

(65) Prior Publication Data

US 2020/0407704 A1 Dec. 31, 2020

Related U.S. Application Data

(63) Continuation of application No. PCT/US2018/062128, filed on Nov. 20, 2018.

(60) Provisional application No. 62/589,502, filed on Nov. 21, 2017.

(51) Int. Cl.
*C12N 9/78* (2006.01)
*A61K 38/00* (2006.01)
*C12N 9/16* (2006.01)
*C12N 15/62* (2006.01)

(52) U.S. Cl.
CPC .............. *C12N 9/78* (2013.01); *C12N 9/16* (2013.01); *C12N 15/62* (2013.01); *A61K 38/00* (2013.01); *C12Y 305/04* (2013.01)

(58) Field of Classification Search
CPC ......... C12N 9/78; C12Y 305/04; A61K 38/00
See application file for complete search history.

(56) References Cited

U.S. PATENT DOCUMENTS

| | | | |
|---|---|---|---|
| 2016/0304846 A1 | 10/2016 | Liu et al. | |
| 2020/0291382 A1* | 9/2020 | Zhang | C12N 9/12 |
| 2022/0010333 A1 | 1/2022 | Mali et al. | |

FOREIGN PATENT DOCUMENTS

| | | |
|---|---|---|
| WO | 2016/094845 A2 | 6/2016 |
| WO | 2019/104094 A1 | 5/2019 |
| WO | 2020/001793 A1 | 1/2020 |

OTHER PUBLICATIONS

George, C.X. et al.; "Editing of Cellular Self-RNAs by Adenosine Deaminase ADAR1 Suppresses Innate Immune Stress Responses"; Journal of Biological Chemistry; vol. 291, No. 12; Mar. 18, 2016; pp. 6158-6168.
Komor, A. C. et al.; "Programmable editing of a target base in genomic DNA without double-stranded DNA cleavage"; Nature; vol. 533, No. 7602; May 19, 2016; pp. 420-424.
Sato, Y. et al.; "Abasic site-binding ligands conjugated with cyanine dyes for "off-on" fluorescence sensing of orphan nucleobases in DNA duplexes and DNA-RNA hybrids"; Chemical Communications; vol. 50, No. 5; Jan. 18, 2014; pp. 515-517.
Sinnamon, J.R. et al.; "Site-directed RNA repair of endogenous Mecp2 RNA in neurons"; Proceedings of the National Academy of Sciences of the U.S.A.; vol. 114, No. 44; Oct. 31, 2017; pp. E9395-E9402.
Yanik, M. et al.; "In vivo genome editing as a potential treatment strategy for inherited retinal dystrophies"; Progress in Retinal and Eye Research; vol. 56; Jan. 2017; pp. 1-18.
Yeo, J. et al.; "RNA editing changes the lesion specificity for the DNA repair enzyme NEIL1"; Proceedings of the National Academy of Sciences of the U.S.A.; vol. 107, No. 48; Nov. 30, 2010; pp. 20715-20719.
Zheng, Y. et al.; "DNA editing in DNA/RNA hybrids by adenosine deaminases that act on RNA"; Nucleic Acids Research; vol. 45, No. 6; Apr. 7, 2017; pp. 3369-3377.
Invitation to Pay Additional Fees mailed Apr. 2, 2019 in International Application No. PCT/US2018/062128, 2 pages.

* cited by examiner

*Primary Examiner* — Maryam Monshipouri
(74) *Attorney, Agent, or Firm* — Kilpatrick Townsend & Stockton LLP

(57) ABSTRACT

In some aspects, the present invention provides methods and compositions for modifying target sites within nucleic acid molecules. In some embodiments, the methods comprise using adenosine deaminases that act on RNA (ADARs), and variants thereof, to modify target sites within DNA-RNA hybrid molecules. In other aspects, ADAR2 variant polypeptides as well as fusion proteins comprising an ADAR catalytic domain and a hybrid nucleic acid binding domain are provided, as are methods for use thereof. Methods for preventing and treating genetic disorders are also provided herein.

12 Claims, 29 Drawing Sheets
Specification includes a Sequence Listing.

(a) 5'-GCUCGCGAUGCUAGAGGGCUCUGC-3'
    3'-CGAGCGCUACGACCCCCCGAGACG-5'

(b) 5'-GCUCGCGAUGCUAGAGGGCUCUGC-3'
    3'-CGAGCGCUACGACCCCCCGAGACG-5'

(c) 5'-GCUCGCGAUGCUAGAGGGCUCUGC-3'
    3'-CGAGCGCUACGACCCCCCGAGACG-5'

| Substrate | $K_{obs}$, min$^{-1}$ | $k_{rel}$ |
|---|---|---|
| (a) | 0.67 ± 0.01 | 1 |
| (b) | 0.045 ± 0.007 | 0.07 |
| (c) | 0.051 ± 0.004 | 0.08 |

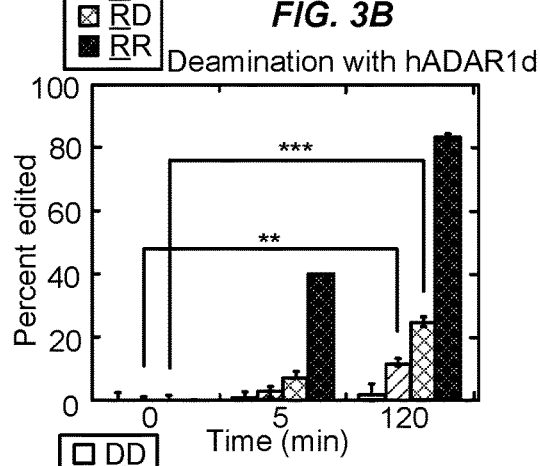
*FIG. 3B* Deamination with hADAR1d
*FIG. 3A*
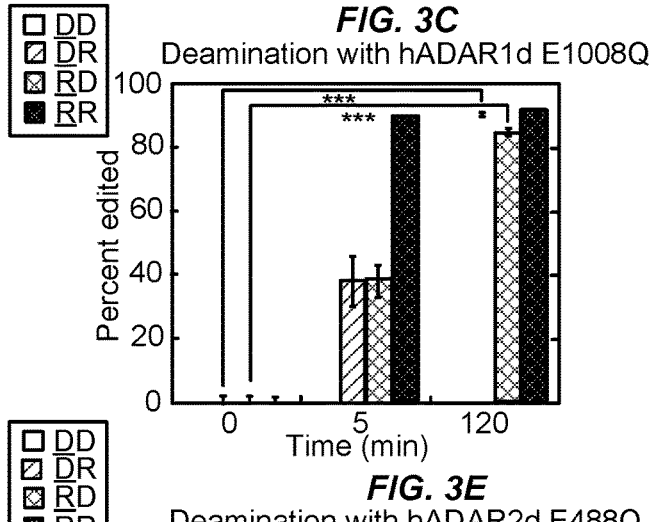
*FIG. 3C* Deamination with hADAR1d E1008Q
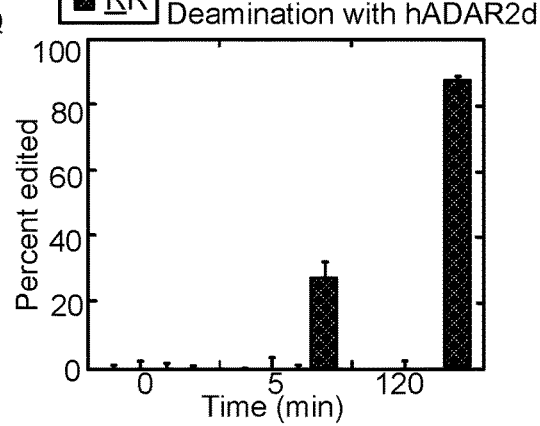
*FIG. 3D* Deamination with hADAR2d
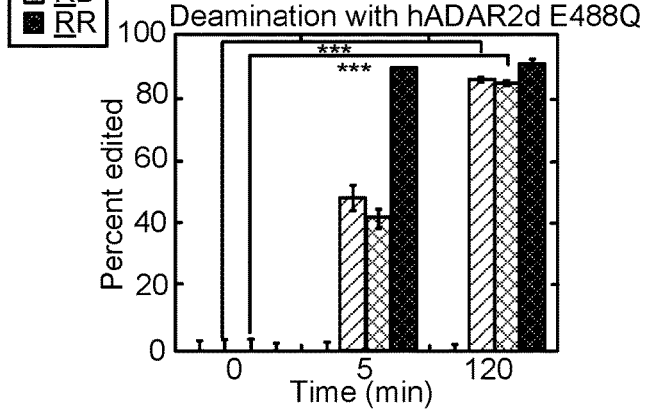
*FIG. 3E* Deamination with hADAR2d E488Q
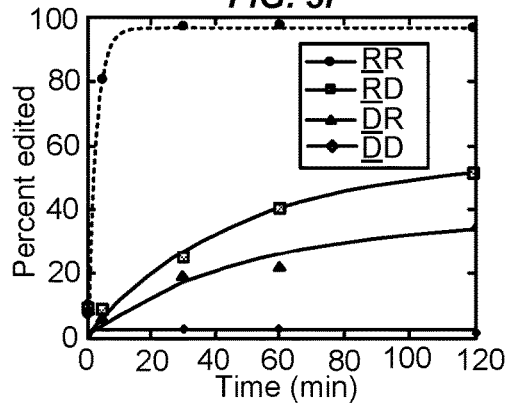
*FIG. 3F*

DD  5'-GCTCGCGATGCTAGAGGGCTCTGC-3'
    3'-CGAGCGCTACGACCCCCGAGACG-5'

DR  5'-GCTCGCGATGCTAGAGGGCTCTGC-3'
    3'-CGAGCGCUACGACCCCCGAGACG-5'

RD  5'-GCUCGCGAUGCUAGAGGGCUCUGC-3'
    3'-CGAGCGCTACGACCCCCGAGACG-5'

Deamination with hADAR2d

X = C or abasic (Ab)

ADAR2-D (WT)

E488F

FIG. 11A
hADAR2d
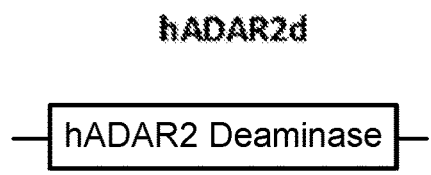
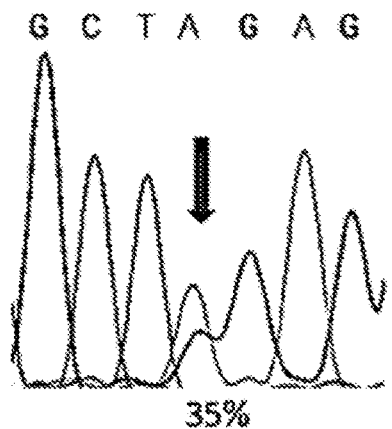
35%
FIG. 11B
HBD-hADAR2d
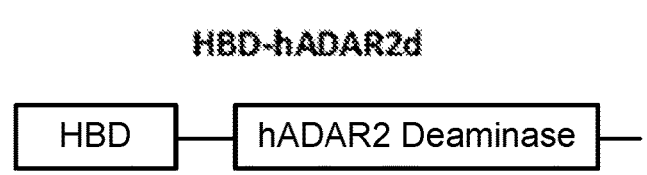
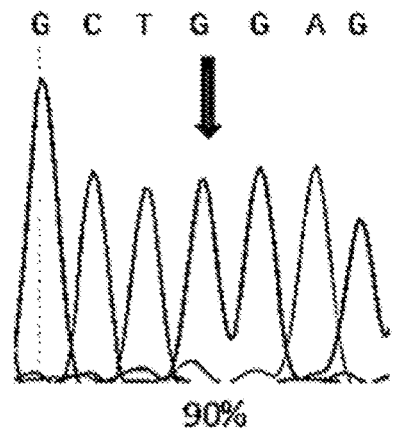
90%

FIG. 13A
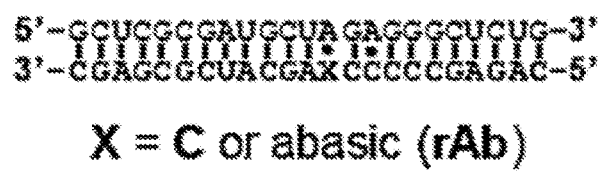
FIG. 13B
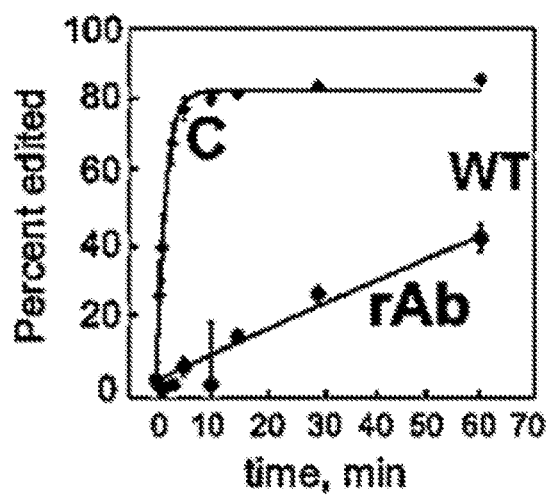
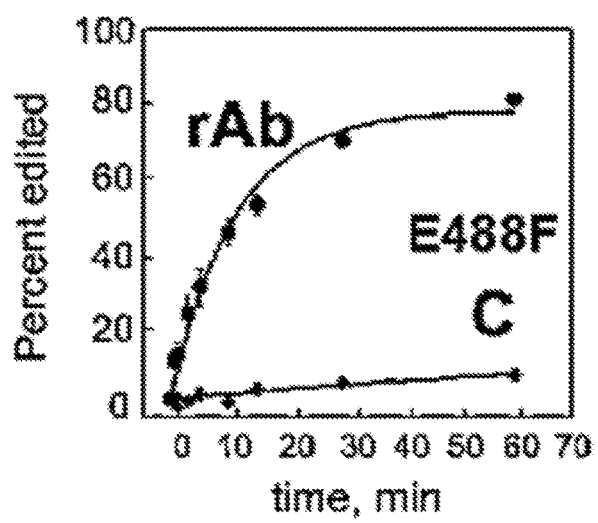
FIG. 13C
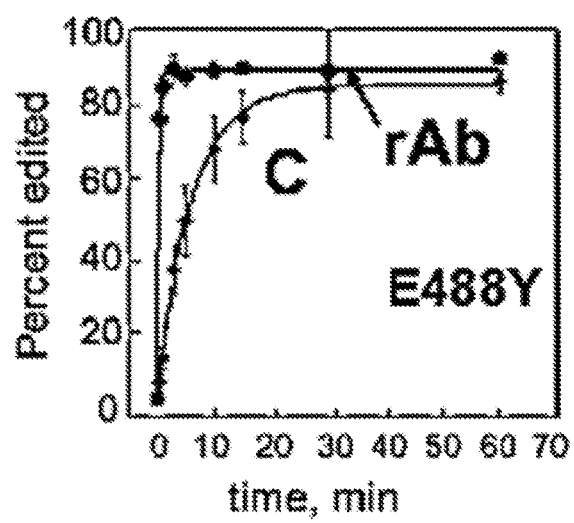
FIG. 13D

FIG. 16A
Off-target 1  Target  Off-target 2
5'─CUAGGCGGACUAUGACUUAGUUUGCGUUACACCCUUUCUUGACAAAACCU─3'
3'─GCCUGAUACUGAAXCAACGCAAUGUGGGAAGAACUGUU─5'
X = C or rAb
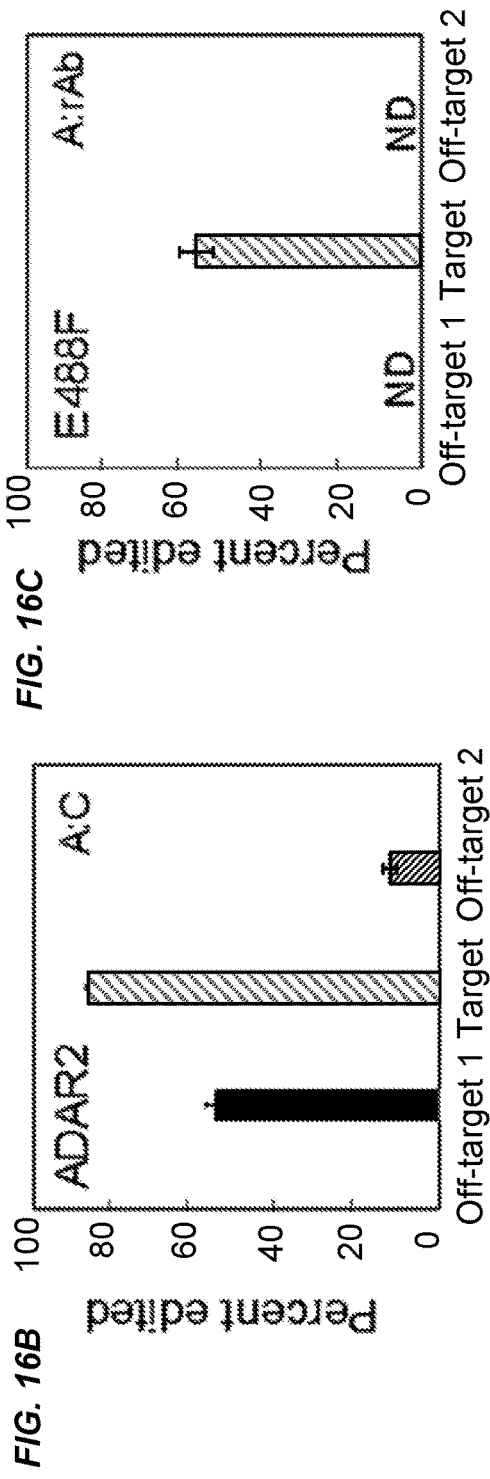
FIG. 16B
FIG. 16C
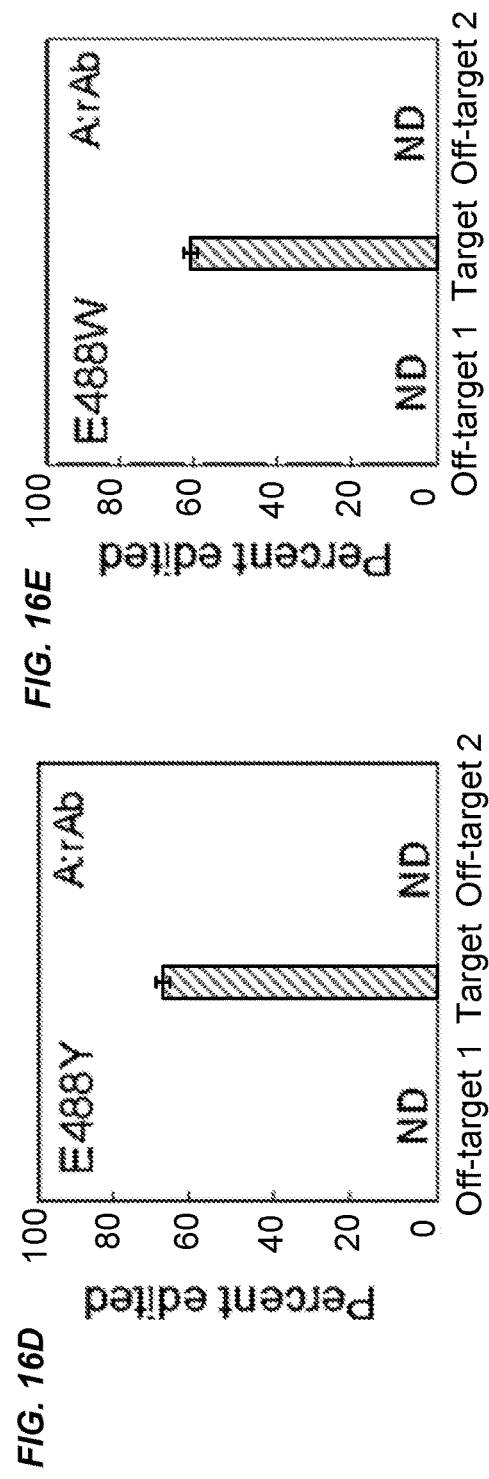
FIG. 16D
FIG. 16E X, Y = C or reduced abasic site (rAb)

FIG. 21

5'-GAAGCAACTCTTGAGTGTTAATATGTTGACCCCTGTATTAGGGATGCGGGAATTGGGTACGAATTCCCCGTACAT
CGCTGTCCACCTTCCAGCAGATGTGGATCAGCAAGCAGGAGTATGACGAGTCCGCCCCTCCATCGTCCACCGCAA
ATGCTTCTAGGCGGACTATGACTTGGTTGCGTTACACCCTTCTTGACAAAACTAACTGCGCAGAAACAAGATG
AGATTGGCATGGCTTTATTTGTTTTTTGTTTTGTTTTTTGGCTTGACTCAGGATTAAAAAC
TGGAACGGGTGAAGGTGACAGCAGTCGGTTGGAGCGAGCATCCCAAAGTTCACAATGTGGCGAGGACTTTGATT
GCACATTGTTGTTTTTTAATAGTCATTCCAAATATGAGATGCGTTGTTACAGGAAGTCCCTTGCCATCCTAAAGCC
ACCCCACTTCTCTAAGGAGAATGGCCCAGTCCTCTCCCAAGTCCACACAGGGAGGTGATAGCATTGCTTTCGTG
TAAATTATGTAATGCAAAATTTTTTAATCTTCGCCTTAATACTTTTTATTTGTTTATTTGAATGATGAGCCTTC
GTGCCCCGGATCCGTGTCGGGATATCACGTGGAATATCGCCGATCCTTGCGTGTTCAATATGCTTGCCGAGCTT
ATCATCT-3'

US 11,407,990 B2

FUSION PROTEINS AND METHODS FOR SITE-DIRECTED GENOME EDITING

CROSS REFERENCE TO RELATED APPLICATIONS

The present application is a continuation of International Application No. PCT/US2018/062128 filed Nov. 20, 2018, which claims priority to U.S. Provisional Application No. 62/589,502, filed Nov. 21, 2017, the disclosures of each of which are herein incorporated by reference in their entireties for all purposes.

STATEMENT AS TO RIGHTS TO INVENTIONS MADE UNDER FEDERALLY SPONSORED RESEARCH AND DEVELOPMENT

This invention was made with Government support under Grant No. R01GM061115, awarded by the National Institutes of Health. The Government has certain rights in this invention.

SEQUENCE LISTING

The present application contains a Sequence Listing which has been submitted electronically in ASCII format and is hereby incorporated by reference in its entirety. Said ASCII copy, created on May 14, 2020, is named 070772-224410US-1192869 SL.txt and is 115,878 bytes in size.

BACKGROUND OF THE INVENTION

Recent years have seen an explosion in the number of new tools to manipulate the genomes of complex organisms, including the use of variants of the CRISPR-Cas9 system. While these tools are powerful, single point mutations introduced with these reagents often require inefficient homology-directed repair. This has stimulated interest in the development of "base editing" methods using Cas9-cytidine deaminase fusion proteins that can be directed to specific sites in the genome with a single guide RNA. While this approach has been shown to be effective for introducing dC to T mutations, the use of only cytidine deaminases for this purpose is limiting. Thus, there is a need for new tools that enable the editing of genomes at specific sites of interest. The present invention satisfies this need, and provides related advantages as well.

BRIEF SUMMARY OF THE INVENTION

In one aspect, methods for modifying a target site within a DNA-RNA hybrid molecule are provided. In some embodiments, the method comprises contacting the hybrid molecule with an adenosine deaminase that acts on RNA (ADAR) or a portion thereof. In some embodiments, the ADAR comprises an ADAR catalytic domain. In some embodiments, the ADAR is selected from the group consisting of ADAR1 and ADAR2. In some embodiments, the ADAR is ADAR1 and the ADAR1 comprises an E1008Q mutation. In some embodiments, the ADAR is ADAR2 and the ADAR2 comprises an E488 mutation. In some embodiments, the E488 mutation is an E488Q, E488Y, E488W, or E488F mutation.

In some embodiments, the target site is modified without introducing a break in the DNA strand of the hybrid molecule. In some embodiments, modifying the target site comprises modifying the DNA strand of the hybrid molecule. In some embodiments, a deoxyadenosine nucleotide is deaminated.

In some embodiments, the RNA strand of the hybrid molecule increases target site modification and/or efficiency. In some embodiments, the RNA strand of the hybrid molecule introduces a deoxyadenosine-cytidine mismatch at the target site. In some embodiments, the RNA strand of the hybrid molecule introduces a deoxyadenosine-cytidine mismatch 5' and/or 3' to the target site. In some embodiments, the ADAR is wild-type ADAR1, ADAR1 comprising an E1008Q mutation, wild-type ADAR2, or ADAR2 comprising an E488Q, E488F, E488Y, or E488W mutation. In some embodiments, target site modification efficiency is increased when the ADAR is wild-type ADAR1, ADAR1 comprising an E1008Q mutation, wild-type ADAR2, or ADAR2 comprising an E488Q, E488F, E488Y, or E488W mutation and the RNA strand of the hybrid molecule introduces a deoxyadenosine-cytidine mismatch at the target site, 5' of the target site, and/or 3' of the target site.

In some embodiments, the RNA strand of the hybrid molecule comprises an abasic site. In some embodiments, the ADAR is ADAR2 and the ADAR2 comprises an E488F, E488Y, or E488W mutation. In some embodiments, target site modification specificity is increased when the ADAR is an ADAR2 comprising an E488F, E488Y, or E488W mutation and the RNA strand of the hybrid molecule comprises an abasic site.

In some embodiments, the target site is modified in vitro. In some embodiments, the hybrid molecule and the ADAR are present within a cell. In some embodiments, the cell is a eukaryotic cell. In some embodiments, an RNA molecule is introduced into the cell and pairs with a DNA strand within the cell to form the hybrid molecule. In some embodiments, 2 or more target loci are modified. In some embodiments, 50 or more target loci are modified.

In some embodiments, the ADAR comprises an ADAR catalytic domain fused to a hybrid nucleic acid binding domain (NBD). In some embodiments, the hybrid NBD comprises ribonuclease H, a type II restriction enzyme, or a portion thereof. In some embodiments, the hybrid NBD comprises ribonuclease H or a portion thereof. In some embodiments, the type II restriction enzyme is selected from the group consisting of EcoRI, HindII, SalI, MspI, HhaI, AluI, TaqI, ThaI, HaeIII, and a combination thereof.

In another aspect, methods for modifying a target site within a nucleic acid are provided that comprise contacting the nucleic acid with a polypeptide provided herein. In some embodiments, the nucleic acid comprises double-stranded RNA. In some embodiments, the nucleic acid comprises a DNA-RNA hybrid molecule. In some embodiments, the nucleic acid comprises an abasic site.

In another aspect, methods for preventing or treating a genetic disorder in a subject are provided. In some embodiments, the method comprises modifying a target site within a DNA-RNA hybrid molecule according to a method provided herein, in order to correct a mutation associated with the genetic disorder. In some embodiments, the target site is modified in vivo. In some embodiments, the target site is modified in vitro and the modified target site is subsequently introduced into the subject.

In some embodiments, the genetic disorder is selected from the group consisting of Rett syndrome, X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disorders, inflammation, immune-related disorders, metabolic disorders, liver disorders, kidney disorders, musculoskeletal disorders, neurological disorders, cardiovascular disorders, pulmonary disorders, ocular disorders, and a combination thereof. In some embodiments, the genetic disorder is Rett syndrome.

In some embodiments, the method comprises a therapeutically effective amount of a pharmaceutical composition provided herein.

In another aspect, isolated polypeptides are provided. In some embodiments, the isolated polypeptide comprises the amino acid sequence set forth in SEQ ID NO:61 or 64.

In another aspect, fusion proteins are provided. In some embodiments, the fusion protein comprises an adenosine deaminase that acts on RNA (ADAR) catalytic domain and a hybrid nucleic acid binding domain (NBD). In some embodiments, the ADAR is selected from the group consisting of ADAR1 and ADAR2. In some embodiments, the ADAR is ADAR1 and the ADAR1 comprises an E1008Q mutation. In some embodiments, the ADAR is ADAR2 and the ADAR2 comprises an E488 mutation. In some embodiments, the E488 mutations is an E488Q, E488Y, E488W, or E488F mutation.

In some embodiments, the hybrid NBD binds to a DNA-RNA hybrid molecule. In some embodiments, the hybrid NBD comprises ribonuclease H, a type II restriction enzyme, or a portion thereof. In some embodiments, the hybrid NBD comprises ribonuclease H or a portion thereof. In some embodiments, the type II restriction enzyme is selected from the group consisting of EcoRI, HindII, SalI, MspI, HhaI, AluI, TaqI, ThaI, HaeIII, and a combination thereof. In some embodiments, the fusion protein further comprises an amino acid linker.

In another aspect, isolated polynucleotides are provided. In some embodiments, the isolated polynucleotide comprises a nucleotide sequence encoding a polypeptide or a fusion protein provided herein.

In yet another aspect, vectors are provided. In some embodiments, the vector comprises a polynucleotide provided herein.

In still another aspect, host cells are provided. In some embodiments, the host cell comprises a polynucleotide provided herein or a vector provided herein.

In another aspect, pharmaceutical compositions are provided. In some embodiments, the pharmaceutical composition comprises a polypeptide provided herein, a fusion protein provided herein, a polynucleotide provided herein, a vector provided herein, or a host cell provided herein and a pharmaceutically acceptable carrier.

In another aspect, a kit for modifying a target site within a DNA-RNA hybrid molecule is provided. In some embodiments, the kit comprises a polypeptide provided herein, a fusion protein provided herein, a polynucleotide provided herein, a vector provided herein, a host cell provided herein, a pharmaceutical composition provided herein, or a combination thereof. In some embodiments, the kit further comprises instructions for use. In some embodiments, the kit further comprises one or more reagents for introducing the polynucleotide or vector into a host cell, contacting the fusion protein or polypeptide with the DNA-RNA hybrid molecule, or a combination thereof.

Other objects, features, and advantages of the present invention will be apparent to one of skill in the art from the following detailed description and figures.

BRIEF DESCRIPTION OF THE DRAWINGS

FIG. 1A shows the structure of hADAR2d bound to duplex RNA (reproduced from (14)). FIG. 1B shows 2'-Hydroxyl contacts to the RNA substrate in the crystal structure (PDB 5ED2).

FIG. 2A shows sequences of deamination substrates (top strands). 2'-deoxynucleotides are labeled in bold. Target sites are underlined. For (a), the sequence of the top strand is set forth in SEQ ID NO:37 and the sequence of the bottom strand is set forth in SEQ ID NO:5. For (b), the sequence of the top strand is set forth in SEQ ID NO:55 and the sequence of the bottom strand is set forth in SEQ ID NO:56. For (c), the sequence of the top strand is set forth in SEQ ID NO:55 and the sequence of the bottom strand is set forth in SEQ ID NO:5. FIG. 2B shows a comparison of deamination product vs. time for the three substrates shown in FIG. 2A with 300 nM hADAR2d. FIG. 2C shows kinetic parameters for the deamination of RNA and partially 2'-deoxy substrates.

FIGS. 3A-3F show a comparison of deamination reactions with DNA/RNA hybrids, all-RNA and all-DNA substrates. FIG. 3A shows sequences of deamination substrates. Editing sites are underlined. 2'-deoxynucleotides are in bold. DD denotes that both strands are DNA. DR denotes that the edited strand is DNA and that the complementary strand is RNA. RD denotes that the edited strand is RNA and that the complementary strand is DNA. RR denotes that both strands are RNA. For DD, the sequence of the top strand is set forth in SEQ ID NO:38 and the sequence of the bottom strand is set forth in SEQ ID NO:8. For DR, the sequence of the top strand is set forth in SEQ ID NO:38 and the sequence of the bottom strand is set forth in SEQ ID NO:5. For RD, the sequence of the top strand is set forth in SEQ ID NO:37 and the sequence of the bottom strand is set forth in SEQ ID NO:8. For RR, the sequence of the top strand is set forth in SEQ ID NO:37 and the sequence of the bottom strand is set forth in SEQ ID NO:5. FIG. 3B shows percent editing for deamination reactions at different time points with 250 nM of hADAR1d. FIG. 3C shows percent editing for deamination reactions at different time points with 250 nM of hADAR1d E1008Q. FIG. 3D shows percent editing for deamination reactions at different time points with 250 nM of hADAR2d. FIG. 3E shows percent editing for deamination reactions at different time points with 250 nM of hADAR2d E488Q. For FIGS. 3B-3E, statistical significance between groups was determined by t tests. *: P-value≤0.001, : P-value≤0.01, *: P-value≤0.05. FIG. 3F shows deamination reaction yield vs. time for 250 nM hADAR2 wt. Kinetic parameters ($k_{obs}$): DD: $k_{obs}$≤0.001 min$^{-1}$, DR: $k_{obs}$=0.02 min$^{-1}$, RD:$k_{obs}$=0.02 min$^{-1}$, RR: $k_{obs}$≥0.4 min$^{-1}$ (n=2, reported value is the average from two trials).

FIG. 4A shows the sequence surrounding three editing sites (A, B, and C). The bold region of the bottom strand marks the sequence of the 24-nt RNA bottom strand with varying X and Y positions. The non-bolded region of the bottom strand corresponds to portions of the 93-nt RNA bottom strand. The sequence of the top strand is set forth in SEQ ID NO:39 and the sequence of the bottom strand is set forth in SEQ ID NO:40. FIGS. 4B-4F show percent editing for sites A, B and C in the different substrate structures (shown at the top of each panel) with either hADAR2 wt or hADAR2d E488Q. For FIGS. 4B-4F, statistical significance between groups was determined by t tests. *: P-value≤0.001, : P-value≤0.01, *: P-value≤0.05.

FIG. 5A shows single-stranded DNA (top strands) containing six target sites. Target sites are the middle nucleotides within the underlined three-nucleotide sequence of each top strand. Bottom strands show the guide RNAs. For the TAG site, the sequence of the top strand is set forth in SEQ ID NO:46 and the sequence of the bottom strand is set forth in SEQ ID NO:19. For the AAG site, the sequence of the top strand is set forth in SEQ ID NO:41 and the sequence of the bottom strand is set forth in SEQ ID NO:22. For the AAT site, the sequence of the top strand is set forth in SEQ ID NO:43 and the sequence of the bottom strand is set forth in SEQ ID NO:20. For the CAC site, the sequence of the top strand is set forth in SEQ ID NO:42 and the sequence of the bottom strand is set forth in SEQ ID NO:21. For the GAA site, the sequence of the top strand is set forth in SEQ ID NO:44 and the sequence of the bottom strand is set forth in SEQ ID NO:24. For the GAC site, the sequence of the top strand is set forth in SEQ ID NO:45 and the sequence of the bottom strand is set forth in SEQ ID NO:23.

FIG. 5B shows percent editing by 500 nM hADAR1d E1008Q at each site shown in FIG. 5A. Statistical significance between groups was determined by t tests. *: P-value≤0.001, : P-value≤0.01, *: P-value≤0.05. FIG. 5C shows a sequence trace of an off-target site found adjacent to the AAT target site. The off-target site is marked with an asterisk in the sequence trace. FIG. 5C discloses SEQ ID NO: 147.

FIG. 6A shows sequences of deamination substrates. Strands in bold are DNA and non-bold strands are RNA. Editing sites are underlined (pa both strands DNA, DR: edited strand DNA, complementary strand RNA; RD: edited strand RNA, complementary strand DNA). For DD, the sequence of the top strand is set forth in SEQ ID NO:38 and the sequence of the bottom strand is set forth in SEQ ID NO:8. For DR, the sequence of the top strand is set forth in SEQ ID NO:38 and the sequence of the bottom strand is set forth in SEQ ID NO:5. For RD, the sequence of the top strand is set forth in SEQ ID NO:37 and the sequence of the bottom strand is set forth in SEQ ID NO:8. FIG. 6B shows percent editing for deamination reactions at different time points with 2 μM of hADAR2d. Statistical significance between groups was determined by t tests. *: P-value≤0.001, : P-value≤0.01, *: P-value≤0.05.

FIG. 8A depicts single-stranded DNA at the GAC target site. The target site is the middle nucleotide within the underlined sequence in the top strand (SEQ ID NO:45). The sequence of the bottom strand (guide RNA) is set forth in SEQ ID NO:23. FIG. 8B shows percent editing by hADAR1d E1008Q at the GAC site (500 nM protein for 2 hours followed by additional 500 nM protein for an additional 2 hours). Statistical significance between groups was determined by t tests. *: P-value≤0.001, : P-value≤0.01, *: P-value≤0.05.

FIG. 10A shows top (SEQ ID NO:51) and bottom (SEQ ID NO:50) RNA strands, wherein an A nucleotide on the top strand was positioned opposite either a C nucleotide or an abasic site, at position X. FIG. 10B shows the results of editing with ADAR2-D (WT). FIG. 10C shows the results of editing with the E488F mutant.

FIGS. 11A and 11B show DNA editing activity of the HBD-ADAR2 deaminase fusion protein. FIG. 11A shows a sequence trace (SEQ ID NO:131) for a reaction mixture after 60 minutes deamination with 250 nM human ADAR2 deaminase domain targeting the DNA strand of a DNA/RNA hybrid duplex. FIG. 11B shows a sequence trace (SEQ ID NO:132) for the same conditions as FIG. 11A, but with the HBD-ADAR2 deaminase fusion protein.

FIG. 12A shows that ADARs catalyze the hydrolytic deamination of adenosine to form the non-canonical nucleoside inosine. FIG. 12B shows the crystal structure of human ADAR2 deaminase domain bound to dsRNA substrate. The ADAR flipping loop contains the intercalating E488 residue, which hydrogen bonds with the orphan base cytidine. FIG. 12C shows that mutation of the 488 residue to phenylalanine (E488F) suggests steric clash ("bump") with orphan base cytidine. FIG. 12D shows that incorporation of a reduced abasic site (rAb) relieves steric clash caused by E488F and acts as the "hole."

FIGS. 13A-13D show ADAR deamination kinetics. FIG. 13A shows the sequence of a deamination substrate. The target site is bolded A in black. The X is the orphan base of the target site either containing cytidine or a reduced abasic site to form a cytidine substrate or a reduced abasic substrate, respectively. Top and bottom sequences are set forth in SEQ ID NOS:51 and 50, respectively. FIGS. 13B-13D show a comparison of deamination product versus time with 300 nM hADAR2-D WT, hADAR2-D E488F and hADAR2-D E488Y, respectively. Deamination kinetics are shown for the reduced abasic substrate (rAb) and cytidine substrate (C). Error bars, s.d. (n=3 technical replicates).

FIG. 14A shows duplex RNA for crystallization. Gli1 duplex had sequence surrounding the human Gli1-mRNA editing site. Adenosine analog 8-azanebularine (N) was across from a reduced abasic site (rAb). N allowed for trapping of the protein-RNA complex in base flipped conformation. Top and bottom sequences are set forth in SEQ ID NOS:71 and 72, respectively. FIG. 14B shows intercalation of Y488 from the minor groove side of RNA duplex in base-flipped conformation. Potential hydrogen bonding at N4 amine of C10'. FIG. 14C shows orphan base, reduced abasic site (rAb), maintains RNA backbone found in other ADAR-RNA structures. Side chain of R510 ion-pairs with the 3'-phosphodiester of orphaned base, rAb11'. See also Table 3 and FIG. 19.

FIG. 15A shows the partial sequence for four different substrates containing different combinations of cytidine or reduced abasic site at orphan base of target. Top and bottom sequences are set forth in SEQ ID NOS:133 and 134, respectively. The results of testing with 150 nM hADAR2-D E488Y (FIG. 15B) and 150 nM hADAR2-D (FIG. 15C) for 15 minutes are shown. Bars are shown for editing at site 1 and site 2. X and Y are orphan base position of site 1 and site 2, respectively. Deamination of hADAR2-D E488W, hADAR2-D E488F and hADAR2-D can be found in FIG. 20 and Table 4. ND=no detected editing. Error bars, s.d. (n=3 technical replicates).

FIGS. 16A-16E show site-directed editing on an overexpressed target site representing a region of the 3'-UTR of β-actin RNA in HEK293T cells. FIG. 16A shows the partial sequence of the target substrate and sequence of guide used. Top and bottom sequences are set forth in SEQ ID NOS:135 and 136, respectively. Shown are target adenosine and adenosine off-targets 1 and 2. All guide nucleotides were 2'-O-methyl modified except those bolded black which are unmodified ribonucleotides. Underlining indicates sites of phosphorothioate modification. X=cytidine (C) or reduced abasic site (rAb). FIG. 16B shows percent editing at target and off-targets on overexpressed β-actin mRNA substrate and cytidine guide RNA with overexpression of hADAR2. FIGS. 16C-16E show percent editing at target and no detected editing (ND) at off-targets on overexpressed β-actin mRNA substrate and reduced abasic guide RNA with overexpression of hADAR2 E488F (FIG. 16C), hADAR2 E488Y (FIG. 16D), and hADAR2 E488W (FIG. 16E). ND=no detected editing. Error bars, s.d. (n=3 biological replicates). See also FIGS. 21 and 22 and Table 5.

FIG. 17A shows directed editing on endogenous 3'-UTR of RAB7A with overexpression of hADAR2 and cytidine guide RNA or overexpression of bulky mutants hADAR2 E488X (X=F, Y, W) and reduced abasic guide RNA. FIG. 17B shows directed editing on endogenous 3'-UTR of β-actin with overexpression of hADAR2 and cytidine guide RNA or overexpression of bulky mutants hADAR2 E488X (X=F, Y, W) and reduced abasic guide RNA. FIG. 17C shows percent editing on various endogenous off-target transcripts: FLNA, TMEM63B, CYFIP2, Gli1 and COG3. Middle bars in each group are off-target site with 5' and 3' flanking sequence. Shown are percent editing of off-target with no transfection and percent editing of off-targets when directing editing at endogenous RAB7A with overexpression of wild-type hADAR2 and cytidine guide RNA. Also shown is percent editing of off-targets when directing editing at endogenous RAB7A with overexpression of hADAR2 E488Y and reduced abasic guide RNA. Percent editing values can be found in Table 7. An asterisk (*) indicates no detected editing. Error bars, s.d. (n=3 biological replicates).

FIG. 19A shows electron density showing lack of density for the hydroxyl group and the two different conformations of Y488 modeled in density. FIG. 19B shows poor stacking of Y488 with G:C pair containing 3' G. Only one conformation of Y488 is shown for clarity. FIG. 19C shows backbone shift of the flipping loop in the direction of the abasic site from overlay with PDB 5ED2.

FIG. 20A shows the sequence of site 1 and site 2 targets in 152 nt substrate; edited A marked at locations 1 and 2 on the top strand. Top and bottom sequences are set forth in SEQ ID NOS:133 and 134, respectively. FIG. 20B shows percent editing by hADAR2-D E488W at site 1 and site 2 with different combinations of orphan base. FIG. 20C shows percent editing by hADAR2-D E488F at site 1 and site 2 with different combinations of orphan base. FIG. 20D shows percent editing by hADAR2-D WT at site 1 and site 2 with different combinations of orphan base. ND denotes no editing detected. Each experiment was carried out in triplicate where percent editing reported is the average of the triplicates±standard deviation.

FIG. 21 shows the sequence (SEQ ID NO:130) of a region of the 3'-UTR of β-actin RNA used for overexpression of directed editing target, related to FIG. 16. The underlined sequences correspond to non-native sequences and the bold adenosine is the target. This sequence was incorporated into pcDNA 3.1 vector via Gibson Assembly.

DETAILED DESCRIPTION OF THE INVENTION

I. Introduction

Figures 1A, 1B:
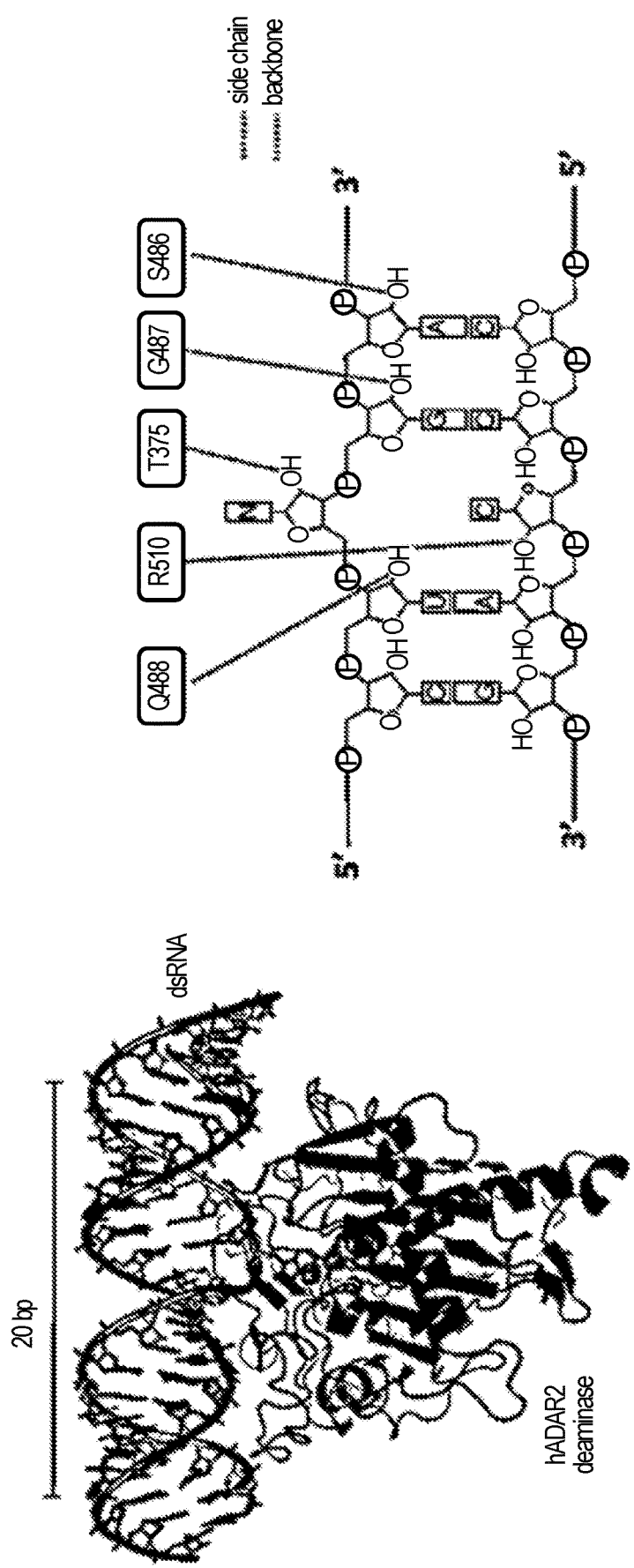
FIGS. 1A and 1B show interactions between hADAR2d and 2'-hydroxyl groups.

Adenosine deaminase that acts on RNA (ADAR) proteins convert adenosine (A) to inosine (I) in duplex RNAs. Since I base pairs with cytidine (C), it functions like guanosine (G) in cellular processes such as splicing, translation, and reverse transcription. Two different enzymes carry out this form of RNA editing in humans; ADAR1 and ADAR2. The ADAR proteins have a modular structure with double-stranded RNA binding domains (dsRBDs) and a C-terminal deaminase domain, and a double helical structure is required for ADAR substrates. The present invention is based, in part, on the discovery that ADAR proteins can act on DNA/RNA hybrid duplex structures and produce dA to dG mutations in DNA. Thus, the present invention provides new genome editing tools based on dA to dI conversions that create specific dA to dG mutations in DNA after replication. The present invention is also based, in part, on the discovery of methods for targeting editing to desired sites, increasing the efficiency of DNA editing by ADAR proteins, and reducing off-target editing events. The methods and compositions described herein are useful for, among other things, preventing or treating a number of genetic disorders.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

The term "adenosine deaminase that acts on RNA" or "ADAR" refers to an enzyme that is encoded by the ADAR gene in humans and converts adenosine (A) to inosine (I) by deamination. In mammals, three types of ADARs are known to exist. ADAR1 and ADAR2 which are both catalytically active, are found in many different tissue types, whereas ADAR3, which is catalytically inactive, is only found in brain tissue. ADAR1 has two known isoforms: ADAR1p110, which is localized to the nucleus, and ADAR1p150, which is found in both the nucleus and cytoplasm of cells. The active site of ADAR contains two or three N-terminal dsRNA binding domains (dsRBDs) and a C-terminal catalytic deaminase domain. ADAR1 contains three regions that bind double-stranded helical RNA (dsRBDs) and two Z-DNA binding domains. Non-limiting examples of ADA sequences are set forth in SEQ ID NOS:48 and 49.

The term "ADAR catalytic domain" refers to the portion of an ADAR that comprises the enzyme's C-terminal catalytic deaminase domain. As a non-limiting example, the catalytic deaminase domain of ADAR1 comprises amino acids 833-1226 of SEQ ID NO:48. As another non-limiting example the catalytic deaminase domain of ADAR2 comprises amino acids 299-701 of SEQ ID NO:49.

The terms "DNA-RNA hybrid molecule," "DNA-RNA hybrid duplex," "hybrid molecule," and the like interchangeably refer to a polynucleotide that comprises both DNA and RNA. In some embodiments, one strand of a hybrid molecule consists entirely of DNA. In some embodiments, one strand of a hybrid molecule consists entirely of RNA. In some embodiments, one strand of a hybrid molecule consists of DNA, and the other strand consists entirely of RNA. In some embodiments, one or both strands of a hybrid molecule contain both RNA and DNA. The two strands of a DNA-RNA hybrid molecule can be completely or partially complementary. In some embodiments, the two strands of a DNA-RNA hybrid molecule have about 10%, 20%, 30%, 40%, 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% complementarity.

The term "abasic site," also known as an "apurinic/apyrimidinic site" or "AP site," refers to a location within a polynucleotide that has neither a purine nor a pyrimidine base. Abasic sites can arise spontaneously (e.g., spontaneous depurination), as intermediates during base excision repair, or can be recombinantly inserted into a polynucleotide.

The term "hybrid nucleic acid binding domain" or "hybrid (NBD)" refers to the portion of a polypeptide or protein that recognizes or binds to a DNA-RNA hybrid molecule. In some embodiments, a hybrid NBD binds to a DNA-RNA hybrid molecule without requiring recognition of a particular nucleotide sequence. In some embodiments, a hybrid NBD recognizes a specific nucleotide sequence.

The term "ribonuclease H" or "RNase H" refers to a family of endonucleases that are not sequence specific and catalyze the hydrolytic cleavage of RNA in RNA-DNA hybrid substrates. The RNase H family is divided into two subtypes, ribonuclease H1 and ribonuclease H2, that exhibit different substrate specificities. In humans, RNase is encoded by four different genes. RNASEH1 encodes the monomeric H1 subtype. RNASEH2A encodes the catalytic subunit of the H2 subtype. RNASEH2B and RNASEH2C encode structural subunits of the H2 subtype. Non-limiting examples of human RNASEH1 amino acid sequences are set forth under NCBI Reference Sequence numbers NP_001273763.1, NP_001273766.1, and NP_002927.2. A non-limiting example of a human RNASEH2A amino acid sequence is set forth under NCBI Reference Sequence numbers NP_006388.2. Non-limiting examples of human RNASEH2B amino acid sequences are set forth under NCBI Reference Sequence numbers NP_001135751.1, NP_078846.2, and NP_078846.2. A non-limiting example of a human RNASEH2C amino acid sequence is set forth under NCBI Reference Sequence numbers NP_115569.2.

The term "type II restriction enzyme" refers to a group of restriction endonucleases classified under Enzyme Commission number 3.1.21.4 that perform endonucleolytic cleavage of DNA to yield double-stranded fragments having 5' phosphates. Type II restriction enzymes typically cleave within a particular recognition site, or within a short distance from a recognition site. Type II restriction enzyme recognition sites are typically 4 to 8 nucleotides in length and are palindromic. Some type II restriction enzymes have the ability to act on DNA-RNA hybrid substrates, non-limiting examples of which include EcoRI, HindII, SalI, MspI, HhaI, AluI, TaqI, ThaI, HaeIII.

The terms "genetic disorder" and "genetic disease" refer to any condition (e.g., a pathological condition) in a subject that arises from a genomic abnormality or is modulated by one or more genetic factors. The term also encompasses conditions that are modulated by environmental factors in addition to genetic factors. A genetic factor can be, for example, the sequence of a gene or the sequence of a regulatory region that controls the expression of a gene. As non-limiting examples, genetic disorders and diseases include those in which the risk of developing the disorder or disease, the age of onset of the disorder or disease, the severity of the disorder or disease, and/or the development of particular signs or symptoms of the disorder or disease are modulated by one or more genetic factors.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions, or additions to a nucleic acid, peptide, polypeptide, or protein sequence which alter, add, or delete a single amino acid or a small percentage of amino acids in the encoded sequence yield a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N. Y. (1984)).

Unless otherwise specified, amino acid residues are numbered according to their relative positions from the left most residue, which is numbered 1, in an unmodified wild-type polypeptide sequence.

The terms "polypeptide," "peptide," and "protein" are used interchangeably herein to refer to a polymer of amino acid residues. All three terms apply to amino acid polymers in which one or more amino acid residues is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The terms "vector" and "expression vector" interchangeably refer to a nucleic acid construct, generated recombinantly or synthetically, with a series of specified nucleic acid elements that permit transcription of a particular polynucleotide sequence (e.g., encoding a fusion protein or polypeptide (e.g., ADAR2 variant polypeptide) of the present invention or a guide RNA molecule) in a host cell. An expression cassette may be part of a plasmid, viral genome, or nucleic acid fragment. Typically, an expression cassette includes a polynucleotide to be transcribed, operably linked to a promoter. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "isolated," as used with reference to a polynucleotide, denotes that the polynucleotide is essentially free of other cellular components with which it is associated in the natural state. It is preferably in a homogeneous state. Purity and homogeneity are typically determined using analytical chemistry techniques such as electrophoresis (e.g., polyacrylamide gel electrophoresis) or chromatography (e.g., high performance liquid chromatography). In some embodiments, an isolated polynucleotide is at least 85% pure, at least 90% pure, at least 95% pure, or at least 99% pure.

The terms "subject," "individual," and "patient" are used interchangeably herein to refer to a vertebrate, preferably a mammal, more preferably a human. Mammals include, but are not limited to, murines, rats, simians, humans, farm animals, sport animals, and pets. Tissues, cells and their progeny of a biological entity obtained in vivo or cultured in vitro are also encompassed.

As used herein, the term "administering" includes oral administration, topical contact, administration as a suppository, intravenous, intraperitoneal, intramuscular, intralesional, intrathecal, intranasal, intraosseous, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, intraosseous, and intracranial. Other modes of delivery include, but are not limited to, the use of liposomal formulations, intravenous infusion, transdermal patches, etc.

The term "treating" refers to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. Therapeutic benefit can also mean to effect a cure of one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "therapeutically effective amount" or "sufficient amount" refers to the amount of a peptide, fusion protein, polypeptide (e.g., ADAR2 variant polypeptide), polynucleotide, or composition that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective to achieve the desired therapeutic effect in a subject suffering from a genetic disorder. The desired therapeutic effect may include, for example, amelioration of undesired symptoms associated with the genetic disorder, prevention of the manifestation of such symptoms before they occur, slowing down the progression of symptoms associated with the genetic disorder, slowing down or limiting any irreversible damage caused by the genetic disorder, lessening the severity of or curing the genetic disorder, or improving the survival rate or providing more rapid recovery from the genetic disorder. Further, in the context of prophylactic treatment the amount may also be effective to prevent the development of the genetic disorder.

The term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor, etc. In some instances, the carrier is an agent that facilitates the delivery of a polypeptide, fusion protein, or polynucleotide to a target cell or tissue. One of skill in the art will recognize that other pharmaceutical carriers are useful in the present invention.

III. Methods for Modifying Target Sites in Nucleic Acids

In one aspect, methods for modifying a target site within a DNA-RNA hybrid molecule are provided. In some embodiments, the method comprises contacting the DNA-RNA hybrid molecule with an adenosine deaminase that acts on RNA (ADAR) protein, e.g., a human ADAR protein. In some embodiments, the method comprises contacting the DNA-RNA hybrid molecule with a portion of an ADAR protein, e.g., a portion that comprises an ADAR catalytic domain. In some embodiments, the target site that is modified is located within the DNA strand of the DNA-RNA hybrid molecule. In some embodiments, the DNA strand is entirely comprised of deoxyribonucleotides. In some embodiments, the DNA strand comprises a mixture of deoxyribonucleotides and ribonucleotides. In some embodiments, a deoxyadenosine nucleotide is deaminated by the ADAR or portion thereof (e.g., comprising the ADAR catalytic domain).

In some embodiments, the ADAR protein is an ADAR1 protein (or an isoform or portion thereof). In some embodiments, the ADAR protein is an ADAR2 protein (or a portion thereof). In some embodiments, the ADAR protein is an ADAR1 protein (or an isoform or portion thereof) or an ADAR2 protein (or a portion thereof). In some embodiments, both an ADAR1 protein (or an isoform thereof) and an ADAR2 protein, or portions thereof, are used in methods of the present invention. As a non-limiting example, an ADAR1 protein can comprise the amino acid sequence set forth in SEQ ID NO:48. As another non-limiting example, an ADAR2 protein can comprise the amino acid sequence set forth in SEQ ID NO:49.

In some embodiments, the DNA strand of a DNA-RNA hybrid molecule is modified (i.e., the target site is located within the DNA strand of the DNA-RNA hybrid molecule). Methods of the present invention are particularly advantageous in that they enable modification of a target site (e.g., for the purposes of gene or genome editing) without having to introduce a break into the DNA strand that is being edited (i.e., without having to introduce a break into the DNA strand of the DNA-RNA hybrid molecule).

In some embodiments, the ADAR protein (e.g., ADAR1 or ADAR2) or portion thereof comprises one or more mutations. As non-limiting examples, the sequences set forth in SEQ ID NOS:48 and/or 49 can comprise one or more mutations. In particular embodiments, the ADAR protein comprises a base flipping loop mutation. One example of a base flipping loop mutation is an E1008 mutation in ADAR1 (e.g., the E1008 position in SEQ ID NO:48 is mutated to any other amino acid). In some instances, the ADAR protein is ADAR1, and the ADAR1 protein comprises an E1008Q or an E1008H mutation. In other instances, the ADAR1 protein comprises a mutation at position E1008 that replaces glutamic acid with a larger amino acid (e.g., an E1008F, E1008Y, E1008W, E1008L, or E1008I mutation).

Another example of a base flipping loop mutation is an E488 mutation in ADAR2 (e.g., the E488 position in SEQ ID NO:49 is mutated to any other amino acid). In some instances, the ADAR protein is ADAR2, and the ADAR2 protein comprises an E488Q or an E488H mutation. In other instances, the ADAR2 protein comprises a mutation at position E488 that replaces glutamic acid with a larger amino acid (e.g., an E488F, E488Y, E488W, E488L, or E488I mutation).

In some embodiments, using an ADAR1 protein comprising an E1008Q or E1008H mutation and/or an ADAR2 protein comprising an E488Q or E488H mutation in methods of the present invention is advantageous in that these base flipping loop mutations can confer increased target site modification efficiency (e.g., increased editing efficiency or activity). In some embodiments, using an ADAR1 protein comprising an E1008F, E1008Y, E1008W, E1008L, or E1008I mutation in methods of the present invention is advantageous in that these mutations can confer increased target site modification specificity (e.g., decreased incidence of off-target editing events), especially when combined with certain modifications of the RNA strand of the hybrid molecule, as discussed below. In further embodiments, using an ADAR2 protein comprising an E488F, E488Y, E488W, E488L, or E488I mutation in methods of the present invention is advantageous in that these mutations can confer increased target site modification specificity (e.g., decreased incidence of off-target editing events), especially when combined with certain modifications of the RNA strand of the hybrid molecule, as discussed below.

In some embodiments, the RNA strand of the DNA-RNA hybrid molecule comprises one or more modifications or features that improve target site modification efficiency and/or specificity. In some embodiments, the RNA strand introduces a dA-C mismatch at the target site. For example, if the target site contains a deoxyadenosine (dA) that is to be deaminated by the ADAR, a cytidine can be introduced into the orphan nucleotide position on the RNA strand (i.e., the position that is complementary to the target site position on the DNA strand) such that a deoxyadenosine-cytidine mismatch is created. Similarly, the RNA strand can contain features or be designed such that one or more dA-C mismatches are introduced 5' and/or 3' of the target site. In some embodiments, the RNA strand introduces one or more dA-C mismatches 5' of the target site. In some embodiments, the RNA strand introduces one or more dA-C mismatches 3' of the target site. In some embodiments, the RNA strand introduces one or more dA-C mismatches 5' of the target site and one or more dA-C mismatches 3' of the target site. As used herein, the terms "5' of the target site" and "3' of the target site" are used with reference to the 5' end of the DNA strand (i.e., the strand of the DNA-RNA hybrid molecule comprising the target site).

In some embodiments, target modification efficiency is increased when the RNA strand of the DNA-RNA hybrid molecule introduces dA-C mismatches at the target site, 5' of the target site, and/or 3' of the target site. In some embodiments, target modification efficiency is increased when the RNA strand of the DNA-RNA hybrid molecule introduces dA-C mismatches at the target site, 5' of the target site, and/or 3' of the target site and the ADAR protein is selected from the group consisting of wild-type ADAR1, ADAR1 comprising an E1008Q or E1008H mutation, wild-type ADAR2, ADAR2 comprising an E488Q or E488H mutation, and a combination thereof.

In some embodiments, target site modification efficiency refers to the number of target sites that are modified after the RNA-DNA hybrid molecule (i.e., comprising the target site) has been contacted with the ADAR for a specific amount of time. In some embodiments, the RNA-DNA hybrid molecule comprises a plurality of target sites, and modification efficiency is taken to be the percentage of target sites that are modified after the hybrid molecule has been contacted with the ADAR for a specific amount of time. In some embodiments, the RNA-DNA hybrid molecule comprises a plurality of such molecules, each containing one or more target sites, and modification efficiency is taken to be the percentage of hybrid molecules in which at least one target site is modified after the plurality of hybrid molecules has been contacted with the ADAR for a specific amount of time. In some embodiments, a plurality of DNA-RNA hybrid molecules, each comprising one or more target sites, are located within a population of host cells, and modification efficiency is taken to be the percentage of the host cell population in which at least one target site is modified after the DNA-RNA hybrid molecules have been contacted with ADAR for a specific amount of time.

In some embodiments, target site modification efficiency is at least about 5%, 10%, 15%, 20%, 25%, 30%, 35%, 40%, 45%, or 50%. In other embodiments, target site modification efficiency is at least about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, target site modification efficiency is increased by at least about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, or 20-fold when an ADAR1 comprising an E1008 mutation, such as an E1008Q or E1008H mutation, and/or an ADAR2 comprising an E488 mutation, such as an E488Q or E488H mutation, is used, compared to when the corresponding wild-type ADAR protein is used.

In some embodiments, target site modification efficiency is increased by at least about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, or 20-fold when the RNA strand of the DNA-RNA hybrid molecule introduces a dA-C mismatch at the target site, 5' of the target site, and/or 3' of the target site (e.g., and when wild-type ADAR1, ADAR1 E1008 (e.g., E1008Q, E1008H), wild-type ADAR2, and/or ADAR2 E488 (e.g., E488Q, E488H) is used), compared to when the dA-C mismatch is not introduced.

In some embodiments, target site modification efficiency is increased by at least about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, or 20-fold when an ADAR1 comprising an E1008 (e.g., E1008Q, E1008H) mutation and/or an ADAR2 comprising an E488 (e.g., E488Q, E488H) mutation is used and the RNA strand of the DNA-RNA hybrid molecule introduces a dA-C mismatch at the target site, 5' of the target site, and/or 3' of the target site, compared to when the corresponding wild-type ADAR protein is used and the dA-C mismatch is not introduced.

In some embodiments, the RNA strand of the DNA-RNA hybrid molecule contains an abasic site. In some embodiments, the abasic site is located at the orphan nucleotide position (i.e., the position that is complementary to the target site position on the DNA strand). In particular embodiments, when methods of the present invention are performed using an RNA strand that has an abasic site at the position on the RNA strand that is complementary to the target site position on the DNA strand, using an ADAR1 comprising an E1008 mutation that replaces glutamic acid with a larger amino acid (e.g., E1008F, E1008Y, E1008W, E1008I, or E1008L) and/or an ADAR2 comprising an E488 mutation that replaces glutamic acid with a larger amino acid (e.g., E488F, E488Y, E488W, E488I, or E488L) increases target site modification efficiency, e.g., compared to when a cytidine or other orphan nucleotide is used.

In some embodiments, target site modification efficiency is at least about 5%, 10%, 15%, 20%, 25%, 30%, 35%, 40%, 45%, or 50% when an ADAR1 comprising an E1008 mutation that replaces glutamic acid with a larger amino acid (e.g., E1008F, E1008Y, E1008W, E1008L, or E1008I ) is used and the RNA strand of the DNA-RNA hybrid molecule comprises an abasic site (e.g., at the position on the RNA strand that is complementary to the target site position on the DNA strand). In other embodiments, target site modification efficiency is at least about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when an ADAR1 comprising an E1008 mutation that replaces glutamic acid with a larger amino acid (e.g., E1008F, E1008Y, E1008W, E1008L, or E1008I) is used and the RNA strand of the DNA-RNA hybrid molecule comprises an abasic site (e.g., at the position on the RNA strand that is complementary to the target site position on the DNA strand).

In some embodiments, target site modification efficiency is increased by at least about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, or 20-fold when an ADAR1 comprising an E1008 mutation that replaces glutamic acid with a larger amino acid (e.g., E1008F, E1008Y, E1008W, E1008L, or E1008I) is used and the RNA strand of the DNA-RNA hybrid molecule comprises an abasic site (e.g., at the position on the RNA strand that is complementary to the target site position on the DNA strand), compared to when a cytidine or other orphan nucleotide is used, or when an abasic site is used and the ADAR1 does not comprise an E1008 mutation that replaces glutamic acid with a larger amino acid.

In some embodiments, target site modification efficiency is at least about 5%, 10%, 15%, 20%, 25%, 30%, 35%, 40%, 45%, or 50% when an ADAR2 comprising an E488 mutation that replaces glutamic acid with a larger amino acid (e.g., E488F, E488Y, E488W, E488L, or E488I ) is used and the RNA strand of the DNA-RNA hybrid molecule comprises an abasic site (e.g., at the position on the RNA strand that is complementary to the target site position on the DNA strand). In other embodiments, target site modification efficiency is at least about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when an ADAR2 comprising an E488 mutation that replaces glutamic acid with a larger amino acid (e.g., E488F, E488Y, E488W, E488L, or E488I) is used and the RNA strand of the DNA-RNA hybrid molecule comprises an abasic site (e.g., at the position on the RNA strand that is complementary to the target site position on the DNA strand).

In some embodiments, target site modification efficiency is increased by at least about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, or 20-fold when an ADAR2 comprising an E488 mutation that replaces glutamic acid with a larger amino acid (e.g., E488F, E488Y, E488W, E488L, or E488I) is used and the RNA strand of the DNA-RNA hybrid molecule comprises an abasic site (e.g., at the position on the RNA strand that is complementary to the target site position on the DNA strand), compared to when a cytidine or other orphan nucleotide is used, or when an abasic site is used and the ADAR2 does not comprise an E488 mutation that replaces glutamic acid with a larger amino acid.

In some embodiments, target site modification specificity is increased. For example, by including an abasic site (e.g., at the position on the RNA strand that is complementary to the target site position on the DNA strand) when an ADAR1 is used that comprises an E1008 mutation, wherein glutamic acid is replaced with a larger amino acid (e.g., an E1008F, E1008Y, E1008W, E1008L, or E1008I mutation), and/or an ADAR2 is used that comprises an E488 mutation, wherein glutamic acid is replaced with a larger amino acid (e.g., an E488F, E488Y, E488W, E488L, or E488I mutation), the specificity of target site modification can be increased (e.g., the incidence of off-target modification events can be reduced). As a non-limiting example, target site modification specificity can be determined by calculating the percentage of all modification or editing events (e.g., that occurred while the DNA-RNA hybrid molecule was contacted with the ADAR) that were modifications of the intended target sites.

Furthermore, target site modification specificity in RNA duplexes can be increased by including an abasic site at a position that is complementary to the target modification site and using an ADAR1 (or a portion thereof) that comprises an E1008 mutation that replaces glutamic acid with a larger amino acid (e.g., E1008F, E1008Y, E1008W, E1008L, or E1008I) and/or an ADAR2 (or a portion thereof) that comprises an E488 mutation that replaces glutamic acid with a larger amino acid (e.g., E488F, E488Y, E488W, E488L, or E488I).

In some embodiments, target site modification specificity is at least about 5%, 10%, 15%, 20%, 25%, 30%, 35%, 40%, 45%, or 50% when an ADAR1 comprising an E1008 mutation that replaces glutamic acid with a larger amino acid (e.g., E1008F, E1008Y, E1008W, E1008L, or E1008I ) is used and the RNA strand of the DNA-RNA hybrid molecule comprises an abasic site (e.g., at the position on the RNA strand that is complementary to the target site position on the DNA strand). In other embodiments, target site modification specificity is at least about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when an ADAR1 comprising an E1008 mutation that replaces glutamic acid with a larger amino acid (e.g., E1008F, E1008Y, E1008W, E1008L, or E1008I) is used and the RNA strand of the DNA-RNA hybrid molecule comprises an abasic site (e.g., at the position on the RNA strand that is complementary to the target site position on the DNA strand).

In some embodiments, target site modification specificity is increased by at least about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, 20-fold, 25-fold, 50-fold, 100-fold, 500-fold, 1,000-fold, 5,000-fold, or 10,000-fold when an ADAR1 comprising an E1008 mutation that replaces glutamic acid with a larger amino acid (e.g., E1008F, E1008Y, E1008W, E1008L, or E1008I) is used and the RNA strand of the DNA-RNA hybrid molecule comprises an abasic site (e.g., at the position on the RNA strand that is complementary to the target site position on the DNA strand), compared to when a cytidine or other orphan nucleotide is used, or when the RNA strand comprises the abasic site and the ADAR does not comprise a mutation at E1008 that replaces glutamic acid with a larger amino acid.

In some embodiments, target site modification specificity is at least about 5%, 10%, 15%, 20%, 25%, 30%, 35%, 40%, 45%, or 50% when an ADAR2 comprising an E488 mutation that replaces glutamic acid with a larger amino acid (e.g., E488F, E488Y, E488W, E488L, or E488I ) is used and the RNA strand of the DNA-RNA hybrid molecule comprises an abasic site (e.g., at the position on the RNA strand that is complementary to the target site position on the DNA strand). In other embodiments, target site modification specificity is at least about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when an ADAR2 comprising an E488 mutation that replaces glutamic acid with a larger amino acid (e.g., E488F, E488Y, E488W, E488L, or E488I) is used and the RNA strand of the DNA-RNA hybrid molecule comprises an abasic site (e.g., at the position on the RNA strand that is complementary to the target site position on the DNA strand).

In some embodiments, target site modification specificity is increased by at least about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, 20-fold, 25-fold, 50-fold, 100-fold, 500-fold, 1,000-fold, 5,000-fold, or 10,000-fold when an ADAR2 comprising an E488 mutation that replaces glutamic acid with a larger amino acid (e.g., E488F, E488Y, E488W, E488L, or E488I) is used and the RNA strand of the DNA-RNA hybrid molecule comprises an abasic site (e.g., at the position on the RNA strand that is complementary to the target site position on the DNA strand), compared to when a cytidine or other orphan nucleotide is used, or when the RNA strand comprises the abasic site and the ADAR does not comprise a mutation at E488 that replaces glutamic acid with a larger amino acid.

In some embodiments, the RNA-DNA hybrid molecule is contacted with ADAR for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 100, 101, 102, 103, 104, 105, 106, 107, 108, 109, 110, 111, 112, 113, 114, 115, 116, 117, 118, 119, or 120 minutes. In some embodiments, the RNA-DNA hybrid molecule is contacted with ADAR for at least about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 hours. In some embodiments, the RNA-DNA hybrid molecule is contacted with ADAR for at least about 1, 1.5, 2, 2.5, 3, 3.5, 4, 4.5, 5, 5.5, 6, 6.5, or 7 days.

In some embodiments, the RNA strand of the DNA-RNA hybrid molecule comprises one or more modifications or features that increase stability (e.g, of the RNA strand). Non-limiting examples of modifications that can be used to increase stability include 2'-O-methyl and phosphorothioate modifications.

In some embodiments, modification of the target site comprises editing a gene. In some embodiments, modification of the target site comprises editing a gene regulatory region (e.g., a region that regulates the expression of a gene). In some embodiments, modification of the target site corrects a defect in a gene product (e.g., a protein that is expressed from a gene).

In some embodiments, modification of the target site increases the expression of a gene product by at least about 1.1-fold, 1.2-fold, 1.3-fold, 1.4-fold, 1.5-fold, 1.6-fold, 1.7-fold, 1.8-fold, 1.9-fold-, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.1-fold, 5.2-fold, 5.3-fold, 5.4-fold, 5.5-fold, 5.6-fold, 5.7-fold, 5.8-fold, 5.9-fold, 6-fold, 6.1-fold, 6.2-fold, 6.3-fold, 6.4-fold, 6.5-fold, 6.6-fold, 6.7-fold, 6.8-fold, 6.9-fold, 7-fold, 7.1-fold, 7.2-fold, 7.3-fold, 7.4-fold, 7.5-fold, 7.6-fold, 7.7-fold, 7.8-fold, 7.9-fold, 8-fold, 8.1-fold, 8.2-fold, 8.3-fold, 8.4-fold, 8.5-fold, 8.6-fold, 8.7-fold, 8.8-fold, 8.9-fold, 9-fold, 9.1-fold, 9.2-fold, 9.3-fold, 9.4-fold, 9.5-fold, 9.6-fold, 9.7-fold, 9.8-fold, 9.9-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, or 20-fold. The increase in expression can be determined, for example, with respect to a control (e.g., expression of the gene when the target site modification has not been made).

In some embodiments, modification of the target site decreases the expression of a gene product by at least about 1.1-fold, 1.2-fold, 1.3-fold, 1.4-fold, 1.5-fold, 1.6-fold, 1.7-fold, 1.8-fold, 1.9-fold-, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.1-fold, 5.2-fold, 5.3-fold, 5.4-fold, 5.5-fold, 5.6-fold, 5.7-fold, 5.8-fold, 5.9-fold, 6-fold, 6.1-fold, 6.2-fold, 6.3-fold, 6.4-fold, 6.5-fold, 6.6-fold, 6.7-fold, 6.8-fold, 6.9-fold, 7-fold, 7.1-fold, 7.2-fold, 7.3-fold, 7.4-fold, 7.5-fold, 7.6-fold, 7.7-fold, 7.8-fold, 7.9-fold, 8-fold, 8.1-fold, 8.2-fold, 8.3-fold, 8.4-fold, 8.5-fold, 8.6-fold, 8.7-fold, 8.8-fold, 8.9-fold, 9-fold, 9.1-fold, 9.2-fold, 9.3-fold, 9.4-fold, 9.5-fold, 9.6-fold, 9.7-fold, 9.8-fold, 9.9-fold, 10-fold, 10.5-fold, 11-fold, 11.5-fold, 12-fold, 12.5-fold, 13-fold, 13.5-fold, 14-fold, 14.5-fold, 15-fold, 15.5-fold, 16-fold, 16.5-fold, 17-fold, 17.5-fold, 18-fold, 18.5-fold, 19-fold, 19.5-fold, or 20-fold. The decrease in expression can be determined, for example, with respect to a control (e.g., expression of the gene when the target site modification has not been made).

In some embodiments, target site modifications (e.g., of a DNA-RNA hybrid molecule) produced by methods and compositions of the present invention will produce a decrease or increase in the level of mRNA expression (e.g., a decrease or increase in transcription of a gene expressed by the target site or under the control of a genetic regulatory element at the target site). Accordingly, the amount of a decrease or increase in expression can be determined or quantified by measuring mRNA levels (e.g., of a gene expressed by the target site or under the control of a genetic regulatory element at the target site). In some embodiments, the amount of a decrease or increase in expression is expressed as a fold change in the level of one or more mRNA transcripts. Exemplary methods for measuring mRNA levels include, without limitation, PCR (e.g., reverse-transcription quantitative PCR) and microarray analysis.

In addition, target site modifications (e.g., of a DNA-RNA hybrid molecule) produced by methods and compositions of the present invention can produce changes in the level of protein expression. Accordingly, the amount of a decrease or increase in expression effected by a target site modification can be determined or quantified by measuring protein levels (e.g., of a protein expressed from a gene expressed by the target site or under the control of a genetic regulatory element at the target site. In some embodiments, the amount of a decrease or increase in expression is expressed as a fold change in the level of one or more proteins. Exemplary methods for determining protein expression or quantifying the presence of other compounds (e.g., metabolites or other biochemicals that can be used to assay metabolic activity) include, without limitation, Western Blot, dot blot, enzyme-linked immunosorbent assay (ELISA), radioimmunoassay (RIA), immunoprecipitation, immunofluorescence, immunohistochemistry (IHC), FACS analysis, chemiluminescence, and multiplex bead assays (e.g., using Luminex or fluorescent microbeads).

Target site modifications (e.g., of a DNA-RNA hybrid molecule) produced according to methods and compositions of the present invention can produce changes in one or more phenotypes (e.g., the level or activity of a biochemical pathway, or the morphology or developmental fate of a cell or tissue). In some embodiments, the effects of target site modifications can be assessed by employing a reporter or selectable marker to examine the phenotype of an organism or a population of organisms. In some instances, the marker produces a visible phenotype, such as the color of an organism or population of organisms. As a non-limiting example, the phenotype can be examined by growing the target organisms (e.g., cells or other organisms that have had their genome modified) and/or their progeny under conditions that result in a phenotype, wherein the phenotype may not be visible under ordinary growth conditions.

In some embodiments, the reporter or selectable marker, used for assessing the effects of a target site modification (e.g., of a DNA-RNA hybrid molecule) made by a method or composition of the present invention, is a fluorescent tagged protein, an antibody, a labeled antibody, a chemical stain, a chemical indicator, or a combination thereof. In other embodiments, the reporter or selectable marker responds to a stimulus, a biochemical, or a change in environmental conditions. In some instances, the reporter or selectable marker responds to the concentration of a metabolic product, a protein product, a synthesized drug of interest, a cellular phenotype of interest, a cellular product of interest, or a combination thereof. A cellular product of interest can be, as a non-limiting example, an RNA molecule (e.g., messenger RNA (mRNA), long non-coding RNA (lncRNA), microRNA (miRNA)), which can be produced, for example, under the control of a target site that is modified by a method or composition of the present invention.

In some embodiments, the target site modification (e.g., of a DNA-RNA hybrid molecule by an ADAR) is produced in vitro. In other embodiments, the DNA-RNA hybrid molecule and the ADAR are in a cell. In some embodiments, an RNA molecule is introduced into the cell and pairs with a DNA strand within the cell to form the DNA-RNA hybrid molecule. In some embodiments, the RNA molecule is a guide RNA (gRNA) molecule. As a non-limiting example, the ADAR, or a combination of the ADAR and an RNA molecule, can be introduced into a cell, and the ADAR subsequently produces a modification (e.g., adenosine deamination) at a target site (e.g., a target site that is present within the cell's genome). Alternatively, a nucleic acid or a vector comprising a polynucleotide sequence encoding the ADAR (or a portion thereof) and/or the RNA molecule can be introduced into a cell, and subsequently the ADAR can be expressed by the cell. The expressed ADAR can then produce a modification at a target site within the cell.

Methods of the present invention can be performed in a multiplex format. In some embodiments, multiplexing comprises introducing two or more RNA molecules into a host cell, or cloning two or more nucleic acids comprising polynucleotide sequences that encode RNA molecules in tandem into a single expression vector (i.e., an expression vector that is subsequently introduced into a host cell). In some instances, at least about 2, 3, 4, 5, 6, 7, 8, 9, 10 15, 20, 25, 30, 35, 40, 45, 50, or more RNA molecules are introduced into a host cell. In some embodiments, at least about 2, 3, 4, 5, 6, 7, 8, 9, 10, or more polynucleotide sequences that encode RNA molecules (e.g., different RNA molecules) are included in a single vector. In some embodiments, at least 2, 3, 4, 5, 6, 7, 8, 9, 10, 15, 20, 25, 30, 35, 40, 45, 50, or more expression vectors are introduced into a host cell. Each of the expression vectors can encode one or more different RNA molecules.

In still other embodiments, multiplexing comprises transfecting a plurality of host cells. Each host cell can be transfected with a single expression vector or multiple different expression vectors. In some embodiments, a plurality of host cells comprises about $10^3$, about $10^4$, about $10^5$, about $10^6$, about 10', or about $10^8$ cells. Also, multiple embodiments of multiplexing can be combined.

By using one or a combination of the various multiplexing embodiments, it is possible to modify any number of target sites within a genome. In some instances, at least about 1, 2, 3, 4, 5, 6, 7, 8, 9, or 10 target sites are modified. In other instances, at least about 10 to about 100 (e.g., at least about 10, 15, 20, 25, 30, 35, 40, 45, 50, 55, 60, 65, 70, 75, 80, 85, 90, 95, or 100) target sites are modified. In some instances, at least about 100 to about 1,000 (e.g., about 100, 200, 300, 400, 500, 600, 700, 800, 900, or 1,000) target sites are modified. In other instances, at least about 1,000 to about 30,000 (e.g., about 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, or 30,000) target sites are modified.

The methods and compositions of the present invention can be used for producing target site modifications (e.g. in a DNA-RNA hybrid molecule) in the genome of any cell of interest. The cell can be a cell from any organism, e.g., a bacterial cell, an archaeal cell, a cell of a single-cell eukaryotic organism, the cell of a multicellular eukaryotic organism, a plant cell (e.g., a rice cell, a wheat cell, a tomato cell, an *Arabidopsis thaliana* cell, a *Zea mays* cell and the like), an algal cell (e.g., *Botryococcus braunii*, *Chlamydomonas reinhardtii*, *Nannochloropsis gaditana*, *Chlorella pyrenoidosa*, *Sargassum patens* C. Agardh, and the like), a fungal cell (e.g., yeast cell, etc.), an animal cell, a cell from an invertebrate animal (e.g., fruit fly, cnidarian, echinoderm, nematode, etc.), a cell from a vertebrate animal (e.g., fish, amphibian, reptile, bird, mammal, etc.), a cell from a mammal, a cell from a human, a cell from a healthy human, a cell from a human patient, a cell from a cancer patient, etc. In some cases, the host cell treated by the method disclosed herein can be transplanted to a subject (e.g., patient). For instance, the cell in which the target site modification is made can be derived from the subject to be treated (e.g., patient).

Furthermore, the cell can be a stem cell, e.g., embryonic stem cell, induced pluripotent stem cell, adult stem cell, e.g., mesenchymal stem cell, neural stem cell, hematopoietic stem cell, organ stem cell, a progenitor cell, a somatic cell, e.g., fibroblast, hepatocyte, heart cell, liver cell, pancreatic cell, muscle cell, skin cell, blood cell, neural cell, immune cell, and any other cell of the body, e.g., human body. The cells can be primary cells or primary cell cultures derived from a subject, e.g., an animal subject or a human subject, and allowed to grow in vitro for a limited number of passages. In some embodiments, target site modifications are made in cells that are disease cells or derived from a subject with a disease. For instance, the cells can be cancer or tumor cells. The cells can also be immortalized cells (e.g., cell lines), for instance, from a cancer cell line.

In any of the embodiments described above, the ADAR can comprise a fusion protein of the present invention described below in Section IV, i.e., an ADAR catalytic domain that is fused to a hybrid nucleic acid binding domain (NBD). In some embodiments, the hybrid NBD comprises ribonuclease H (RNase H), a type II restriction enzyme, or a portion thereof. In particular embodiments, the hybrid NBD comprises RNase H or a portion thereof. In some embodiments, the type II restriction enzyme or portion thereof is one that can recognize or bind to a DNA-RNA hybrid molecule. In particular embodiments, the hybrid NBD comprises 1, 2, 3, 4, 5, 6, 7, 8, or 9 type II restriction enzymes (or a portion thereof) selected from the group consisting of EcoRI, HindII, SalI, MspI, HhaI, AluI, TaqI, ThaI, and HaeIII. In some embodiments, the hybrid NBD comprises RNase H (or a portion thereof) and 1, 2, 3, 4, 5, 6, 7, 8, or 9 type II restriction enzymes (or a portion thereof) selected from the group consisting of EcoRI, HindII, SalI, MspI, HhaI, AluI, TaqI, ThaI, and HaeIII (or a portion thereof). Furthermore, in any of the embodiments described above, the ADAR can comprise a variant ADAR2 polypeptide described below in Section IV, e.g., a variant ADAR2 polypeptide comprising a mutation at position 488, wherein position 488 is determined with reference to the full-length amino acid sequence set forth in SEQ ID NO:49.

IV. Fusion Proteins and Polypeptides

In another aspect, fusion proteins are provided. The fusion proteins of the present invention can be used in the practice of any of the methods of the present invention as described above in Section III.

In some embodiments, the fusion protein comprises the catalytic domain of an adenosine deaminase that acts on RNA (ADAR) protein (e.g., a human ADAR protein) and a hybrid nucleic acid binding domain (NBD). In some embodiments, the ADAR catalytic domain of the fusion protein deaminates a deoxyadenosine nucleotide, e.g., located within the DNA strand of a DNA-RNA hybrid molecule.

In some embodiments, the ADAR catalytic domain is an ADAR1 catalytic domain. In some embodiments, the ADAR catalytic domain is an ADAR2 catalytic domain. In some embodiments, the fusion protein comprises an ADAR1 catalytic domain or an ADAR2 catalytic domain. In some embodiments, the fusion protein comprises both an ADAR1 catalytic domain and an ADAR2 catalytic domain. As a non-limiting example, the ADAR1 catalytic domain can comprise amino acids 833-1226 of the amino acid sequence set forth in SEQ ID NO:48. As another non-limiting example, the ADAR2 catalytic domain can comprise amino acids 299-701 of the amino acid sequence set forth in SEQ ID NO:49.

In some embodiments, the fusion protein modifies a target site without having to introduce a break into the DNA strand that is being edited (i.e., without having to introduce a break into the DNA strand of the DNA-RNA hybrid molecule).

In some embodiments, the ADAR catalytic domain (e.g., ADAR1 or ADAR2 catalytic domain) comprises one or more mutations. In particular embodiments, the ADAR catalytic domain comprises a base flipping loop mutation. One example of a base flipping loop mutation is an E1008 mutation in ADAR1 (e.g., the E1008 position in SEQ ID NO:48 is mutated to any other amino acid). In some instances, the ADAR1 catalytic domain comprises an E1008Q mutation, wherein the E1008 position is determined in reference to the full-length ADAR1 sequence set forth in SEQ ID NO:48. In other instances, the ADAR1 catalytic domain comprises an E1008H mutation, wherein the E1008 position is determined in reference to the full-length ADAR1 sequence set forth in SEQ ID NO:48. In some instances, the ADAR1 catalytic domain comprises a mutation at position E1008, determined in reference to the full-length ADAR1 sequence set forth in SEQ ID NO:48, that replaces glutamic acid with a larger amino acid (e.g., an E1008F, E1008Y, E1008W, E1008L, or E1008I mutation)).

Another example of a base flipping loop mutation is an E488 mutation in ADAR2 (e.g., the E488 position in SEQ ID NO:49 is mutated to any other amino acid). In some instances, the ADAR2 catalytic domain comprises an E488Q mutation, wherein the E488 position is determined in reference to the full-length ADAR2 sequence set forth in SEQ ID NO:49. In other instances, the ADAR2 catalytic domain comprises an E488H mutation, wherein the E488 position is determined in reference to the full-length ADAR2 sequence set forth in SEQ ID NO:49. In some instances, the ADAR2 catalytic domain comprises a mutation at position E488, determined in reference to the full-length ADAR2 sequence set forth in SEQ ID NO:49, that replaces glutamic acid with a larger amino acid (e.g., an E488F, E488Y, E488W, E488L, or E488I mutation).

In some embodiments, the hybrid NBD recognizes or binds a DNA-RNA hybrid molecule. In some embodiments, the hybrid NBD comprises ribonuclease H (RNase H), a type II restriction enzyme, or a portion thereof. In particular embodiments, the hybrid NBD comprises RNase H or a portion thereof. In some embodiments, the type II restriction enzyme or portion thereof is one that can recognize or bind to a DNA-RNA hybrid molecule. In particular embodiments, the hybrid NBD comprises 1, 2, 3, 4, 5, 6, 7, 8, or 9 type II restriction enzymes (or a portion thereof) selected from the group consisting of EcoRI, HindII, SalI, MspI, HhaI, AluI, TaqI, ThaI, and HaeIII. In some embodiments, the hybrid NBD comprises RNase H (or a portion thereof) and 1, 2, 3, 4, 5, 6, 7, 8, or 9 type II restriction enzymes (or a portion thereof) selected from the group consisting of EcoRI, HindII, SalI, MspI, HhaI, AluI, TaqI, ThaI, and HaeIII (or a portion thereof).

In some embodiments, the fusion protein further comprises an amino acid linker. In particular embodiments, the amino acid linker is located between an ADAR catalytic domain and a hybrid NBD. In some embodiments, the amino acid linker is about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In some instances, the amino acid linker is about 21 amino acids in length. The amino acid linker can comprise any amino acid or combination of amino acids. In some embodiments, the amino acid linker comprises G and/or S. A non-limiting example of a suitable amino acid linker sequence is set forth under SEQ ID NO:141.

In another aspect, isolated polypeptides that are variants of ADAR2 are provided. The isolated polypeptides of the present invention can be used in the practice of any of the methods of the present invention as described above in Section III.

In some embodiments, the isolated polypeptide comprises an amino acid sequence having at least about 75% identity (e.g., at least about 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to the amino acid sequence set forth in SEQ ID NO:49. In some embodiments, position 488, determined with reference to the full-length ADAR2 sequence set forth in SEQ ID NO:49, is not used to determine percent identity. In some embodiments, the isolated polypeptide does not comprise the amino acid sequence set forth in SEQ ID NO:49.

In some embodiments, the isolated polypeptide comprises an E488 mutation, wherein the E488 position is determined with reference to the full-length ADAR2 sequence set forth in SEQ ID NO:49. In some embodiments, the isolated polypeptide comprises an E488Y, E488I, E488C, E488D, E488G, E488K, E488P, E488T, or E488V mutation, wherein the E488 position is determined with reference to the full-length ADAR2 sequence set forth in SEQ ID NO:49. In some embodiments, the isolated polypeptide comprises an E488Y or E488I mutation, wherein the E488 position is determined with reference to the full-length ADAR2 sequence set forth in SEQ ID NO:49. In some embodiments, the isolated polypeptide comprises an E488Y mutation. In some embodiments, the isolated polypeptide comprises an E488I mutation. In some embodiments, the isolated polypeptide comprises an E488C mutation. In some embodiments, the isolated polypeptide comprises an E488D mutation. In some embodiments, the isolated polypeptide comprises an E488G mutation. In some embodiments, the isolated polypeptide comprises an E488K mutation. In some embodiments, the isolated polypeptide comprises an E488P mutation. In some embodiments, the isolated polypeptide comprises an E488T mutation. In some embodiments, the isolated polypeptide comprises an E488V mutation.

In some embodiments, the isolated polypeptide comprises an amino acid sequence having at least about 75% identity (e.g., at least about 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to the amino acid sequence set forth in SEQ ID NO:61. In some embodiments, position 488, determined with reference to the full-length ADAR2 sequence set forth in SEQ ID NO:61, is not used to determine percent identity. In some embodiments, the isolated polypeptide comprises the amino acid sequence set forth in SEQ ID NO:61, or the catalytic domain thereof.

In some embodiments, the isolated polypeptide comprises an amino acid sequence having at least about 75% identity (e.g., at least about 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to the amino acid sequence set forth in SEQ ID NO:64. In some embodiments, position 488, determined with reference to the full-length ADAR2 sequence set forth in SEQ ID NO:64, is not used to determine percent identity. In some embodiments, the isolated polypeptide comprises the amino acid sequence set forth in SEQ ID NO:64 or the catalytic domain thereof.

ADAR2 variant polypeptides of the present invention (e.g., isolated ADAR2 variant polypeptides) and compositions comprising the ADAR2 variant polypeptides can be used, for example, to modify target sites within nucleic acids (e.g., by contacting the ADAR2 variant polypeptide or a composition comprising the ADAR2 variant polypeptide with a nucleic acid). In some embodiments, the nucleic acid comprises double-stranded RNA. In other embodiments, the nucleic acid comprises a DNA-RNA hybrid molecule. In some embodiments, the nucleic acid comprises an abasic site. In some instances, the RNA strand within the DNA-RNA hybrid molecule comprises an abasic site. In other instances, an orphan nucleotide position in the double-stranded RNA molecule (i.e., the position occupying the complementary position to the target modification site on the other RNA strand) comprises an abasic site.

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, Tetrahedron Lett. 22: 1859-1862 (1981), using an automated synthesizer, as described in Van Devanter et. al., Nucleic Acids Res. 12: 6159-6168 (1984). Purification of oligonucleotides is performed using any art-recognized strategy, e.g., native acrylamide gel electrophoresis or anion-exchange HPLC as described in Pearson & Reanier, I Chrom. 255: 137-149 (1983).

The sequence of a protein domain or gene of interest can be verified after cloning or subcloning using, e.g., the chain termination method for sequencing double-stranded templates of Wallace et al., Gene 16: 21-26 (1981).

A large number of possible tags may be used for practicing the present invention. Non-limiting examples include: biotin (small molecule); StrepTag (Strepll) (8 a.a.); SBP (38 a.a.); biotin carboxyl carrier protein or BCCP (100 a.a.); epitope tags such as FLAG (8 a.a.), 3×FLAG (22 a.a.), and my c (22 a.a.); S-tag (Novagen) (15 a.a.); Xpress (Invitrogen) (25 a.a.); eXact (Bio-Rad) (75 a.a.); HA (9 a.a.); VSV-G (11 a.a.); Protein A/G (280 a.a.); HIS (6-10 a.a.) (SEQ ID NO: 143); glutathione s-transferase or GST (218 a.a.); maltose binding protein or MBP (396 a.a.); CBP (28 a.a.); CYD (5 a.a.); HPC (12 a.a.); CBD intein-chitin binding domain (51 a.a.); Trx (Invitrogen) (109 a.a.); NorpA (5 a.a.); and NusA (495 a.a.). Furthermore, the tag may be linked to a cleavage sequence such that the tag can be removed from a protein of interest (e.g., fusion protein of the present invention), if so desired. As a non-limiting example, a tobacco etch virus (TEV) protease cleavage sequence (e.g., SEQ ID NO:142) can be used.

B. Coding Sequence for a Protein of Interest

In another aspect, the present invention provides polynucleotides (e.g., isolated polynucleotides) that comprise a nucleotide sequence encoding a fusion protein or polypeptide (e.g., ADAR2 variant polypeptide) of the present invention. The rapid progress in the studies of human genome has made possible a cloning approach where a human or other model organism DNA sequence database can be searched for any gene segment that has a certain percentage of sequence homology to a known nucleotide sequence, such as one encoding an ADAR or a hybrid NBD described herein. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full-length coding sequence from a human or other model organism cDNA or genomic library using a synthetic probe may be necessary to obtain a larger gene.

Alternatively, a nucleic acid sequence can be isolated from a cDNA or genomic DNA library (e.g., human or rodent cDNA or genomic DNA library) using standard cloning techniques such as polymerase chain reaction (PCR), where homology-based primers can often be derived from a known nucleic acid sequence. Most commonly used techniques for this purpose are described in standard texts, e.g., Sambrook and Russell, supra.

cDNA libraries may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, Gene, 25: 263-269 (1983); Ausubel et al., supra). Upon obtaining an amplified segment of nucleotide sequence by PCR, the segment can be further used as a probe to isolate the full-length polynucleotide sequence encoding the protein of interest from the cDNA library. A general description of appropriate procedures can be found in Sambrook and Russell, supra.

A similar procedure can be followed to obtain a full-length sequence encoding a protein of interest from a human or other model organism genomic library. Genomic libraries are commercially available or can be constructed according to various art-recognized methods. As a non-limiting example, to construct a genomic library, the DNA is first extracted from a tissue where a protein of interest is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, *PCR Technology,* CRC Press Inc. 1994) to amplify a segment of nucleotide sequence from a cDNA or genomic library. Using the amplified segment as a probe, the full-length nucleic acid encoding a protein of interest is obtained.

Upon acquiring a nucleic acid sequence encoding a protein of interest, such as an ADAR or a hybrid NBD, the coding sequence can be further modified by a number of well-known techniques such as restriction endonuclease digestion, PCR, and PCR-related methods to generate coding sequences, including mutants and variants derived from the wild-type protein. The polynucleotide sequence encoding the desired polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding a protein of interest. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortie, Science, 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other possible methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

C. Modification of Nucleic Acids for Preferred Codon Usage in a Host Organism

The polynucleotide comprising a nucleotide sequence encoding a protein of interest, e.g., a fusion protein or polypeptide (e.g., ADAR2 variant polypeptide) of the present invention or a portion thereof (e.g., an ADAR catalytic domain or hybrid NBD), can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell. This analysis is preferably limited to genes that are highly expressed by the host cell.

At the completion of modification, the coding sequences are verified by sequencing and are then subcloned into an appropriate expression vector for recombinant production of a protein of interest, such as an ADAR2 variant polypeptide or a fusion protein comprising an ADAR catalytic domain or a variant thereof and a hybrid NBD or a variant thereof.

Following verification of the coding sequence, a fusion protein or polypeptide (e.g., ADAR2 variant polypeptide) of the present invention can be produced using routine techniques in the field of recombinant genetics, relying on the nucleotide sequences encoding the polypeptide disclosed herein.

D. Expression Systems

To obtain high level expression of a nucleic acid encoding a fusion protein or polypeptide (e.g., ADAR2 variant polypeptide) of this invention, one typically subclones a polynucleotide encoding the protein of interest (e.g., a polynucleotide of the present invention comprising a nucleotide sequence encoding a fusion protein or polypeptide of the present invention) in the correct reading frame into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli, Bacillus* sp., *Salmonella,* and *Caulobacter.* Kits for such expression systems are commercially available. Eukaryotic expression systems for mammalian cells (including human cells), yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In another aspect, the present invention provides host cells that have been transfected by expression vectors of the present invention (i.e., expression vectors comprising polynucleotides that comprise nucleotide sequences encoding fusion proteins or polypeptides (e.g., ADAR2 variant polypeptides) of the present invention). The compositions and methods of the present invention can be used for producing target site modifications (e.g., in a DNA-RNA hybrid molecule) in the genome of any host cell of interest. The host cell can be a cell from any organism, e.g., a bacterial cell, an archaeal cell, a cell of a single-cell eukaryotic organism, a plant cell (e.g., a rice cell, a wheat cell, a tomato cell, an *Arabidopsis thaliana* cell, a *Zea mays* cell and the like), an algal cell (e.g., *Botryococcus braunii, Chlamydomonas reinhardtii, Nannochloropsis gaditana, Chlorella pyrenoidosa, Sargassum patens* C. Agardh, and the like), a fungal cell (e.g., yeast cell, etc.), an animal cell, a cell from an invertebrate animal (e.g., fruit fly, cnidarian, echinoderm, nematode, etc.), a cell from a vertebrate animal (e.g., fish, amphibian, reptile, bird, mammal, etc.), a cell from a mammal, a cell from a human, a cell from a healthy human, a cell from a human patient, a cell from a cancer patient, etc. In some cases, the host cell treated by the method disclosed herein can be transplanted to a subject (e.g., patient). For instance, the host cell in which the target site modification is made can be derived from the subject to be treated (e.g., patient).

Target site modifications (e.g., in a DNA-RNA hybrid molecule) by fusion proteins or polypeptides (e.g., ADAR2 variant polypeptides) of the present invention can be made in any cell of interest, such as a stem cell, e.g., embryonic stem cell, induced pluripotent stem cell, adult stem cell, e.g., mesenchymal stem cell, neural stem cell, hematopoietic stem cell, organ stem cell, a progenitor cell, a somatic cell, e.g., fibroblast, hepatocyte, heart cell, liver cell, pancreatic cell, muscle cell, skin cell, blood cell, neural cell, immune cell, and any other cell of the body, e.g., human body. The cells can be primary cells or primary cell cultures derived from a subject, e.g., an animal subject or a human subject, and allowed to grow in vitro for a limited number of passages. In some embodiments, target site modifications are made in cells that are disease cells or derived from a subject with a disease. For instance, the cells can be cancer or tumor cells. The cells can also be immortalized cells (e.g., cell lines), for instance, from a cancer cell line.

Depending on the host cell and expression system used, the expression vector (e.g., for expression of a fusion protein or polypeptide (e.g., ADAR2 variant polypeptide) of the present invention and/or a RNA molecule) may contain transcription and translation control elements, including promoters, transcription enhancers, transcription terminators, and the like. Useful promoters can be derived from viruses, or any organism, e.g., prokaryotic or eukaryotic organisms. Promoters may also be inducible (i.e., capable of responding to environmental factors and/or external stimuli that can be artificially controlled). For expressing fusion proteins or polypeptides of the present invention, non-limiting examples of promoters that find utility in expression vectors of the present invention include RNA polymerase II promoters (e.g., pGAL7 and pTEF1), RNA polymerase III promoters (e.g., RPR-tetO, SNR52, and tRNA-tyr), the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc. Suitable terminators for use in fusion protein-expressing and polypeptide-expressing vectors of the present invention include, but are not limited to SNR52 and RPR terminator sequences, which can be used with transcripts created under the control of a RNA polymerase III promoter. Additionally, various primer binding sites may be incorporated into a vector to facilitate vector cloning, sequencing, genotyping, and the like. Other suitable promoter, enhancer, terminator, and primer binding sequences will readily be known to one of skill in the art.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the protein of interest under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transfected host cells.

When periplasmic expression of a fusion protein or polypeptide (e.g., ADAR2 variant polypeptide) of the present invention is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

A person skilled in the art will recognize that various conservative substitutions can be made to any wild-type or mutant/variant protein to produce a fusion protein or polypeptide (e.g., ADAR2 variant polypeptide) of the present invention. Moreover, modifications of a polynucleotide coding sequence may also be made to accommodate preferred codon usage in a particular expression host without altering the resulting amino acid sequence.

E. Transfection Methods

Standard transfection methods are used to produce bacterial, mammalian, yeast, insect, or plant cell lines that express large quantities of a recombinant fusion protein or polypeptide (e.g., ADAR2 variant polypeptide) of this invention, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351(1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the fusion protein or polypeptide (e.g., ADAR2 variant polypeptide) of this invention.

V. Therapeutic Methods

In another aspect, pharmaceutical compositions are provided. In some embodiments, the pharmaceutical composition comprises a fusion protein or polypeptide (e.g., ADAR2 variant polypeptide) of the present invention, a polynucleotide of the present invention, a vector of the present invention, and/or a host cell of the present invention and a pharmaceutically acceptable carrier.

The methods, fusion proteins, polypeptides (e.g., ADAR2 variant polypeptides), and compositions of the present invention are useful for preventing or treating any number of genetic disorders (e.g., in a subject in need thereof). In some embodiments, the method of preventing or treating a genetic disorder comprises administering a therapeutically effective amount of a pharmaceutical composition of the present invention to the subject. In some embodiments, the method comprises using a method, fusion protein, polypeptide (e.g., ADAR2 variant polypeptide), or composition of the present invention to modify a target site within a DNA-RNA hybrid molecule in order to correct a mutation that is associated with the genetic disorder. In some embodiments, the subject is treated (e.g., a target site within a DNA-RNA hybrid molecule in the subject is modified) before any symptoms or sequelae of the genetic disorder develop. In other embodiments, the subject has symptoms or sequelae of the genetic disorder. In some instances, treatment results in a reduction or elimination of the symptoms or sequelae of the genetic disorder.

In some embodiments, treatment (e.g., modification of a target site within a DNA-RNA hybrid molecule in the subject) includes administering pharmaceutical compositions (e.g., comprising fusion proteins, polypeptides (e.g., ADAR2 variant polypeptides), nucleic acids, expression vectors, or cells) of the present invention directly to a subject. As a non-limiting example, pharmaceutical compositions of the present invention (e.g., comprising a fusion protein, polypeptide (e.g., ADAR2 variant polypeptide), nucleic acid, expression vector, or cell of the present invention and a pharmaceutically acceptable carrier) can be delivered directly to a subject (e.g., by local injection or systemic administration). In other embodiments, the compositions of the present invention are delivered to a host cell or population of host cells, and then the host cell or population of host cells is administered or transplanted into the subject. The host cell or population of host cells can be administered or transplanted with a pharmaceutically acceptable carrier. In some instances, modification of the target site (e.g., within the host cell genome) has not yet been completed prior to administration or transplantation to the subject. In other instances, modification of the target site has been completed when administration or transplantation occurs. In certain instances, progeny of the host cell or population of host cells are transplanted into the subject. In some embodiments, correct target site modification within the host cell or population of host cells, or the progeny thereof, is verified before administering or transplanting cells containing modified target sites or the progeny thereof into a subject. Procedures for transplantation, administration, and verification of correct target site modification will be known to one of skill in the art.

Compositions of the present invention, including cells and/or progeny thereof that have had their target sites modified by the methods, fusion proteins, polypeptides (e.g., ADAR2 variant polypeptides), and/or compositions of the present invention, may be administered as a single dose or as multiple doses, for example two doses administered at an interval of about one month, about two months, about three months, about six months or about 12 months. Other suitable dosage schedules can be determined by a medical practitioner.

In some embodiments, the genetic disorder that is prevented or treating is selected from the group consisting of the genetic disorder is selected from the group consisting of Rett syndrome, X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disorders, inflammation, immune-related disorders, metabolic disorders, liver disorders, kidney disorders, musculoskeletal disorders, neurological disorders, cardiovascular disorders, pulmonary disorders, ocular disorders, and a combination thereof. In particular embodiments, the genetic disorder is Rett syndrome.

VI. Kits

In another aspect, the present invention provides kits for modifying a target site within a nucleic acid, such as an RNA molecule (e.g., double-stranded RNA molecule) and/or a DNA-RNA hybrid molecule. In some embodiments, the kit comprises a fusion protein of the present invention, a polypeptide (e.g., ADAR2 variant polypeptide) of the present invention, a polynucleotide of the present invention, a vector of the present invention, a host cell of the present invention, a pharmaceutical composition of the present invention, or any combination thereof. The kit may further comprise an RNA molecule (e.g., a gRNA molecule) or a polynucleotides or expression vector containing a nucleic acid sequence encoding the RNA molecule.

Kits of the present invention can be packaged in a way that allows for safe or convenient storage or use (e.g., in a box or other container having a lid), Typically, kits of the present include one or more containers, each container storing a particular kit component such as a reagent, a control sample, and so on. The choice of container will depend on the particular form of its contents, e.g., a kit component that is in liquid form, powder form, etc. Furthermore, containers can be made of materials that are designed to maximize the shelf-life of the kit components. As a non-limiting example, kit components that are light-sensitive can be stored in containers that are opaque.

In some embodiments, the kit contains one or more reagents. In some instances, the reagents are useful for transfecting a host cell with a nucleic acid (e.g., encoding a fusion protein or polypeptide (e.g., ADAR2 variant polypeptide) of the present invention), expression vector (e.g., comprising a nucleic acid of the present invention), or a plurality thereof, and/or inducing expression from the nucleic acid(s) and/or expression vector(s). The kit may further comprise one or more reagents useful for delivering fusion proteins or polypeptides of the present invention into a host cell and/or for contacting a fusion protein or polypeptide of the present invention with a nucleic acid molecule (e.g., an RNA molecule and/or DNA-RNA hybrid molecule (e.g., containing a target site to be modified)). In yet other embodiments, the kit further comprises instructions for use.

VII. Examples

The present invention will be described in greater detail by way of a specific example. The following example is offered for illustrative purposes only, and is not intended to limit the invention in any manner. Those of skill in the art will readily recognize a variety of noncritical parameters which can be changed or modified to yield essentially the same results.

Example 1. DNA Editing in DNA/RNA Hybrids by Adenosine Deaminases that Act on RNA Introduction Adenosine deaminases that act on RNA (ADARs) convert adenosine (A) to inosine (I) in duplex RNAs (1-3). Since I base pairs with cytidine (C), it functions like guanosine (G) in cellular processes such as splicing, translation and reverse transcription (1,4). The A to I modification is known to alter miRNA recognition sites, redirect splicing and change the meaning of specific codons (5-7). Two different enzymes carry out this form of RNA editing in humans; ADAR1 and ADAR2 (8). Dysregulated ADAR activity is associated with human disease (9-13). For instance, mutations in the ADAR1 gene are known to cause the autoimmune disease Aicardi-Goutieres Syndrome (AGS) (11,12). The ADAR proteins have a modular structure with double stranded RNA binding domains (dsRBDs) and a C-terminal deaminase domain (3). Double helical structure is required for ADAR substrates. Indeed, recent X-ray crystal structures of the human ADAR2 deaminase domain bound to substrate RNAs revealed a 20 bp binding site with extensive contacts in the minor groove near the editing site and in the two adjacent major grooves (14) (FIG. 1A). In addition, these structures suggested the mechanism by which the reactive nucleotide gains access to the deaminase active site would require an A-form like double helix (14). Interestingly, these structures also identified five direct contacts to 2'-hydroxyls in the minor groove near the editing site with only four of these common to the two different RNA sequences crystallized (14) (FIG. 1B). These observations led to the question of whether 2'-hydroxyl contacts are required for an ADAR reaction and, if not, could the reaction take place in the context of a DNA/RNA hybrid duplex which maintains an A-form helical conformation. This was an important question for multiple reasons. First, a recent literature report suggested that overexpression of human ADAR1 can lead to dA to dG mutations in DNA, yet no evidence had been provided for direct deamination in a DNA strand by an ADAR (15). Second, mutations in other AGS-related genes (e.g., TREX1, RNAseH2 and SAMHD1) lead to an accumulation of DNA/RNA hybrids, suggesting that the ability to regulate DNA/RNA hybrid levels could be a common link among gene products mutated in this disease (16). Finally, the development of adenosine deaminases that act on DNA could lead to new genome editing tools based on dA to dI conversion creating specific dA to dG mutations in the DNA after replication. This is similar in concept to the recently reported dC to dU base editing systems involving cytidine deaminase-Cas9 fusion proteins and single guide RNAs (17,18). For these reasons, the reactivity of ADARs with DNA/RNA hybrid substrates was examined, as described below.

Materials and Methods

Protein Overexpression and Purification hADAR1 deaminase domain (hADAR1d), hADAR1 deaminase domain E1008Q (hADAR1d E1008Q), hADAR2 deaminase domain (hADAR2d), hADAR2 deaminase domain E488Q (hADAR2d E488Q) and wild-type hADAR2 (hADAR2 wt) were expressed and purified as previously described (19). Protein concentrations were determined using BSA standards visualized by SYPRO Orange staining of SDS-polyacrylamide gels. Purified hADAR1d and hADAR1d E1008Q were stored in 50 mM Tris-HCl, pH 8.0, 200 mM KCl, 5 mM EDTA pH 8.0, 10% glycerol, 0.01% NP-40, and 1 mM DTT at −70° C. Purified hADAR2d, hADAR2d E488Q, and hADAR2 wt were stored in 20 mM Tris-HCL pH 8.0, 100 mM NaCl, 20% glycerol, and 1 mM 2-mercaptoethanol at −70° C.

Oligonucleotide Purification

Single-stranded RNA and DNA oligonucleotides were purified by denaturing polyacrylamide gel electrophoresis and visualized using UV shadowing. Bands were excised from the gel, crushed and soaked overnight at 4° C. in 500 mM NH$_4$OAc and 100 mM EDTA. Polyacrylamide fragments were removed using a 0.2 µm filter, followed by phenol-chloroform extraction and ethanol precipitation. The final solutions were lyophilized to dryness, resuspended in nuclease-free water, quantified by absorbance at 260 nm and stored at −20° C. The oligonucleotides were later heated at 95° C. for 5 min and then slowly cooled to room temperature in 10 mM Tris-HCl, 0.1 mM EDTA pH 7.5, 100 mM NaCl to allow them to hybridize.

Generation and Deamination of Internally $^{32}$P-Labeled Substrates

Oligonucleotides were purified as described above. The 3' 12-nt oligonucleotides of the top (i.e., edited) strand were radiolabeled with [γ-$^{32}$P] ATP at the 5' end with T4 polynucleotide kinase as described previously (20). About 30 pmols of labeled 3' top strand 12 nt oligonucleotide was redissolved with 3 µL of 10 µM DNA splint, 2 µL of 20 µM 5' top strand 12 nt oligonucleotide, 0.5 µL of RNasin (1.6 units/4), 2 µL of NEB T4 DNA ligase 10× buffer, and 5 µL of water. This reconstituted solution was heated to 65° C. for 5 minutes. After the solution was slowly cooled to room temperature, 1.5 μL of RNasin (1.6 units/4), 5 μL of 4 mM ATP, and 1 μL of T4 DNA ligase (400 U/μL) were added to the solution so that the final reaction volume was 20 μL. The reaction was incubated at 30° C. for 2 hours, then 2 μL of 40 μM trap DNA were added to the splint ligation reaction. The splint ligation products were purified as described above. Purified $^{32}$P labeled top strand was hybridized with the corresponding bottom strand 24-nt oligonucleotide as described above. Oligonucleotide sequences are shown in Table 1. Deamination reactions were carried out as previously described (21) with the following modifications. For the partially 2'-deoxy-modified substrates, the final reaction volume was 10 μL. The final enzyme concentration was 300 nM. The final RNA concentration was 10 nM. The final reaction solution contained 16 mM Tris-HCl, pH 7.4, 3.3% glycerol, 1.6 mM EDTA, 0.003% NP-40, 60 mM KCl, 7.1 mM NaCl, 0.5 mM DTT, 160 units/mL RNasin, and 1 μg/mL yeast tRNA. Reactions were quenched by adding 190 μL 95° C. nuclease-free water followed by incubation at 95° C. for 5 minutes. Deaminated products were purified by phenol-chloroform extraction and ethanol precipitation. The product-containing solution was lyophilized to dryness and suspended in 50 μL of 1×TE solution, followed by digestion with nuclease P1. The resulting 5'-mononucleotides were resolved by thin-layer chromatography (TLC, Macherey-Nagel) (22). The TLC was visualized by exposure to storage phosphor imaging plates (Molecular Dynamics) on a Typhoon phosphorimager (Molecular Dynamics) and quantified by volume integration using ImageQuant software (Molecular Dynamics). Data were fitted to the equation: $[P]_t = \alpha[1-e^{k_{obs}t}]$, where $[P]_t$ is the percent edited at time t, α is the fitted reaction end point, and $k_{obs}$ is the fitted rate constant using KaleidaGraph. Each experiment was carried out in triplicate, and the rate constant reported in the text are average values±standard deviations. For the DD, DR, RD, RR substrates, deaminations were performed as above with following modifications. The final enzyme concentration was 250 nM. The final reaction solution for hADAR2d, hADAR2d E488Q, and hADAR2 wt contained 17 mM Tris-HCl, pH 7.4, 4.2% glycerol, 1.6 mM EDTA, 0.003% NP-40, 60 mM KCl, 11.6 mM NaCl, 0.5 mM DTT, 160 units/mL RNasin, and 1 μg/mL yeast tRNA. The final reaction solution for hADAR1d, and hADAR1d E1008Q contained 12 mM Tris-HCl, pH 7.2, 3.3% glycerol, 1 mM EDTA, 0.002% NP-40, 40.5 mM potassium glutamate, 6.5 mM KCl, 6 mM NaCl, 0.5 mM DTT, 160 units/mL RNasin, and 1 μg/mL yeast tRNA. The editing level for the corresponding zero time point was subtracted from each data point as background subtraction. Statistical significance between groups was determined by t tests using QuickCalcs (GraphPad Software). hADAR2 wt deamination was carried out twice, deamination with other proteins was carried out in triplicate.

Preparation and Deamination with 90-Nt DNA+RNA Hybrid Substrates

The 90-nt DNA top strand and 24-nt RNA bottom strands were purchased from Integrated DNA Technology and purified as described above. The 90 nt DNA was PCR amplified with a T7 promoter-containing primer to generate a T7 RNA polymerase transcription template. Primer sequences are shown in Table 1. PCR products were purified by agarose gel and extracted from the gel (QIAquick Gel Extraction Kit, Qiagen). The 93-nt RNA bottom strand was transcribed from this DNA template with MEGAscript® T7 Kit (ThermoFisher) and purified with polyacrylamide gel as described above. The 90-nt DNA was hybridized with corresponding RNAs. The bottom RNA to top DNA molar ratio was 3:1 for each hybridization. Deamination reactions were carried out as previously described (21) with the following modifications. The final reaction volume was 10 μL. hADAR2d E488Q and hADAR2 wt were used for the reaction and the final enzyme concentration was 250 nM. The final RNA concentration was 10 nM. The final reaction solution contained 17 mM Tris-HCl, pH 7.4, 4.2% glycerol, 1.6 mM EDTA, 0.003% NP-40, 60 mM KCl, 11.6 mM NaCl, 0.5 mM DTT, 160 units/mL RNasin, and 1 μg/mL yeast tRNA. Reactions were quenched by adding 190 μL 95° C. nuclease-free water followed by incubation at 95° C. for 5 minutes. Reaction products were PCR amplified with extended primers using GoTaq® DNA Polymerase (Promega). Primer sequences are shown in Table 1. PCR products were purified with DNA clean & concentrator (Zymo) and sequenced. The sequencing peak heights were measured with Chromas for calculating the editing level. Each experiment was carried out in triplicate. The editing level for the corresponding zero time point was subtracted from each data point as background subtraction. Statistical significance between groups was determined by t tests using QuickCalcs (GraphPad Software).

Deamination in the M13 Genome

M13 genomic ssDNA (New England Biolabs) was hybridized with the corresponding guide RNAs. The guide RNA to genomic DNA molar ratio was 20:1 for each hybridization. Deamination reactions were carried out as previously described (21) with the following modifications. The final reaction volume was 10 μL. hADAR1d E1008Q was used for the reaction and the final enzyme concentration was 500 nM. The final RNA concentration was 2.8 nM. The final reaction solution contained 13 mM Tris-HCl, pH 7.2, 3.6% glycerol, 1.2 mM EDTA, 0.002% NP-40, 40.5 mM potassium glutamate, 12.5 mM KCl, 6 mM NaCl, 0.6 mM DTT, 160 units/mL RNasin, and 1 μg/mL yeast tRNA. Reactions were quenched by adding 190 μL 95° C. nuclease-free water followed by incubation at 95° C. for 5 minutes. The target regions of the reaction products were PCR amplified with primers using GoTaq® DNA Polymerase (Promega). Primer sequences are shown in Table 1. PCR products were purified by agarose gel, extracted using a QIAquick Gel Extraction Kit (Qiagen), and sequenced with the forward PCR primers. The sequencing peak heights were measured with Chromas for calculating the editing level. Each experiment was carried out in triplicate. The editing level for the corresponding zero time point was subtracted from each data point as background subtraction. Statistical significance between groups was determined by t tests using QuickCalcs (GraphPad Software).

Deamination of GAC Site in the M13 Genome with 1000 nM Enzyme

Figure 8B:
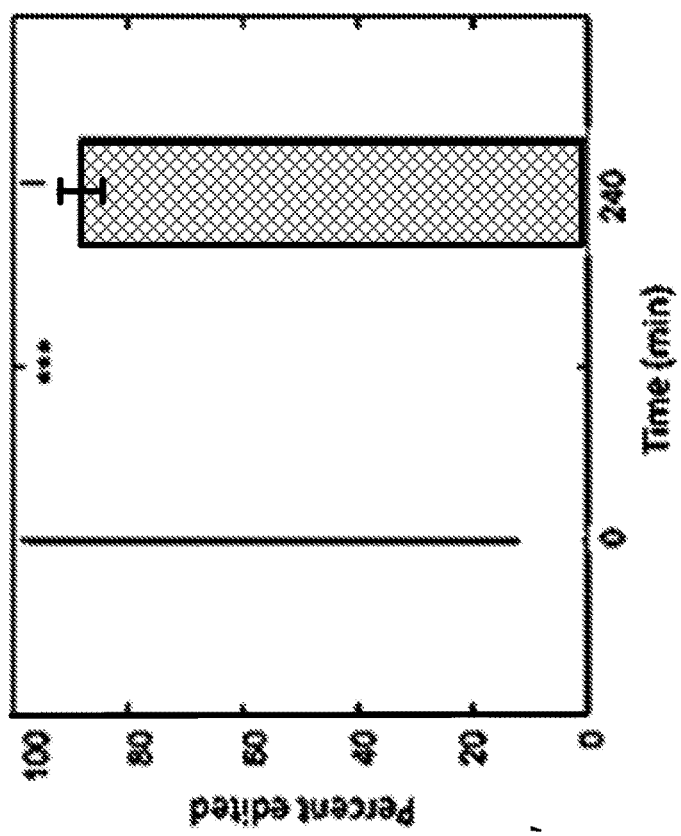
FIGS. 8A and 8B show editing of the GAC site in the ssDNA genome of M13 bacteriophage.
Figure 8A:
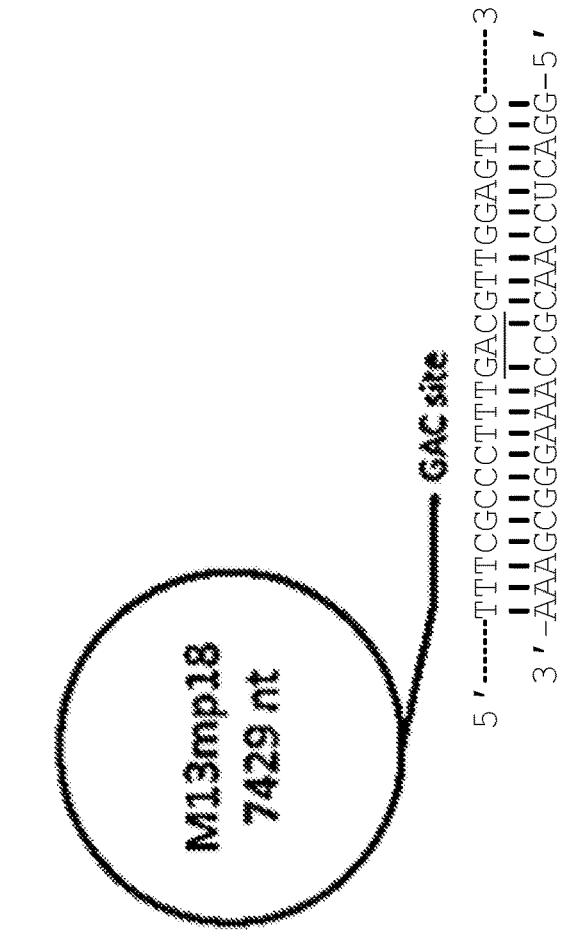

M13 genomic ssDNA (New England Biolabs) was hybridized with the GAC guide RNA. The guide RNA to genomic DNA molar ratio was 20:1 for each hybridization. Deamination reactions were carried out as previously described (21) with following modifications. The final reaction volume was 20 μL. hADAR1d E1008Q was used for the reaction and final enzyme concentration was 1000 nM. Half the protein sample was added at the beginning of the reaction, while the remainder was added at the 2-hour time point. The final RNA concentration was 2.8 nM. The final reaction solution contained 16 mM Tris-HCl, pH 7.2, 4.2% glycerol, 1.5 mM EDTA, 0.003% NP-40, 40.5 mM potassium glutamate, 24.5 mM KCl, 12 mM NaCl, 0.7 mM DTT, 160 units/mL RNasin, and 1 μg/mL yeast tRNA. Reactions were quenched by adding 180 μL 95° C. nuclease-free water followed by incubation at 95° C. for 5 minutes. The target region of the reaction product was PCR amplified with primers using GoTaq® DNA Polymerase (Promega). Primer sequences are shown in Table 1. PCR products were purified by agarose gel, extracted (QIAquick Gel Extraction Kit, Qiagen) and sequenced with the forward PCR primers. The sequencing peak heights were measured with Chromas for calculating the editing level. Editing level of corresponding zero-time point was subtracted from each data point as background subtraction. Statistical significance between groups was determined by t tests using QuickCalcs (GraphPad Software). This experiment was carried out in triplicate and editing values are reported as the average±standard deviation (FIG. 8).

Results

The Importance of 2'-Hydroxyl Contacts to the ADAR Deaminase Domain

Figures 2A, 2B, 2C:
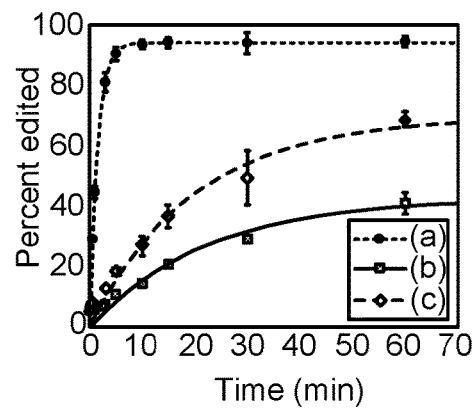
FIGS. 2A-2C show deamination kinetics for an RNA duplex and partially 2'-deoxyribose-substituted substrates.

To determine if the 2'-hydroxyl contacts observed in X-ray crystal structures of the human ADAR2 deaminase domain (hADAR2d) bound to substrate RNAs are required for an editing reaction, a chimeric substrate was prepared with each nucleotide contacted at its 2'-hydroxyl replaced with the corresponding 2'-deoxynucleotide. The substrate used in these experiments was similar to the human glioma factor 1 (hGli1)-derived substrate crystallized with hADAR2d that had five direct contacts to 2'-hydroxyl groups, including at each nucleotide in the UAGA sequence surrounding the editing site (underlined) and the nucleotide on the non-edited strand paired with the edited base (FIG. 1B and FIG. 2, substrate a). It was observed found that removal of the five 2'-hydroxyl contacts slowed the rate of reaction at the editing site with hADAR2d by approximately 15-fold (FIG. 2, substrate b). A similar rate was observed for a substrate with 2'-deoxy substitutions only on the edited strand (FIG. 2, substrate c). These results indicated that while the 2'-hydroxyl contacts made by hADAR2d contribute to editing efficiency, they are not absolutely required for the reaction, suggesting that ADARs may react with DNA/RNA hybrids.

Deamination of Duplexes with Different DNA/RNA Strand Combinations

Figures 6A, 6B:
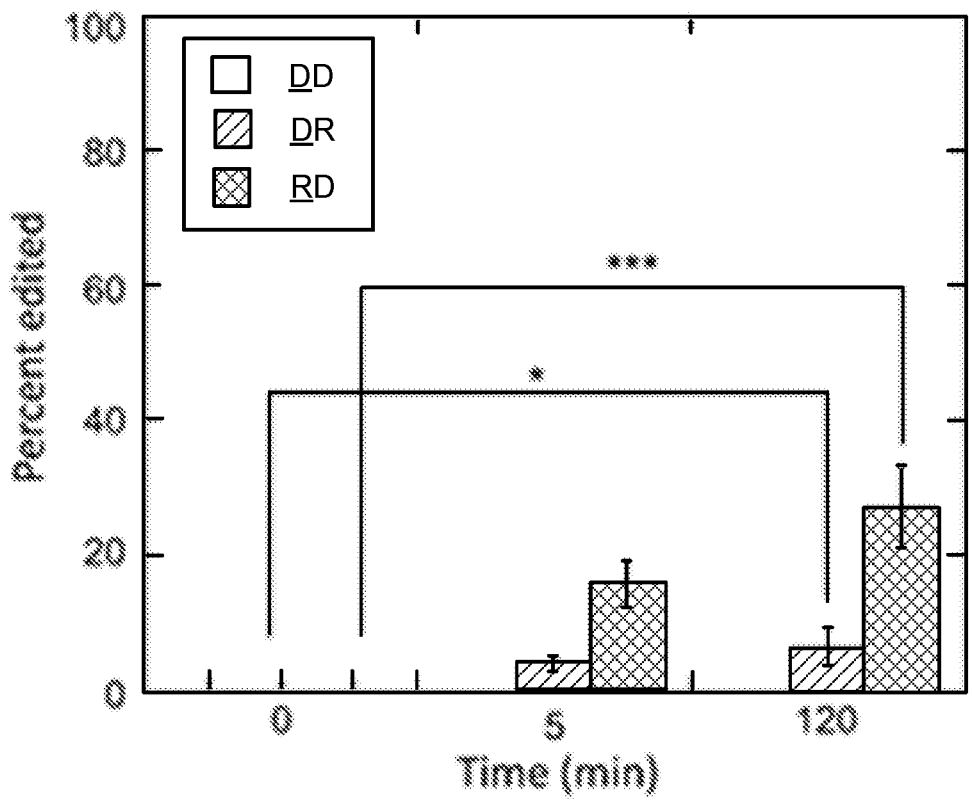
FIGS. 6A and 6B describe hADAR2 deamination reactions with DNA/RNA hybrid, all RNA, and all DNA substrates.

To test for reactivity in DNA/RNA hybrids and compare this to reactions in similar all RNA or all DNA substrates, four new 24-bp duplexes were prepared, each having the hGli1 substrate sequence but varying the backbone structure of the component strands (e.g. DNA or RNA) (FIG. 3). We then measured editing activity at the position corresponding to the hGli1 editing site using internally $^{32}$P-labelled substrates and a standard thin layer chromatography assay (23). hADAR2d and a mutant with enhanced editing activity (hADAR2d E488Q) (24) were tested. In addition, the human ADAR1 deaminase domain (hADAR1d) and its activated mutant (E1008Q) (25) were also tested. Unsurprisingly, for each of the deaminase domains tested, the all-RNA substrate (RR) was the most efficiently deaminated (FIGS. 3B-3E) (underlining indicates substrate strand). Also, no reaction was observed in the all-DNA substrate (DD) with any of the deaminase domains tested under any condition (FIGS. 3B-3E). However, for both DNA/RNA hybrids (RD and DR), hADAR1d E1008Q and hADAR2d E488Q produced significant deamination (e.g., >40%) after a five-minute reaction time with complete editing observed at 120 minutes (FIGS. 3B-3E). Lower reactivity was observed for the wild-type deaminase domains with the hybrid substrates under these conditions. Indeed, observation of reaction of wild type hADAR2d in the hybrid substrates required a higher concentration of enzyme (FIG. 6).

To determine the effects of dsRBDs on these reactions, full-length hADAR2 was tested with the four 24-bp duplex substrates (RR, DD, RD, and DR) (FIG. 3F). Again, the RR substrate was deaminated most rapidly and no product was observed with the DD substrate. However, unlike the case of 250 nM wild type hADAR2d where little product was observed throughout the two-hour time course, this concentration of full-length hADAR2 clearly produced deamination product in both DNA/RNA hybrids (FIG. 3F). Thus, the presence of hADAR2's dsRBDs enhanced reaction efficiency with hybrid substrates. While it is known that a duplex with two RNA strands is the preferred binding site for dsRBDs, dsRBD binding to DNA/RNA hybrids has been reported (26).

The Effects of Mismatches and Length of DNA/RNA Hybrid Substrates

Figure 4A:
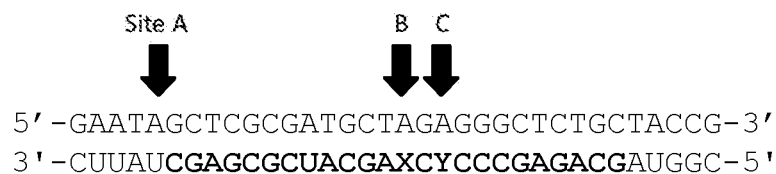
FIGS. 4A-4F shows deamination in the DNA strand of DNA/RNA hybrid duplexes and the effects of mismatches and duplex length. In all panels, the top strand is the DNA strand and the bottom strand is the RNA strand.
Figure 4B:
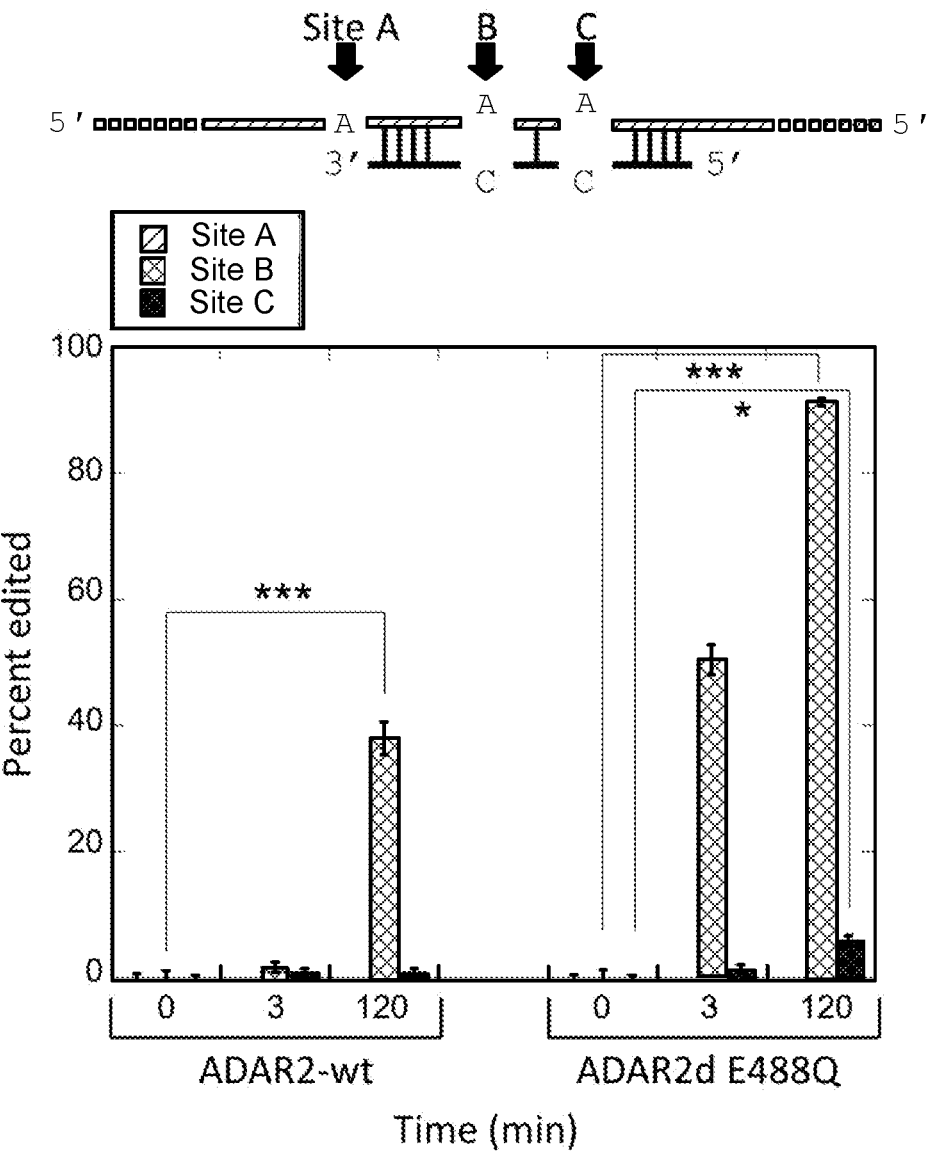
Figure 4C:
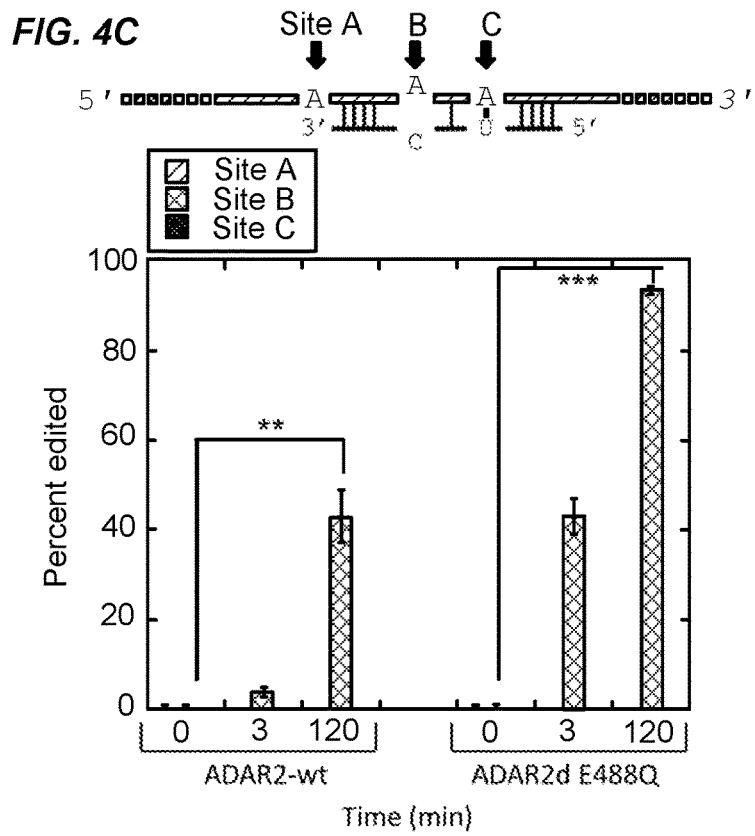
Figure 4D:
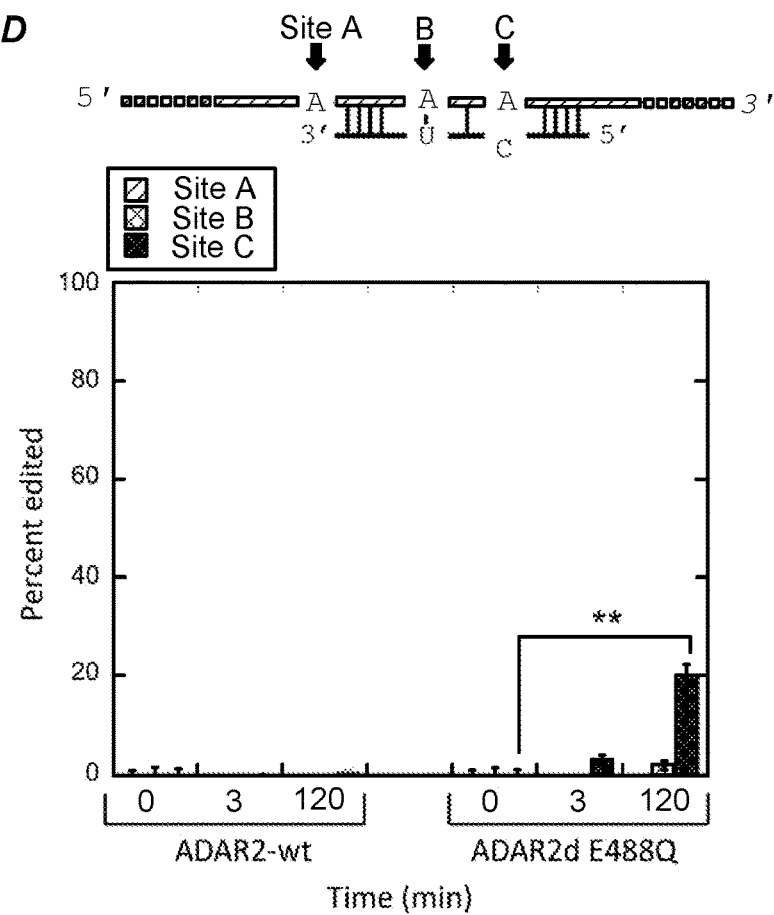
Figure 4E:
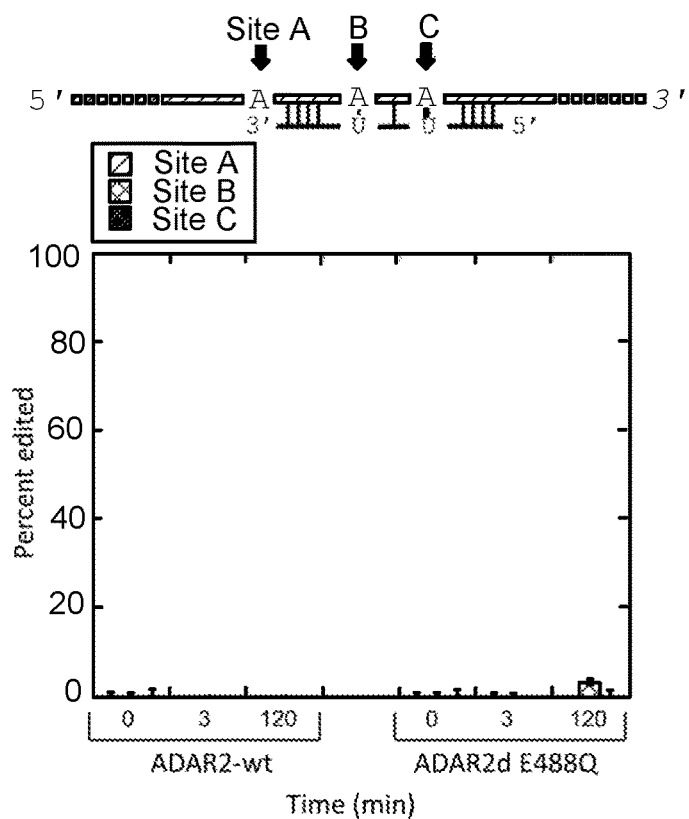
Figure 4F:
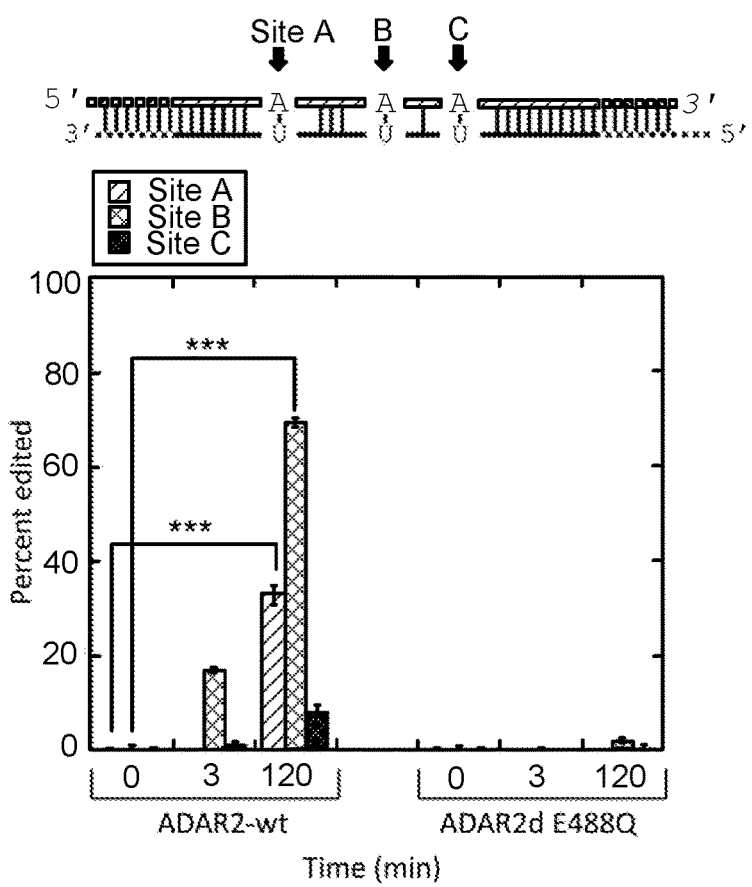
Figure 7:
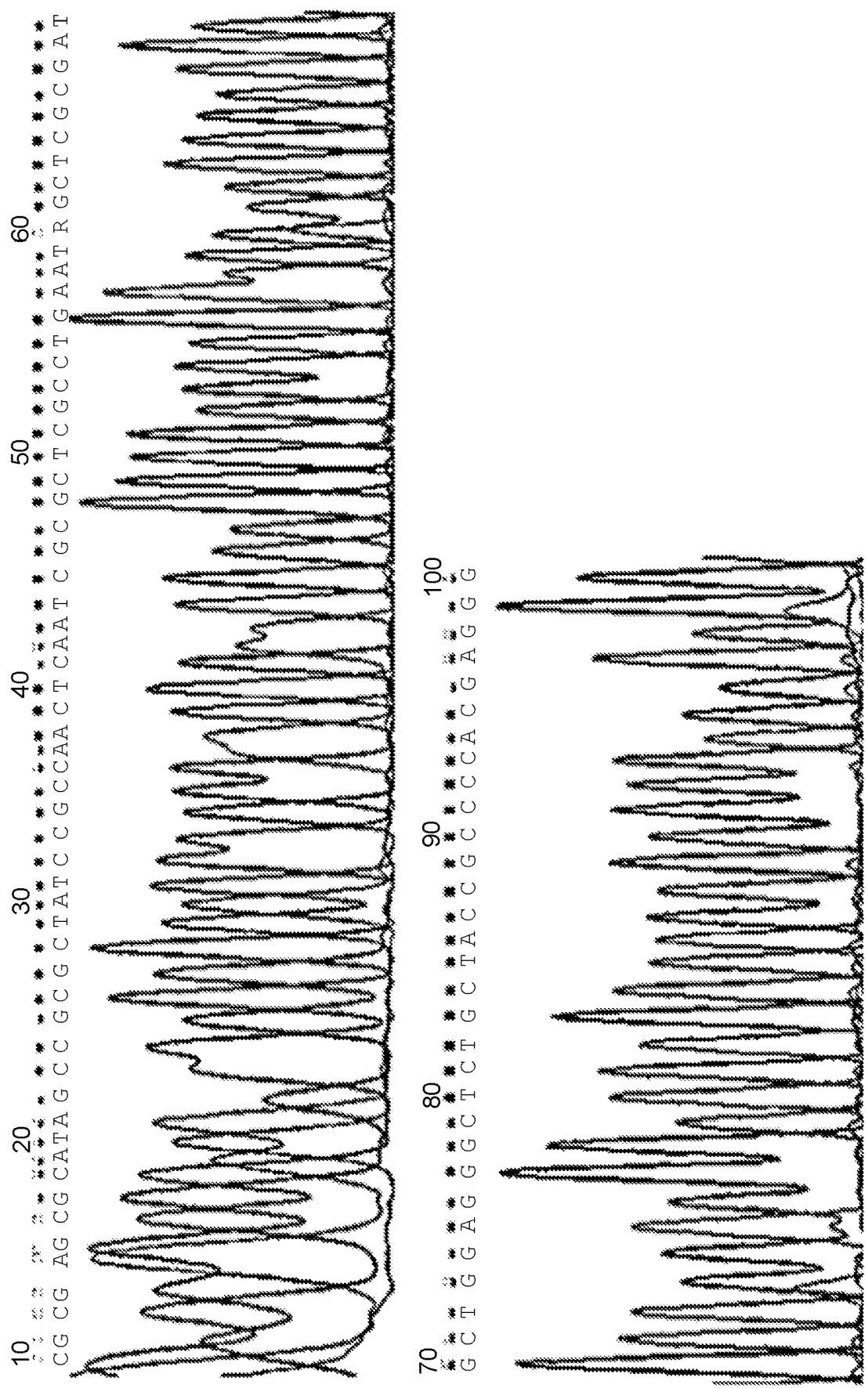
FIG. 7 shows a sequencing trace of the 90-mer substrate treated with hADAR2 wt for 120 minutes. The sequence shown above the trace is set forth in SEQ ID NO:47.

The 24-bp hGli1-derived duplex substrates each had an A-C mismatch at the editing site and an A-C mismatch at the 3' next nearest neighbor position (FIG. 3A). To determine the role of these mismatches in the reaction of the DNA strand in a DNA/RNA hybrid and to test the effect of duplex length, new substrate structures were generated containing a longer DNA strand (90 nt) with the editing site hybridized to different RNAs that vary in sequence and in length (FIG. 4). The longer DNA substrate strand allowed for PCR amplification of the reaction products and Sanger sequencing to be used to assess editing on this strand. Five different DNA/RNA hybrid substrates were prepared. Four had 24-nt RNA strands complementary to the sequence surrounding the editing site but varied in the identity of the nucleotides paired with the editing site dA or 3' next nearest neighbor dA such that either a dA-C mismatch or a dA-U pair was formed at each site (FIGS. 4B-4E). An additional substrate was formed with a complementary 93-nt RNA generating a 90 bp DNA/RNA hybrid duplex with a three-nucleotide overhang (FIG. 4F). The reaction of full-length, wild-type hADAR2 was compared to that of the hADAR2d E488Q mutant at different times and at three different positions in the DNA strand (FIG. 4, sites A, B, and C). Both full-length hADAR2 and hADAR2d E488Q deaminated the dA at site B in the substrate bearing two A-C mismatches, with the deaminase domain mutant showing higher levels of editing at the 3-minute and 120-minute time points (FIG. 4B). Converting the dA-C mismatch at site C to an dA-U pair reduced reaction at this site, as expected, but had very little effect on editing at the B site (FIG. 4C). In addition, a dA-C mismatch at site B significantly enhanced editing at this site, as indicated by the very low B site editing levels observed in FIG. 4D. Little editing was observed at either site for both proteins for the substrate with a fully complementary 24-nt RNA (FIG. 4E). However, for the 90 bp DNA/RNA hybrid, full-length hADAR2 reacted at all three sites A, B, and C, with site B being the most efficiently edited (FIG. 4F). No additional editing sites were observed for full-length ADAR2 on this substrate (FIG. 7). Site A was not base paired in substrates with the 24-nt RNA strands and no editing was observed at site A in those substrates. Importantly, hADAR2d E488Q did not edit the fully matched hybrid duplex, illustrating the importance of a dA-C mismatch in directing editing for this protein. This result also highlights the effect of hADAR2's dsRBDs in allowing editing in long, perfectly matched DNA/RNA hybrids. The presence of the RNA-binding N-terminal fragment containing the dsRBDs allowed ADAR2 to edit the DNA strand of a long DNA-RNA hybrid without the requirement for an A-C mismatch at the editing site. Without being bound by any particular theory, it is likely that the enhanced binding affinity afforded by the N-terminal fragment compensated for the lower reactivity of an A-U pair.

Selective Editing within the M13 Bacteriophage ssDNA Genome

Figure 5A:
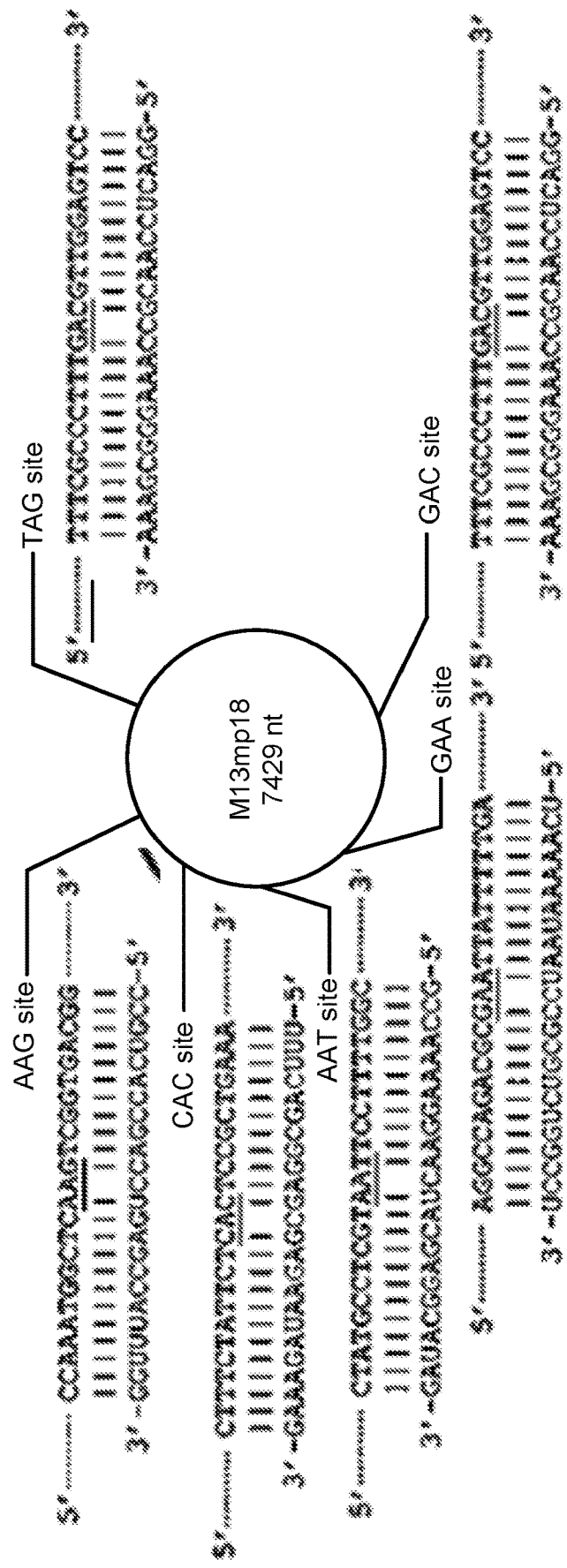
FIGS. 5A-5C show selective editing of multiple sites in the ssDNA genome of M13 bacteriophage.
Figure 5B:
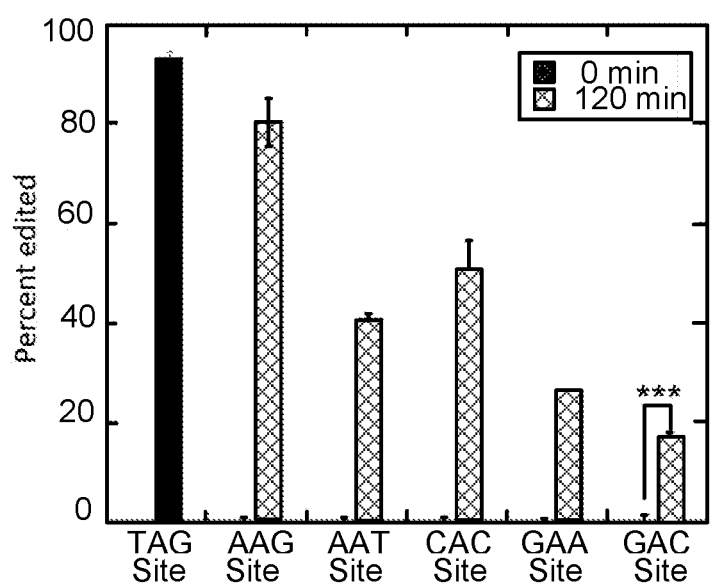
Figure 5C:
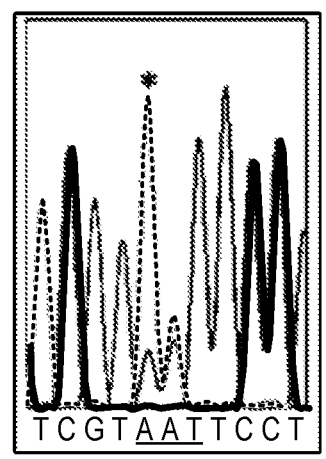

The results described above indicated that RNA oligonucleotides could be used in combination with an ADAR or ADAR deaminase domain to direct editing at specific 2'-deoxyadenosines in a DNA strand. To further define the scope and limitations of this reaction, six different 24-nt guide RNAs were designed that were complementary to different locations in the single-stranded DNA genome of the M13 bacteriophage such that different 2'-deoxyadenosines would be targeted for deamination by an ADAR deaminase domain in a DNA/RNA hybrid duplex (FIG. 5A). Each RNA strand was designed to form a dA-C mismatch at the targeted site in the center of a 24 bp hybrid duplex. The six 2'-deoxyadenosines had different nearest neighbor nucleotides so it could be determined if preferences for the ADAR reaction in a DNA strand matched those known for RNA strands (27). For these experiments, 500 nM hADAR1d E1008Q was used as the deaminase and each reaction was allowed to proceed for two hours. With this approach, it was possible to direct editing at each of the six targeted 2'-deoxyadenosines (FIG. 5B). The extent of editing that was observed varied among the target sites with the following yields: TAG site (94%), AAG site (81%), AAT site (43%), CAC site (53%), GAA site (27%), and the GAC site (19%). These trends closely matched the known nearest neighbor preferences for hADAR1d in RNA substrates (27). The editing yield at difficult sites (e.g., GAC site) can be enhanced with additional enzyme and longer incubation times. Indeed, two additions, each of 500 nM of hADAR1 E1008Q, over a total of four hours resulted in 89% editing at the GAC site (FIG. 8). Editing for each target site was monitored by amplification and sequencing of about 800 bp of the M13 genome surrounding that site. The only editing that was observed was at the six targeted 2'-deoxyadenosines and one additional off-target site. This off-target dA was edited to 15% yield and was located adjacent to the targeted dA of the AAT site (FIG. 5C).

Discussion

ADARs were first identified for their ability to unwind duplex RNA (28,29). This effect arises from the conversion of A-U pairs in a duplex substrate to less stable I-U pairs resulting in duplex denaturation (2). Early studies also showed that preincubation with an excess of duplex RNA but not single-stranded RNA, double-stranded DNA, single-stranded DNA, or tRNA, inhibited the unwinding reaction (29). Later it was recognized that ADARs can also deaminate adenosines in duplex regions of more complex, folded RNAs (21,30-34). However, there have been no previous reports describing the ability of an ADAR to edit the strands of DNA/RNA hybrid substrates. Recently reported crystal structures of hADAR2d bound to duplex RNA showed the complex trapped at a point in the reaction with the reactive nucleotide flipped into the deaminase active site and suggested that base flipping by ADARs requires an A-form helix (14). DNA/RNA hybrids maintain an A-form like conformation so ADAR-induced base flipping might occur with such a substrate structure (35-37). However, the crystal structures also identified five direct contacts to 2'-hydroxyl groups in the RNA substrates. The experiments described here with chimeric substrates bearing 2'-deoxynucleotides at all the contact sites indicated that interactions with 2'-hydroxyls are not absolutely required for deaminase activity (FIG. 2).

The observation that ADARs can deaminate 2'-deoxyadenosines in the DNA strands of DNA/RNA hybrids has implications for understanding known ADAR properties. For instance, a recent report showed that overexpression of ADAR1 induced adenosine-targeted DNA mutations in a class switch recombination region (Ig-Sµ) in IgM B cells from ADAR1 transgenic mice and in the region as well as the c-Myc gene in wild type MEFs (15). This study suggested that ADAR1 is an inducer of somatic mutations like activation-induced deaminase (AID) but provided no mechanistic rationale for how ADAR1 expression could cause mutations in DNA. Since both class switch regions and the c-Myc gene are known to be genomic loci where DNA/RNA hybrids occur (in the form of R-loops) (38,39), ADAR1-induced DNA mutations at these sites could arise from reaction of the DNA strand of the hybrid duplex in an R-loop. 2'-deoxyinosine residues in DNA are subject to repair by endonuclease V (EndoV), an enzyme that cleaves the strand at the second phosphodiester bond 3' to the lesion (40,41). Additional enzymes are necessary to remove dI and complete the repair, but the subsequent steps of the repair of dI in dsDNA are poorly understood and completely unknown for dI in DNA/RNA hybrids (41,42). Overexpression of an ADAR may overwhelm dI repair pathways, allowing replication to render the dA to dG mutation permanent.

AGS is a severe childhood autoimmune disease that is characterized by overexpression of interferon α and increased innate immune response (11,12). This disease is caused by mutations in multiple genes whose protein products, including ADAR1, are all involved in nucleic acid metabolism (11). Recent studies suggested that the presence of increased levels of cytosolic double stranded RNA arising from defects in ADAR1 activity caused by AGS mutations leads to interferon induction (43,44). Interestingly, a common feature of cells isolated from patients with mutations in different AGS genes is the accumulation of DNA/RNA hybrid structures (16). It has been suggested that DNA/RNA hybrids represent a common immunogenic form of nucleic acids in AGS (16). It is possible that normal ADAR1 function leads to deamination and denaturation (or degradation triggered by EndoV) of DNA/RNA hybrids. ADAR1 mutations that disrupt deaminase activity could then lead to their accumulation. Further study of the possible role of DNA/RNA hybrids in ADAR-linked AGS is justified.

The observations described here that the mutants of ADAR deaminase domains can efficiently edit DNA strands in DNA/RNA hybrids also has practical implications for the development of new genome editing tools. Recent years have seen an explosion in the number of new tools to manipulate the genomes of complex organisms, primarily by use of variants of the CRISPR-Cas9 system (45,46). While these tools are powerful, single point mutations introduced with these reagents require inefficient homology-directed repair (47,48). This has stimulated others to develop "base editing" methods using Cas9-cytidine deaminase fusion proteins that can be directed to specific sites in the genome with a single guide RNA (17,18). While this approach has been shown to be effective for introducing dC to T mutations, the use of only cytidine deaminases for this purpose is limiting. Here it has been shown that an ADAR deaminase domain bearing an E to Q mutation in the enzyme's base flipping loop can be directed to edit specific dA-C mismatches in hybrid duplexes formed by the binding of 24-nt guide RNAs. Fusion of ADAR catalytic domains with nucleic acid binding domains, particularly hybrid binding domains, and activation with additional specific mutations are likely to enhance reactivity with DNA-RNA hybrids even further. This RNA-guided ADAR reaction in DNA can be directed to specific locations in the genomes of complex organisms to induce single dA to dG mutations. Efficient and selective dA deamination in the M13 bacteriophage genome was possible here with the hADAR1 deaminase domain bearing a flipping loop mutation (hADAR1d E1008Q) and by targeting dA-C mismatches. The mutated residue is responsible for contacting the orphan base when the edited nucleotide occupies the deaminase active site (14). When this base is a C, a protonated E1008 side chain likely donates a hydrogen bond to N3 of C. The E1008Q mutant does not require protonation to hydrogen bond to N3 of C leading to an increase in editing activity. Off-target editing was minimized by using a relatively short 24-nt guiding RNA that is near the minimum length required for full contact to the deaminase domain. Since ADARs do not deaminate single strands, editing would not be expected outside the DNA/RNA hybrid duplex. Indeed, this was the case since no editing sites were observed in the regions of the M13 genome sequenced after the reaction besides those found within the region bound by the guide RNAs. Also, by positioning the targeted dA near the center of the 24 bp duplex, editing was restricted to an approximately four bp window in the center of the guide RNA-target DNA duplex. The ADAR catalytic domain would not fully engage the duplex for editing sites outside this region (14,49). The one off-target site observed is consistent with this hypothesis. The off-target dA is located immediately adjacent to the targeted dA of the AAT target site (FIG. 5C). Furthermore, the off-target dA had a 5' T, the best 5' nearest neighbor for an ADAR editing site (27). It is possible to reduce this rare type of off-target editing by introducing an unfavorable mismatch (e.g., dA-G) at this site in the DNA/RNA hybrid (50).

Overall, the ADAR-catalyzed editing of the DNA strands in DNA/RNA hybrids reported here expands the scope of possible biological functions of ADARs and points to potential applications in genome editing.

In Table 1 below, deoxyribonucleotides are bold and underlined, whereas ribonucleotides are neither bold nor underlined.

TABLE 1

Oligonucleotide and Primer Sequences

| SEQ ID NO: | Sequence | Description |
|---|---|---|
| Sequences for internally $^{32}$P-labeled partially 2'-deoxyribose-substituted substrates | | |
| 1 | 5'-AGAGGGCUCUGC-3' | 3' partially deoxy top strand |
| 2 | 5'-GCUCGCGAUGCU-3' | 5' partially deoxy top strand |
| 57 | 5'-AGAGGGCUCUGC-3' | 3' RNA top strand |
| 58 | 5'-GCUCGCGAUGCU-3' | 5' RNA top strand |
| 3 | 5'-TTTTTGCAGAGCCCTCTAGCATCGCGAGCTTTTT-3' | Splint DNA |
| 4 | 5'-AAAAAGCTCGCGATGCTAGAGGGCTCTGCAAAAA-3' | Trap DNA |
| 56 | 5'-GCAGAGCCCCCCAGCAUCGCGAGC-3' | Partially deoxy bottom strand |
| 5 | 5'-GCAGAGCCCCCCAGCAUCGCGAGC-3' | RNA bottom strand |
| Sequences for internally $^{32}$P-labeled DD, DR, RD, RR substrates | | |
| 6 | 5'-AGAGGGCTCTGC-3' | 3' DNA top strand |
| 7 | 5'-GCTCGCGATGCT-3' | 5' DNA top strand |
| 8 | 5'-GCAGAGCCCCCCAGCATCGCGAGC-3' | DNA bottom strand |
| 57 | 5'-AGAGGGCUCUGC-3' | 3' RNA top strand |
| 58 | 5'-GCUCGCGAUGCU-3' | 5' RNA top strand |

TABLE 1-continued

Oligonucleotide and Primer Sequences

| SEQ ID NO: | Sequence | Description |
|---|---|---|
| 5 | 5'-GCAGAGCCCCCCAGCAUCGCGAGC-3' | RNA bottom strand |

Sequences for 90 nt DNA + RNA hybrid substrates

| SEQ ID NO: | Sequence | Description |
|---|---|---|
| 9 | 5'-GCGCATAGCCGCGCTATCCGCCAACTCAATCGCGCTCGCCTGAATAGCTCGCGATGCTAGAGGGCTCTGCTACCGCCCCACGAGGGCCAG-3' | 90 nt DNA strand |
| 10 | 5'-TAATACGACTCACTATAGGGCTGGCCCTCGTGGGGCGGTA-3' | T7 promoter extend reverse primer |
| 11 | 5'-GCGCATAGCCGCGCTATCCG-3' | T7 promoter extend forward primer |
| 12 | 5'-CTGGCCCTCGTGGGGCGGTA-3' | 90 nt DNA PCR reverse primer |
| 13 | 5'-GAGCGCTGAAGGTCTCTTCTTCTCATGACTGAACTCGCGAGCGCATAGCCGCGCTATCCG-3' | PCR extend forward primer |
| 14 | 5'-GAGCGCTGAAGGTCTCTTCT-3' | Sequencing primer |
| 15 | 5'-GCAGAGCCCUCUAGCAUCGCGAGC-3' | No mismatch RNA bottom strand |
| 16 | 5'-GCAGAGCCCUCCAGCAUCGCGAGC-3' | Mismatch site B RNA bottom strand |
| 17 | 5'-GCAGAGCCCCCUAGCAUCGCGAGC-3' | Mismatch site C RNA bottom strand |
| 5 | 5'-GCAGAGCCCCCCAGCAUCGCGAGC-3' | Mismatch site B + C RNA bottom strand |
| 18 | 5'-GGGCUGGCCCUCGUGGGGCGGUAGCAGAGCCCUCUAGCAUCGCGAGCUAUUCAGGCGAGCGCGAUUGAGUUGGCGGAUAGCGCGGCUAUGCGC-3' | 93 nt bottom RNA |

Sequences for M13 phage substrates

| SEQ ID NO: | Sequence | Description |
|---|---|---|
| 19 | 5'-AUCCGGUAUUCCAAGAACGCGAGG-3' | TAG site guide RNA |
| 20 | 5'-GCCAAAAGGAACUACGAGGCAUAG-3' | AAT site guide RNA |
| 21 | 5'-UUUCAGCGGAGCGAGAAUAGAAAG-3' | CAC site guide RNA |
| 22 | 5'-CCGUCACCGACCUGAGCCAUUUGG-3' | AAG site guide RNA |
| 23 | 5'-GGACUCCAACGCCAAAGGGCGAAA-3' | GAC site guide RNA |

TABLE 1-continued

Oligonucleotide and Primer Sequences

| SEQ ID NO: | Sequence | Description |
|---|---|---|
| 24 | 5'-UCAAAAAUAAUCCGCGUCUGGCCU-3' | GAA site guide RNA |
| 25 | 5'-CTTGTGGGTTATCTCTCTGATATTAGCGCTC-3' | TAG site PCR forward primer |
| 26 | 5'-GAATAACCTTGCTTCTGTAAATCGTCGCTAT-3' | TAG site PCR reverse primer |
| 27 | 5'-CTACTCGTTCGCAGAATTGGGAATC-3' | AAT site PCR forward primer |
| 28 | 5'-GAACGAGGCGCAGACGGTCAATC-3' | AAT site PCR reverse primer |
| 29 | 5'-GATTGACCGTCTGCGCCTCGTTC-3' | CAC site PCR forward primer |
| 30 | 5'-CAGTGCCTTGAGTAACAGTGCCCG-3' | CAC site PCR reverse primer |
| 31 | 5'-CGGGCACTGTTACTCAAGGCACTG-3' | AAG site PCR forward primer |
| 32 | 5'-GAGCGCTAATATCAGAGAGATAACCCACAAG-3' | AAG site PCR reverse primer |
| 33 | 5'-CTGGATATTACCAGCAAGGCCGATAG-3' | GAC site PCR forward primer |
| 34 | 5'-GCTCGAATTCGTAATCATGGTCATAGC-3' | GAC site PCR reverse primer |
| 35 | 5'-GCTATGACCATGATTACGAATTCGAGC-3' | GAA site PCR forward primer |
| 36 | 5'-GATTCCCAATTCTGCGAACGAGTAG-3' | GAA site PCR reverse primer |

Example 2. hADAR2-D and hADAR2-D E488F Deamination of Duplexes

Figure 9:
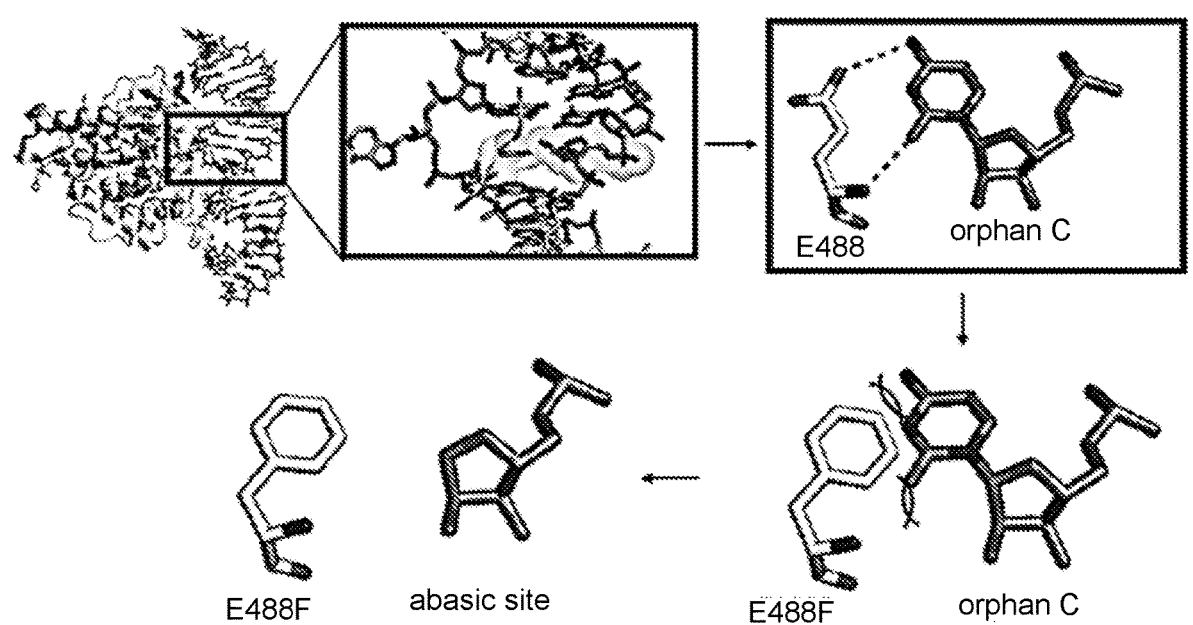
FIG. 9 illustrates aspects of an orthogonal A-to-I editing system. R denotes an ambiguous base call at the indicated position.
Figure 10A:
FIGS. 10A-10C describes the use of an orthogonal A-to-I editing system.
Figure 10B:
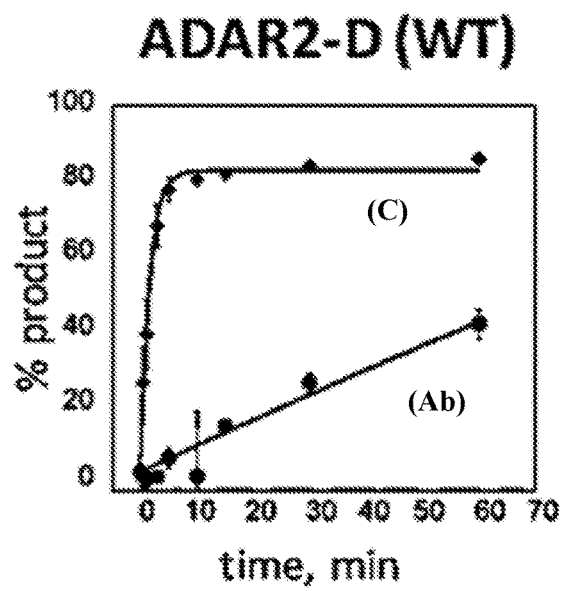
Figure 10C:
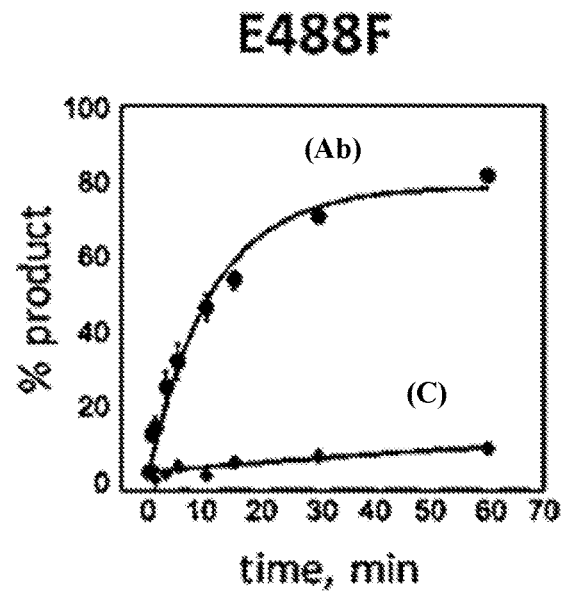

To determine reactivity and selectivity of the human ADAR2 deaminase domain (hADAR2d) E488F on a 24-bp duplex containing hGli1 sequence, two different duplexes were prepared. One duplex contained a cytidine (C) across from the target site while the other contained a reduced abasic site across from the target site (FIG. 9). Editing activity was measured by using an internally $^{32}$P-labeled target and a thin layer chromatography assay. hADAR2d and hADAR2d E488F were used to perform deamination reactions with both the C-containing and reduced abasic target site substrates. After the reaction was quenched and purified, the RNA was nuclease digested and spotted for thin layer chromatography (TLC). Analysis of TLC plates using phosphoimaging and ImageQuant software showed that hADARd E488F exhibited high editing activity for the substrate containing the reduced abasic site and poor editing activity with the native substrate (FIG. 10C).

Purification of Oligonucleotides

RNA strands were purified by denaturing polyacrylamide gel electrophoresis and visualized using UV shadowing. Bands were excised from the gel and were crushed and soaked overnight at 4° C. in 500 mM NH₄OAc, and 100 mM EDTA. Polyacrylamide fragments were removed using a 0.2 µm filter, ethanol precipitated, and lyophilized to dryness. Oligonucleotides were then resuspended in nuclease free water and stored at −20° C. Upon hybridization, the internally labeled hGli1 top strand (see, section titled "Internal labeling of ³²P-substrate" below) and corresponding bottom strand (wherein the position marked X in FIG. 10A was a C-containing site or an abasic site) were heated to 95° C. for 5 minutes and then slowly cooled to room temperature in 10 mM Tris-HCl, 0.1 mM EDTA pH 7.5, and 100 mM NaCl.

Internal Labeling of ³²P-Substrate

The 3' 12-nucleotide oligonucleotide of the top strand was radiolabeled with [γ-³²P] ATP at the 5' end with T4 polynucleotide kinase. About 30 pmol of labeled 3' top strand was dissolved with 40 pmol of 5' 12-nucleotide top strand, 30 pmol of DNA splint, 0.5 µL of RNasin (1.6 units/4), 2 µL of NEB T4 DNA ligase 10× buffer, and 5 µL of nuclease free water. The solution was heated at 65° C. for 5 minutes and slowly cooled to room temperature. After the addition of 1.5 µL of RNasin (1.6 units/4), 5 µL of 4 mM ATP, and 1 µL of T4 DNA ligase (400 U/4), the reaction incubated at 30° C. for two hours. Splint-ligated product was purified as described above.

Deamination Experimental

Deamination reactions had a final volume of 10 µL with concentrations of 10 nM RNA and 300 nM hADAR2d or hADAR2d E488F. The final reaction solution contained 16 mM Tris-HCl, pH 7.4, 3.3% glycerol, 1.6 mM EDTA, 0.003% NP-40, 60 mM KCl, 7.1 mM NaCl, 0.5 mM DTT, 1.6 units/4 RNasin, and 1 µg/mL yeast tRNA. Reactions were quenched by adding 190 µL of 95° C. nuclease free water followed by vortexing of the solution and incubating at 95° C. for 5 minutes. Deaminated RNA was purified by phenol-chloroform extraction and ethanol precipitation. The deaminated product solution was lyophilized to dryness and resuspended in 50 µL of 1×TE solution followed by digestion with nuclease P1. The subsequent 5'-mononucleotides were resolved by thin-layer chromatography (TLC). The TLC was visualized by exposure to a storage phosphor imaging plate on a Typhoon phosphoimager. TLC was then quantified by volume integration using ImageQuant software where the data were fitted to the equation: $[P]_t = \alpha [1-e^{k_{obs}t}]$, where $[P]_t$ is the percent edited at time t, a is the fitted end point, and $k_{obs}$ is the observed rate constant. Each experiment was carried out in triplicate.

Example 3. ADAR2 Deaminase Domain-HBD Fusion Protein Shows Enhanced DNA Editing Efficiency The 50 amino acid hybrid binding domain from human RNase H1 was fused to the 382 amino acid deaminase domain from human ADAR2 with a 21 amino acid linker (SEQ ID NO:140). This protein showed enhanced editing efficiency at a 2'-deoxyadenosine residue in the DNA strand of a DNA/RNA hybrid duplex (90%) when compared to the ADAR2 deaminase domain alone (35%) (FIG. 11). These results show that ADAR-catalyzed DNA editing efficiency can be improved using fusion proteins to enhance binding to the substrate DNA.

Example 4. A Bump-Hole Approach for Directed RNA Editing

This example describes the use of a bump-hole strategy to develop highly selective combinations of mutant ADARs and directing oligonucleotides. Site-directed RNA editing (SDRE) (e.g., of endogenous targets) was shown in vitro and in human cells using bulky mutant ADAR2 proteins and guide RNAs with reduced off-target activity. Furthermore, the crystal structure of ADAR2-D E488Y with a RNA duplex containing a reduced abasic site is shown.

Molecules capable of directing changes to nucleic acid sequences are powerful tools for molecular biology and promising candidates for the therapeutic correction of disease-causing mutations. However, unwanted reactions at off target sites complicate their use. Here we report selective combinations of mutant editing enzyme and directing oligonucleotide. Mutations in human ADAR2 (adenosine deaminase acting on RNA 2) that introduce aromatic amino acids at position 488 reduce background RNA editing. This residue is juxtaposed to the nucleobase that pairs with the editing site adenine, suggesting a steric clash for the bulky mutants. Replacing this nucleobase with a hydrogen atom removes the clash and restores editing activity. A crystal structure of the E488Y mutant bound to abasic site-containing RNA shows the accommodation of the tyrosine side chain. Finally, we demonstrate directed RNA editing in vitro and in human cells using mutant ADAR2 proteins and modified guide RNAs with reduced off target activity.

Introduction

Figure 12A:
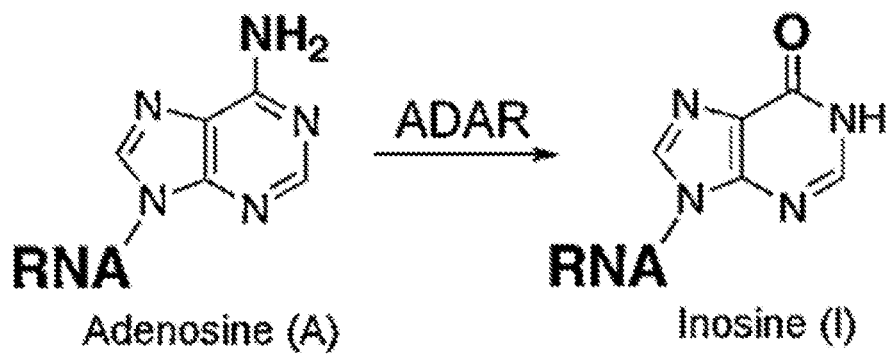
FIGS. 12A-12D show a bump-hole approach for orthogonal site-directed RNA editing with ADAR.

A variety of systems have been developed for directing reactions that change nucleic acid sequence, either in DNA (e.g., for genome editing) or in RNA (e.g., for transcriptome editing) (Montiel-Gonzalez et al., 2013; Montiel-Gonzalez et al., 2016; Nunez et al., 2016; Ran et al., 2013; Hsu et al., 2014; Cox et al., 2017; Gaudelli et al., 2017; Stafforst and Schneider, 2012). CRISPR-Cas-mediated selective cleavage of duplex DNA coupled with homology-directed repair with appropriately designed donor DNA fragments has become a popular approach for introducing specific sequence changes in genomes (Nunez et al., 2016; Ran et al., 2013; Hsu et al., 2014). Nucleotide-specific editors have been reported recently that use cleavage inactive Cas mutants fused to either cytidine or adenosine deaminase domains (Gaudelli et al., 2017; Komor et al., 2016). In complex with the appropriate single guide RNAs (sgRNAs), these proteins are capable of directing specific single nucleotide changes (C to T or A to G) in the genomes of bacteria, mammalian cells and mice (Gaudelli et al., 2017; Gao et al., 2018; Kim et al., 2017; Komor et al., 2016). Methods for directing the deamination of specific adenosines in RNA have also been described including a recent report of Cas13 fusion proteins capable of RNA editing for Programmable A to I replacement (REPAIR) (Cox et al., 2017; Hanswillemenke et al., 2015; Montiel-Gonzalez et al., 2016). This and other systems designed to direct RNA editing reactions use deaminase domains from the ADAR enzymes (Hanswillemenke et al., 2015; Montiel-Gonzalez et al., 2013; Montiel-Gonzalez et al., 2016; Cox et al., 2017; Stafforst and Schneider, 2012). ADARs (adenosine deaminases that act on RNA) are known to convert A to inosine (I) in duplex RNA (Bass, 2002; Bass and Weintraub, 1988; Goodman et al., 2012). Since I base pairs with C, it functions like G in cellular processes such as splicing, translation and reverse transcription (FIG. 12A) (Bass, 2002; Nishikura, 2010). Among its many consequences on RNA function, ADAR-mediated A to I editing can alter miRNA recognition sites, redirect splicing and change the meaning of specific codons (Wang et al., 2013; Rueter et al., 1999; Yeo et al., 2010). The ability of ADARs to convert A to I has spurred efforts to develop new proteins capable of directing ADAR-catalyzed deamination to specific adenosines present in mRNAs because of disease-associated G to A mutations in the genome (Cox et al., 2017; Montiel-Gonzalez et al., 2013; Vallecillo-Viejo et al., 2018). However, in each of the reported directed RNA editing systems, off target activity is observed (Cox et al., 2017; Montiel-Gonzalez et al., 2013; Montiel-Gonzalez et al., 2016; Vallecillo-Viejo et al., 2018; Wettengel et al., 2017; Vogel et al., 2018). This is because ADAR catalytic domains are used for their deaminase activity and these domains can react with RNA substrates in the absence of a targeting domain (Zheng et al., 2017; Montiel-Gonzalez et al., 2013; Eifler et al., 2013; Hanswillemenke et al., 2015; Wang and Beal, 2016; Matthews et al., 2016; Phelps et al., 2015). Here we describe efforts to reshape an ADAR-RNA interface such that high levels of A to I editing activity are only observed at specific target sites thus reducing unwanted off target editing.

Results

A Bump-Hole Approach to an Orthogonal A to I Editing System

Figure 12B:
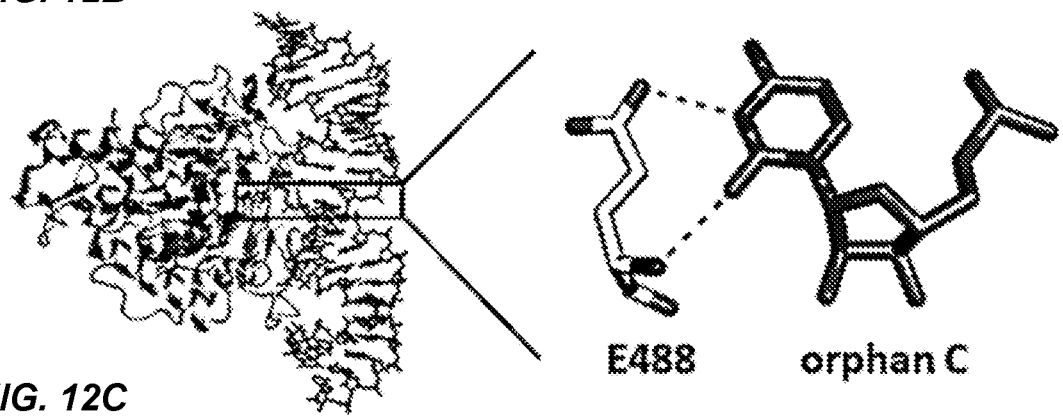
Figure 12C:
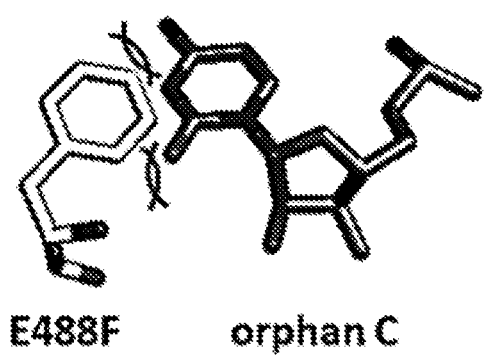
Figure 12D:
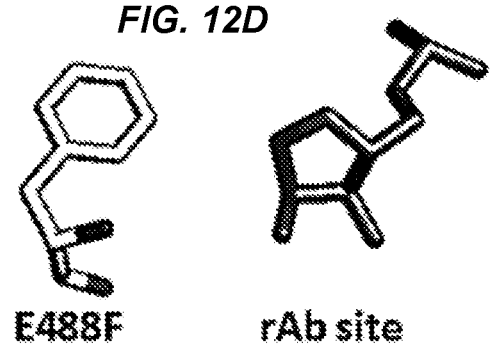

Our recent structural studies of the ADAR2 deaminase domain bound to RNA revealed a loop on the protein surface involved in the base flipping step of the deamination reaction (i.e., flipping loop, S486-T490) (Matthews et al., 2016). The side chain of E488 inserts into the space vacated when the reacting nucleotide occupies the deaminase active site, making direct contact to the "orphan base"; a cytosine or uracil in substrate RNAs bearing either A-C or A-U pairs at the site of reaction (FIG. 12B). Interestingly, in a screen for active and inactive mutants of human ADAR2, Kuttan and Bass identified E488F and E488Y in the pool of inactive clones (Kuttan and Bass, 2012). The low activity of these mutants with typical RNA substrates is explained by the steric clash that would occur between the side chains of these large, aromatic amino acids and the orphan base (FIG. 12C). However, we reasoned these mutants might be active if additional space were created in the complex to accommodate their large side chains. Furthermore, if the clash could be relieved, the ability of the aromatic side chains to engage in 7E stacking interactions in the RNA duplex might be advantageous. To test this idea, we overexpressed and purified the E488F and E488Y mutant ADAR2 deaminase domains. In addition, we prepared a duplex RNA substrate bearing an A-C mismatch at the target site (i.e., the optimal pairing interaction for a wild type ADAR reaction) and a substrate in which the target adenosine was paired with a reduced abasic (rAb) site (FIGS. 12D and 13A) (Lehmann and Bass, 2000; Wong et al., 2001). The duplex sequence used here is derived from that found near a known editing site in the human glioma factor 1 mRNA and was used in our earlier structural studies (Matthews et al., 2016). The abasic site, lacking a nucleobase, provides the "hole" to accommodate the "bump" of the E488F and E488Y mutant proteins (Alaimo et al., 2001; Belshaw et al., 1995). We evaluated the effects of these structural changes by measuring deamination rate constants under single turnover conditions (Zheng et al., 2017; Phelps et al., 2015). The combination of the wild type ADAR2 deaminase domain and an RNA substrate with an A-C mismatch led to a deamination $k_{obs}=0.7\pm0.2$ min$^{-1}$, whereas this protein deaminated the substrate with an A-rAb combination nearly 100-fold more slowly ($k_{obs}=8.9\times10^{-3}\pm0.4\times10^{-3}$ min$^{-1}$) (FIG. 13B and Table 2). This result clearly demonstrates the importance of the E488-orphan base interaction for the reaction of the wild type enzyme. Importantly, the E488F mutant shows the opposite reactivity preference with the A-rAb substrate converted to product with a $k_{obs}=0.09\pm0.02$ min$^{-1}$ and the A-C substrate reacting 71-fold more slowly at a $k_{obs}=1.4\times10^{-3}\pm0.3\times10^{-3}$ min$^{-1}$ (FIG. 13C and Table 2). The E488Y mutant also preferentially reacts with the A-rAb substrate ($k_{obs}>3$ min$^{-1}$) in comparison to the A-C substrate RNA ($k_{obs}=0.17\pm0.04$ min$^{-1}$) (FIG. 13D and Table 2). Interestingly, the E488Y mutant was substantially more reactive than the E488F mutant on both RNA substrates. The E488Y mutant also had at least a five-fold higher rate of editing on the A-rAb substrate compared to the wild type protein on the A-C mismatch in an optimal flanking sequence for ADARs.

High-Resolution Structure of an Engineered Protein-RNA Interface.

Figure 14A:
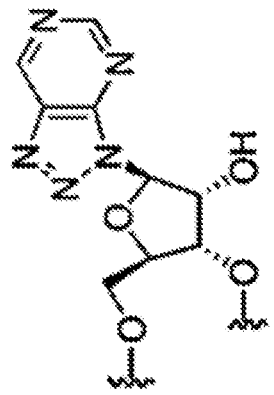
FIGS. 14A-14C show the crystal structure of hADAR2-D E488Y bound to reduced abasic-containing RNA substrate.

The high editing rate for the E488Y/A-rAb combination prompted us to characterize this interaction further by x-ray crystallography. For this purpose, we generated a duplex RNA with the nucleoside analog 8-azanebularine in place of the reactive adenosine paired with an rAb site (FIG. 14A). We had previously shown that the 8-azanebularine modification allows one to trap the ADAR2-RNA complex in the base-flipped conformation for crystallography (Matthews et al., 2016). Crystals of hADAR2-D E488Y/A-rAb combination were grown at room temperature by the sitting drop vapor diffusion method and took several days to form. X-ray diffraction data were collected to 2.55 Å resolution. The structure was solved by molecular replacement using the previously determined structure of ADAR2 deaminase domain complexed with Gli1 RNA (PDBID: 5ED2) (Matthews et al., 2016), and refined to a final $R_{factor}/R_{free}$ of 19.0 and 25.5% respectively. (Table 3).

Figure 14C:
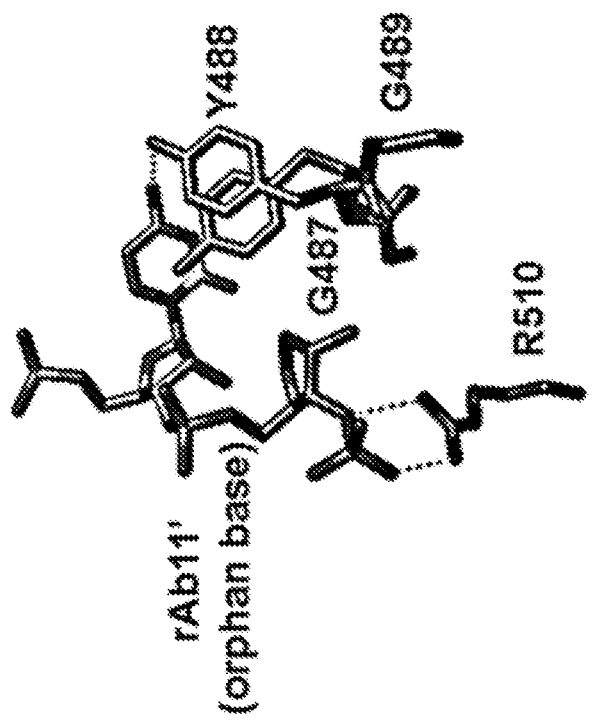
Figure 14B:
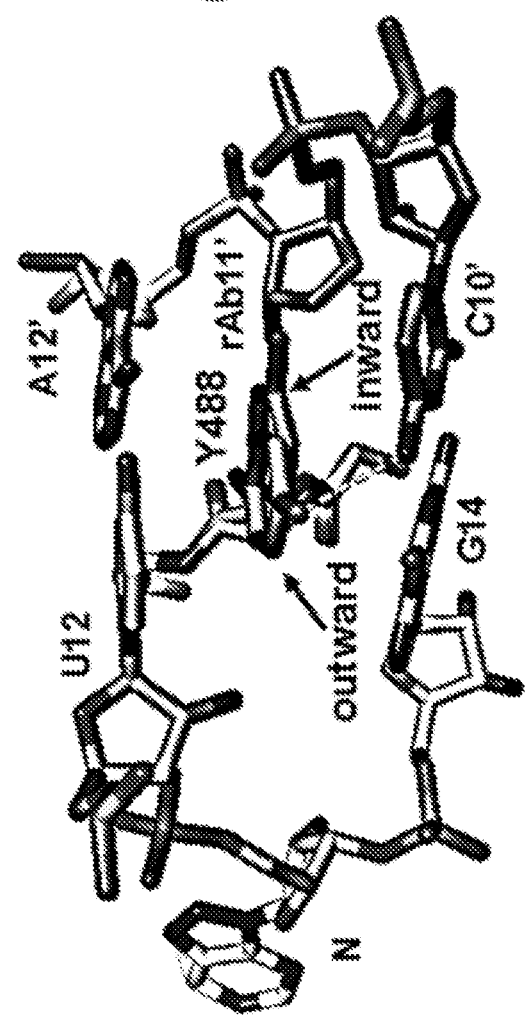
Figure 18:
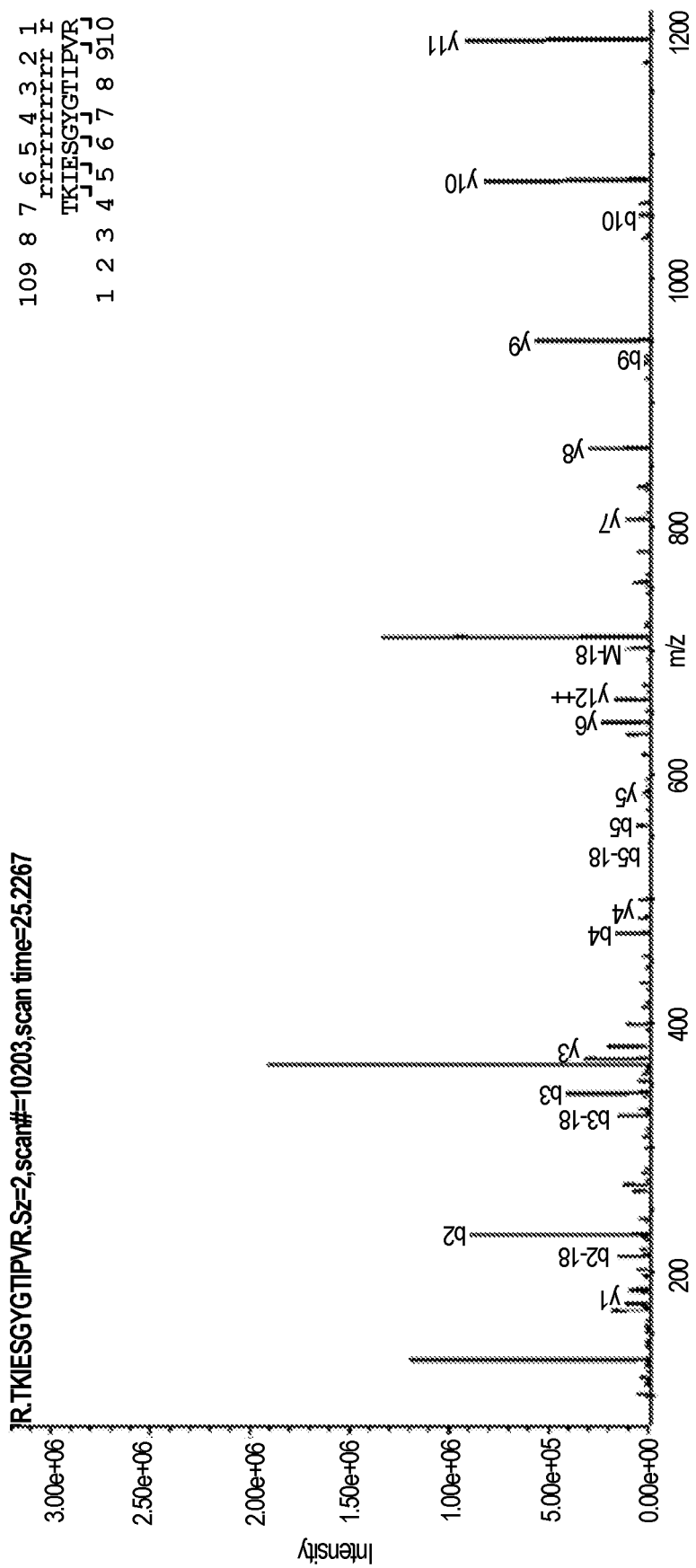
FIG. 18 shows tandem mass spectra for tryptic digest of ADAR2-D E488Y, related to FIG. 14, indicating peptide identification of E488Y presence. Peptide sequence shown in upper left and right corners of figure is SEQ ID NO:129.
Figure 19B:
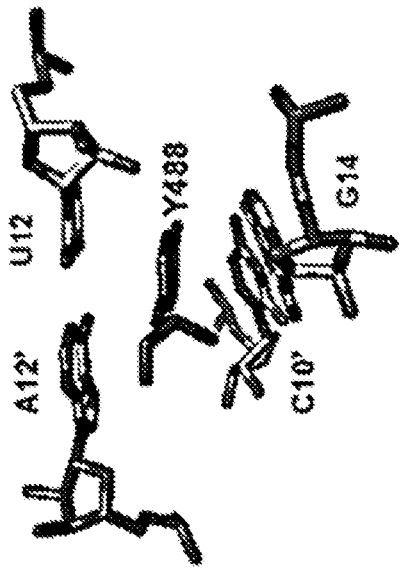
FIGS. 19A-19C show ADAR2 deaminase domain E488Y bound to reduced abasic-containing RNA, related to FIG. 14.
Figure 19A:
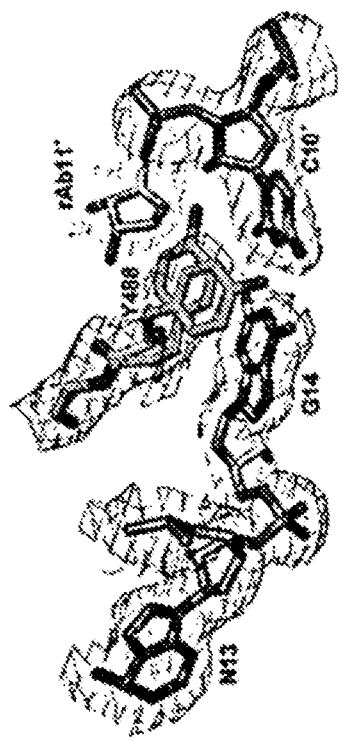

As seen in the previous structures, the side chain of residue 488 in the base flipping loop intercalates into the RNA substrate (Matthews et al., 2016). Here, the tyrosine side chain fills the void created by the flipped-out base and the abasic site and stacks between the editing site flanking base pairs. However, while the electron density clearly defined the benzyl-ring of Y488, no density was observed for the hydroxyl group (FIG. 19A). The presence of the E488Y mutant in the crystals was confirmed by mass spectrometry (FIG. 18). Therefore, we reasoned that the mutant base-flipping loop approaching a "hole" containing substrate would likely adopt multiple conformations. Accordingly, Y488 was modeled in two conformations where the benzyl rings occupy the well-defined electron density, but the hydroxyl groups point to different positions, thus averaging out the density (FIGS. 19A and 19B). In one conformation, the Y488 side chain adopts a more "outward" position relative to the central axis of the double helix whereas in the other conformation, Y488 is more "inward". In the "outward" conformation of Y488, the Y488 hydroxyl group is in close proximity (2.7 Å) to the cytosine N4 amine of the G:C pair containing the 3' G, suggesting potential for hydrogen bonding although the geometry is not ideal (FIG. 14B). Also, since the residue 488 may be responsible for displacing the modified base, a more "outward" position could be more effective in preventing the premature return of the flipped-out base before deamination occurs. However, the side-chain rotamer for the "outward" position is extremely uncommon, according to the MolProbity rotamer probability distribution (Lovell et al., 2000). In the case of F488, the "outward" conformation would be less stable since there is no potential for hydrogen bonding to stabilize it. Thus, the likelihood of F488 adopting this conformation is lower, which would increase the chances of the flipped-out base returning prematurely to the double-helix. This is one possible explanation for why the E488Y mutant may be more active than E488F.

Figure 19C:
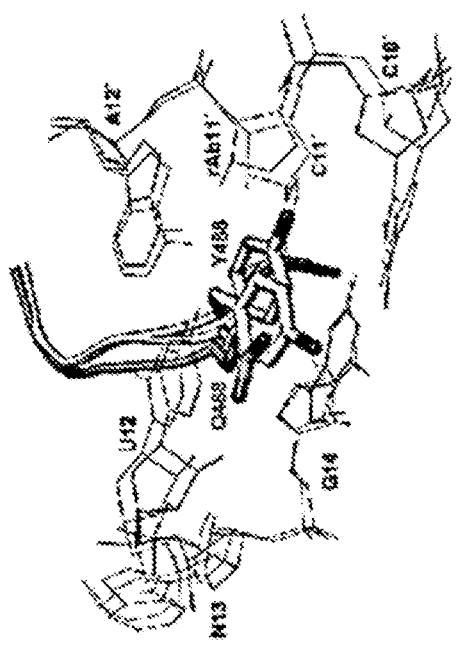
Figure 20A:
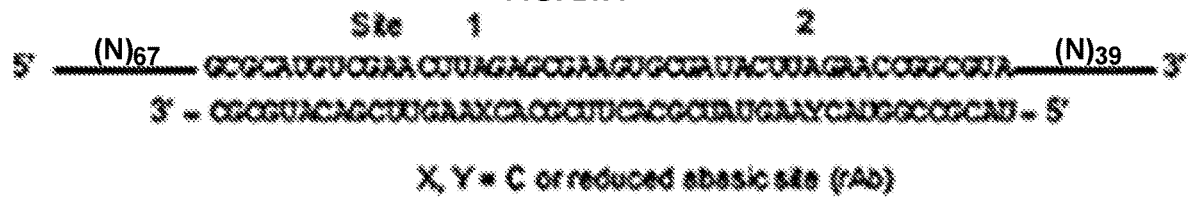
FIGS. 20A-20D show selective editing of 152 nt with hADAR2-D E488W, hADAR2-D E488F, and hADAR2-D WT, related to FIG. 15. Deamination reactions had a final volume of 10 μL with concentrations of 10 nM RNA and 300 nM hADAR2-D E488W, 1.2 μM hADAR2-D E488F, or 1.2 μM hADAR2-D WT. Reactions were quenched after 30 min.
Figure 20B:
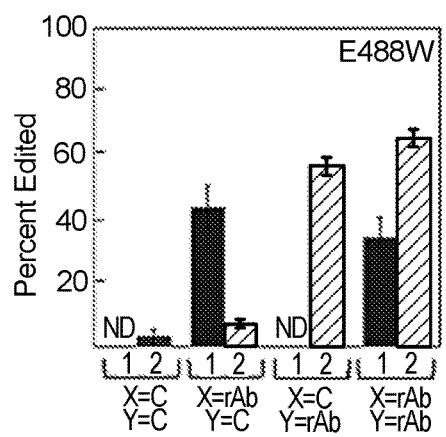
Figure 20C:
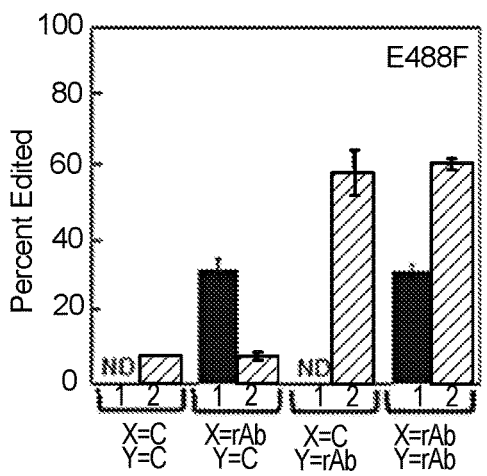
Figure 20D:
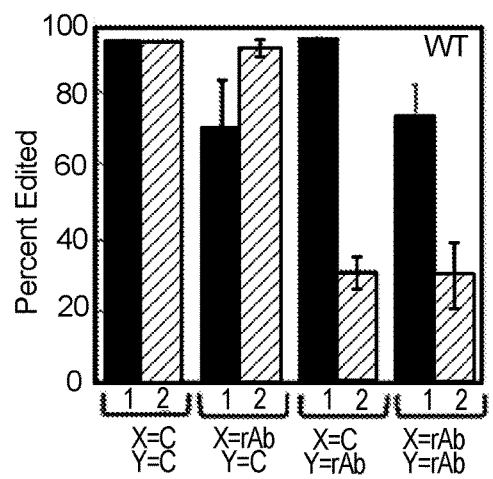
Figure 22A:
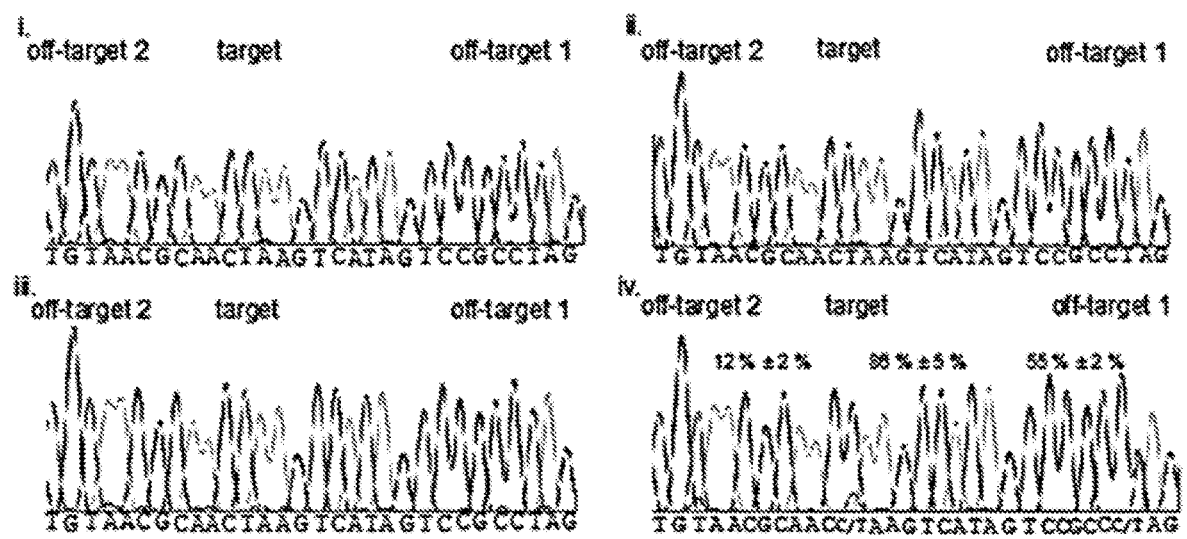
FIGS. 22A-22D show sequencing traces of controls and directed editing of overexpressed β-actin target and corresponding off-targets when hADAR2 wt (FIG. 22A), hADAR2 E488F (FIG. 22B), hADAR2 E488Y (FIG. 22C), and hADAR2 E488W (FIG. 22D) was overexpressed in HEK293-T cells, related to FIG. 16. Each panel consists of (i) overexpressed β-actin, (ii) overexpressed β-actin with guide RNA, (iii) overexpressed β-actin with overexpressed hADAR2 (wt or E488X (X=F, Y, W), and (iv) overexpressed β-actin and guide RNA with overexpressed hADAR2 (wt or E488X (X=F, Y, W). Cytidine guide RNA was used in FIG. 22A and reduced abasic guide RNA was used in FIGS. 22B-22D. The sequence shown in (i), (ii), and (iii) of FIGS. 22A-22D is set forth in SEQ ID NO:137. The sequence shown in (iv) of FIG. 22A is set forth in SEQ ID NO:138. The sequence shown in (iv) of FIGS. 22B-22D is set forth in SEQ ID NO:139.
Figure 22B:
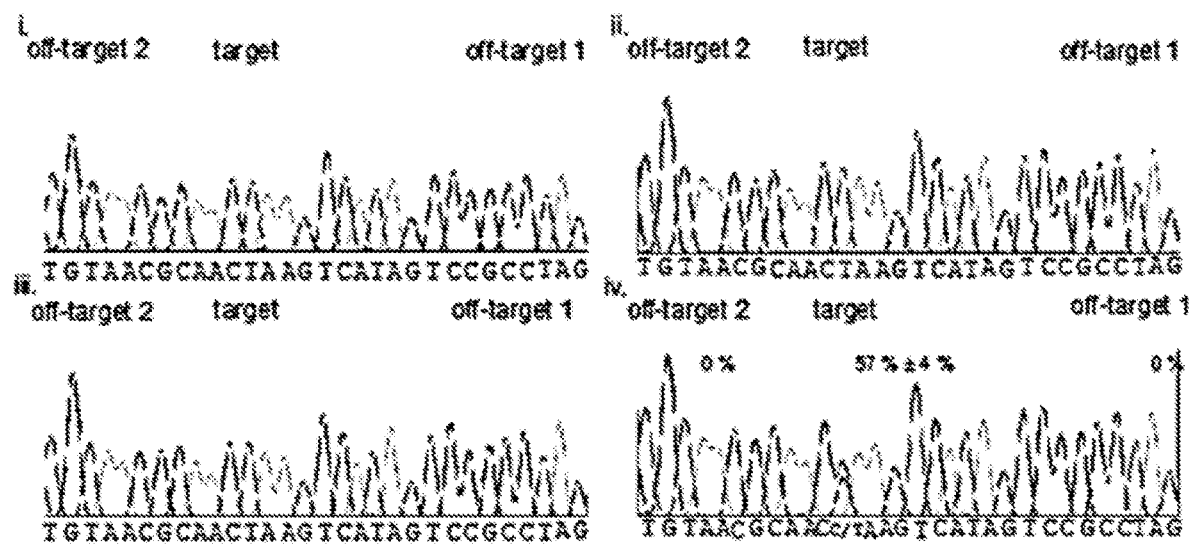
Figure 22C:
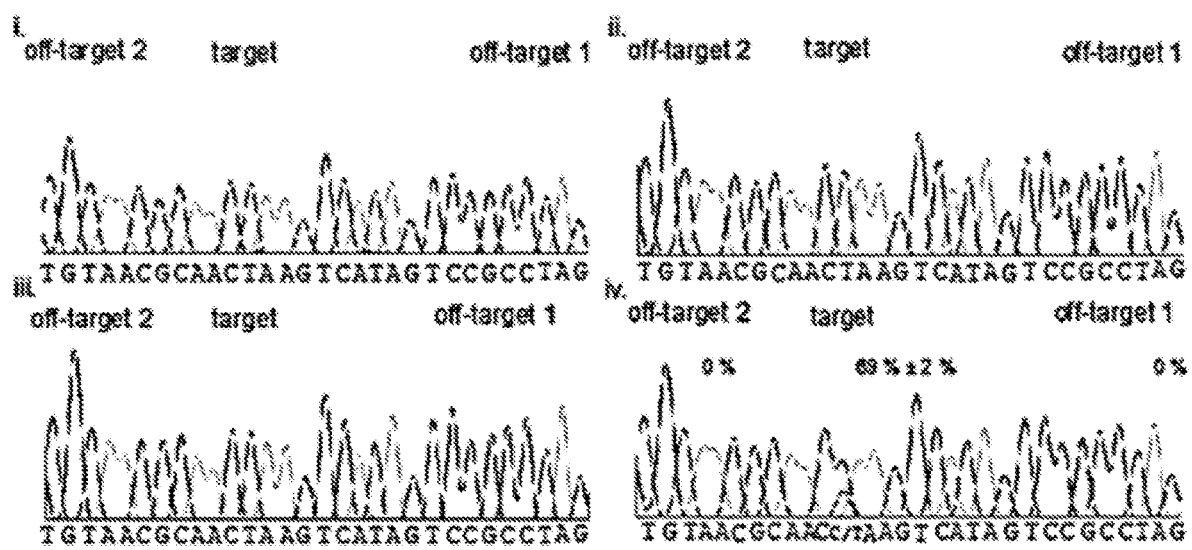
Figure 22D:
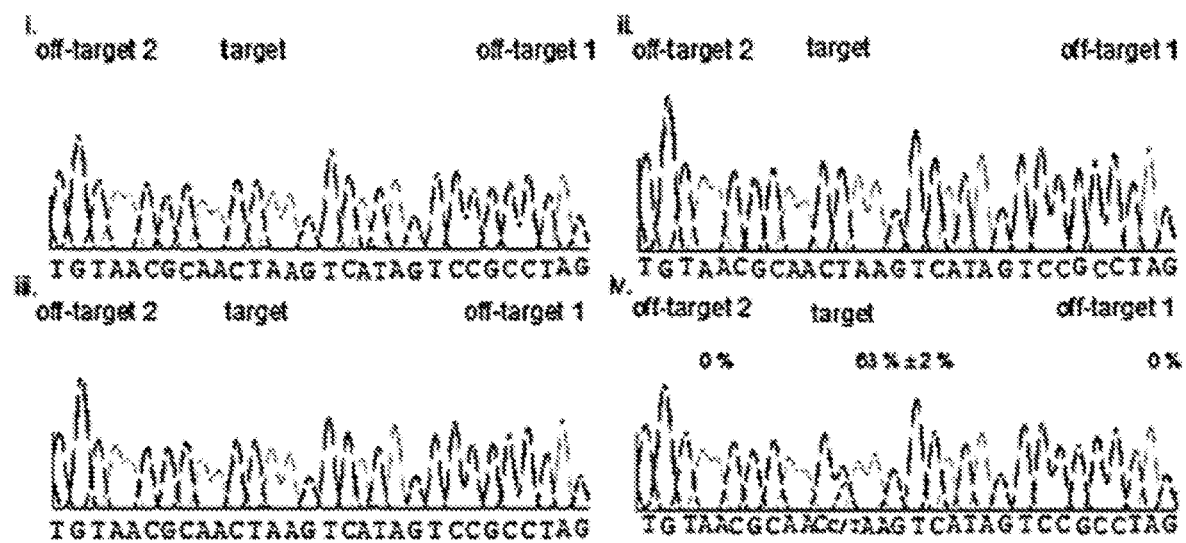

The plane of the tyrosine phenol is parallel to that of the flanking U-A pair containing the U on the 5' side of the editing site and, thus, 7E stacking of the tyrosine appears best with this base pair. The plane of the G-C pair containing the 3' G is at an angle resulting in poor 7E overlap with the Y488 side chain (FIG. 19B). In addition, overlay with previous structures shows the protein backbone of the base flipping loop bearing E488Y shifts (~1.5 Å) to allow the tyrosine side chain to more effectively fill the void created by the abasic site (FIG. 19C). This clearly indicates flexibility in this loop to adjust positioning of the intercalating side chain in the presence of the reduced abasic site at the orphan base position. The reduced abasic site maintains the RNA backbone conformation found in previous structures and is stabilized by contact to the side chain of R510 (FIG. 14C) (Matthews et al., 2016).

Figures 15A, 15B, 15C:
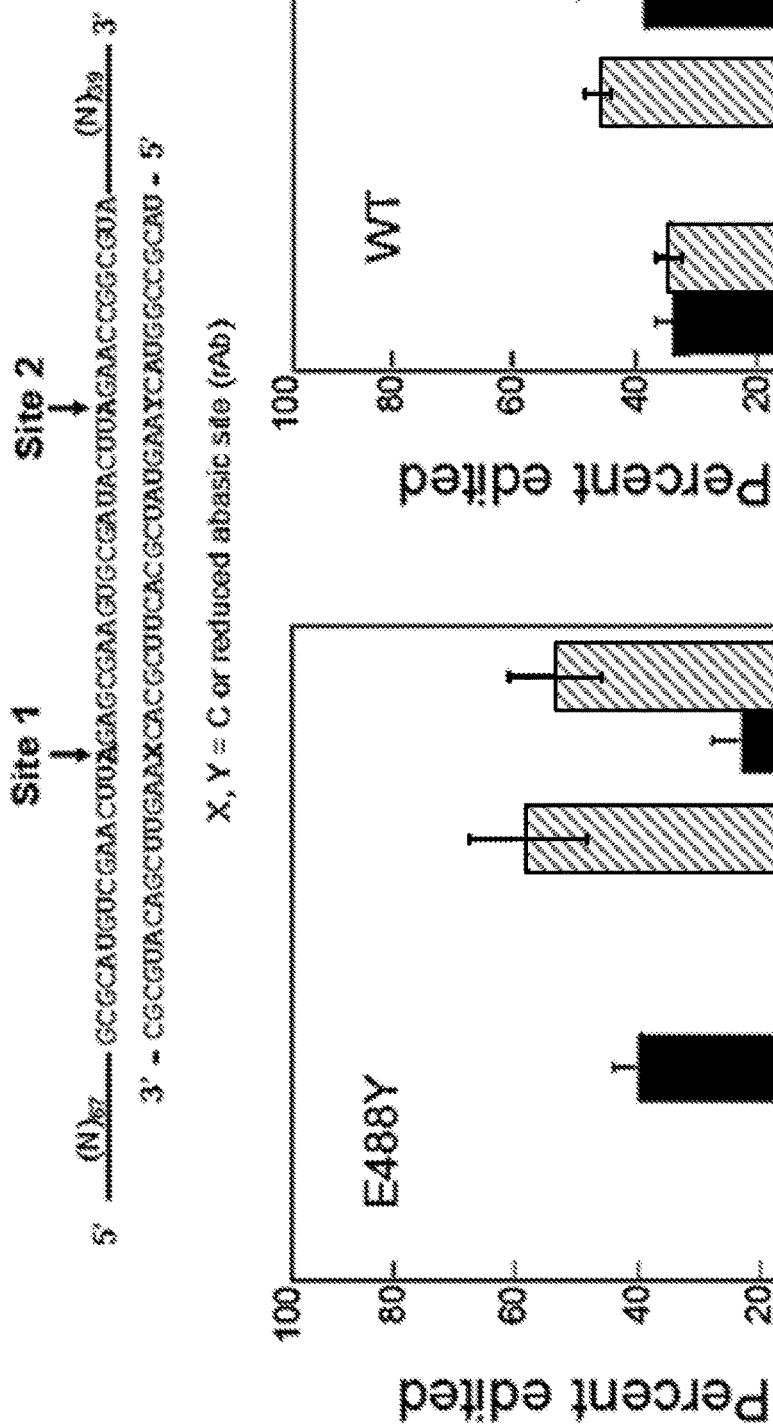
FIGS. 15A-15C show selective editing on 152 nt RNA containing target site 1 and site 2 in optimal ADAR flanking sequence.

Duplex RNA Substrate with Two Good Target Sequences Provides an In Vitro Test for Selectivity The preferential reactivity of the bulky ADAR2 E488X mutants suggested ADAR reaction selectivity could be controlled for substrates with multiple reactive adenosines by the appropriate positioning of the rAb site in a guide strand. To test this idea, we generated a 152 nt RNA with two adenosines with similar flanking sequences separated by 18 nt. This RNA was hybridized to four different 46 nt guide strands with each target adenosine (site 1 or site 2) paired with either C or rAb (FIG. 15A). With both adenosines paired with C, the ADAR2 deaminase domain deaminated site 1 and site 2 adenosines to a yield of 36±3% and 37±2%, respectively (FIG. 15C). Conversely, with both adenosines paired with C, the ADAR2 deaminase domain E488Y mutant deaminated the site 2 adenosine to a yield of 10±2%, while the site 1 adenosine was not deaminated by this enzyme under these conditions (FIG. 15B). However, when rAb was paired with the site 1 adenosine, the editing yield for the E488Y mutant rose from undetectable to 42±4% while the site 2 editing yield remained largely unchanged at 11±2% under these conditions. If, on the other hand, the rAb was paired with the site 2 adenosine instead of site 1, the editing yield at this site rose to 61±9%. When both site 1 and site 2 adenosines were paired with rAb, the editing yields were 24±5% and 55±8%, respectively (FIG. 15B). These results clearly show that the reaction of the E488Y ADAR2 deaminase domain mutant can be directed to different positions in a target RNA by pairing the desired site with the rAb nucleoside analog. We have also shown that the ADAR2 deaminase domain E488F and E488W mutants show similar selectivity and dependence on rAb positioning in the guide strand for the 152 nt RNA target (FIG. 20 and Table 4). At this time, reasons for differences in reactivity of site 1 and site 2 when both are paired with either C or rAb are not known, but may arise from differences in the RNA substrate at the contact site for the 5' binding loop of the deaminase domain (Matthews et al., 2016; Wang and Beal, 2016; Wang et al., 2018).

Figure 23:
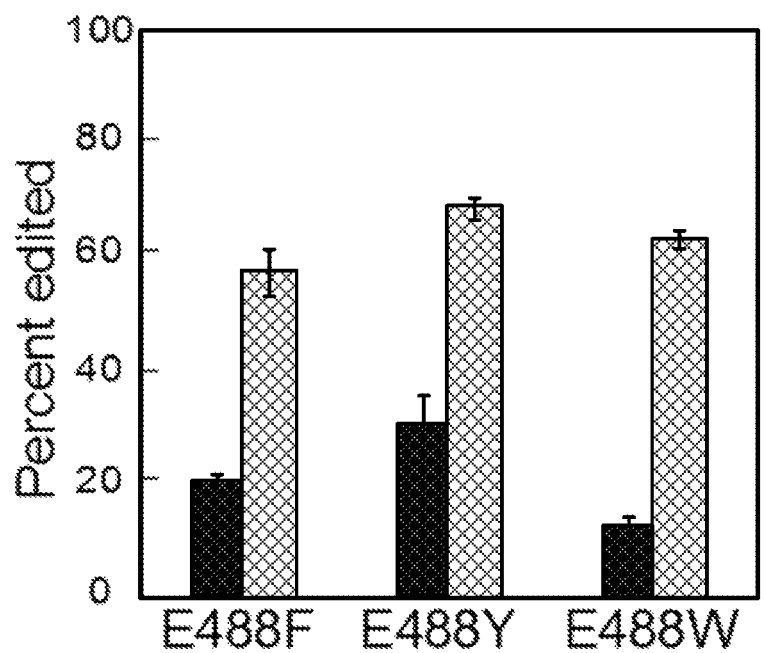
FIG. 23 shows a comparison of percent editing on overexpressed β-actin target with cytidine guide RNA (A:C, left bar in each pair) and reduced abasic guide RNA (A:rAb, right bar in each pair) by mutants hADAR2 E488X (X=F, Y, W), related to FIG. 16. Each experiment was carried out in biological triplicate where percent editing reported is the average of the triplicates±standard deviation.
Figure 24:
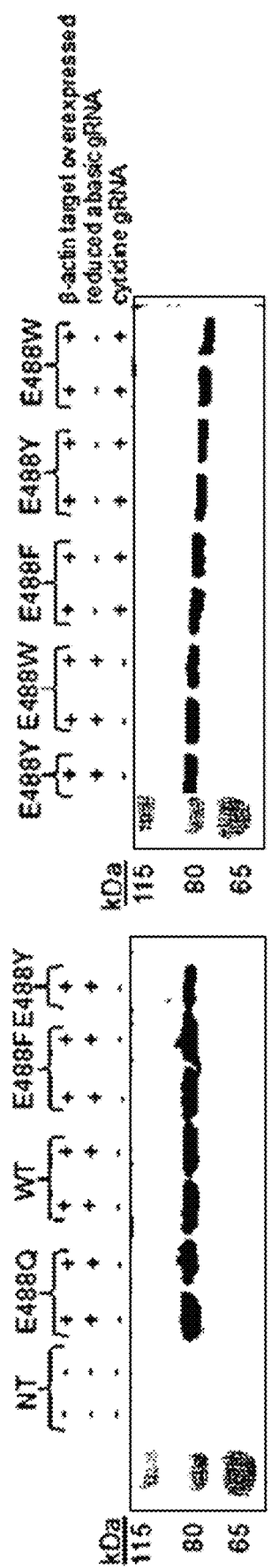
FIG. 24 shows Western blot analysis of whole cell lysates from HEK293T cells expressing full-length ADAR2 and E488X (X=F, Y, W) transfected in with β-actin target and either cytidine guide RNA or reduced abasic guide RNA, related to FIG. 16. No transfection (NT) lanes contained whole cell lysate from HEK293T cells and lanes containing full-length ADAR2 WT or E488X (X=F, Y, W) contained 500 ng pcDNA3.1 containing ADAR gene, 500 ng containing pcDNA3.1 containing region of 3'-UTR β-actin target, and 50 nM of appropriate guide RNA. Cells were lysed 24 hours after transfection.
Figure 25:
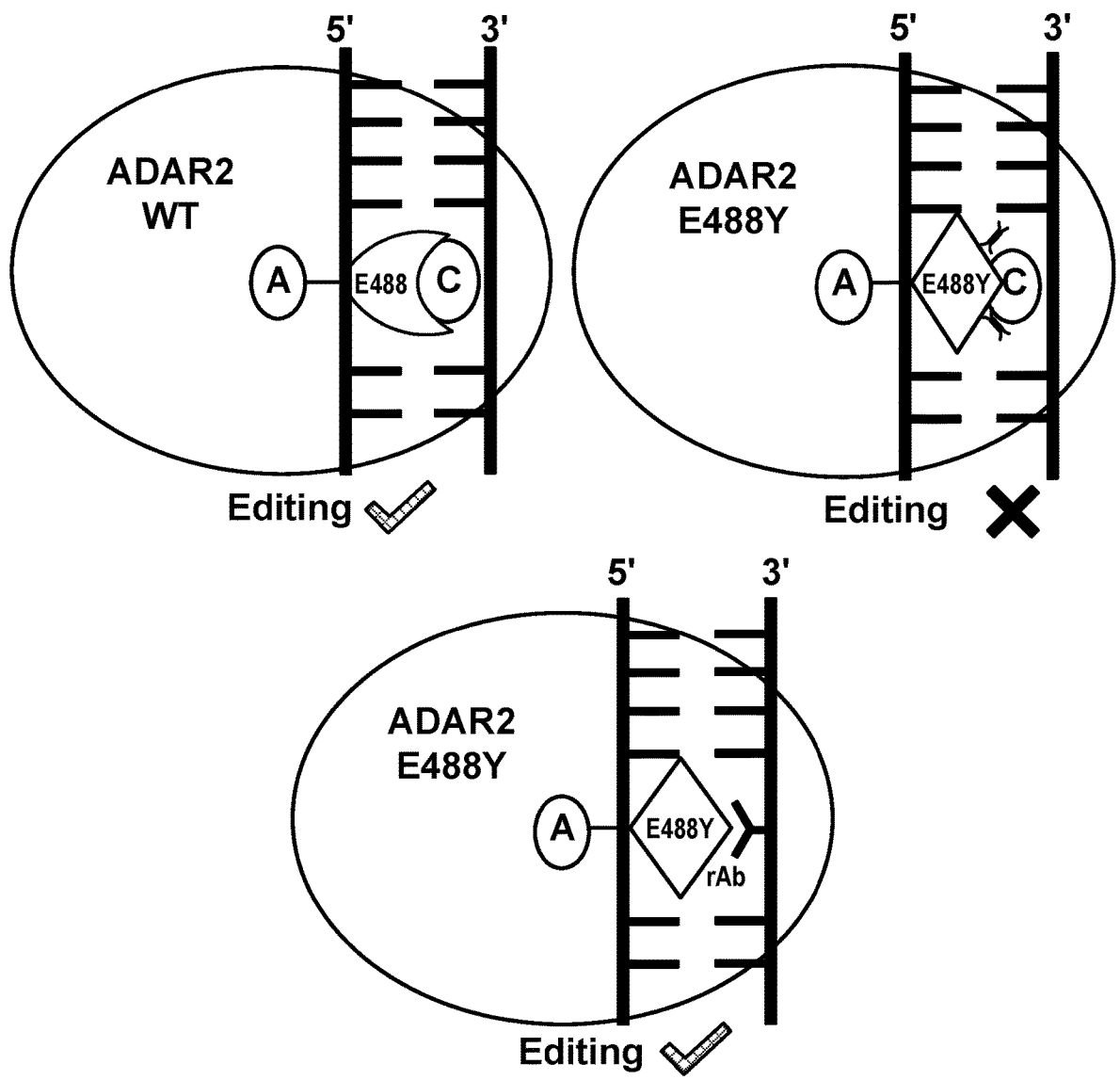
FIG. 25 shows a summary of some aspects of the invention described in Example 4.

Selective Oligonucleotide-Directed Editing in Human Cells with ADAR2 E488F, Y and W Mutants The studies described above suggested the combination of bulky mutations in human ADAR2 at position 488 and a guide strand bearing a rAb site opposite the targeted adenosine could be highly selective in directed RNA editing. To determine if the approach could work in living cells, we synthesized a guide oligonucleotide to direct editing by full-length ADAR2 (with its two double stranded RNA binding domains (dsRBDs)) to an overexpressed target site representing a region of the 3'-UTR of β-actin mRNA (FIG. 21) (Vogel et al., 2014; Vogel and Stafforst, 2014; Schneider et al., 2014). The guide RNA was designed to form a duplex containing an adenosine within a 5'-UAG-3' sequence, the optimal flanking sequence for a human ADAR2 target (FIG. 16A) (Li et al., 2009; Eifler et al., 2013; Matthews et al., 2016; Eggington et al., 2011). Opposite the targeted adenosine, the guide strand had either a cytidine or a rAb site. The guide RNA was additionally stabilized with 2'-O-methyl and phosphorothioate modifications, as previously described for directed editing in cells with chemically synthesized guide strands (Vogel et al., 2014; Schneider et al., 2014; Woolf et al., 1995). Expression of wild type human ADAR2 in HEK293T cells transfected with the guide designed to form an A-C mismatch led to 87±8% editing at the target site (FIG. 16B). Two other adenosines near the target site (off target 1 and off target 2, FIG. 16A) were also edited under these conditions (55±2% and 12±2%, respectively). Expression of ADAR and transfection of the guide were both required to observe editing on this RNA (FIGS. 22A-22D). Importantly, the E488F, E488Y and E488W mutants of ADAR2 induced high levels of target site editing (57±4%, 68±2% and 63±2%, respectively) in the presence of the rAb guide with no editing detected at the two off target sites (FIGS. 16C-16E and Table 5). This was not simply a result of lowering the overall ADAR activity since substantially lower levels of editing are observed with these mutants and the cytidine-containing guide (E488F, E488Y and E488W having editing levels of 21±1%, 31±5% and 13±2%, respectively) (FIGS. 23 and 24, Table 6).

Figure 17C:
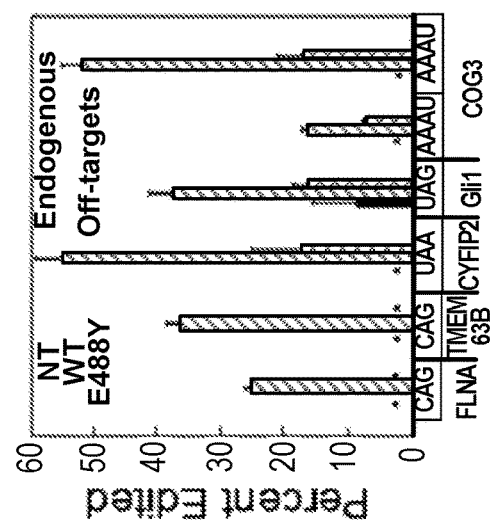
FIGS. 17A-17C show directed editing on endogenous targets and observed endogenous off-targets.
Figure 17B:
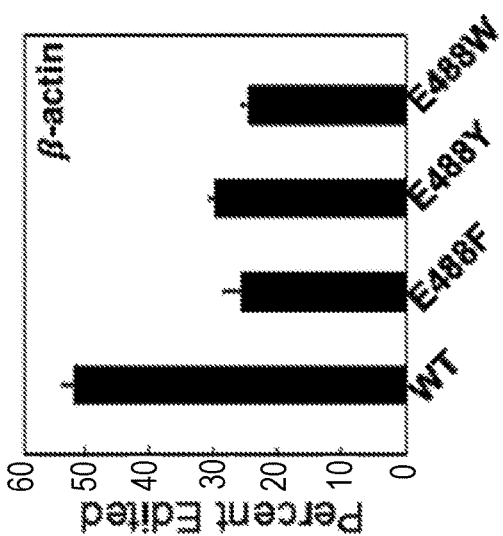
Figure 17A:
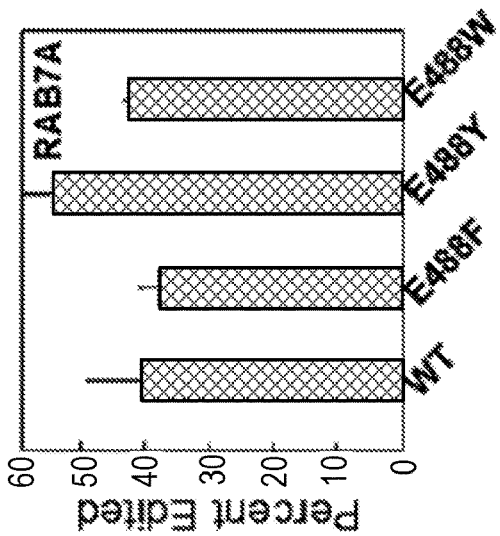

We next tested the ability of the E488X mutant ADARs and modified guide RNAs to direct editing to specific adenosines present on endogenous mRNAs in human cells (FIG. 17 and Table 7). The transcripts chosen (RAB7A and β-actin) both contain adenosines in the 5'-UAG-3' sequence context in their 3'-UTRs and both have been previously targeted for directed RNA editing (Wettengel et al., 2017). As discussed above, guide RNAs were designed to have a cytidine or a reduced abasic site across from the targeted adenosine and were further stabilized by 2'-O-methyl and phosphorothioate modifications. Under the conditions described above for targeting the overexpressed β-actin 3' UTR fragment, no editing was observed on the endogenous β-actin mRNA. However, after optimization of the transfection of the ADAR encoding plasmid and guide RNA (see Method Details for conditions) targeted editing was observed on both the endogenous β-actin and RAB7A transcripts in HEK293T cells. Wild type ADAR2 in the presence of the RAB7A cytidine guide RNA led to an editing level of 41±9%, whereas overexpression of the E488F, E488Y and E488W ADAR2 mutants in the presence of the rAb guide RNA led to editing levels of 38±3%, 55±5% and 43±1%, respectively (FIG. 17B). Thus, for this endogenous target, the ADAR2 E488X mutant/modified guide combinations led to on-target editing yields equivalent to (E488F and E488W) or superior to (E488Y) the wild type enzyme. In contrast, wild type ADAR2 edited the endogenous β-actin target in the presence of cytidine guide RNA to a level of 52±2%, whereas the E488F, E488Y and E488W mutants with the reduced abasic guide RNA induced editing levels to an approximately two-fold lower level (26±3%, 30±1% and 25±1%, respectively) (FIG. 17A). Since expression of the E488Y ADAR2 mutant in the presence of the RAB7A rAb guide led to the highest efficiency of on target editing, we evaluated off target editing under these conditions. Importantly, we found that expression of the E488Y mutant induced less efficient off-target editing in comparison to the wild type enzyme for several previously reported endogenous substrate RNAs for human ADAR2 (FIG. 17C and Table 7). The sites analyzed included one that is edited by endogenous ADARs in HEK293T cells (Gli1) and five sites that are only edited in these cells with overexpressed ADAR (FLNA, TMEM63B, CYFIP2 and COG3). No editing was observed for FLNA and TMEM63B when E488Y was overexpressed while overexpression of the wild type ADAR2 clearly induced editing at these sites (FLNA 26±1% and TMEM63B 37±2%). For the Gli1 site, overexpression of wild type ADAR2 increased editing approximately 4-fold from 9±6% to 38±4%, whereas E488Y led to a 2-fold increase in editing to 17±2%. Overexpression of wild-type ADAR2 increased editing on the CYFIP2 site from not detectable to 55±4%, whereas E488Y caused only 18±8%, editing at this site. Finally, at the COG3 sites, wild type ADAR2 increased editing from not detectable at both sites to 17±1% and 52±3%, while E488Y mutant had editing levels of 7.6±0.4% and 18±4%, respectively. Thus, for all six sites analyzed, a clear reduction in off target editing is observed for the E488Y mutant.

Discussion

Redirecting the ADAR reaction to adenosines present in RNA as a result of disease-associated G to A mutations is a promising approach for the development of novel therapeutics (Reenan, 2014; Sinnamon et al., 2017; Heep et al., 2017; Wettengel et al., 2017). This is conceptually similar to base-specific gene editing using deaminase-Cas9 fusion proteins but with RNA, not DNA, as the target (Komor et al., 2016; Hsu et al., 2014). Directed RNA editing provides an important alternative to Cas-mediated genome editing because the RNA editing effect is transient in nature and, thus, reversible. Editing the transcriptome is inherently less risky than directing permanent sequence changes to the genome. In addition, RNA editing is possible in post-mitotic cells. For example, directing RNA editing to "repair" specific disease associated G to A mutations in the MeCP2 mRNA present in post-mitotic neurons has therapeutic potential for Rett Syndrome (Sinnamon et al., 2017). However, the intrinsic reactivity of ADAR deaminase domains, particularly hyperactive variants that have been used in some cases, can lead to off target RNA editing (Cox et al., 2017; Montiel-Gonzalez et al., 2013; Montiel-Gonzalez et al., 2016; Wettengel et al., 2017; Vogel et al., 2018). An important challenge is to identify methods that reduce off target editing activity while maintaining (or enhancing) the desired on-target, directed editing. Rosenthal has addressed this issue by targeting ADAR fusion proteins to the nucleus where off-target editing is less efficient (Vallecillo-Viejo et al., 2018). Zhang described the use of mutant ADAR catalytic domains with lower overall deaminase activity (Cox et al., 2017). Using the ADAR2 deaminase domain mutant (E488Q/T375G) fused to dCas13b, Zhang observed a decrease in off-target editing, however on-target editing was also compromised (Cox et al., 2017). Stafforst has used modified guide RNAs to block editing within the duplex containing the guide and genomic integration of the deaminase to reduce off targeting due to overexpression (Vogel et al., 2014; Vogel et al., 2018). Here we described a structure-guided approach that combines the idea of reducing ADAR activity by mutagenesis and the use of chemically-modified guide strands to re-shape the ADAR-RNA interface such that only a target adenosine opposite a nucleoside analog (e.g., a rAb site) in the guide is efficiently edited. This is an example of the bump-hole approach for controlling ligand-receptor interactions (Alaimo et al., 2001; Belshaw et al., 1995).

The abasic site was a simple starting point for modification at the orphan base position, however other modifications have potential to lead to an even more selective A to I editing systems. The high-resolution crystal structure presented here provides additional insight into other potential modifications that could be incorporated into the guide strand to facilitate editing with ADAR mutants. For instance, since the most efficient stacking of the Y488 side chain appears to occur with the U-A pair containing the 5' U (FIG. 14B), adenosine analogs with altered π-stacking properties could be beneficial in the guide strand at this position. In addition, using our structure as a starting point, one could carry out computational screening of ribose analogs to identify derivatives uniquely suited for accommodating various E488X mutants (Suter et al., 2016; Onizuka et al., 2013). Furthermore, only the 488 position was mutated here but one can easily imagine extending this concept to other residues whose side chains approach the guide strand. Combinations of specific mutations and compensatory guide strand modifications would be expected to increase further overall editing selectivity.

Other directed RNA editing approaches use artificial targeting domains fused to ADAR deaminase domains (Hanswillemenke et al., 2015; Montiel-Gonzalez et al., 2013; Montiel-Gonzalez et al., 2016; Sinnamon et al., 2017). For the directed editing in human cells described here, our editing enzymes have human ADAR2's native targeting domain (i.e., the natural N-terminal domain containing two dsRBDs). We believe this is a demanding test of the effects of our bump-hole approach, since all natural ADAR2 sites are potential off-target sites. Interestingly, the guide RNA used to direct editing to the overexpressed β-actin 3' UTR fragment induced wild type ADAR2 to deaminate three adenosines within a 26 nt segment of the target, including one (off target 1) that is outside the predicted binding site for the guide (FIG. 16). Editing efficiency was reduced with the ADAR2 E488X mutants at both the off target sites, even though off target site 1 adenosine is not predicted to pair with a guide RNA nucleotide. While the basis for the reduced activity for this site cannot be firmly established at this time, off target site 1 may exist in duplex structure native to the overexpressed β-actin 3' UTR fragment (Vogel et al., 2018).

We have shown that the bump-hole combinations described here can be used to direct efficient RNA editing to two different endogenous transcripts (RAB7A and (3-actin) (FIGS. 17A and 17B). Directed editing of the RAB7A target with the bulky ADAR2 mutant/rAb guide combination occurred at levels equal to, or higher than, the wild type ADAR2/cytidine guide combination (FIG. 17A). For the β-actin target, wild type ADAR2/cytidine guide was 1.7-fold more efficient than the best bulky mutant (E488Y)/rAb guide combination (FIG. 17B). A variety of factors could be responsible for transcript-specific differences in targeting efficiencies, including differences in transcript expression levels, target accessibility and differences in the metabolic stabilities of the different guide RNAs used. Additional studies are necessary to determine the relative importance of these different parameters in controlling on-target editing yield. Nevertheless, these results show that the bulky ADAR mutant/rAb guide combinations can lead to directed editing yields comparable (within 2-fold) to the wild type ADAR2/cytidine guide for endogenous transcripts.

Importantly, for each of the six ADAR2 sites analyzed for off target editing, the E488Y mutant induced lower editing levels than the wild type enzyme (FIG. 17C). The full extent of off target editing with the bulky ADAR2 mutants described here will require transcriptome sequencing under the directed editing conditions and a comparison to wild type ADAR2 (Vogel et al., 2018). The results reported here show that, under the conditions of a directed editing scenario where efficient editing is observed with an endogenous target (e.g., RAB7A editing=55%), off target editing is reduced through the use of a bump-hole combination. Off target activity is not completely eliminated, since some editing is observed with the E488Y mutant on the CYFIP2, Gli1 and COG3 off target sites. However, further optimization is likely possible with additional mutagenesis to disrupt the ADAR-RNA interface and new compensating guide RNA modifications. Such efforts are currently underway in our laboratory.

Significance

Genome and transcriptome editing tools have the potential to revolutionize molecular biology and medicine. However, it is essential that such tools be highly precise as unexpected changes in nucleic acid sequences could be lethal. Here we show the classic bump-hole approach from chemical biology can be applied to controlling the selectivity of directed RNA editing by adenosine deamination. In principle, this approach could be applied to each of the published directed RNA editing platforms that use ADAR-derived adenosine deaminase domains and guide RNAs. Furthermore, the bump-hole approach described here for optimizing targeted nucleic acid editing should prove useful for other systems where use of native components leads to unacceptable levels of off targeting and high resolution structures of the protein-nucleic acid complexes exist.

Methods

Experimental Model and Subject Details

HEK293T cells (sex-female) were purchased from ATCC and used in this study. HEK293T cells were cultured in Dulbecco's modified Eagle's medium (DMEM), 10% fetal bovine serum, and 1% anti-anti at 37° C., 5% $CO_2$. HEK293T cells were used at less than 15 passages. *Saccharomyces cerevisiae* BCY123 was used in this study. *S. cerevisiae* BCY123 were grown in media without uracil (6.7 g/liter yeast nitrogen base containing $(NH_4)_2SO_4$ and lacking amino acids, 10 g/liter succinic acid, 6 g/liter NaOH, 1.92 g/liter yeast synthetic dropout media without uracil, 22 mg/liter adenine hemisulfate) with 2% dextrose (Macbeth and Bass, 2007).

Purification of Oligonucleotides

Unless otherwise noted oligonucleotides were purchased from either Dharmacon or Integrated DNA Technologies. Oligonucleotides were purified by denaturing polyacrylamide gel electrophoresis (PAGE) and visualized using UV shadowing. Bands were excised from gel and gel slices were crushed and soaked overnight at 4° C. in 500 mM $NH_4OAc$ and 100 mM EDTA. Polyacrylamide fragments were removed using a 0.2 μm filter. Oligonucleotides were ethanol precipitated and lyophilized to dryness. Oligonucleotides were then resuspended in nuclease-free water and stored at −20° C. All oligonucleotide sequences can be found in Table 8.

Protein Overexpression and Purification

Mutagenesis of hADAR2-D and full-length hADAR2 was performed using QuickChange XL Site-Directed Mutagenesis (Agilent) and transformed into XL10-Gold Ultracompetent cells (Agilent). Primers for mutagenesis were purified as described above. hADAR2-D wt and hADAR2-D E488X (X=F, Y, W) were expressed and purified as previously described (Macbeth and Bass, 2007; Matthews et al., 2016). In brief, *S. cerevisiae* BCY123 cells were transformed with a pSc-ADAR construct encoding hADAR2-D WT or hADAR2-D E488X (X=F, Y, W). Cells were streaked on yeast minimal medium minus uracil (Cm-ura) plates. A single colony was used to inoculate a 15 mL Cm-ura starter culture, which was shaken at 300 r.p.m. at 30° C. overnight. The starter culture was used to inoculate 1.5 L yeast growth medium. After 24 hours, cells were induced with 165 mL of sterile 30% galactose, and protein was expressed for 5 hours. Cells were collected by centrifugation and stored at −80° C. Cells were lysed in 20 mM Tris-HCl, pH 8.0, 5% glycerol, 1 mM BME, 750 mM NaCl, 35 mM imidazole, 0.01% NP-40 supplemented with cOmplete EDTA-free protease inhibitor (Sigma Aldrich). Cell lysate was clarified by centrifugation (19,000 rpm, 50 min). Lysate was passed over a 5 mL Ni-NTA column, which was then washed with 50 mL of each wash buffer: wash I buffer (20 mM Tris-HCl, pH 8.0, 5% glycerol, 1 mM BME, 1 M NaCl, 35 mM imidazole), wash II buffer (20 mM Tris-HCl, pH 8.0, 5% glycerol, 1 mM BME, 500 mM NaCl, 35 mM imidazole), and wash III buffer (20 mM Tris-HCl, pH 8.0, 5% glycerol, 1 mM BME, 100 mM NaCl, 35 mM imidazole). Protein was eluted with 20 mM Tris-HCl, pH 8.0, 5% glycerol, 1 mM BME, 400 mM imidazole and 100 mM NaCl. Fractions containing protein were dialyzed against 20 mM Tris-HCl, pH 8.0, 20% glycerol, 1 mM BME and 100 mM NaCl. Protein concentration was determined through BSA standards visualized by SYPRO Orange (ThermoFisher Scientific) staining on SDS-polyacrylamide gels. Purified protein was stored at −70° C. in 20 mM Tris-HCl pH 8.0, 100 mM NaCl, 20% glycerol and 1 mM 2-mercaptoethanol.

Crystallography

The 8-azanebularine (8AN) phosphoramidite was synthesized as previously described and incorporated into RNA as mentioned prior (Haudenschild et al., 2004; Pokharel et al., 2009). RNA for crystallography was purified as described previously (Matthews et al., 2016). In brief, RNA for crystallography was purified by denaturing PAGE and visualized with UV shadowing. Bands were excised from gel and gel slices were crushed and soaked overnight at 4° C. in 500 mM $NH_4OAc$ and 100 mM EDTA. Polyacrylamide fragments were removed using a 0.2 μm filter and followed up by desalting on a C18 Sep-Pak column. RNA solutions were lyophilized to dryness, resuspended in nuclease-free water and quantified by absorbance at 260 nm. Oligonucleotide mass was confirmed by electrospray ionization mass spectrometry. Duplex RNA was hybridized in a 1:1 ratio by heating to 95° C. for 5 min and slow cooling to 25° C. Protein, hADAR2-D E488Y, was expressed, purified and quantified as described above with the following exceptions (Matthews et al., 2016; Macbeth and Bass, 2007). After elution from first Ni-NTA column, fractions containing hADAR2-D E488Y were pooled and purified on a 2 mL GE Healthcare Lifesciences Hi-Trap Heparin HP column in the absence of BME. The His10 fusion protein ("His10" disclosed as SEQ ID NO: 144) was cleaved with an optimized ratio of 1 mg of TEV protease per 1 mg of protein. Cleavage was carried out for 1-2 hours before the product was passed over another Ni-NTA column at 0.5 mL/min. The flow through and wash were collected; dialyzed against 20 mM Tris, pH 8.0, 200 mM NaCl, 5% glycerol, and 1 mM BME; and concentrated to just under 1 mL for gel filtration on a GE Healthcare HiLoad 16/600 Superdex 200 PG column. Fractions containing hADAR2-D E488Y were pooled and concentrated to 5-7 mg/mL for crystallography trials (Matthews et al., 2016). Crystals of hADAR2-D E488Y+Gli1_reduced abasic RNA complex were grown at room temperature by the sitting drop vapor diffusion method. A solution of 0.5 μL volume containing 4.5 mg/mL protein and 100 μM of Gli1_reduced abasic RNA (1:1 hADAR2-D:RNA molar ratio) was mixed with 0.5 μL of 0.1 M MES:NaOH pH 6.5 and 14% PEG 20,000. Crystals took a few days to grow at 21° C. Crystals were flashed-cooled in liquid nitrogen using 30% glycerol as a cryo-protectant. X-ray diffraction data were collected at 100K on beamline 12-2 at the Stanford Synchrotron Radiation Lightsource. Diffraction data were processed with XDS and scaled with XSCALE with an $R_{merge}$=6.3% to 2.55 Å resolution (Kabsch, 2010). Structure was solved by molecular replacement using the previously determined ADAR2-Gli1 RNA complex X-ray structure (PDBID: 5ED2) and the model was refined with Refmac5 (CCP4) and built using COOT (Murshudov et al., 2011; Emsley and Cowtan, 2004). Data processing and refinement statistics can be found in Table 4. Atomic coordinates and structure factors have been deposited in the Protein Data Bank (PDBID: 6D06).

Mass Spectrometry Analysis of Proteins Present in ADAR-RNA Crystals

Crystals of hADAR2-D E488Y+Gli1_reduced abasic RNA complex were pooled and carefully washed in a solution of diluted mother liquor. Sample was added to 10 µl of 4% SDS and heated at 95° C. for 5 min. Sample was run down SDS-PAGE gel and visualized with Coomassie blue (Bio-Rad). The gel was excised and diced into 1 mm cubes using a sterile blade. Briefly, proteins were reduced and alkylated according to previously described procedures and digested with sequencing grade tryspin per manufacturer's recommendations (Promega) (Shevchenko et al., 1996). Peptides were dried down in a vacuum concentrator after digestion, then resolubilized in 2% acetonitrile/0.1% trifluoroacetic acid. Digested peptides were analyzed by LC-MS/MS on a Thermo Scientific Q Exactive Plus Orbitrap Mass spectrometer in conjunction with Proxeon Easy-nLC II HPLC (ThermoScientific) and Proxeon nanospray source. The digested peptides were loaded on a 100 µm×25 mm Magic C18 100 Å 5 U reverse phase trap where they were desalted online before being separated using a 75×150 mm Magic C18 200 Å 3 U reverse phase column. Peptides were eluted using a 60 min gradient with a flow rate of 300 nL/min. An MS survey scan was obtained for the m/z range 350-1600, MS/MS spectra were acquired using a top 15 method, where the top 15 ions in the MS spectra were subjected to HCD (High Energy Collisional Dissociation). An isolation mass window of 1.6 m/z was for the precursor ion selection, and normalized collision energy of 27% was used for fragmentation. A 15-second duration was used for the dynamic exclusion.

Tandem mass spectra were extracted and charge state deconvoluted by Proteome Discoverer (ThermoScientific). All MS/MS samples were analyzed using X! Tandem (thegpm.org; version Alanine (2017. 2. 1.4)). X! Tandem was set up to search Uniprot *Saccharomyces cerevisiae* database (January 2018, 6079 entries), the cRAP database of common laboratory contaminants (thegpm.org/crap; 114 entries), the ADAR2 catalytic domain sequence plus an equal number of reverse protein sequences assuming the digestion enzyme trypsin. X! Tandem was searched with a fragment ion mass tolerance of 20 PPM and a parent ion tolerance of 20 PPM. Iodoacetamide derivative of cysteine was specified in X! Tandem as a fixed modification. Deamidation of asparagine and glutamine, oxidation of methionine and tryptophan, sulphone of methionine, tryptophan oxidation to formylkynurenin of tryptophan and acetylation of the N-terminus were specified in X! Tandem as variable modifications.

Criteria for Protein Identification: Version Scaffold 4.8.4 (Proteome Software Inc., Portland, Oreg.) was used to validate MS/MS-based peptide and protein identifications. Peptide identifications were accepted if they exceeded specific database search engine thresholds. X! Tandem identifications required at least −Log (Expect Scores) scores of greater than 2.0 with a mass accuracy of 5 ppm. Protein identifications were accepted if they contained at least 2 identified peptides. Peptides pertinent to the sequence analysis were visually inspected for validation (FIG. 18).

Deamination Kinetics for hADAR2-D E488F and hADAR2-D E488Y

Generation of internally $^{32}$P-labeled strand: The 3' 11 nucleotide oligonucleotide of the top (edited) strand was radiolabeled with [γ-$^{32}$P] ATP (PerkinElmer Life Sciences) at the 5' end with T4 polynucleotide kinase as previously described (Phelps et al., 2014). About 30 pmol of labeled 3' top strand was dissolved with 40 pmol of 5' 12 nucleotide top strand, 30 pmol of DNA splint, 0.5 µL of RNasin (1.6 U/µL), 2 µL of T4 DNA ligase 10× buffer (NEB) and 5 µL of nuclease free water (Zheng et al., 2017). The solution was heated at 65° C. for 5 min and slowly cooled to room temperature. After the addition of 1.5 µL of RNasin (1.6 U/µL), 5 µL of 4 mM ATP and 1 µL of T4 DNA ligase (NEB, 400 U/µL), reaction incubated at 30° C. for 2 hours. Splint-ligated product was purified as described above. Upon hybridization internally labeled top strand and corresponding bottom strand (X=C or rAb) were heated to 95° C. for 5 min and then slowly cooled to room temperature in 10 mM Tris-HCl, 0.1 mM EDTA pH 7.5, and 100 mM NaCl.

Deamination reactions had a final volume of 10 µL with concentrations of 10 nM RNA and 300 nM hADAR2-D wt, hADAR2-D E488F, or hADAR2-D E488Y. The final reaction solution contained 16 mM Tris-HCl, pH 7.4, 3.3% glycerol, 1.6 mM EDTA, 0.003% NP-40, 60 mM KCl, 7.1 mM NaCl, 0.5 mM DTT, 1.6 U/µL RNasin and 1 µg/mL yeast tRNA. Reactions were quenched by adding 190 µl of 95° C. nuclease-free water followed by vortex of the solution and incubating at 95° C. for 5 min. Deaminated sample was purified by phenol-chloroform extraction and ethanol precipitation. The deaminated sample was lyophilized to dryness and resuspended in 50 µL of 1×TE solution followed by digestion with nuclease P1 (Sigma Aldrich). The subsequent 5'-mononucleotides were resolved by thin-layer chromatography (TLC, Macherey-Nagel). The TLC plate was visualized by exposure to a storage phosphor imaging plate (Molecular Dynamics) on a Typhoon phosphoimager (Molecular Dynamics) (O'Connell and Keller, 1994). Radioactive spots were then quantified by volume integration using ImageQuant (Molecular Dynamics) where the data were fitted in KaleidaGraph to the equation: $[P]_t = \alpha[1-e^{-k_{obs}t}]$, where $[P]_t$ is percent edited at time t, a is the fitted end point, and $k_{obs}$ is the observed rate constant. Each experiment was carried out in triplicate where the observed rate stated is the average of the replicates±standard deviation.

Selective Editing on 152 nt Multiple Target Substrate

Using extended primers containing BamHI and HindIII restriction sites, 74 nt multiple target substrate was PCR amplified using Phusion Hot Start DNA Polymerase (ThermoScientific). PCR product was purified by agarose gel and Qiagen Gel Extraction kit. Sample was then resuspended in nuclease-free water and double digested at BamHI and HindIII restriction sites (NEB). Double-digested product was inserted into a T7-promoter-containing vector by standard cloning procedures. Plasmid containing 152 nt target substrate was single-digested by BamHI and 152 nt RNA was transcribed from this DNA template with MEGA-script® T7 Kit (ThermoFisher). Transcribed product was purified as described above.

RNA bottom strands containing orphan nucleotide for site 1 (3 nmols) were first phosphorylated by T4 PNK (NEB, 10,000 U/mL) in 10×T4 PNK buffer and 100 mM ATP. After denaturation of PNK, RNA bottom strand containing orphan nucleotide for site 2 (3 nmols), DNA splint (3 nmols) and RNasin (1.6 U/μL) were dissolved in solution with phosphorylated RNA bottom strand containing site 1. Solution was heated to 95° C. for 5 min and then slowly cooled to room temperature. Additional RNasin (1.6 U/μL) was added to the cooled solution followed by T4 DNA ligase (400 U/μL). The reaction was incubated at 30° C. for 2 hours. Ligated sample was then phenol-chloroform extracted, ethanol precipitated, lyophilized to dryness, and resuspended in nuclease-free water. Samples were then DNase treated with RQ1 RNase-free DNase (Promega). DNase-treated splint ligated product was purified as described above. Upon hybridization, 152 nt transcribed top strand and corresponding ligated bottom strand (varying X and Y containing C or rAb) were heated to 95° C. for 5 min and then slowly cooled to room temperature in 10 mM Tris-HCl, 0.1 mM EDTA pH 7.5 and 100 mM NaCl.

Deamination reactions had a final volume of 10 μL with concentrations of 10 nM RNA and 1.2 μM hADAR2-D E488F, 150 nM hADAR2-D E488Y, or 300 nM hADAR2-D E488W. The final reaction solution contained 16 mM Tris-HCl, pH 7.4, 3.3% glycerol, 1.6 mM EDTA, 0.003% NP-40, 60 mM KCl, 7.1 mM NaCl, 0.5 mM DTT, 1.6 U/μL RNasin, and 1 μg/mL yeast tRNA. Reaction was quenched as described above. Reaction was quenched after 30 min, 15 min, and 30 min for hADAR2-D E488F, hADAR2-D E488Y, and hADAR2-D E488W, respectively. RT-PCR of deaminated samples was performed using Access RT-PCR kit (Promega) for 24 cycles. PCR product was purified using Zygmo DNA Clean and Concentrator kit. Purified samples were submitted for Sanger Sequencing and sequence traces were analyzed by 4 Peaks (Nucleobytes) to quantify percent editing.

Directed Editing on Overexpressed β-Actin in HEK293T Cells and Analysis

Full-length hADAR2 wt and HA tag were subcloned into pcDNA3.1 vector using a Gibson Assembly Cloning Kit (NEB). QuickChange XL Site-Directed Mutagenesis (Agilent) was used to incorporate a E488X (X=F, Y, W) mutation in a pcDNA3.1 vector containing a hADAR2 sequence. Plasmid containing β-actin target sequence was ordered from ThermoFisher. β-actin target region was amplified by PCR using primers containing non-native sequence at 5' ends of forward and reverse primers (FIG. 19). β-actin target was then subcloned into pcDNA3.1 vector using Gibson Assembly Cloning Kit (NEB). HEK293T cells were cultured in Dulbecco's modified Eagle's medium (DMEM), 10% fetal bovine serum, and 1% anti-anti at 37° C., 5% $CO_2$. Once cultivated cells reached 70-90% confluency, $1.5 \times 10^5$ cells were seeded into 24-well plates. Cells were transfected 24 hours later using Lipofectamine 2000 (ThermoFisher Scientific). Transfection of plasmids and guide RNA was as followed: 500 ng ADAR plasmid, 500 ng β-actin plasmid, and 50 nM chemically synthesized guide RNA. After incubation of transfection reagent, specified plasmids and guide RNAs in Opti-MEM Reduced Serum Media (ThermoFisher Scientific) solution were added to designated wells and incubated at 37° C., 5% $CO_2$ for 24 hours. Total RNA was then collected using RNAqueous Total RNA Isolation Kit (ThermoFisher Scientific) and DNase treated with RQ1 RNase-free DNase (Promega). Nested RT-PCR was performed using Access RT-PCR kit (Promega) for 15 cycles and then followed by Phusion Hot Start DNA Polymerase (ThermoScientific) for the second PCR of 25 cycles. PCR product was purified by agarose gel and Qiagen Gel Extraction kit. Product was submitted for Sanger Sequencing and sequence traces were analyzed by 4 Peaks (Nucleobytes) to quantify percent editing.

Directed Editing on RAB7A and Endogenous β-Actin in HEK293T Cells and Analysis

HEK293T cells were cultured in Dulbecco's modified Eagle's medium (DMEM), 10% fetal bovine serum, and 1% anti-anti at 37° C., 5% $CO_2$. Once cultivated cells reached 70-90% confluency, $6.4 \times 10^3$ cells were seeded into 96-well plates. Cells were transfected 24 hours later using Lipofectamine 2000 (ThermoFisher Scientific). Transfection of plasmids and guide RNA was as followed: 500 ng ADAR plasmid and 50 nM chemically synthesized guide RNA. After incubation of transfection reagent, specified plasmids and guide RNAs in Opti-MEM Reduced Serum Media (ThermoFisher Scientific), solution was added to designated well and incubated at 37° C., 5% $CO_2$ for 48 hours. Total RNA was then collected using RNAqueous Total RNA Isolation Kit (ThermoFisher Scientific) and DNase treated with RQ1 RNase-free DNase (Promega). Nested RT-PCR was performed using Access RT-PCR kit (Promega) for 20 cycles and then followed by Phusion Hot Start DNA Polymerase (ThermoScientific) for the second PCR of 30 cycles. PCR product was purified by agarose gel and Qiagen Gel Extraction kit. Product was submitted for Sanger Sequencing and sequence traces were analyzed by 4 Peaks (Nucleobytes) to quantify percent editing.

Detection of Full-Length ADAR2 Proteins in Transfected HEK293T Cells

Transfection for Western blotting was performed as described above. Cells were lysed with 300 μL of lysis buffer (50 mM Tris-HCl, pH 8.0, 150 mM NaCl, 1% (v/v) NP-40 supplemented with Halt protease inhibitor cocktail) (ThermoFisher) by shaking at 4° C. for 30 min. Samples were resolved on an SDS-PAGE gel alongside PageRuler Prestained Plus Protein Ladder (ThermoFisher Scientific). Western blotting was carried out using primary antibody HA Tag Monoclonal Antibody (2-2.2.14) (ThermoFisher) at 1:10,000 dilution and anti-mouse IgG with alkaline phosphatase-conjugated secondary antibody (Santa Cruz Biotechnology) at 1:2,000 dilution. The ADAR proteins were detected using ECF substrate (GE Healthcare) on a Typhoon Trio Variable Mode Imager (GE Healthcare).

Quantification and Statistical Analysis

Statistical details can be found in corresponding figure legends. Bar graphs are plotted as means±SD. Error bars represent standard deviation of n=3 replicates. Quantification of Western blots was carried out using ImageQuant. Sanger Sequencing and sequence traces were analyzed by 4 Peaks (Nucleobytes) to quantify percent editing.

Data and Software Availability

The atomic coordinates and structure factors for hADAR2-D E488Y:hGli1_abasic-8AN reported in this paper, have been deposited in the Protein Data Bank (rcsb.org) under the accession code 6D06.

Tables

Table 2 below shows inetic parameters for the deamination of cytidine substrate and reduced abasic substrate with hADAR2 deaminase domains of WT, E488F, and E488Y. $^a$Selectivity reported is ratio $k_{obs}$ for rAb orphan/$k_{obs}$ for C orphan.

TABLE 2

Kinetic Paramters for Deamination

| Enzyme | Orphan | Rate constant, min$^{-1}$ | Selectivity for abasic site$^a$ |
|---|---|---|---|
| ADAR2-D WT | C | 0.7 ± 0.2 | 0.01 |
| ADAR2-D WT | rAb | 8.9 × 10$^{-3}$ ± 0.4 × 10$^{-3}$ | — |
| ADAR2-D E488F | C | 1.4 × 10$^{-3}$ ± 0.3 × 10$^{-3}$ | 71 |
| ADAR2-D E488F | rAb | 0.09 ± 0.02 | — |
| ADAR2-D E488Y | C | 0.17 ± 0.04 | >18 |
| ADAR2-D E488Y | rAb | >3 | — |

Table 3 below shows data processing and refinement statistics for hADAR2-D E488Y: hGli1_abasic-8AN, related to FIG. 14. a $R_{merge}=[\Sigma_h\Sigma_i|I_h-I_{hi}|/\Sigma_h\Sigma_iI_{hi}]$ where $I_h$ is the mean of $I_{hi}$ observations of reflection h. Numbers in parenthesis represent highest resolution shell. $^b$ R-Factor and $^c$ $R_{free}=\Sigma||F_{obs}|-|F_{calc}||/\Sigma|F_{obs}|\times100$ for 95% of recorded data (R–Factor) or 5% data (Rfree). $^d$ Ramachandran plot statistics from MolProbity (Kabsch, 2010).

TABLE 3

Data Processing and Refinement Statistics

| Synchrotron (Beamline) | SSRL (12-2) |
|---|---|
| Wavelength (Å) | 0.97946 |
| Space Group | C2 |
| Unit Cell Parameters (Å) | a = 174.68 |
|  | b = 63.44 |
|  | c = 132.06 |
| Resolution Range (Å) | 50.0-2.55 (2.62-2.55) |
| No. observed reflections | 128,317 (9,614) |
| No. unique reflections | 37,329 (2,749) |
| Completeness (%) | 97.4 (98.1) |
| I/σ (I) | 15.27 (2.07) |
| $R_{merge}{}^a$ (%) | 6.3 (72.3) |
| $CC_{1/2}$ (%) | 99.8 (73.6) |
| Protein Monomers per ASU | 2 |
| Matthew's Coefficient (Å$^3$/Da) | 2.21 |
| Solvent Content (%) | 50.28 |
| Refinement Statistics | |
| No of reflections (F > 0) | 35,463 |
| $R_{factor}{}^b$ (%) | 19.01 |
| $R_{free}{}^b$ (%) | 25.52 |
| RMS bond length (Å) | 0.0121 |
| RMS bond angle (°) | 1.751 |
| Coordinate Error$^c$ (Å) | 0.245 |
| Ramachandran Plot Statistics$^d$ | |
| Favored (%) | 94.09 |
| Allowed (%) | 5.36 |
| Outliers (%) | 0.55 |
| No. of atoms | |
| Protein | 5777 |
| RNA | 967 |
| Inositol Hexakisphosphate (IHP) | 73 |
| Zn | 2 |
| Waters | 48 |

Table 4 below shows selective editing of 152 nt substrate with different combinations of orphan base by hADAR2-D E488F, hADAR2-D E488Y, hADAR2-D E488W, and hADAR2-D WT, related to FIG. 15. Deamination reactions had a final volume of 10 μL with concentrations of 10 nM RNA and 1.2 μM hADAR2-D E488F, 150 nM hADAR2-D E488Y, or 300 nM hADAR2-D E488W. Reaction was quenched after 30 min, 15 min, and 30 min for hADAR2-D E488F, hADAR2-D E488Y, and hADAR2-D E488W, respectively. Deamination reactions for hADAR2-D WT had a final volume of 10 μL with concentrations of 10 nM RNA and either 150 nM hADAR2-D or 1.2 μM hADAR2-D. Reaction was quenched at 15 min or 30 min for reaction containing 150 nM hADAR2-D or 1.2 μM hADAR2-D, respectively. ND denotes no editing detected. Each experiment was carried out in triplicate where percent editing reported is the average of the triplicates±standard deviation.

TABLE 4

Selective Editing of 152 nt Substrate

| hADAR2-D E488F | | | | |
|---|---|---|---|---|
| Target Site | X = C, Y = C | X = rAb, Y = C | X = C, Y = rAb | X = rAb, Y = rAb |
| Site 1 (X) | ND | 32% ± 3% | ND | 31% ± 2% |
| Site 2 (Y) | 7.6% ± 0.4% | 7% ± 1% | 59% ± 6% | 61% ± 2% |

| hADAR2-D E488Y | | | | |
|---|---|---|---|---|
| Target Site | X = C, Y = C | X = rAb, Y = C | X = C, Y = rAb | X = rAb, Y = rAb |
| Site 1 (X) | ND | 42% ± 4% | ND | 24% ± 5% |
| Site 2 (Y) | 10% ± 2% | 11% ± 2% | 61% ± 9% | 55% ± 8% |

| hADAR2-D E488W | | | | |
|---|---|---|---|---|
| Target Site | X = C, Y = C | X = rAb, Y = C | X = C, Y = rAb | X = rAb, Y = rAb |
| Site 1 (X) | ND | 44% ± 7% | ND | 34% ± 7% |
| Site 2 (Y) | 3% ± 2% | 7% ± 2% | 57% ± 3% | 65% ± 3% |

| hADAR2-D 150 nM, 15 min | | | | |
|---|---|---|---|---|
| Target Site | X = C, Y = C | X = rAb, Y = C | X = C, Y = rAb | X = rAb, Y = rAb |
| Site 1 (X) | 36% ± 3% | 7% ± 2% | 41% ± 11% | 5% ± 1% |
| Site 2 (Y) | 37% ± 2% | 48% ± 3% | ND | ND |

TABLE 4-continued

Selective Editing of 152 nt Substrate hADAR2-D 1.2 µM, 30 min

| Target Site | X = C, Y = C | X = rAb, Y = C | X = C, Y = rAb | X = rAb, Y = rAb |
|---|---|---|---|---|
| Site 1 (X) | 96.0% ±0.3% | 71% ± 14% | 97.1% ± 0.3% | 74% ± 10% |
| Site 2 (Y) | 96.1% ± 0.4% | 94% ± 2% | 31% ± 4% | 30% ± 9% |

Table 5 below shows percent editing for target and off-targets in overexpressed β-actin substrate by hADAR2 wt with cytidine guide RNA and by mutants E488X (X=F, Y, W) with reduced abasic guide RNA in HEK293-T cells, related to FIG. 16. ND denotes no editing detected. Each experiment was carried out in biological triplicate where percent editing reported is the average of the triplicates±standard deviation.

TABLE 5

Percent Editing in Overexpressed β-actin Substrate

| Enzyme | Off-target 1 | Target | Off-target 2 |
|---|---|---|---|
| WT | 55% ± 2% | 86.5% ± 0.8% | 12% ± 2% |
| E488F | ND | 57% ± 4% | ND |
| E488Y | ND | 69% ± 2% | ND |
| E488W | ND | 63% ± 2% | ND |

Table 6 below shows comparisons of percent editing by mutants hADAR2 E488X (X=F, Y, W) on overexpressed β-actin target with cytidine guide RNA (orphan base C) and reduced abasic guide RNA (orphan base rAb) in HEK293-T cells, related to FIG. 16. Each experiment was carried out in biological triplicate where percent editing reported is the average of the triplicates±standard deviation.

TABLE 6

Comparisons of Percent Editing in Overexpressed β-actin Substrate

| | Orphan Base | |
|---|---|---|
| Enzyme | C | rAb |
| E488F | 21% ± 1% | 57% ± 4% |
| E488Y | 31% ± 5% | 69% ± 2% |
| E488W | 13% ± 2% | 63% ± 2% |

Table 7 below shows percent editing for endogenous targets β-actin and RAB7A and endogenous off-targets in HEK293-T cells, related to FIG. 17. Overexpression of wild-type hADAR2 with cytidine guide RNA and overexpression of hADAR2 E488X (X=F, Y, W) with reduced abasic guide RNA. Endogenous off-targets percent edited was taken from total RNA used for directed editing of RAB7A target. NT denotes no transfection. ND denotes no editing detected. Each experiment was carried out in biological triplicate where percent editing reported is the average of the triplicates±standard deviation.

TABLE 7

Percent Editing for Endogenous β-actin and RAB7A Targets and Off-Targets

Endogenous β-actin Target

| Enzyme | Percent Edited |
|---|---|
| WT | 52% ± 2% |
| E488F | 26% ± 3% |
| E488Y | 30% ± 1% |
| E488W | 25% ± 1% |

Endogenous RAB7A Target

| Enzyme | Percent Edited |
|---|---|
| WT | 41% ± 9% |
| E488F | 38% ± 3% |
| E488Y | 55% ± 5% |
| E488W | 43% ± 1% |

Endogenous Off-targets

Off-target Sites Percent Edited

| Enzyme | FLNA (CAG) | TMEM63B (CAG) | CYFIP2 (UAA) | Gli1 (UAG) | COG3 (AAAU) | COG3 (AAAU) |
|---|---|---|---|---|---|---|
| NT | ND | ND | ND | 9% ± 6% | ND | ND |
| WT | 26% ± 1% | 37% ± 2% | 55% ± 4% | 38% ± 4% | 16.8% ± 0.8% | 52% ± 3% |
| E488Y | ND | ND | 18% ± 8% | 17% ± 2% | 7.7% ± 0.4% | 18% ± 4% |

Tables 8(a)-8(i) below show sequences for oligonucleotides (reduced abasic site indicated by rAb), related to the Methods section above.

| Tables 8(a)-8(i) Oligonucleotide Sequences | | |
|---|---|---|
| 8(a). Sequences for mutagenesis of hADAR2 and hADAR2-D | | |
| E488F FWD | 5'-GACCAAAATAGAGTCTGGTTTTGGGACGATTCCAGTGCGCTC-3' | SEQ ID NO: 65 |
| E488F RVS | 5'-GAGCGCACTGGAATCGTCCCAAAACCAGACTCTATTTTGGTC-3' | SEQ ID NO: 66 |
| E488Y FWD | 5'-GACCAAAATAGAGTCTGGTTATGGGACGATTCCAGTGCGCTC-3' | SEQ ID NO:67 |
| E488Y RVS | 5'-GAGCGCACTGGAATCGTCCCATAACCAGACTCTATTTTGGTC-3' | SEQ ID NO: 68 |
| E488W FWD | 5'-GACCAAAATAGAGTCTGGTTGGGGGACGATTCCAGTGCGCTC-3' | SEQ ID NO:69 |
| E488W RVS | 5'-GAGCGCACTGGAATCGTCCCCCAACCAGACTCTATTTTGGTC-3' | SEQ ID NO: 70 |
| 8(b). Sequences for E488Y/A:rAb crystallography | | |
| hGLi1 top containing 8-azaN (N) | 5'-GCUCGCGAUGCUNGAGGGCUCUG-3' | SEQ ID NO: 71 |
| hGLi1 bottom containing reduced abasic site (rAb), denoted by X | 5'-CAGAGCCCCCXAGCAUCGCGAGC-3' | SEQ ID NO: 72 |
| 8(c). Sequences for generation of internally labeled top strand and non-edited bottom strand for hGli1 substrate | | |
| 3' top strand | 5'-AGAGGGCUCUG-3' | SEQ ID NO: 73 |
| 5' top strand | 5'-GCUCGCGAUGCU-3' | SEQ ID NO: 58 |
| Top strand DNA splint | 5'-CAGAGCCCCCCAGCATCGCGAGC-3' | SEQ ID NO: 74 |
| Bottom RNA strand (orphan base C) | 5'-CAGAGCCCCCCAGCAUCGCGAGC-3' | SEQ ID NO: 75 |
| Bottom RNA strand (orphan base rAb) | 5'-CAGAGCCCCCrAbAGCAUCGCGAGC-3' | SEQ ID NO: 72 |
| 8(d). Sequences for 152 nt selective editing substrate | | |
| Bottom RNA Strand Site 1 (C) | 5'-UUCGCACCAAGUUCGACAUGCGC-3' | SEQ ID NO: 76 |
| Bottom RNA Strand Site 2 (C) | 5'-UACGCCGGUACCAAGUAUCGCAC-3' | SEQ ID NO: 77 |
| Bottom RNA Strand Site 1 (rAb) | 5'-UUCGCACrAbAAGUUCGACAUGCGC-3' | SEQ ID NO: 78 |
| Bottom RNA Strand Site 2 (rAb) | 5'-UACGCCGGUACrAbAAGUAUCGCAC-3' | SEQ ID NO: 79 |
| Bottom Strand Splint | 5'-GCGCATGTCGAACTTGGTGCGAAGTGCGATACTTGGTACCGGCGTACATTGGTATCCACCGACGTGACGCGTCT-3' | SEQ ID NO: 80 |
| 74 nt multiple target substrate | 5'-GCGCATGTCGAACTTAGAGCGAAGTGCGATACTTAGAACCGGCGTACATTAGAATCCACCGACGTGACGCGTCT-3' | SEQ ID NO: 81 |
| Forward with HindIII restriction site | 5'-GTGTGTGTAAGCTTTCGTGGTCCTTAGACTTCGTGCACATACAGGCGCATGTCGAACTTAGAGCGAAG-3' | SEQ ID NO: 82 |

-continued

Tables 8(a)-8(i)
Oligonucleotide Sequences

| | | |
|---|---|---|
| Reverse with BamHI restriction site | 5'-GTGTGTGTGGATCCCTGCAAGACGCGTC ACGTCGGTGGATTC-3' | SEQ ID NO: 83 |
| RT-PCR FWD and sequencing primer | 5'-TGGGTACGAATTCCCCGTACAAGCTT-3' | SEQ ID NO: 84 |
| RT-PCR RVS primer | 5'-AGACGCGTCACGTCGGTGGATT-3' | SEQ ID NO: 85 |

8(e). Sequences for incorporation of HA tag and hADAR2 sequence into pcDNA3.1 vector via Gibson Assembly (italicized region corresponds to HA tag, underlined region corresponds to ADAR2 sequence, bold region overlaps with pcDNA3.1 vector)

| | | |
|---|---|---|
| Gibson FWD containing HA tag | 5'-ATCTCAGAGGAGGACCTGGAATTCA TGGG*ATACCCCTACGACGTGCCCGACTAC GCC*GGATCCGCCGAGATCAAGGAGAAAA TCTGC-3' | SEQ ID NO: 86 |
| Gibson RVS | 5'-AGGGCCCTCTAGATGCATGCTCGAG CGGCCGCTCATACTGGGCAGAGATAAAA GTTCTTTTCCT-3' | SEQ ID NO: 87 |

8(f). Sequences for β-actin overexpressed target (italicized region corresponds to non-native; bold region overlaps with pcDNA3.1 vector)

| | | |
|---|---|---|
| Non-specific sequence FWD | 5'-*GAAGCAACTCTTGAGTGTTAATATGTTGA CCCCTGTATTAGGGATGCGGGAATTGGGT*ACGAATTCCCCGTACATCGCTGTCCACCT-3' | SEQ ID NO: 88 |
| Non-specific sequence RVS | 5'-*AGATGATAAGCTCCGGCAAGCAATATTGA CAACGCAAGGATCGGCGATATTC*CACGTG ATATCCCGACACGGATCCGGGGCA-3' | SEQ ID NO: 89 |
| Gibson FWD | 5'-GACTCACTATAGGGAGACCCAGAAG CAACTCTTGAGTGTTAATATGTTGACCCC TGTATTAGGGATGCGGG-3' | SEQ ID NO: 90 |
| Gibson RVS | 5'-TAGGGCCCTCTAGATGCATGCTCGA AGATGATAAGCTCCGGCAAGCAATATTG AACAACGCAAGGATCGGCG-3' | SEQ ID NO: 91 |

8(g). Sequences of guide RNAs for RNA site-directed editing in HEK293T cells (phosphorothioate modification marked with asterisk, ribonucleotides underlined; all other nucleotides are 2'-O-methylated)

| | | |
|---|---|---|
| Overexpressed and endogenous β-actin RNA bottom strand (C) | 5'-U*U*GUCAAGAAAGGGUGUAACGCAA <u>CCAAG</u>UCAUAGUC*C*G-3' | SEQ ID NO: 92 |
| Overexpressed and endogenous β-actin RNA bottom strand (rAb) | 5'-U*U*GUCAAGAAAGGGUGUAACGCAA <u>CrAbAAG</u>UCAUAGUC*C*G-3' | SEQ ID NO: 93 |
| Endogenous RAB7A RNA bottom strand (C) | 5'-U*G*UCUACUGUACAGAAUACUGCCG <u>CCAGC</u>UGGAUUUC*C*C-3 | SEQ ID NO: 94 |
| Endogenous RAB7A RNA bottom strand (rAb) | 5'-U*G*UCUACUGUACAGAAUACUGCCG <u>CrAbAGC</u>UGGAUUUC*C*C-3' | SEQ ID NO: 95 |

8(h). Sequences for nested RT-PCR of β-actin and RAB7A in HEK293T cells

| | | |
|---|---|---|
| Overexpressed β-actin RT FWD | 5'-AGACCCAGAAGCAACTCTTGAGTGTTA ATATGTTGACCCCT-3' | SEQ ID NO: 96 |
| Overexpressed β-actin RT RVS | 5'-GCATGCTCGAAGATGATAAGCTCCGGCAA GCA-3' | SEQ ID NO: 97 |
| Overexpressed β-actin Nest FWD | 5'-GTATTAGGGATGCGGGAATTGGGTACG AATTCCCCGTACATCGCT-3' | SEQ ID NO: 98 |
| Overexpressed β-actin Nest RVS | 5'-ATATTGAACAACGCAAGGATCGGCGAT ATTCCACGTGATATCCCG-3' | SEQ ID NO: 99 |

Tables 8(a)-8(i)
Oligonucleotide Sequences

| | | |
|---|---|---|
| Endogenous β-actin RT FWD | 5'-CAGCAGATGTGGATCAGCAAGCAGGAG-3' | SEQ ID NO: 100 |
| Endogenous β-actin RT RVS | 5'-GGAAGGGGGGGCACGAAGGCTCATC-3' | SEQ ID NO: 101 |
| Endogenous β-actin Nest FWD | 5'-TATGACGAGTCCGGCCCCTCCATCGT-3' | SEQ ID NO: 102 |
| Endogenous β-actin Nest RVS | 5'-GCAATGCTATCACCTCCCCTGTGTGGACT-3' | SEQ ID NO: 103 |
| Overexpressed and endogenous β-actin sequence primer | 5'-AACAAATAAAGCCATGCCAATCTCATCTTGTT-3' | SEQ ID NO: 104 |
| Endogenous RAB7A RT FWD | 5'-GCAACCAATTAAAATGTATAAATTAGTGTAAGAAATT-3' | SEQ ID NO: 105 |
| Endogenous RAB7A RT RVS | 5'-GCTACAATGCAGGGGCAGATCCTAGGAAG-3' | SEQ ID NO: 106 |
| Endogenous RAB7A Nest FWD | 5'-CTTGGATTATGTGTTTAAGTCCTGTAATGCAGGCC-3' | SEQ ID NO: 107 |
| Endogenous RAB7A Nest RVS | 5'-GGAGCAGAACTGCCAGGGTTCCAACC-3' | SEQ ID NO: 108 |

8(i). Sequences for nested RT-PCR of endogenous off-targets in HEK293T cells

| | | |
|---|---|---|
| TMEM63B RT FWD | 5'-CCGCTGGCTCTTTGATAAGAAATTCTTGGCTGAGG-3' | SEQ ID NO: 109 |
| TMEM63B RT RVS | 5'-AGCCAGAAGAGGCAGAGGATGGGCG-3' | SEQ ID NO: 110 |
| TMEM63B Nest FWD | 5'-CAGCTATTCGGTTTGAGTGTGTGTTCC-3 | SEQ ID NO: 111 |
| TMEM63B Nest RVS | 5'-CGGCCACCACCTGGTTCACAGCCC-3' | SEQ ID NO: 112 |
| CYFIP2 RT FWD | 5'-TCCTGGCCAACCACAACAGGATCACCCAGTGTC-3' | SEQ ID NO: 113 |
| CYFIP2 RT RVS | 5'-TAGGTCGAAGAGCTCGCGATACTCCTCGTCTG-3' | SEQ ID NO: 114 |
| CYFIP2 Nest FWD | 5'-TCCACCAGCAACTTGAAGTGATCCCAGGCTATGA-3' | SEQ ID NO: 115 |
| CYFIP2 Nest RVS | 5'-ACTTCTGGCTGTCCAGCCCTGAGCCCG-3' | SEQ ID NO: 116 |
| FLNA RT FWD | 5'-TCAGTATCTGGACCCGGGAAGCTGGTGC-3' | SEQ ID NO: 117 |
| FLNA RT RVS | 5'-TGCCGTTGAACTTGACGTCAATCAGGTAAACGCC-3' | SEQ ID NO: 118 |
| FLNA Nest FWD | 5'-TGGAGGCCTGGCCATTGCTGTCGAGGG-3' | SEQ ID NO: 119 |
| FLNA Nest RVS | 5'-ATTCTCCCGAGGGATGAAGCGCACAGC-3' | SEQ ID NO: 120 |

Tables 8(a)-8(i)
Oligonucleotide Sequences

| | | |
|---|---|---|
| COG3 RT FWD | 5'-CAGATGCATAGATAGGGCAGTGTTCCAAGGA-3' | SEQ ID NO: 121 |
| COG3 RT RVS | 5'-ACCTTTGTCATGAACTCCTCCAGCTGTTC-3' | SEQ ID NO: 122 |
| COG3 Nest FWD | 5'-TTATCACAGGAAGCATTGTCTGCCTGCATTCAGTC-3' | SEQ ID NO: 123 |
| COG3 Nest RVS | 5'-TACAAACAGCTTGGTCTGCTGCTGAAT-3' | SEQ ID NO: 124 |
| Gli1 RT FWD | 5'-CGAGCCGAGTATCCAGGATACAAC-3' | SEQ ID NO: 125 |
| Gli1 RT RVS | 5'-CCCATATCCCAGAGTATCAGTAGGTGG-3' | SEQ ID NO: 126 |
| Gli1 Nest FWD | 5'-CCCAATGCAGGGGTCACCCGGAGGG-3' | SEQ ID NO: 127 |
| Gli1 Nest RVS | 5'-GAAGTCCATATAGGGGTTCAGACCACTGCCCAC-3' | SEQ ID NO: 128 |

REFERENCES FOR EXAMPLE 4

Alaimo, P. J., Shogren-Knaak, M. A. and Shokat, K. M. (2001). Chemical genetic approaches for the elucidation of signaling pathways. Curr Opin Chem Biol 5, 360-367.

Bass, B. L. (2002). RNA editing by adenosine deaminases that act on RNA. Annu. Rev. of Biochem. 71, 817-846.

Bass, B. L. and Weintraub, H. (1988). An unwinding activity that covalently modifies its double-stranded RNA substrate. Cell 55, 1089-1098.

Belshaw, P. J., Schoepfer, J. G., Liu, K. Q., Morrison, K. L. and Schreiber, S. L. (1995). Rational Design of Orthogonal Receptor-Ligand Combinations. Angew. Chem. 34, 2129-2132.

Cox, D. B. T., Gootenberg, J. S., Abudayyeh, O. O., Franklin, B., Kellner, M. J., Joung, J. and Zhang, F. (2017). RNA editing with CRISPR-Cas13. Science 358, 1019-1027.

Eggington, J. M., Greene, T. and Bass, B. L. (2011). Predicting sites of ADAR editing in double-stranded RNA. Nat. Commun. 2, 319.

Eifler, T., Pokharel, S. and Beal, P. A. (2013). RNA-Seq analysis identifies a novel set of editing substrates for human ADAR2 present in Saccharomyces cerevisiae. Biochemistry 52, 7857-7869.

Emsley, P. and Cowtan, K. (2004). Coot: model-building tools for molecular graphics. Acta Crystallogr. D Biol. Crystallogr. 60, 2126-2132.

Gao, X., Tao, Y., Lamas, V., Huang, M., Yeh, W. H., Pan, B., Hu, Y. J., Hu, J. H., Thompson, D. B., Shu, Y., Li, Y., Wang, H., Yang, S., Xu, Q., Polley, D. B., Liberman, M. C., Kong, W. J., Holt, J. R., Chen, Z. Y. and Liu, D. R. (2018). Treatment of autosomal dominant hearing loss by in vivo delivery of genome editing agents. Nature 553, 217-221.

Gaudelli, N. M., Komor, A. C., Rees, H. A., Packer, M. S., Badran, A. H., Bryson, D. I. and Liu, D. R. (2017). Programmable base editing of A*T to G*C in genomic DNA without DNA cleavage. Nature 551, 464-471.

Goodman, R. A., Macbeth, M. R. and Beal, P. A. (2012). ADAR proteins: structure and catalytic mechanism. Curr. Top. Microbiol. 353, 1-33.

Hanswillemenke, A., Kuzdere, T., Vogel, P., Jekely, G. and Stafforst, T. (2015). Site-Directed RNA Editing in Vivo Can Be Triggered by the Light-Driven Assembly of an Artificial Riboprotein. J. Am. Chem. Soc. 137, 15875-15881.

Haudenschild, B. L., Maydanovych, O., Veliz, E. A., Macbeth, M. R., Bass, B. L. and Beal, P. A. (2004). A transition state analogue for an RNA-editing reaction. J. Am. Chem. Soc. 126, 11213-11219.

Heep, M., Mach, P., Reautschnig, P., Wettengel, J. and Stafforst, T. (2017). Applying Human ADAR1p110 and ADAR1p150 for Site-Directed RNA Editing-G/C Substitution Stabilizes GuideRNAs against Editing. Genes (Basel) 8.

Hsu, P. D., Lander, E. S. and Zhang, F. (2014). Development and applications of CRISPR-Cas9 for genome engineering. Cell 157, 1262-1278.

Kabsch, W. (2010). XDS. Acta Crystallogr D Biol Crystallogr 66, 125-132.

Kim, K., Ryu, S. M., Kim, S. T., Baek, G., Kim, D., Lim, K., Chung, E., Kim, S. and Kim, J. S. (2017). Highly efficient RNA-guided base editing in mouse embryos. Nat Biotechnol 35, 435-437.

Komor, A. C., Kim, Y. B., Packer, M. S., Zuris, J. A. and Liu, D. R. (2016). Programmable editing of a target base in genomic DNA without double-stranded DNA cleavage. Nature 533, 420-424.

Kuttan, A. and Bass, B. L. (2012). Mechanistic insights into editing-site specificity of ADARs. Proc. Natl. Acad. Sci. U.S.A 109, E3295-3304.

Lehmann, K. A. and Bass, B. L. (2000). Double-stranded RNA adenosine deaminases ADAR1 and ADAR2 have overlapping specificities. Biochemistry 39, 12875-12884.

Li, J. B., Levanon, E. Y., Yoon, J. K., Aach, J., Xie, B., Leproust, E., Zhang, K., Gao, Y. and Church, G. M. (2009). Genome-wide identification of human RNA editing sites by parallel DNA capturing and sequencing. Science 324, 1210-1213.

Lovell, S. C., Word, J. M., Richardson, J. S. and Richardson, D. C. (2000). The penultimate rotamer library. Proteins 40, 389-408.

Macbeth, M. R. and Bass, B. L. (2007). Large-scale overexpression and purification of ADARs from *Saccharomyces cerevisiae* for biophysical and biochemical studies. Methods Enzymol. 424, 319-331.

Matthews, M. M., Thomas, J. M., Zheng, Y., Tran, K., Phelps, K. J., Scott, A. I., Havel, J., Fisher, A. J. and Beal, P. A. (2016). Structures of human ADAR2 bound to dsRNA reveal base-flipping mechanism and basis for site selectivity. Nat. Struct. Mol. Biol. 23, 426-433.

Montiel-Gonzalez, M. F., Vallecillo-Viejo, I., Yudowski, G. A. and Rosenthal, J. J. (2013). Correction of mutations within the cystic fibrosis transmembrane conductance regulator by site-directed RNA editing. Proc. Natl. Acad. Sci. U.S.A 110, 18285-18290.

Montiel-Gonzalez, M. F., Vallecillo-Viejo, I. C. and Rosenthal, J. J. (2016). An efficient system for selectively altering genetic information within mRNAs. Nucleic Acids Res. 44, e157.

Murshudov, G. N., Skubak, P., Lebedev, A. A., Pannu, N. S., Steiner, R. A., Nicholls, R. A., Winn, M. D., Long, F. and Vagin, A. A. (2011). REFMACS for the refinement of macromolecular crystal structures. Acta Crystallogr D Biol Crystallogr 67, 355-367.

Nishikura, K. (2010). Functions and regulation of RNA editing by ADAR deaminases. Annual Review of Biochemistry 79, 321-349.

Nunez, J. K., Harrington, L. B. and Doudna, J. A. (2016). Chemical and Biophysical Modulation of Cas9 for Tunable Genome Engineering. ACS Chem. Biol. 11, 681-688.

O'connell, M. A. and Keller, W. (1994). Purification and properties of double-stranded RNA-specific adenosine deaminase from calf thymus. Proc. Natl. Acad. Sci. U.S.A 91, 10596-10600.

Onizuka, K., Harrison, J. G., Ball-Jones, A. A., Ibarra-Soza, J. M., Zheng, Y., Ly, D., Lam, W., Mac, S., Tantillo, D. J. and Beal, P. A. (2013). Short interfering RNA guide strand modifiers from computational screening. J. Am. Chem. Soc. 135, 17069-17077.

Phelps, K. J., Ibarra-Soza, J. M., Tran, K., Fisher, A. J. and Beal, P. A. (2014). Click modification of RNA at adenosine: structure and reactivity of 7-ethynyl- and 7-triazolyl-8-aza-7-deazaadenosine in RNA. ACS Chem. Biol. 9, 1780-1787.

Phelps, K. J., Tran, K., Eifler, T., Erickson, A. I., Fisher, A. J. and Beal, P. A. (2015). Recognition of duplex RNA by the deaminase domain of the RNA editing enzyme ADAR2. Nucleic Acids Res. 43, 1123-1132.

Pokharel, S., Jayalath, P., Maydanovych, O., Goodman, R. A., Wang, S. C., Tantillo, D. J. and Beal, P. A. (2009). Matching active site and substrate structures for an RNA editing reaction. J. Am. Chem. Soc. 131, 11882-11891.

Ran, F. A., Hsu, P. D., Wright, J., Agarwala, V., Scott, D. A. and Zhang, F. (2013). Genome engineering using the CRISPR-Cas9 system. Nat. Protoc. 8, 2281-2308.

Reenan, R. (2014). Correcting mutations by RNA repair. N. Engl. J. Med. 370, 172-174.

Rueter, S. M., Dawson, T. R. and Emeson, R. B. (1999). Regulation of alternative splicing by RNA editing. Nature 399, 75-80.

Schneider, M. F., Wettengel, J., Hoffmann, P. C. and Stafforst, T. (2014). Optimal guideRNAs for re-directing deaminase activity of hADAR1 and hADAR2 in trans. Nucleic Acids Res. 42, e87.

Shevchenko, A., Wilm, M., Vorm, O. and Mann, M. (1996). Mass spectrometric sequencing of proteins silver-stained polyacrylamide gels. Anal. Chem. 68, 850-858.

Sinnamon, J. R., Kim, S. Y., Corson, G. M., Song, Z., Nakai, H., Adelman, J. P. and Mandel, G. (2017). Site-directed RNA repair of endogenous Mecp2 RNA in neurons. Proc. Natl. Acad. Sci. U.S.A 114, 9395-9402.

Stafforst, T. and Schneider, M. F. (2012). An RNA-deaminase conjugate selectively repairs point mutations. Angew. Chem. Int. Ed. Engl. 51, 11166-11169.

Suter, S. R., Sheu-Gruttadauria, J., Schirle, N. T., Valenzuela, R., Ball-Jones, A. A., Onizuka, K., Macrae, I. J. and Beal, P. A. (2016). Structure-Guided Control of siRNA Off-Target Effects. J. Am. Chem. Soc. 138, 8667-8669.

Vallecillo-Viejo, I. C., Liscovitch-Brauer, N., Montiel-Gonzalez, M. F., Eisenberg, E. and Rosenthal, J. J. C. (2018). Abundant off-target edits from site-directed RNA editing can be reduced by nuclear localization of the editing enzyme. RNA Biol. 15, 104-114.

Vogel, P., Moschref, M., Li, Q., Merkle, T., Selvasaravanan, K. D., Li, J. B. and Stafforst, T. (2018). Efficient and precise editing of endogenous transcripts with SNAP-tagged ADARs. Nat. Methods 15, 535-538.

Vogel, P., Schneider, M. F., Wettengel, J. and Stafforst, T. (2014). Improving site-directed RNA editing in vitro and in cell culture by chemical modification of the guideRNA. Angew. Chem. Int. Ed. Engl. 53, 6267-6271.

Vogel, P. and Stafforst, T. (2014). Site-directed RNA editing with antagomir deaminases—a tool to study protein and RNA function. ChemMedChem 9, 2021-2025.

Wang, Q., Hui, H., Guo, Z., Zhang, W., Hu, Y., He, T., Tai, Y., Peng, P. and Wang, L. (2013). ADAR1 regulates ARHGAP26 gene expression through RNA editing by disrupting miR-30b-3p and miR-573 binding. RNA 19, 1525-1536.

Wang, Y. and Beal, P. A. (2016). Probing RNA recognition by human ADAR2 using a high-throughput mutagenesis method. Nucleic Acids Res. 44, 9872-9880.

Wang, Y., Park, S. and Beal, P. A. (2018). Selective Recognition of RNA Substrates by ADAR Deaminase Domains. Biochemistry 57, 1640-1651.

Wettengel, J., Reautschnig, P., Geisler, S., Kahle, P. J. and Stafforst, T. (2017). Harnessing human ADAR2 for RNA repair—Recoding a PINK1 mutation rescues mitophagy. Nucleic Acids Res. 45, 2797-2808.

Wong, S. K., Sato, S. and Lazinski, D. W. (2001). Substrate recognition by ADAR1 and ADAR2. RNA 7, 846-858.

Woolf, T. M., Chase, J. M. and Stinchcomb, D. T. (1995). Toward the therapeutic editing of mutated RNA sequences. Proc. Natl. Acad. Sci. U.S.A 92, 8298-8302.

Yeo, J., Goodman, R. A., Schirle, N. T., David, S. S. and Beal, P. A. (2010). RNA editing changes the lesion specificity for the DNA repair enzyme NEIL1. Proc. Natl. Acad. Sci. U.S.A. 107, 20715-20719.

Zheng, Y., Lorenzo, C. and Beal, P. A. (2017). DNA editing in DNA/RNA hybrids by adenosine deaminases that act on RNA. Nucleic Acids Res. 45, 3369-3377.

VIII. References

1. Bass, B. L. (2002) RNA Editing by Adenosine Deaminases That Act on RNA. *Annu. Rev. Biochem,* 71, 817-846.

2. Bass, B. L. and Weintraub, H. (1988) An unwinding activity that covalently modifies its double-stranded RNA substrate. *Cell*, 55, 1089-1098.

3. Goodman, R. A., Macbeth, M. R. and Beal, P. A. (2012) In Samuel, C. E. (ed.), *Adenosine Deaminases Acting on RNA (ADARs) and A-to-I Editing*. Springer Berlin Heidelberg, Berlin, Heidelberg, pp. 1-33.

4. Nishikura, K. (2010) Functions and regulation of RNA editing by ADAR deaminases. *Annu. Rev. Biochem*, 79, 321-349.

5. Wang, Q., Hui, H., Guo, Z., Zhang, W., Hu, Y., He, T., Tai, Y., Peng, P. and Wang, L. (2013) ADAR1 regulates ARHGAP26 gene expression through RNA editing by disrupting miR-30b-3p and miR-573 binding. *RNA*, 19, 1525-1536.

6. Rueter, S. M., Dawson, T. R. and Emeson, R. B. (1999) Regulation of alternative splicing by RNA editing. *Nature*, 399, 75-80.

7. Yeo, J., Goodman, R. A., Schirle, N. T., David, S. S. and Beal, P. A. (2010) RNA editing changes the lesion specificity for the DNA repair enzyme NEIL1. *Proc. Natl. Acad. Sci. USA.*, 107, 20715-20719.

8. Bass, B. L., Nishikura, K., Keller, W., Seeburg, P. H., Emeson, R. B., O'Connell, M. A., Samuel, C. E. and Herbert, A. (1997) A standardized nomenclature for adenosine deaminases that act on RNA. *RNA*, 3, 947-949.

9. Miyamura, Y., Suzuki, T., Kono, M., Inagaki, K., Ito, S., Suzuki, N. and Tomita, Y. (2003) Mutations of the RNA-Specific Adenosine Deaminase Gene (DSRAD) Are Involved in Dyschromatosis Symmetrica Hereditaria. *Amer. J. Hum. Genet.*, 73, 693-699.

10. Zhang, G., Shao, M., Li, Z., Gu, Y., Du, X., Wang, X. and Li, M. (2016) Genetic spectrum of dyschromatosis symmetrica hereditaria in Chinese patients including a novel nonstop mutation in ADAR1 gene. *BMC Med. Genet.*, 17, 14.

11. Livingston, J. H. and Crow, Y. J. (2016) Neurologic Phenotypes Associated with Mutations in TREX1, RNASEH2A, RNASEH2B, RNASEH2C, SAMHD1, ADAR1, and IFIH1: Aicardi-Goutiéres Syndrome and Beyond. Neuropediatrics, 47, 355-360.

12. Rice, G. I., Kasher, P. R., Forte, G. M. A., Mannion, N. M., Greenwood, S. M., Szynkiewicz, M., Dickerson, J. E., Bhaskar, S. S., Zampini, M., Briggs, T. A. et al. (2012) Mutations in ADAR1 cause Aicardi-Goutieres syndrome associated with a type I interferon signature. *Nat. Genet.*, 44, 1243-1248.

13. Slotkin, W. and Nishikura, K. (2013) Adenosine-to-inosine RNA editing and human disease. Genome Med, 5, 105.

14. Matthews, M. M., Thomas, J. M., Zheng, Y., Tran, K., Phelps, K. J., Scott, A. I., Havel, J., Fisher, A. J. and Beal, P. A. (2016) Structures of human ADAR2 bound to dsRNA reveal base-flipping mechanism and basis for site selectivity. *Nat. Struct. Mol. Biol.*, 23, 426-433.

15. Tsuruoka, N., Arima, M., Yoshida, N., Okada, S., Sakamoto, A., Hatano, M., Satake, H., Arguni, E., Wang, J.-Y. Y., Yang, J.-H. H. et al. (2013) ADAR1 protein induces adenosine-targeted DNA mutations in senescent Bcl6 gene-deficient cells. *J. Biol. Chem.*, 288, 826-836.

16. Lim, Y. W., Sanz, L. A., Xu, X., Hartono, S. R. and Chédin, F. (2015) Genome-wide DNA hypomethylation and RNA:DNA hybrid accumulation in Aicardi-Goutières syndrome. *eLife*, 4, e08007.

17. Komor, A. C., Kim, Y. B., Packer, M. S., Zuris, J. A. and Liu, D. R. (2016) Programmable editing of a target base in genomic DNA without double-stranded DNA cleavage. *Nature*, 533, 420-424.

18. Nishida, K., Arazoe, T., Yachie, N., Banno, S., Kakimoto, M., Tabata, M., Mochizuki, M., Miyabe, A., Araki, M., Hara, K. Y. et al. (2016) Targeted nucleotide editing using hybrid prokaryotic and vertebrate adaptive immune systems. *Science*, 353.

19. Mizrahi, R. A., Phelps, K. J., Ching, A. Y. and Beal, P. A. (2012) Nucleoside analog studies indicate mechanistic differences between RNA-editing adenosine deaminases. *Nucleic Acids Res.*, 40, 9825-9835.

20. Phelps, K. J., Ibarra-Soza, J. M. M., Tran, K., Fisher, A. J. and Beal, P. A. (2014) Click modification of RNA at adenosine: structure and reactivity of 7-ethynyl- and 7-triazolyl-8-aza-7-deazaadenosine in RNA. *ACS Chem. Biol.*, 9, 1780-1787.

21. Eifler, T., Pokharel, S. and Beal, P. A. (2013) RNA-Seq Analysis Identifies a Novel Set of Editing Substrates for Human ADAR2 Present in *Saccharomyces cerevisiae*. *Biochemistry*, 52, 7857-7869.

22. O'Connell, M. A. and Keller, W. (1994) Purification and properties of double-stranded RNA-specific adenosine deaminase from calf thymus. *Proc. Natl. Acad. Sci. U S. A.*, 91, 10596-10600.

23. Lehmann, K. A. and Bass, B. L. (1999) The importance of internal loops within RNA substrates of ADAR1. *J. Mol. Biol.*, 291, 1-13.

24. Kuttan, A. and Bass, B. L. (2012) Mechanistic insights into editing-site specificity of ADARs. *Proc. Natl. Acad. Sci. U.S.A.*, 109, 304.

25. Wang, Y., Havel, J. and Beal, P. A. (2015) A Phenotypic Screen for Functional Mutants of Human Adenosine Deaminase Acting on RNA 1. *ACS Chem. Biol.*, 10, 2512-2519.

26. Vukovic, L., Koh, H. R., Myong, S. and Schulten, K. (2014) Substrate Recognition and Specificity of Double Stranded RNA Binding Proteins. *Biochemistry*, 53, 3457-3466.

27. Eggington, J. M., Greene, T. and Bass, B. L. (2011) Predicting sites of ADAR editing in double-stranded RNA. *Nat. Commun.*, 2, 319.

28. Bass, B. L. and Weintraub, H. (1987) A developmentally regulated activity that unwinds RNA duplexes. *Cell*, 48, 607-613.

29. Wagner, R. W. and Nishikura, K. (1988) Cell cycle expression of RNA duplex unwindase activity in mammalian cells. *Mol. Cell. Biol.*, 8, 770-777.

30. Niswender, C. M., Sanders-Bush, E. and Emeson, R. B. (1998) Identification and characterization of RNA editing events within the 5-HT2C receptor. *Ann. N. Y. Acad. Sci.*, 861, 38-48.

31. Sommer, B., Kohler, M., Sprengel, R. and Seeburg, P. H. (1991) RNA editing in brain controls a determinant of ion flow in glutamate-gated channels. *Cell*, 67, 11-19.

32. Melcher, T., Maas, S., Herb, A., Sprengel, R., Seeburg, P. H. and Higuchi, M. (1996) A mammalian RNA editing enzyme. *Nature*, 379, 460-464.

33. Burns, C. M., Chu, H., Rueter, S. M., Hutchinson, L. K., Canton, H., Sanders-Bush, E. and Emeson, R. B. (1997) Regulation of serotonin-2C receptor G-protein coupling by RNA editing. *Nature*, 387, 303-308.

34. Li, J. B., Levanon, E. Y., Yoon, J.-K., Aach, J., Xie, B., LeProust, E., Zhang, K., Gao, Y. and Church, G. M.

(2009) Genome-Wide Identification of Human RNA Editing Sites by Parallel DNA Capturing and Sequencing. *Science,* 324, 1210-1213.
35. Xiong, Y. and Sundaralingam, M. (2000) Crystal structure of a DNA.RNA hybrid duplex with a polypurine RNA r(gaagaagag) and a complementary polypyrimidine DNA d(CTCTTCTTC). *Nucleic Acids Res.,* 28, 2171-2176.
36. Conn, G. L., Brown, T. and Leonard, G. A. (1999) The crystal structure of the RNA/DNA hybrid r(GAAGAGAAGC). d(GCTTCTCTTC) (SEQ ID NOS 145 and 146, respectively) shows significant differences to that found in solution. *Nucleic Acids Res.,* 27 , 555-561.
37. Davis, R. R., Shaban, N. M., Perrino, F. W. and Hollis, T. (2015) Crystal structure of RNA-DNA duplex provides insight into conformational changes induced by RNase H binding. *Cell Cycle,* 14, 668-673.
38. Yang, Y., McBride, K. M., Hensley, S., Lu, Y., Chedin, F. and Bedford, M. T. (2014) Arginine methylation facilitates the recruitment of TOP3B to chromatin to prevent R loop accumulation. *Mol. Cell,* 53, 484-497.
39. Yu, K., Chedin, F., Hsieh, C.-L. L., Wilson, T. E. and Lieber, M. R. (2003) R-loops at immunoglobulin class switch regions in the chromosomes of stimulated B cells. *Nat. Immunol.,* 4, 442-451.
40. Yao, M., Hatahet, Z., Melamede, R. J. and Kow, Y. W. (1994) Deoxyinosine 3' endonuclease, a novel deoxyinosine-specific endonuclease from *Escherichia coli. Ann. N. Y. Acad. Sci.,* 726, 315-316.
41. Mi, R., Alford-Zappala, M., Kow, Y. W., Cunningham, R. P. and Cao, W. (2012) Human endonuclease V as a repair enzyme for DNA deamination. *Mutat. Res.,* 735, 12-18.
42. Lee, C.-C. C., Yang, Y.-C. C., Goodman, S. D., Yu, Y.-H. H., Lin, S.-B. B., Kao, J.-T. T., Tsai, K.-S. S. and Fang, W.-H. H. (2010) Endonuclease V-mediated deoxyinosine excision repair in vitro. *DNA Repair,* 9, 1073-1079.
43. Liddicoat, B. J., Piskol, R., Chalk, A. M., Ramaswami, G., Higuchi, M., Hartner, J. C., Li, J. B., Seeburg, P. H. and Walkley, C. R. (2015) RNA editing by ADAR1 prevents MDA5 sensing of endogenous dsRNA as nonself. *Science,* 349, 1115-1120.
44. Mannion, Niamh M., Greenwood, S. M., Young, R., Cox, S., Brindle, J., Read, D., Nellåker, C., Vesely, C., Ponting, Chris P., McLaughlin, Paul J. et al. (2014) The RNA-Editing Enzyme ADAR1 Controls Innate Immune Responses to RNA. *Cell Rep.,* 9, 1482-1494.
45. Wang, H., La Russa, M. and Qi, L. S. (2016) CRISPR/Cas9 in Genome Editing and Beyond. *Annu. Rev. Biochem,* 85, 227-264.
46. Doudna, J. A. and Charpentier, E. (2014) Genome editing. The new frontier of genome engineering with CRISPR-Cas9. *Science,* 346, 1258096.
47. Ran, F. A., Hsu, P. D., Wright, J., Agarwala, V., Scott, D. A. and Zhang, F. (2013) Genome engineering using the CRISPR-Cas9 system. *Nat. Protoc.,* 8, 2281-2308.
48. Cong, L., Ran, F. A., Cox, D., Lin, S., Barretto, R., Habib, N., Hsu, P. D., Wu, X., Jiang, W., Marraffini, L. A. et al. (2013) Multiplex genome engineering using CRISPR/Cas systems. *Science,* 339, 819-823.
49. Phelps, K. J., Tran, K., Eifler, T., Erickson, A. I., Fisher, A. J. and Beal, P. A. (2015) Recognition of duplex RNA by the deaminase domain of the RNA editing enzyme ADAR2. *Nucleic Acids Res.,* 43, 1123-1132.
50. Wong, S. K., Sato, S. and Lazinski, D. W. (2001) Substrate recognition by ADAR1 and ADAR2. *RNA,* 7, 846-858.

IX. Exemplary Embodiments

Exemplary embodiments provided in accordance with the presently disclosed subject matter include, but are not limited to, the claims and the following embodiments:

1. A method for modifying a target site within a DNA-RNA hybrid molecule, the method comprising contacting the hybrid molecule with an adenosine deaminase that acts on RNA (ADAR) or a portion thereof.
2. The method of embodiment 1, wherein the ADAR comprises an ADAR catalytic domain.
3. The method of embodiment 1 or 2, wherein the ADAR is selected from the group consisting of ADAR1 and ADAR2.
4. The method of any one of embodiments 1 to 3, wherein the ADAR is ADAR1 and wherein the ADAR1 comprises an E1008Q mutation.
5. The method of any one of embodiments 1 to 3, wherein the ADAR is ADAR2 and wherein the ADAR2 comprises an E488 mutation.
6. The method of embodiment 5, wherein the E488 mutation is an E488Q, E488Y, E488W, or E488F mutation.
7. The method of any one of embodiments 1 to 6, wherein the target site is modified without introducing a break in the DNA strand of the hybrid molecule.
8. The method of any one of embodiments 1 to 7, wherein modifying the target site comprises modifying the DNA strand of the hybrid molecule.
9. The method of embodiment 8, wherein a deoxyadenosine nucleotide is deaminated.
10. The method of any one of embodiments 1 to 9, wherein the RNA strand of the hybrid molecule increases target site modification efficiency and/or specificity.
11. The method of embodiment 10, wherein the RNA strand of the hybrid molecule introduces a deoxyadenosine-cytidine mismatch at the target site.
12. The method of embodiment 10 or 11, wherein the RNA strand of the hybrid molecule introduces a deoxyadenosine-cytidine mismatch 5' and/or 3' to the target site.
13. The method of embodiment 11 or 12, wherein the ADAR is wild-type ADAR1, ADAR1 comprising an E1008Q mutation, wild-type ADAR2, or ADAR2 comprising an E488Q, E488F, E488Y, or E488W mutation.
14. The method of embodiment 13, wherein target site modification efficiency is increased.
15. The method of embodiment 10, wherein the RNA strand of the hybrid molecule comprises an abasic site.
16. The method of embodiment 15, wherein the ADAR is ADAR2 and the ADAR2 comprises an E488F, E388Y, or E488W mutation.
17. The method of embodiment 16, wherein target site modification specificity is increased.
18. The method of any one of embodiments 1 to 17, wherein the target site is modified in vitro.
19. The method of any one of embodiments 1 to 17, wherein the hybrid molecule and the ADAR are present within a cell.
20. The method of embodiment 19, wherein the cell is a eukaryotic cell.
21. The method of embodiment 19 or 20, wherein an RNA molecule is introduced into the cell and pairs with a DNA strand within the cell to form the hybrid molecule.
22. The method of any one of embodiments 1 to 21, wherein 2 or more target loci are modified.
23. The method of any one of embodiments 1 to 22, wherein 50 or more target loci are modified.
24. The method of any one of embodiments 1 to 23, wherein the ADAR comprises an ADAR catalytic domain fused to a hybrid nucleic acid binding domain (NBD).

25. The method of embodiment 24, wherein the hybrid NBD comprises ribonuclease H, a type II restriction enzyme, or a portion thereof.

26. The method of embodiment 25, wherein the hybrid NBD comprises ribonuclease H or a portion thereof.

27. The method of embodiment 25, wherein the type II restriction enzyme is selected from the group consisting of EcoRI, HindII, SalI, MspI, HhaI, AluI, TaqI, ThaI, HaeIII, and a combination thereof.

28. A method for preventing or treating a genetic disorder in a subject, the method comprising modifying a target site within a DNA-RNA hybrid molecule according to the method of any one of embodiments 1 to 27 to correct a mutation associated with the genetic disorder.

29. The method of embodiment 28, wherein the target site is modified in vivo.

30. The method of embodiment 28, wherein the target site is modified in vitro and the modified target site is subsequently introduced into the subject.

31. The method of any one of embodiments 28 to 30, wherein the genetic disorder is selected from the group consisting of Rett syndrome, X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disorders, inflammation, immune-related disorders, metabolic disorders, liver disorders, kidney disorders, musculoskeletal disorders, neurological disorders, cardiovascular disorders, pulmonary disorders, ocular disorders, and a combination thereof.

32. The method of embodiment 31, wherein the genetic disorder is Rett syndrome.

33. An isolated polypeptide comprising the amino acid sequence set forth in SEQ ID NO:61 or 64.

34. A fusion protein comprising an adenosine deaminase that acts on RNA (ADAR) catalytic domain and a hybrid nucleic acid binding domain (NBD).

35. The fusion protein of embodiment 34, wherein the ADAR is selected from the group consisting of ADAR1 and ADAR2.

36. The fusion protein of embodiment 34 or 35, wherein the ADAR is ADAR1 and wherein the ADAR1 comprises an E1008Q mutation.

37. The fusion protein of embodiment 34 or 35, wherein the ADAR is ADAR2 and wherein the ADAR2 comprises an E488 mutation.

38. The fusion protein of embodiment 37, wherein the E488 mutation is an E488Q, E488Y, E488W, or E488F mutation.

39. The fusion protein of any one of embodiments 34 to 38, wherein the hybrid NBD binds to a DNA-RNA hybrid molecule.

40. The fusion protein of any one of embodiments 34 to 39, wherein the hybrid NBD comprises ribonuclease H, a type II restriction enzyme, or a portion thereof.

41. The fusion protein of embodiment 40, wherein the hybrid NBD comprises ribonuclease H or a portion thereof.

42. The fusion protein of embodiment 40, wherein the type II restriction enzyme is selected from the group consisting of EcoRI, HindII, SalI, MspI, HhaI, AluI, TaqI, ThaI, HaeIII, and a combination thereof.

43. The fusion protein of any one of embodiments 34 to 42, further comprising an amino acid linker.

44. An isolated polynucleotide comprising a nucleotide sequence encoding the polypeptide of embodiment 33 or the fusion protein of any one of embodiments 34 to 43.

45. A vector comprising the polynucleotide of embodiment 44.

46. A host cell comprising the polynucleotide of embodiment 44 or the vector of embodiment 45.

47. A pharmaceutical composition comprising the polypeptide of embodiment 33, the fusion protein of any one of embodiments 34 to 43, the polynucleotide of embodiment 44, the vector of embodiment 45, or the host cell of embodiment 46, and a pharmaceutically acceptable carrier.

48. A kit for modifying a target site within a DNA-RNA hybrid molecule, the kit comprising the polypeptide of embodiment 33, the fusion protein of any one of embodiments 34 to 43, the polynucleotide of embodiment 44, the vector of embodiment 45, the host cell of embodiment 46, the pharmaceutical composition of embodiment 47, or a combination thereof.

49. The kit of embodiment 48, further comprising instructions for use.

50. The kit of embodiment 48 or 49, further comprising one or more reagents for introducing the nucleic acid or vector into a host cell, contacting the polypeptide or fusion protein with the DNA-RNA hybrid molecule, or a combination thereof.

51. A method for preventing or treating a genetic disorder in a subject, the method comprising administering to the subject a therapeutically effective amount of the pharmaceutical composition of embodiment 47.

52. The method of embodiment 51, wherein the genetic disorder is selected from the group consisting of Rett syndrome, X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disorders, inflammation, immune-related disorders, metabolic disorders, liver disorders, kidney disorders, musculoskeletal disorders, neurological disorders, cardiovascular disorders, pulmonary disorders, ocular disorders, and a combination thereof.

53. The method of embodiment 52, wherein the genetic disorder is Rett syndrome.

54. A method for modifying a target site within a nucleic acid, the method comprising contacting the nucleic acid with the polypeptide of embodiment 33.

55. The method of embodiment 54, wherein the nucleic acid comprises a double-stranded RNA molecule.

56. The method of embodiment 54, wherein the nucleic acid comprises a DNA-RNA hybrid molecule.

57. The method of any one of embodiments 54 to 56, wherein the nucleic acid comprises an abasic site.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| | Informal Sequence Listing | |
|---|---|---|
| SEQ ID NO: | Sequence | Description |
| 1 | 5'-<u>AGA</u>GGGCUCUGC-3' | 3' partially deoxy top strand sequence (deoxy nucleotides underlined) |
| 2 | 5'-GCUCGCGAUGC<u>U</u>-3' | 5' partially deoxy top strand sequence (deoxy nucleotide underlined) |
| 3 | 5'-TTTTTGCAGAGCCCTCTAGCATCGCGAGCTTTTT-3' | Splint DNA |
| 4 | 5'-AAAAAGCTCGCGATGCTAGAGGGCTCTGCAAAAA-3' | Trap DNA |
| 5 | 5'-GCAGAGCCCCCCAGCAUCGCGAGC-3' | RNA bottom strand |
| 6 | 5'-AGAGGGCTCTGC-3' | 3' DNA top strand |
| 7 | 5'-GCTCGCGATGCT-3' | 5' DNA top strand |
| 8 | 5'-GCAGAGCCCCCCAGCATCGCGAGC-3' | DNA bottom strand |
| 9 | 5'-GCGCATAGCCGCGCTATCCGCCAACTCAATCGCGCTCG CCTGAATAGCTCGCGATGCTAGAGGGCTCTGCTACCGCCC CACGAGGGCCAG-3' | 90 nt DNA strand |
| 10 | 5'-TAATACGACTCACTATAGGGCTGGCCCTCGTGGGCGG TA-3' | T7 promoter extend reverse primer |
| 11 | 5'-GCGCATAGCCGCGCTATCCG-3' | T7 promoter extend forward primer |
| 12 | 5'-CTGGCCCTCGTGGGCGGTA-3' | 90 nt DNA PCR reverse primer |
| 13 | 5'-GAGCGCTGAAGGTCTCTTCTTCTCATGACTGAACTCGCG AGCGCATAGCCGCGCTATCCG-3' | PCR extend forward primer |
| 14 | 5'-GAGCGCTGAAGGTCTCTTCT-3' | Sequencing primer |
| 15 | 5'-GCAGAGCCCUCUAGCAUCGCGAGC-3' | No mismatch RNA bottom strand |
| 16 | 5'-GCAGAGCCCUCCAGCAUCGCGAGC-3' | Mismatch site B RNA bottom strand |
| 17 | 5'-GCAGAGCCCCCUAGCAUCGCGAGC-3' | Mismatch site C RNA bottom strand |
| 18 | 5'-GGGCUGGCCCUCGUGGGGCGGUAGCAGAGCCCUCUAG CAUCGCGAGCUAUUCAGGCGAGCGCGAUUGAGUUGGCG GAUAGCGCGGCUAUGCGC-3' | 93 nt Bottom RNA |
| 19 | 5'-AUCCGGUAUUCCAAGAACGCGAGG-3' | TAG site guide RNA |
| 20 | 5'-GCCAAAAGGAACUACGAGGCAUAG-3' | AAT site guide RNA |
| 21 | 5'-UUUCAGCGGAGCGAGAAUAGAAAG-3' | CAC site guide RNA |
| 22 | 5'-CCGUCACCGACCUGAGCCAUUUGG-3' | AAG site guide RNA |
| 23 | 5'-GGACUCCAACGCCAAAGGGCGAAA-3' | GAC site guide RNA |
| 24 | 5'-UCAAAAAUAAUCCGCGUCUGGCCU-3' | GAA site guide RNA |
| 25 | 5'-CTTGTGGGTTATCTCTCTGATATTAGCGCTC-3' | TAG site PCR forward primer |
| 26 | 5'-GAATAACCTTGCTTCTGTAAATCGTCGCTAT-3' | TAG site PCR reverse primer |
| 27 | 5'-CTACTCGTTCGCAGAATTGGGAATC-3' | AAT site PCR Forward primer |
| 28 | 5'-GAACGAGGCGCAGACGGTCAATC-3' | AAT site PCR reverse primer |
| 29 | 5'-GATTGACCGTCTGCGCCTCGTTC-3' | CAC site PCR forward primer |
| 30 | 5'-CAGTGCCTTGAGTAACAGTGCCCG-3' | CAC site PCR reverse primer |
| 31 | 5'-CGGGCACTGTTACTCAAGGCACTG-3' | AAG site PCR forward primer |
| 32 | 5'-GAGCGCTAATATCAGAGAGATAACCCACAAG-3' | AAG site PCR reverse primer |
| 33 | 5'-CTGGATATTACCAGCAAGGCCGATAG-3' | GAC site PCR forward primer |
| 34 | 5'-GCTCGAATTCGTAATCATGGTCATAGC-3' | GAC site PCR reverse primer |

|  |  |  |
|---|---|---|
| | Informal Sequence Listing | |
| SEQ ID NO: | Sequence | Description |
| 35 | 5'-GCTATGACCATGATTACGAATTCGAGC-3' | GAA site PCR forward primer |
| 36 | 5'-GATTCCCAATTCTGCGAACGAGTAG-3' | GAA site PCR reverse primer |
| 37 | 5'-GCUCGCGAUGCUAGAGGGCUCUGC-3' | Combined top strand sequence (RNA) |
| 38 | 5'-GCTCGCGATGCTAGAGGGCTCTGC-3' | Combined top strand sequence (DNA) |
| 39 | 5'-GAATAGCTCGCGATGCTAGAGGGCTCTGCTACCG-3' | Partial 90 nt DNA strand |
| 40 | 5'-CGGUAGCAGAGCCCYCXAGCAUCGCGAGCUAUUC-3' | Partial 90 nt bottom strand |
| 41 | 5'-CCAAATGGCTCAAGTCGGTGACGG-3' | AAG site |
| 42 | 5'-CTTTCTATTCTCACTCCGCTGAAA-3' | CAC site |
| 43 | 5'-CTATGCCTCGTAATTCCTTTTGGC-3' | AAT site |
| 44 | 5'-AGGCCAGACGCGAATTATTTTTGA-3' | GAA site |
| 45 | 5'-TTTCGCCCTTTGACGTTGGAGTCC-3' | GAC site |
| 46 | 5'-CCTCGCGTTCTTAGAATACCGGAT-3' | TAG site |
| 47 | 5'-CGCGAGCGCATAGCCGCGCTATCCGCCAACTCAATCGCGCTCGCCTGAATRGCTCGCGATGCTGGAGGGCTCTGCTACCGCCCCACGAGGG-3' | DNA sequence trace readout |
| 48 | MNPRQGYSLSGYYTHPFQGYEHRQLRYQQPGPGSSPSSFLLKQIEFLKGQLPEAPVIGKQTPSLPPSLPGLRPRFPVLLASSTRGRQVDIRGVPRGVHLRSQGLQRGFQHPSPRGRSLPQRGVDCLSSHFQELSIYQDQEQRILKFLEELGEGKATTAHDLSGKLGTPKKEINRVLYSLAKKGKLQKEAGTPPLWKIAVSTQAWNQHSGVVRPDGHSQGAPNSDPSLEPEDRNSTSVSEDLLEPFIAVSAQAWNQHSGVVRPDSHSQGSPNSDPGLEPEDSNSTSALEDPLEFLDMAEIKEKICDYLFNVSDSSALNLAKNIGLTKARDINAVLIDMERQGDVYRQGTTPPIWHLTDKKRERMQIKRNTNSVPETAPAAIPETKRNAEFLTCNIPTSNASNNMVFEEKVENGQEPVIKLENRQEARPEPARLKPPVHYNGPSKAGYVDFENGQWATDDIPDDLNSIRAAPGEFRAIMEMPSFYSHGLPRCSPYKKLTECQLKNPISGLLEYAQFASQTCEFNMIEQSGPPHEPRFKFQVVINGREFPPAEAGSKKVAKQDAAMKAMTILLEEAKAKDSGKSEESSHYSTEKESEKTAESQTPTPSATSFFSGKSPVTTLLECMHKLGNSCEFRLLSKEGPAHEPKFQYCVAVGAQTFPSVSAPSKKVAKQMAAEEAMKALHGEATNSMASDNQPEGMISESLDNLESMMPNKVRKIGELVRYLNTNPVGGLLEYARSHGFAAEFKLVDQSGPPHEPKFVYQAKVGGRWFPAVCAHSKKQGKQEAADAALRVLIGENEKAERMGFTEVTPVTGASLRRTMLLLSRSPEAQPKTLPLTGSTFHDQIAMLSHRCFNTLTNSFQPSLLGRKILAAIIMKKDSEDMGVVVSLGTGNRCVKGDSLSLKGETVNDCHAEIISRRGFIRFLYSELMKYNSQTAKDSIFEPAKGGEKLQIKKTVSFHLYISTAPCGDGALFDKSCSDRAMESTESRHYPVFENPKQGKLRTKVENGEGTIPVESSDIVPTWDGIRLGERLRTMSCSDKILRWNVLGLQGALLTHFLQPIYLKSVTLGYLFSQGHLTRAICCRVTRDGSAFEDGLRHPFIVNHPKVGRVSIYDSKRQSGKTKETSVNWCLADGYDLEILDGTRGTVDGPRNELSRVSKKNIFLLFKKLCSFRYRRDLLRLSYGEAKKAARDYETAKNYFKKGLKDMGYGNWISKPQEEKNFYLCPV | hADAR1 sequence (catalytic deaminase domain underlined) |
| 49 | MDIEDEENMSSSTDVKENRNLDNVSPKDGSTPGPGEGSQLSNGGGGGPGRKRPLEEGSNGHSKYRLKKRRKTPGPVLPKNALMQLNEIKPGLQYTLLSQTGPVHAPLFVMSVEVNGQVFEGSGPTKKKAKLHAAEKALRSFVQFPNASEAHLAMGRTLSVNTDFTSDQADFPDTLFNGFETPDKAEPPFYVGSNGDDSFSSSGDLSLSASPVPASLAQPPLPVLPPFPPPSGKNPVMILNELRPGLKYDFLSESGESHAKSFVMSVVVDGQFFEGSGRNKKLAKARAAQSALAAIFNL | hADAR2 sequence (catalytic deaminase domain underlined) |

| SEQ ID NO: | Sequence | Description |
|---|---|---|
|  | HLDQTPSRQPIPSEGLQLHLPQVLADAVSRLVLGKFGD LTDNFSSPHARRKVLAGVVMTTGTDVKDAKVISVSTG TKCINGEYMSDRGLALNDCHAEIISRRSLLRFLYTQLEL YLNNKDDQKRSIFQKSERGGFRLKENVQFHLYISTSPC GDARIFSPHEPILEEPADRHPNRKARGQLRTKIESGEGT IPVRSNASIQTWDGVLQGERLLTMSCSDKIARWNVVGI QGSLLSIFVEPIYFSSIILGSLYHGDHLSRAMYQRISNIE DLPPLYTLNKPLLSGISNAEARQPGKAPNFSVNWTVGD SAIEVINATTGKDELGRASRLCKHALYCRWMRVHGK VPSHLLRSKITKPNVYHESKLAAKEYQAAKARLFTAFI KAGLGAWVEKPTEQDQFSLTP |  |
| 50 | 5'-CAGAGCCCCCXAGCAUCGCGAGC-3' | RNA bottom strand (X is C or abasic (rAb)) |
| 51 | 5'-GCUCGCGAUGCUAGAGGGCUCUG-3' | RNA top strand |
| 52 | MDIEDEENMSSSTDVKENRNLDNVSPKDGSTPGPGEGSQLS NGGGGGPGRKRPLEEGSNGHSKYRLKKRRKTPGPVLPKNAL MQLNEIKPGLQYTLLSQTGPVHAPLFVMSVEVNGQVFEGSG PTKKKAKLHAAEKALRSFVQFPNASEAHLAMGRTLSVNTDF TSDQADFPDTLFNGFETPDKAEPPFYVGSNGDDSFSSSGDLSL SASPVPASLAQPPLPVLPPFPPPSGKNPVMILNELRPGLKYDF LSESGESHAKSFVMSVVVDGQFFEGSGRNKKLAKARAAQSA LAAIFNLHLDQTPSRQPIPSEGLQLHLPQVLADAVSRLVLGKF GDLTDNFSSPHARRKVLAGVVMTTGTDVKDAKVISVSTGTK CINGEYMSDRGLALNDCHAEIISRRSLLRFLYTQLELYLNNK DDQKRSIFQKSERGGFRLKENVQFHLYISTSPCGDARIFSPHE PILEEPADRHPNRKARGQLRTKIESGFGTIPVRSNASIQTWDG VLQGERLLTMSCSDKIARWNVVGIQGSLLSIFVEPIYFSSIILG SLYHGDHLSRAMYQRISNIEDLPPLYTLNKPLLSGISNAEARQ PGKAPNFSVNWTVGDSAIEVINATTGKDELGRASRLCKHAL YCRWMRVHGKVPSHLLRSKITKPNVYHESKLAAKEYQAAK ARLFTAFIKAGLGAWVEKPTEQDQFSLTP | ADAR2 E488F sequence (catalytic deaminase domain underlined) |
| 53 | MNPRQGYSLSGYYTHPFQGYEHRQLRYQQPGPGSSPSSFLLK QIEFLKGQLPEAPVIGKQTPSLPPSLPGLRPRFPVLLASSTRGR QVDIRGVPRGVHLRSQGLQRGFQHPSPRGRSLPQRGVDCLSS HFQELSIYQDQEQRILKFLEELGEGKATTAHDLSGKLGTPKK EINRVLYSLAKKGKLQKEAGTPPLWKIAVSTQAWNQHSGVV RPDGHSQGAPNSDPSLEPEDRNSTSVSEDLLEPFIAVSAQAW NQHSGVVRPDSHSQGSPNSDPGLEPEDSNSTSALEDPLEFLD MAEIKEKICDYLFNVSDSSALNLAKNIGLTKARDINAVLIDM ERQGDVYRQGTTPPIWHLTDKKRERMQIKRNTNSVPETAPA AIPETKRNAEFLTCNIPTSNASNNMVTTEKVENGQEPVIKLEN RQEARPEPARLKPPVHYNGPSKAGYVDFENGQWATDDIPDD LNSIRAAPGEFRAIMEMPSFYSHGLPRCSPYKKLTECQLKNPI SGLLEYAQFASQTCEFNMIEQSGPPHEPRFKFQVVINGREFPP AEAGSKKVAKQDAAMKAMTILLEEAKAKDSGKSEESSHYST EKESEKTAESQTPTPSATSFFSGKSPVTTLLECMHKLGNSCEF RLLSKEGPAHEPKFQYCVAVGAQTFPSVSAPSKKVAKQMAA EEAMKALHGEATNSMASDNQPEGMISESLDNLESMMPNKV RKIGELVRYLNTNPVGGLLEYARSHGFAAEFKLVDQSGPPHE PKFVYQAKVGGRWFPAVCAHSKKQGKQEAADAALRVLIGE NEKAERMGFTEVTPVTGASLRRTMLLLSRSPEAQPKTLPLTG STFHDQIAMLSHRCFNTLTNSFQPSLLGRKILAAIIMKKDSED MGVVVSLGTGNRCVKGDSLSLKGETVNDCHAEIISRRGFIRF LYSELMKYNSQTAKDSIFEPAKGGEKLQIKKTVSFHLYISTAP CGDGALFDKSCSDRAMESTESRHYPVFENPKQGKLRTKVEN GQGTIPVESSDIVPTWDGIRLGERLRTMSCSDKILRWNVLGL QGALLTHFLQPIYLKSVTLGYLFSQGHLTRAICCRVTRDGSA FEDGLRHPFIVNHPKVGRVSIYDSKRQSGKTKETSVNWCLAD GYDLEILDGTRGTVDGPRNELSRVSKKNIFLLFKKLCSFRYR RDLLRLSYGEAKKAARDYETAKNYFKKGLKDMGYGNWISK PQEEKNFYLCPV | ADAR1 E1008Q sequence (catalytic deaminase domain underlined) |
| 54 | MDIEDEENMSSSTDVKENRNLDNVSPKDGSTPGPGEGSQLS NGGGGGPGRKRPLEEGSNGHSKYRLKKRRKTPGPVLPKNAL MQLNEIKPGLQYTLLSQTGPVHAPLFVMSVEVNGQVFEGSG PTKKKAKLHAAEKALRSFVQFPNASEAHLAMGRTLSVNTDF TSDQADFPDTLFNGFETPDKAEPPFYVGSNGDDSFSSSGDLSL SASPVPASLAQPPLPVLPPFPPPSGKNPVMILNELRPGLKYDF LSESGESHAKSFVMSVVVDGQFFEGSGRNKKLAKARAAQSA | ADAR2 E488Q sequence (catalytic deaminase domain underlined) |

| SEQ ID NO: | Sequence | Description |
|---|---|---|
| | LAAIFNLHLDQTPSRQPIPSEGLQLHLPQVLADAVSRLVLGKF GDLTDNFSSPHARRKVLAGVVMTTGTDVKDAKVISVSTGTK CINGEYMSDRGLALNDCHAEIISRRSLLRFLYTQLELYLNNK DDQKRSIFQKSERGGFRLKENVQFHLYISTSPCGDARIFSPHE PILEEPADRHPNRKARGQLRTKIESGQGTIPVRSNASIQTWDG VLQGERLLTMSCSDKIARWNVVGIQGSLLSIFVEPIYFSSIILG SLYHGDHLSRAMYQRISNIEDLPPLYTLNKPLLSGISNAEARQ PGKAPNFSVNWTVGDSAIEVINATTGKDELGRASRLCKHAL YCRWMRVHGKVPSHLLRSKITKPNVYHESKLAAKEYQAAK ARLFTAFIKAGLGAWVEKPTEQDQFSLTP | |
| 55 | 5'-GCUCGCGAUGCUAGAGGGCUCUGC-3' | Partially deoxy combined top strand sequence (deoxy nucleotides underlined) |
| 56 | 5'-GCAGAGCCCCCCAGCAUCGCGAGC-3' | Partially deoxy bottom strand (deoxy nucleotide underlined) |
| 57 | 5'-AGAGGGCUCUGC-3' | 3' RNA top strand sequence |
| 58 | 5'-GCUCGCGAUGCU-3' | 5' RNA top strand sequence |
| 59 | MDIEDEENMSSSSTDVKENRNLDNVSPKDGSTPGPGEGSQLS NGGGGGPGRKRPLEEGSNGHSKYRLKKRRKTPGPVLPKNAL MQLNEIKPGLQYTLLSQTGPVHAPLFVMSVEVNGQVFEGSG PTKKKAKLHAAEKALRSFVQFPNASEAHLAMGRTLSVNTDF TSDQADFPDTLFNGFETPDKAEPPFYVGSNGDDSFSSSGDLSL SASPVPASLAQPPLPVLPPFPPPSGKNPVMILNELRPGLKYDF LSESGESHAKSFVMSVVVDGQFFEGSGRNKKLAKARAAQSA LAAIFNLHLDQTPSRQPIPSEGLQLHLPQVLADAVSRLVLGKF GDLTDNFSSPHARRKVLAGVVMTTGTDVKDAKVISVSTGTK CINGEYMSDRGLALNDCHAEIISRRSLLRFLYTQLELYLNNK DDQKRSIFQKSERGGFRLKENVQFHLYISTSPCGDARIFSPHE PILEEPADRHPNRKARGQLRTKIESGXGTIPVRSNASIQTWDG VLQGERLLTMSCSDKIARWNVVGIQGSLLSIFVEPIYFSSIILG SLYHGDHLSRAMYQRISNIEDLPPLYTLNKPLLSGISNAEARQ PGKAPNFSVNWTVGDSAIEVINATTGKDELGRASRLCKHAL YCRWMRVHGKVPSHLLRSKITKPNVYHESKLAAKEYQAAK ARLFTAFIKAGLGAWVEKPTEQDQFSLTP | ADAR2 E488X sequence (catalytic deaminase domain underlined; X can be any amino acid) |
| 60 | MDIEDEENMSSSSTDVKENRNLDNVSPKDGSTPGPGEGSQLS NGGGGGPGRKRPLEEGSNGHSKYRLKKRRKTPGPVLPKNAL MQLNEIKPGLQYTLLSQTGPVHAPLFVMSVEVNGQVFEGSG PTKKKAKLHAAEKALRSFVQFPNASEAHLAMGRTLSVNTDF TSDQADFPDTLFNGFETPDKAEPPFYVGSNGDDSFSSSGDLSL SASPVPASLAQPPLPVLPPFPPPSGKNPVMILNELRPGLKYDF LSESGESHAKSFVMSVVVDGQFFEGSGRNKKLAKARAAQSA LAAIFNLHLDQTPSRQPIPSEGLQLHLPQVLADAVSRLVLGKF GDLTDNFSSPHARRKVLAGVVMTTGTDVKDAKVISVSTGTK CINGEYMSDRGLALNDCHAEIISRRSLLRFLYTQLELYLNNK DDQKRSIFQKSERGGFRLKENVQFHLYISTSPCGDARIFSPHE PILEEPADRHPNRKARGQLRTKIESGHGTIPVRSNASIQTWDG VLQGERLLTMSCSDKIARWNVVGIQGSLLSIFVEPIYFSSIILG SLYHGDHLSRAMYQRISNIEDLPPLYTLNKPLLSGISNAEARQ PGKAPNFSVNWTVGDSAIEVINATTGKDELGRASRLCKHAL YCRWMRVHGKVPSHLLRSKITKPNVYHESKLAAKEYQAAK ARLFTAFIKAGLGAWVEKPTEQDQFSLTP | ADAR2 E488H sequence (catalytic deaminase domain underlined) |
| 61 | MDIEDEENMSSSSTDVKENRNLDNVSPKDGSTPGPGEGSQLS NGGGGGPGRKRPLEEGSNGHSKYRLKKRRKTPGPVLPKNAL MQLNEIKPGLQYTLLSQTGPVHAPLFVMSVEVNGQVFEGSG PTKKKAKLHAAEKALRSFVQFPNASEAHLAMGRTLSVNTDF TSDQADFPDTLFNGFETPDKAEPPFYVGSNGDDSFSSSGDLSL SASPVPASLAQPPLPVLPPFPPPSGKNPVMILNELRPGLKYDF LSESGESHAKSFVMSVVVDGQFFEGSGRNKKLAKARAAQSA LAAIFNLHLDQTPSRQPIPSEGLQLHLPQVLADAVSRLVLGKF GDLTDNFSSPHARRKVLAGVVMTTGTDVKDAKVISVSTGTK CINGEYMSDRGLALNDCHAEIISRRSLLRFLYTQLELYLNNK DDQKRSIFQKSERGGFRLKENVQFHLYISTSPCGDARIFSPHE PILEEPADRHPNRKARGQLRTKIESGYGTIPVRSNASIQTWDG VLQGERLLTMSCSDKIARWNVVGIQGSLLSIFVEPIYFSSIILG SLYHGDHLSRAMYQRISNIEDLPPLYTLNKPLLSGISNAEARQ PGKAPNFSVNWTVGDSAIEVINATTGKDELGRASRLCKHAL | ADAR2 E488Y sequence (catalytic deaminase domain underlined) |

| SEQ ID NO: | Sequence | Description |
|---|---|---|
| | YCRWMRVHGKVPSHLLRSKITKPNVYHESKLAAKEYQAAK<br>ARLFTAFIKAGLGAWVEKPTEQDQFSLTP | |
| 62 | MDIEDEENMSSSTDVKENRNLDNVSPKDGSTPGPGEGSQLS<br>NGGGGGPGRKRPLEEGSNGHSKYRLKKRRKTPGPVLPKNAL<br>MQLNEIKPGLQYTLLSQTGPVHAPLFVMSVEVNGQVFEGSG<br>PTKKKAKLHAAEKALRSFVQFPNASEAHLAMGRTLSVNTDF<br>TSDQADFPDTLFNGFETPDKAEPPFYVGSNGDDSFSSSGDLSL<br>SASPVPASLAQPPLPVLPPFPPPSGKNPVMILNELRPGLKYDF<br>LSESGESHAKSFVMSVVVDGQFFEGSGRNKKLAKARAAQSA<br>LAAIFNLHLDQTPSRQPIPSEGLQLHLPQVLADAVSRLVLGKF<br>GDLTDNFSSPHARRKVLAGVVMTTGTDVKDAKVISVSTGTK<br>CINGEYMSDRGLALNDCHAEIISRRSLLRFLYTQLELYLNNK<br>DDQKRSIFQKSERGGFRLKENVQFHLYISTSPCGDARIFSPHE<br>PILEEPADRHPNRKARGQLRTKIESGWGTIPVRSNASIQTWD<br>GVLQGERLLTMSCSDKIARWNVVGIQGSLLSIFVEPIYFSSIIL<br>GSLYHGDHLSRAMYQRISNIEDLPPLYTLNKPLLSGISNAEAR<br>QPGKAPNFSVNWTVGDSAIEVINATTGKDELGRASRLCKHA<br>LYCRWMRVHGKVPSHLLRSKITKPNVYHESKLAAKEYQAA<br>KARLFTAFIKAGLGAWVEKPTEQDQFSLTP | ADAR2 E488W sequence (catalytic deaminase domain underlined) |
| 63 | MDIEDEENMSSSTDVKENRNLDNVSPKDGSTPGPGEGSQLS<br>NGGGGGPGRKRPLEEGSNGHSKYRLKKRRKTPGPVLPKNAL<br>MQLNEIKPGLQYTLLSQTGPVHAPLFVMSVEVNGQVFEGSG<br>PTKKKAKLHAAEKALRSFVQFPNASEAHLAMGRTLSVNTDF<br>TSDQADFPDTLFNGFETPDKAEPPFYVGSNGDDSFSSSGDLSL<br>SASPVPASLAQPPLPVLPPFPPPSGKNPVMILNELRPGLKYDF<br>LSESGESHAKSFVMSVVVDGQFFEGSGRNKKLAKARAAQSA<br>LAAIFNLHLDQTPSRQPIPSEGLQLHLPQVLADAVSRLVLGKF<br>GDLTDNFSSPHARRKVLAGVVMTTGTDVKDAKVISVSTGTK<br>CINGEYMSDRGLALNDCHAEIISRRSLLRFLYTQLELYLNNK<br>DDQKRSIFQKSERGGFRLKENVQFHLYISTSPCGDARIFSPHE<br>PILEEPADRHPNRKARGQLRTKIESGLGTIPVRSNASIQTWDG<br>VLQGERLLTMSCSDKIARWNVVGIQGSLLSIFVEPIYFSSIILG<br>SLYHGDHLSRAMYQRISNIEDLPPLYTLNKPLLSGISNAEARQ<br>PGKAPNFSVNWTVGDSAIEVINATTGKDELGRASRLCKHAL<br>YCRWMRVHGKVPSHLLRSKITKPNVYHESKLAAKEYQAAK<br>ARLFTAFIKAGLGAWVEKPTEQDQFSLTP | ADAR2 E488L sequence (catalytic deaminase domain underlined) |
| 64 | MDIEDEENMSSSTDVKENRNLDNVSPKDGSTPGPGEGSQLS<br>NGGGGGPGRKRPLEEGSNGHSKYRLKKRRKTPGPVLPKNAL<br>MQLNEIKPGLQYTLLSQTGPVHAPLFVMSVEVNGQVFEGSG<br>PTKKKAKLHAAEKALRSFVQFPNASEAHLAMGRTLSVNTDF<br>TSDQADFPDTLFNGFE,TPDKAEPPFYVGSNGDDSFSSSGDLSL<br>SASPVPASLAQPPLPVLPPFPPPSGKNPVMILNELRPGLKYDF<br>LSESGESHAKSFVMSVVVDGQFFEGSGRNKKLAKARAAQSA<br>LAAIFNLHLDQTPSRQPIPSEGLQLHLPQVLADAVSRLVLGKF<br>GDLTDNFSSPHARRKVLAGVVMTTGTDVKDAKVISVSTGTK<br>CINGEYMSDRGLALNDCHAEIISRRSLLRFLYTQLELYLNNK<br>DDQKRSIFQKSERGGFRLKENVQFHLYISTSPCGDARIFSPHE<br>PILEEPADRHPNRKARGQLRTKIESGIGTIPVRSNASIQTWDG<br>VLQGERLLTMSCSDKIARWNVVGIQGSLLSIFVEPIYFSSIILG<br>SLYHGDHLSRAMYQRISNIEDLPPLYTLNKPLLSGISNAEARQ<br>PGKAPNFSVNWTVGDSAIEVINATTGKDELGRASRLCKHAL<br>YCRWMRVHGKVPSHLLRSKITKPNVYHESKLAAKEYQAAK<br>ARLFTAFIKAGLGAWVEKPTEQDQFSLTP | ADAR2 E488I sequence (catalytic deaminase domain underlined) |
| 65 | 5'-GACCAAAATAGAGTCTGGTTTTGGGACGATTCCAGTGCGCTC-3' | E488F FWD |
| 66 | 5'-GAGCGCACTGGAATCGTCCCAAAACCAGACTCTATTTTGGTC-3' | E488F RVS |
| 67 | 5'-GACCAAAATAGAGTCTGGTTATGGGACGATTCCAGTGCGCTC-3' | E488Y FWD |
| 68 | 5'-GAGCGCACTGGAATCGTCCCATAACCAGACTCTATTTTGGTC-3' | E488Y RVS |

-continued

| SEQ ID NO: | Sequence | Description |
|---|---|---|
| 69 | 5'-GACCAAAATAGAGTCTGGTTGGGGGACGATTCCAGTGCGCTC-3' | E488W FWD |
| 70 | 5'-GAGCGCACTGGAATCGTCCCCCAACCAGACTCTATTTTGGTC-3' | E488W RVS |
| 71 | 5'-GCUCGCGAUGCUNGAGGGCUCUG-3' | hGLi1 top containing 8-azaN (N) |
| 72 | 5'-CAGAGCCCCCXAGCAUCGCGAGC-3' | hGLi1 bottom containing reduced abasic site (rAb) (denoted by X) |
| 73 | 5'-AGAGGGCUCUG-3' | 3' top strand |
| 74 | 5'-CAGAGCCCCCCAGCATCGCGAGC-3' | Top strand DNA splint |
| 75 | 5'-CAGAGCCCCCCAGCAUCGCGAGC-3' | Bottom RNA strand (orphan base C) |
| 76 | 5'-UUCGCACCAAGUUCGACAUGCGC-3' | Bottom RNA Strand Site 1 (C) |
| 77 | 5'-UACGCCGGUACCAAGUAUCGCAC-3' | Bottom RNA Strand Site 2 (C) |
| 78 | 5'-UUCGCACrAbAAGUUCGACAUGCGC-3' | Bottom RNA Strand Site 1 (rAb denotes reduced abasic site) |
| 79 | 5'-UACGCCGGUACrAbAAGUAUCGCAC-3' | Bottom RNA Strand Site 2 (rAb denotes reduced abasic site) |
| 80 | 5'-GCGCATGTCGAACTTGGTGCGAAGTGCGATACTTGGTACCGGCGTACATTGGTATCCACCGACGTGACGCGTCT-3' | Bottom Strand Splint |
| 81 | 5'-GCGCATGTCGAACTTAGAGCGAAGTGCGATACTTAGAACCGGCGTACATTAGAATCCACCGACGTGACGCGTCT-3' | 74 nt multiple target substrate |
| 82 | 5'-GTGTGTGTAAGCTTTCGTGGTCCTTAGACTTCGTGCACATACAGGCGCATGTCGAACTTAGAGCGAAG-3' | Forward with HindIII restriction site |
| 83 | 5'-GTGTGTGTGGATCCCTGCAAGACGCGTCACGTCGGTGGATTC-3' | Reverse with BamHI restriction site |
| 84 | 5'-TGGGTACGAATTCCCCGTACAAGCTT-3' | RT-PCR FWD and sequencing primer |
| 85 | 5'-AGACGCGTCACGTCGGTGGATT-3' | RT-PCR RVS primer |
| 86 | 5'-ATCTCAGAGGAGGACCTGGAATTCATGGGA*TACCCCTACGACGTGCCCGACTACGCCG*GATCC<u>GCCGAGATCAAGGAGAAAATCTGC</u>-3' | Gibson FWD containing HA tag (italicized region corresponds to HA tag, underlined region corresponds to ADAR2 sequence, bold region overlaps with pcDNA3.1 vector) |
| 87 | 5'-AGGGCCCTCTAGATGCATGCTCGAGCGGCCGCTCA<u>TACTGGGCAGAGATAAAAGTTCTTTTCCT</u>-3 | Gibson RVS (underlined region corresponds to ADAR2 sequence, bold region overlaps with pcDNA3.1 vector) |
| 88 | 5'-*GAAGCAACTCTTGAGTGTTAATATGTTGACCCCTGTATTAGGGATGCGGG*AATTGGGTACGAATTCCCCGTACATCGCTGTCCACCT-3' | Non-specific sequence FWD |
| 89 | 5'-*AGATGATAAGCTCCGGCAAGCAATATTGAACAACGCAAGGATCGGCGATATT*CCACGTGATATCCCGACACGGATCCGGGGCA-3' | Non-specific sequence RVS |
| 90 | 5'-GACTCACTATAGGGAGACCCAGAAGCAACTCTTGAGTGTTAATATGTTGACCCCTGTATTAGGGATGCGGG-3' | Gibson FWD (italicized region corresponds to non-native) |
| 91 | 5'-TAGGGCCCTCTAGATGCATGCTCGAAGATGATAAGCTCCGGCAAGCAATATTGAACAACGCAAGGATCGGCG-3' | Gibson RVS (bold region overlaps with pcDNA3.1 vector) |

| SEQ ID NO: | Sequence | Description |
|---|---|---|
| 92 | 5'-U*U*GUCAAGAAAGGGUGUAACGCAA<u>CCAAG</u>UCAUAGUC*C*G-3' | Overexpressed and endogenous β-actin RNA bottom strand (C) (phosphorothioate modification marked with asterisk, ribonucleotides underlined; all other nucleotides are 2'-O-methylated) |
| 93 | 5'-U*U*GUCAAGAAAGGGUGUAACGCAA<u>CrAbAAG</u>UCAUAGUC*C*G-3' | Overexpressed and endogenous β-actin RNA bottom strand (rAb) (phosphorothioate modification marked with asterisk, ribonucleotides underlined; all other nucleotides are 2'-O-methylated) |
| 94 | 5'-U*G*UCUACUGUACAGAAUACUGCCG<u>CCAGC</u>UGGAUUUC*C*C-3' | Endogenous RAB7A RNA bottom strand (C) (phosphorothioate modification marked with asterisk, ribonucleotides underlined; all other nucleotides are 2'-O-methylated) |
| 95 | 5'-U*G*UCUACUGUACAGAAUACUGCCG<u>CrAbAGC</u>UGGAUUUC*C*C-3' | Endogenous RAB7A RNA bottom strand (rAb) (phosphorothioate modification marked with asterisk, ribonucleotides underlined; all other nucleotides are 2'-O-methylated) |
| 96 | 5'-AGACCCAGAAGCAACTCTTGAGTGTTAATATGTTGACCCCT-3' | Overexpressed β-actin RT FWD |
| 97 | 5'-GCATGCTCGAAGATGATAAGCTCCGGCAAGCA-3' | Overexpressed β-actin RT RVS |
| 98 | 5'-GTATTAGGGATGCGGGAATTGGGTACGAATTCCCCGTACATCGCT-3' | Overexpressed β-actin Nest FWD |
| 99 | 5'-ATATTGAACAACGCAAGGATCGGCGATATTCCACGTGATATCCCG-3' | Overexpressed β-actin Nest RVS |
| 100 | 5'-CAGCAGATGTGGATCAGCAAGCAGGAG-3' | Endogenous β-actin RT FWD |
| 101 | 5'-GGAAGGGGGGGCACGAAGGCTCATC-3' | Endogenous β-actin RT RVS |
| 102 | 5'-TATGACGAGTCCGGCCCCTCCATCGT-3' | Endogenous β-actin Nest FWD |
| 103 | 5'-GCAATGCTATCACCTCCCCTGTGTGGACT-3' | Endogenous β-actin Nest RVS |
| 104 | 5'-AACAAATAAAGCCATGCCAATCTCATCTTGTT-3 | Overexpressed and endogenous β-actin sequence primer |
| 105 | 5'-GCAACCAATTAAAATGTATAAATTAGTGTAAGAAATT-3' | Endogenous RAB7A RT FWD |
| 106 | 5'-GCTACAATGCAGGGGCAGATCCTAGGAAG-3' | Endogenous RAB7A RT RVS |
| 107 | 5'-CTTGGATTATGTGTTTAAGTCCTGTAATGCAGGCC-3' | Endogenous RAB7A Nest FWD |
| 108 | 5'-GGAGCAGAACTGCCAGGGTTCCAACC-3' | Endogenous RAB7A Nest RVS |
| 109 | 5'-CCGCTGGCTCTTTGATAAGAAATTCTTGGCTGAGG-3' | TMEM63B RT FWD |
| 110 | 5'-AGCCAGAAGAGGCAGAGGATGGGCG-3' | TMEM63B RT RVS |
| 111 | 5'-CAGCTATTCGGTTTGAGTGTGTGTTCC-3' | TMEM63B Nest FWD |
| 112 | 5'-CGGCCACCACCTGGTTCACAGCCC-3' | TMEM63B Nest RVS |
| 113 | 5'-TCCTGGCCAACCACAACAGGATCACCCAGTGTC-3' | CYFIP2 RT FWD |
| 114 | 5'-TAGGTCGAAGAGCTCGCGATACTCCTCGTCTG-3' | CYFIP2 RT RVS |
| 115 | 5'-TCCACCAGCAACTTGAAGTGATCCCAGGCTATGA-3' | CYFIP2 Nest FWD |
| 116 | 5'-ACTTCTGGCTGTCCAGCCCTGAGCCCG-3' | CYFIP2 Nest RVS |

Informal Sequence Listing

| SEQ ID NO: | Sequence | Description |
|---|---|---|
| 117 | 5'-TCAGTATCTGGACCCGGGAAGCTGGTGC-3' | FLNA RT FWD |
| 118 | 5'-TGCCGTTGAACTTGACGTCAATCAGGTAAACGCC-3' | FLNA RT RVS |
| 119 | 5'-TGGAGGCCTGGCCATTGCTGTCGAGGG-3' | FLNA Nest FWD |
| 120 | 5'-ATTCTCCCGAGGGATGAAGCGCACAGC-3' | FLNA Nest RVS |
| 121 | 5'-CAGATGCATAGATAGGGCAGTGTTCCAAGGA-3' | COG3 RT FWD |
| 122 | 5'-ACCTTTGTCATGAACTCCTCCAGCTGTTC-3' | COG3 RT RVS |
| 123 | 5'-TTATCACAGGAAGCATTGTCTGCCTGCATTCAGTC-3' | COG3 Nest FWD |
| 124 | 5'-TACAAACAGCTTGGTCTGCTGCTGAAT-3' | COG3 Nest RVS |
| 125 | 5'-CGAGCCGAGTATCCAGGATACAAC-3' | Gli1 RT FWD |
| 126 | 5'-CCCATATCCCAGAGTATCAGTAGGTGG-3' | Gli1 RT RVS |
| 127 | 5'-CCCAATGCAGGGGTCACCCGGAGGG-3' | Gli1 Nest FWD |
| 128 | 5'-GAAGTCCATATAGGGGTTCAGACCACTGCCCAC-3' | Gli1 Nest RVS |
| 129 | TKIESGYGTIPVR | Peptide sequence |
| 130 | 5'-<u>GAAGCAACTCTTGAGTGTTAATATGTTGACCCCTGTATT<br>AGGG</u>ATGCGGGAATTGGGTACGAATTCCCCGTACATCGCT<br>GTCCACCTTCCAGCAGATGTGGATCAGCAAGCAGGAGTAT<br>GACGAGTCCGGCCCCTCCATCGTCCACCGCAAATGCTTCT<br>AGGCGGACTATGACTTAGTTGCGTTACACCCTTTCTTGAC<br>AAAACCTAACTTGCGCAGAAAACAAGATGAGATTGCAT<br>GGCTTTATTTGTTTTTTTGTTTTGTTTTGGTTTTTTTTTTT<br>TTTTGGCTTGACTCAGGATTTAAAAACTGGAACGGTGAAG<br>GTGACAGCAGTCGGTTGGAGCGAGCATCCCCCAAAGTTCA<br>CAATGTGGCCGAGGACTTTGATTGCACATTGTTGTTTTTTT<br>AATAGTCATTCCAAATATGAGATGCGTTGTTACAGGAAGT<br>CCCTTGCCATCCTAAAAGCCACCCCACTTCTCTCTAAGGA<br>GAATGGCCCAGTCCTCTCCCAAGTCCACACAGGGGAGGTG<br>ATAGCATTGCTTTCGTGTAAATTATGTAATGCAAAATTTTT<br>TTAATCTTCGCCTTAATACTTTTTTATTTTGTTTTATTTTGA<br>ATGATGAGCCTTCGTGCCCCGGATCCGTGTCGGGATATCA<br>CGTGGAA<u>TATCGCCGATCCTTGCGTTGTTCAATATTGCTTG<br>CCGGAGCTTATCATCT</u>-3' | Sequence of a region of the 3'-UTR of β-actin RNA used for overexpression of directed editing target (Underlined corresponds to non-native sequence and bold is target A) |
| 131 | 5'-GCTAGAG-3' | Trace sequence |
| 132 | 5'-GCTGGAG-3' | Trace sequence |
| 133 | 5'-<br>(N)$_{67}$GCGCAUGUCGAACUUAGAGCGAAGUGCGAUACUUA<br>GAACCGGCGUA(N)$_{39}$-3' | Top strand sequence |
| 134 | 5'-<br>UACGCCGGUACYAAGUAUCGCACUUCGCACXAAGUUCGA<br>CAUGCGC-3' | Bottom strand sequence (X and Y denote C or reduced abasic site (rAb)) |
| 135 | 5'-<br>CUAGGCGGACUAUGACUUAGUUGCGUUACACCCUUUCU<br>UGACAAAACCU-3' | Top strand sequence |
| 136 | 5'-<br><u>UUG</u>UCAAGAAAGGGUGUAACGCAACXAAGUCAUAGU<u>CC<br>G</u>-3' | Bottom strand sequence (All nucleotides are 2'-O-methyl modified except those bolded black which are unmodified ribonucleotides. Underlining indicates sites of phosphorothioate modification. X = cytidine (C) or reduced abasic site (rAb)) |

Informal Sequence Listing

| SEQ ID NO: | Sequence | Description |
|---|---|---|
| 137 | TGTAACGCAACTAAGTCATAGTCCGCCTAG | Trace sequence |
| 138 | TGTAACGCAACX$_1$AAGTCATAGTCCGCCX$_2$AG, wherein X$_1$ is C or T and X$_2$ is C or T | Trace sequence |
| 139 | TGTAACGCAACX1AAGTCATAGTCCGCCTAG, wherein X$_1$ is C or T | Trace sequence |
| 140 | HHHHHHHHHHENLYFQGMFYAVRRGRKTGVFLTWNECRA QVDRFPAARFKKFATEDEAWAFVRKSASLHLDQTPSRQPIPS EGLQLHLPQVLADAVSRLVLGKFGDLTDNFSSPHARRKVLA GVVMTTGTDVKDAKVISVSTGTKCINGEYMSDRGLALNDC HAEIISRRSLLRFLYTQLELYLNNKDDQKRSIFQKSERGGFRL KENVQFHLYISTSPCGDARIFSPHEPILEEPADRHPNRKARGQ LRTKIESGEGTIPVRSNASIQTWDGVLQGERLLTMSCSDKIAR WNVVGIQGSLLSIFVEPIYFSSIILGSLYHGDHLSRAMYQRISN IEDLPPLYTLNKPLLSGISNAEARQPGKAPNFSVNWTVGDSAT EVINATTGKDELGRASRLCKHALYCRWMRVHGKVPSHLLRS KITKPNVYHESKLAAKEYQAAKARLFTAFIKAGLGAWVEKP TEQDQFSLTP | ADAR2-HBD fusion protein sequence (His tag: 1-10; TEV cleavage sequence: 11-17; HBD: 18-67; linker; 68-88; ADAR: 89-470) |
| 141 | LHLDQTPSRQPIPSEGLQLHL | Amino acid linker |
| 142 | ENLYFQG | TEV cleavage sequence |

What is claimed is:

1. A fusion protein comprising a human adenosine deaminase that acts on RNA (ADAR1) catalytic domain linked via an amino acid linker to a hybrid nucleic acid binding domain (NBD) from a human ribonuclease H that binds to a DNA-RNA hybrid molecule.

2. The fusion protein of claim 1, wherein the human ADAR1 catalytic domain comprises an E1008 mutation and the E1008 position is determined with reference to the sequence set forth in SEQ ID NO:48.

3. A pharmaceutical composition comprising the fusion protein of claim 1 and a pharmaceutically acceptable carrier.

4. A method for preventing or treating a genetic disorder in a subject, the method comprising administering to the subject a therapeutically effective amount of the pharmaceutical composition of claim 3.

5. The fusion protein of claim 1, wherein the human ADAR1 catalytic domain comprises amino acids 833-1226 of SEQ ID NO:48.

6. The fusion protein of claim 1, wherein the fusion protein modifies a target site without having to introduce a break into the DNA strand of the DNA-RNA hybrid molecule.

7. The fusion protein of claim 1, wherein the RNA strand of the DNA-RNA hybrid molecule comprises an abasic site.

8. The fusion protein of claim 7, wherein the human ADAR1 catalytic domain comprises an E1008W, E1008Y, or E1008F mutation and the E1008 position is determined with reference to the sequence set forth in SEQ ID NO:48.

9. The fusion protein of claim 2, wherein the E1008 mutation comprises an E1008Q mutation.

10. The fusion protein of claim 2, wherein the E1008 mutation comprises an E1008H mutation.

11. The fusion protein of claim 2, wherein the E1008 mutation comprises an E1008W, E1008Y, or E1008F mutation.

12. The fusion protein of claim 1, wherein the human ribonuclease H comprises human ribonuclease H1.

* * * * *

SEQUENCE LISTING

<160> NUMBER OF SEQ ID NOS: 147

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 1
agagggcucu gc                                                          12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 2
gcucgcgaug cu                                                          12

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

```
<400> SEQUENCE: 3
tttttgcaga gccctctagc atcgcgagct tttt                              34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaagctcg cgatgctaga gggctctgca aaaa                              34

<210> SEQ ID NO 5
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gcagagcccc ccagcaucgc gagc                                         24

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agagggctct gc                                                      12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gctcgcgatg ct                                                      12

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcagagcccc ccagcatcgc gagc                                         24

<210> SEQ ID NO 9
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 9
gcgcatagcc gcgctatccg ccaactcaat cgcgctcgcc tgaatagctc gcgatgctag    60
agggctctgc taccgcccca cgagggccag                                      90

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taatacgact cactataggg ctggccctcg tggggcggta                            40

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgcatagcc gcgctatccg                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctggccctcg tggggcggta                                                 20

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagcgctgaa ggtctcttct tctcatgact gaactcgcga gcgcatagcc gcgctatccg    60

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gagcgctgaa ggtctcttct                                                 20

<210> SEQ ID NO 15
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 15
gcagagcccu cuagcaucgc gagc                                            24

<210> SEQ ID NO 16
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gcagagcccu ccagcaucgc gagc                                            24

<210> SEQ ID NO 17
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gcagagcccc cuagcaucgc gagc                                            24

<210> SEQ ID NO 18
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gggcuggccc ucguggggcg guagcagagc ccucuagcau cgcgagcuau ucaggcgagc     60
gcgauugagu uggcggauag cgcggcuaug cgc                                  93

<210> SEQ ID NO 19
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
auccgguauu ccaagaacgc gagg                                            24

<210> SEQ ID NO 20
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gccaaaagga acuacgaggc auag                                            24

<210> SEQ ID NO 21
<211> LENGTH: 24
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 21
uuucagcgga gcgagaauag aaag                                          24

<210> SEQ ID NO 22
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ccgucaccga ccugagccau uugg                                          24

<210> SEQ ID NO 23
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ggacuccaac gccaaagggc gaaa                                          24

<210> SEQ ID NO 24
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ucaaaaauaa uccgcgucug gccu                                          24

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cttgtgggtt atctctctga tattagcgct c                                  31

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaataacctt gcttctgtaa atcgtcgcta t                                  31

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctactcgttc gcagaattgg gaatc                                    25

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaacgaggcg cagacggtca atc                                      23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gattgaccgt ctgcgcctcg ttc                                      23

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cagtgccttg agtaacagtg cccg                                     24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgggcactgt tactcaaggc actg                                     24

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gagcgctaat atcagagaga taacccacaa g                             31

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 33
ctggatatta ccagcaaggc cgatag                                        26

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gctcgaattc gtaatcatgg tcatagc                                       27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gctatgacca tgattacgaa ttcgagc                                       27

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gattcccaat tctgcgaacg agtag                                         25

<210> SEQ ID NO 37
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gcucgcgaug cuagagggcu cugc                                          24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gctcgcgatg ctagagggct ctgc                                          24

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
```
gaatagctcg cgatgctaga gggctctgct accg                               34

<210> SEQ ID NO 40
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cgguagcaga gcccycyagc aucgcgagcu auuc                               34

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ccaaatggct caagtcggtg acgg                                          24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctttctattc tcactccgct gaaa                                          24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctatgcctcg taattccttt tggc                                          24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aggccagacg cgaattattt ttga                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
tttcgcccatt tgacgttgga gtcc                                          24
```

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
cctcgcgttc ttagaatacc ggat                                           24
```

<210> SEQ ID NO 47
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
cgcgagcgca tagccgcgct atccgccaac tcaatcgcgc tcgcctgaat rgctcgcgat    60
gctggagggc tctgctaccg ccccacgagg g                                   91
```

<210> SEQ ID NO 48
<211> LENGTH: 1226
<212> TYPE: PRT
<213> ORGANISM: Homo sapiens

<400> SEQUENCE: 48

```
Met Asn Pro Arg Gln Gly Tyr Ser Leu Ser Gly Tyr Tyr Thr His Pro
1               5                   10                  15

Phe Gln Gly Tyr Glu His Arg Gln Leu Arg Tyr Gln Gln Pro Gly Pro
            20                  25                  30

Gly Ser Ser Pro Ser Ser Phe Leu Leu Lys Gln Ile Glu Phe Leu Lys
        35                  40                  45

Gly Gln Leu Pro Glu Ala Pro Val Ile Gly Lys Gln Thr Pro Ser Leu
    50                  55                  60

Pro Pro Ser Leu Pro Gly Leu Arg Pro Arg Phe Pro Val Leu Leu Ala
65                  70                  75                  80

Ser Ser Thr Arg Gly Arg Gln Val Asp Ile Arg Gly Val Pro Arg Gly
                85                  90                  95

Val His Leu Arg Ser Gln Gly Leu Gln Arg Gly Phe Gln His Pro Ser
            100                 105                 110

Pro Arg Gly Arg Ser Leu Pro Gln Arg Gly Val Asp Cys Leu Ser Ser
        115                 120                 125

His Phe Gln Glu Leu Ser Ile Tyr Gln Asp Gln Gln Arg Ile Leu
    130                 135                 140

Lys Phe Leu Glu Glu Leu Gly Glu Gly Lys Ala Thr Thr Ala His Asp
145                 150                 155                 160

Leu Ser Gly Lys Leu Gly Thr Pro Lys Lys Glu Ile Asn Arg Val Leu
                165                 170                 175

Tyr Ser Leu Ala Lys Lys Gly Lys Leu Gln Lys Glu Ala Gly Thr Pro
            180                 185                 190

Pro Leu Trp Lys Ile Ala Val Ser Thr Gln Ala Trp Asn Gln His Ser
        195                 200                 205

Gly Val Val Arg Pro Asp Gly His Ser Gln Gly Ala Pro Asn Ser Asp
    210                 215                 220
```

```
Pro Ser Leu Glu Pro Glu Asp Arg Asn Ser Thr Ser Val Ser Glu Asp
225                 230                 235                 240

Leu Leu Glu Pro Phe Ile Ala Val Ser Ala Gln Ala Trp Asn Gln His
            245                 250                 255

Ser Gly Val Val Arg Pro Asp Ser His Ser Gln Gly Ser Pro Asn Ser
                260                 265                 270

Asp Pro Gly Leu Glu Pro Glu Asp Ser Asn Ser Thr Ser Ala Leu Glu
            275                 280                 285

Asp Pro Leu Glu Phe Leu Asp Met Ala Glu Ile Lys Glu Lys Ile Cys
            290                 295                 300

Asp Tyr Leu Phe Asn Val Ser Asp Ser Ser Ala Leu Asn Leu Ala Lys
305                 310                 315                 320

Asn Ile Gly Leu Thr Lys Ala Arg Asp Ile Asn Ala Val Leu Ile Asp
                325                 330                 335

Met Glu Arg Gln Gly Asp Val Tyr Arg Gln Gly Thr Thr Pro Pro Ile
            340                 345                 350

Trp His Leu Thr Asp Lys Lys Arg Glu Arg Met Gln Ile Lys Arg Asn
            355                 360                 365

Thr Asn Ser Val Pro Glu Thr Ala Pro Ala Ala Ile Pro Glu Thr Lys
370                 375                 380

Arg Asn Ala Glu Phe Leu Thr Cys Asn Ile Pro Thr Ser Asn Ala Ser
385                 390                 395                 400

Asn Asn Met Val Thr Thr Glu Lys Val Glu Asn Gly Gln Glu Pro Val
                405                 410                 415

Ile Lys Leu Glu Asn Arg Gln Glu Ala Arg Pro Glu Pro Ala Arg Leu
                420                 425                 430

Lys Pro Pro Val His Tyr Asn Gly Pro Ser Lys Ala Gly Tyr Val Asp
            435                 440                 445

Phe Glu Asn Gly Gln Trp Ala Thr Asp Asp Ile Pro Asp Asp Leu Asn
            450                 455                 460

Ser Ile Arg Ala Ala Pro Gly Glu Phe Arg Ala Ile Met Glu Met Pro
465                 470                 475                 480

Ser Phe Tyr Ser His Gly Leu Pro Arg Cys Ser Pro Tyr Lys Lys Leu
                485                 490                 495

Thr Glu Cys Gln Leu Lys Asn Pro Ile Ser Gly Leu Leu Glu Tyr Ala
            500                 505                 510

Gln Phe Ala Ser Gln Thr Cys Glu Phe Asn Met Ile Glu Gln Ser Gly
            515                 520                 525

Pro Pro His Glu Pro Arg Phe Lys Phe Gln Val Val Ile Asn Gly Arg
            530                 535                 540

Glu Phe Pro Pro Ala Glu Ala Gly Ser Lys Lys Val Ala Lys Gln Asp
545                 550                 555                 560

Ala Ala Met Lys Ala Met Thr Ile Leu Leu Glu Glu Ala Lys Ala Lys
                565                 570                 575

Asp Ser Gly Lys Ser Glu Glu Ser Ser His Tyr Ser Thr Glu Lys Glu
            580                 585                 590

Ser Glu Lys Thr Ala Glu Ser Gln Thr Pro Thr Pro Ser Ala Thr Ser
            595                 600                 605

Phe Phe Ser Gly Lys Ser Pro Val Thr Thr Leu Leu Glu Cys Met His
            610                 615                 620

Lys Leu Gly Asn Ser Cys Glu Phe Arg Leu Leu Ser Lys Glu Gly Pro
625                 630                 635                 640
```

```
Ala His Glu Pro Lys Phe Gln Tyr Cys Val Ala Val Gly Ala Gln Thr
            645                 650                 655

Phe Pro Ser Val Ser Ala Pro Ser Lys Lys Val Ala Lys Gln Met Ala
        660                 665                 670

Ala Glu Glu Ala Met Lys Ala Leu His Gly Glu Ala Thr Asn Ser Met
        675                 680             685

Ala Ser Asp Asn Gln Pro Glu Gly Met Ile Ser Glu Ser Leu Asp Asn
    690                 695                 700

Leu Glu Ser Met Met Pro Asn Lys Val Arg Lys Ile Gly Glu Leu Val
705                 710                 715                 720

Arg Tyr Leu Asn Thr Asn Pro Val Gly Gly Leu Leu Glu Tyr Ala Arg
                725                 730                 735

Ser His Gly Phe Ala Ala Glu Phe Lys Leu Val Asp Gln Ser Gly Pro
            740                 745                 750

Pro His Glu Pro Lys Phe Val Tyr Gln Ala Lys Val Gly Gly Arg Trp
        755                 760                 765

Phe Pro Ala Val Cys Ala His Ser Lys Lys Gln Gly Lys Gln Glu Ala
        770                 775                 780

Ala Asp Ala Ala Leu Arg Val Leu Ile Gly Glu Asn Glu Lys Ala Glu
785                 790                 795                 800

Arg Met Gly Phe Thr Glu Val Thr Pro Val Thr Gly Ala Ser Leu Arg
                805                 810                 815

Arg Thr Met Leu Leu Ser Arg Ser Pro Glu Ala Gln Pro Lys Thr
                820                 825                 830

Leu Pro Leu Thr Gly Ser Thr Phe His Asp Gln Ile Ala Met Leu Ser
            835                 840                 845

His Arg Cys Phe Asn Thr Leu Thr Asn Ser Phe Gln Pro Ser Leu Leu
        850                 855                 860

Gly Arg Lys Ile Leu Ala Ala Ile Ile Met Lys Lys Asp Ser Glu Asp
865                 870                 875                 880

Met Gly Val Val Val Ser Leu Gly Thr Gly Asn Arg Cys Val Lys Gly
                885                 890                 895

Asp Ser Leu Ser Leu Lys Gly Glu Thr Val Asn Asp Cys His Ala Glu
            900                 905                 910

Ile Ile Ser Arg Arg Gly Phe Ile Arg Phe Leu Tyr Ser Glu Leu Met
        915                 920                 925

Lys Tyr Asn Ser Gln Thr Ala Lys Asp Ser Ile Phe Glu Pro Ala Lys
        930                 935                 940

Gly Gly Glu Lys Leu Gln Ile Lys Lys Thr Val Ser Phe His Leu Tyr
945                 950                 955                 960

Ile Ser Thr Ala Pro Cys Gly Asp Gly Ala Leu Phe Asp Lys Ser Cys
            965                 970                 975

Ser Asp Arg Ala Met Glu Ser Thr Glu Ser Arg His Tyr Pro Val Phe
        980                 985                 990

Glu Asn Pro Lys Gln Gly Lys Leu Arg Thr Lys Val Glu Asn Gly Glu
        995                 1000                1005

Gly Thr Ile Pro Val Glu Ser Ser Asp Ile Val Pro Thr Trp Asp
        1010                1015                1020

Gly Ile Arg Leu Gly Glu Arg Leu Arg Thr Met Ser Cys Ser Asp
        1025                1030                1035

Lys Ile Leu Arg Trp Asn Val Leu Gly Leu Gln Gly Ala Leu Leu
        1040                1045                1050

Thr His Phe Leu Gln Pro Ile Tyr Leu Lys Ser Val Thr Leu Gly
```

```
            1055                1060                1065

Tyr Leu Phe Ser Gln Gly His Leu Thr Arg Ala Ile Cys Cys Arg
            1070                1075                1080

Val Thr Arg Asp Gly Ser Ala Phe Glu Asp Gly Leu Arg His Pro
            1085                1090                1095

Phe Ile Val Asn His Pro Lys Val Gly Arg Val Ser Ile Tyr Asp
            1100                1105                1110

Ser Lys Arg Gln Ser Gly Lys Thr Lys Glu Thr Ser Val Asn Trp
            1115                1120                1125

Cys Leu Ala Asp Gly Tyr Asp Leu Glu Ile Leu Asp Gly Thr Arg
            1130                1135                1140

Gly Thr Val Asp Gly Pro Arg Asn Glu Leu Ser Arg Val Ser Lys
            1145                1150                1155

Lys Asn Ile Phe Leu Leu Phe Lys Lys Leu Cys Ser Phe Arg Tyr
            1160                1165                1170

Arg Arg Asp Leu Leu Arg Leu Ser Tyr Gly Glu Ala Lys Lys Ala
            1175                1180                1185

Ala Arg Asp Tyr Glu Thr Ala Lys Asn Tyr Phe Lys Lys Gly Leu
            1190                1195                1200

Lys Asp Met Gly Tyr Gly Asn Trp Ile Ser Lys Pro Gln Glu Glu
            1205                1210                1215

Lys Asn Phe Tyr Leu Cys Pro Val
            1220                1225

<210> SEQ ID NO 49
<211> LENGTH: 701
<212> TYPE: PRT
<213> ORGANISM: Homo sapiens

<400> SEQUENCE: 49

Met Asp Ile Glu Asp Glu Glu Asn Met Ser Ser Ser Thr Asp Val
1               5                   10                  15

Lys Glu Asn Arg Asn Leu Asp Asn Val Ser Pro Lys Asp Gly Ser Thr
                20                  25                  30

Pro Gly Pro Gly Glu Gly Ser Gln Leu Ser Asn Gly Gly Gly Gly
        35                  40                  45

Pro Gly Arg Lys Arg Pro Leu Glu Glu Gly Ser Asn Gly His Ser Lys
    50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
                100                 105                 110

Val Glu Val Asn Gly Gln Val Phe Glu Gly Ser Gly Pro Thr Lys Lys
            115                 120                 125

Lys Ala Lys Leu His Ala Ala Glu Lys Ala Leu Arg Ser Phe Val Gln
        130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
                180                 185                 190
```

-continued

Gly Ser Asn Gly Asp Asp Ser Phe Ser Ser Gly Asp Leu Ser Leu
            195                 200                 205

Ser Ala Ser Pro Val Pro Ala Ser Leu Ala Gln Pro Pro Leu Pro Val
210                 215                 220

Leu Pro Pro Phe Pro Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
    290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
            340                 345                 350

Ala Gly Val Val Met Thr Thr Gly Thr Asp Val Lys Asp Ala Lys Val
        355                 360                 365

Ile Ser Val Ser Thr Gly Thr Lys Cys Ile Asn Gly Glu Tyr Met Ser
    370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
        435                 440                 445

Ser Pro Cys Gly Asp Ala Arg Ile Phe Ser Pro His Glu Pro Ile Leu
    450                 455                 460

Glu Glu Pro Ala Asp Arg His Pro Asn Arg Lys Ala Arg Gly Gln Leu
465                 470                 475                 480

Arg Thr Lys Ile Glu Ser Gly Glu Gly Thr Ile Pro Val Arg Ser Asn
                485                 490                 495

Ala Ser Ile Gln Thr Trp Asp Gly Val Leu Gln Gly Glu Arg Leu Leu
            500                 505                 510

Thr Met Ser Cys Ser Asp Lys Ile Ala Arg Trp Asn Val Val Gly Ile
        515                 520                 525

Gln Gly Ser Leu Leu Ser Ile Phe Val Glu Pro Ile Tyr Phe Ser Ser
    530                 535                 540

Ile Ile Leu Gly Ser Leu Tyr His Gly Asp His Leu Ser Arg Ala Met
545                 550                 555                 560

Tyr Gln Arg Ile Ser Asn Ile Glu Asp Leu Pro Pro Leu Tyr Thr Leu
                565                 570                 575

Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
        595                 600                 605

Ile Glu Val Ile Asn Ala Thr Thr Gly Lys Asp Glu Leu Gly Arg Ala

```
                610                 615                 620
Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
            645                 650                 655

Val Tyr His Glu Ser Lys Leu Ala Ala Lys Glu Tyr Gln Ala Ala Lys
            660                 665                 670

Ala Arg Leu Phe Thr Ala Phe Ile Lys Ala Gly Leu Gly Ala Trp Val
        675                 680                 685

Glu Lys Pro Thr Glu Gln Asp Gln Phe Ser Leu Thr Pro
690                 695                 700

<210> SEQ ID NO 50
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: c or reduced abasic nucleotide

<400> SEQUENCE: 50
cagagccccc nagcaucgcg agc                                         23

<210> SEQ ID NO 51
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gcucgcgaug cuagagggcu cug                                         23

<210> SEQ ID NO 52
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Asp Ile Glu Asp Glu Glu Asn Met Ser Ser Ser Thr Asp Val
1               5                   10                  15

Lys Glu Asn Arg Asn Leu Asp Asn Val Ser Pro Lys Asp Gly Ser Thr
            20                  25                  30

Pro Gly Pro Gly Glu Gly Ser Gln Leu Ser Asn Gly Gly Gly Gly
        35                  40                  45

Pro Gly Arg Lys Arg Pro Leu Glu Glu Gly Ser Asn Gly His Ser Lys
    50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110
```

```
Val Glu Val Asn Gly Gln Val Phe Glu Gly Ser Gly Pro Thr Lys Lys
            115                 120                 125

Lys Ala Lys Leu His Ala Glu Lys Ala Leu Arg Ser Phe Val Gln
130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
                180                 185                 190

Gly Ser Asn Gly Asp Asp Ser Phe Ser Ser Gly Asp Leu Ser Leu
            195                 200                 205

Ser Ala Ser Pro Val Pro Ala Ser Leu Ala Gln Pro Pro Leu Pro Val
            210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Asp Gly Gln
            260                 265                 270

Phe Phe Glu Gly Ser Gly Arg Asn Lys Lys Leu Ala Lys Ala Arg Ala
            275                 280                 285

Ala Gln Ser Ala Leu Ala Ala Ile Phe Asn Leu His Leu Asp Gln Thr
            290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
                340                 345                 350

Ala Gly Val Val Met Thr Thr Gly Thr Asp Val Lys Asp Ala Lys Val
            355                 360                 365

Ile Ser Val Ser Thr Gly Thr Lys Cys Ile Asn Gly Glu Tyr Met Ser
370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
            435                 440                 445

Ser Pro Cys Gly Asp Ala Arg Ile Phe Ser Pro His Glu Pro Ile Leu
    450                 455                 460

Glu Glu Pro Ala Asp Arg His Pro Asn Arg Lys Ala Arg Gly Gln Leu
465                 470                 475                 480

Arg Thr Lys Ile Glu Ser Gly Phe Gly Thr Ile Pro Val Arg Ser Asn
                485                 490                 495

Ala Ser Ile Gln Thr Trp Asp Gly Val Leu Gln Gly Glu Arg Leu Leu
            500                 505                 510

Thr Met Ser Cys Ser Asp Lys Ile Ala Arg Trp Asn Val Val Gly Ile
            515                 520                 525

Gln Gly Ser Leu Leu Ser Ile Phe Val Glu Pro Ile Tyr Phe Ser Ser
```

```
                    530                 535                 540
Ile Ile Leu Gly Ser Leu Tyr His Gly Asp His Leu Ser Arg Ala Met
545                 550                 555                 560

Tyr Gln Arg Ile Ser Asn Ile Glu Asp Leu Pro Pro Leu Tyr Thr Leu
                    565                 570                 575

Asn Lys Pro Leu Leu Ser Gly Ile Ser Asn Ala Glu Ala Arg Gln Pro
                580                 585                 590

Gly Lys Ala Pro Asn Phe Ser Val Asn Trp Thr Val Gly Asp Ser Ala
            595                 600                 605

Ile Glu Val Ile Asn Ala Thr Thr Gly Lys Asp Glu Leu Gly Arg Ala
        610                 615                 620

Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
                660                 665                 670

Ala Arg Leu Phe Thr Ala Phe Ile Lys Ala Gly Leu Gly Ala Trp Val
            675                 680                 685

Glu Lys Pro Thr Glu Gln Asp Gln Phe Ser Leu Thr Pro
        690                 695                 700

<210> SEQ ID NO 53
<211> LENGTH: 1226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Asn Pro Arg Gln Gly Tyr Ser Leu Ser Gly Tyr Tyr Thr His Pro
1               5                   10                  15

Phe Gln Gly Tyr Glu His Arg Gln Leu Arg Tyr Gln Pro Gly Pro
            20                  25                  30

Gly Ser Ser Pro Ser Ser Phe Leu Leu Lys Gln Ile Glu Phe Leu Lys
        35                  40                  45

Gly Gln Leu Pro Glu Ala Pro Val Ile Gly Lys Gln Thr Pro Ser Leu
    50                  55                  60

Pro Pro Ser Leu Pro Gly Leu Arg Pro Arg Phe Pro Val Leu Leu Ala
65                  70                  75                  80

Ser Ser Thr Arg Gly Arg Gln Val Asp Ile Arg Gly Val Pro Arg Gly
                85                  90                  95

Val His Leu Arg Ser Gln Gly Leu Gln Arg Gly Phe Gln His Pro Ser
            100                 105                 110

Pro Arg Gly Arg Ser Leu Pro Gln Arg Gly Val Asp Cys Leu Ser Ser
        115                 120                 125

His Phe Gln Glu Leu Ser Ile Tyr Gln Asp Gln Gln Arg Ile Leu
    130                 135                 140

Lys Phe Leu Glu Glu Leu Gly Glu Gly Lys Ala Thr Thr Ala His Asp
145                 150                 155                 160

Leu Ser Gly Lys Leu Gly Thr Pro Lys Lys Glu Ile Asn Arg Val Leu
                165                 170                 175

Tyr Ser Leu Ala Lys Lys Gly Lys Leu Gln Lys Glu Ala Gly Thr Pro
            180                 185                 190
```

-continued

```
Pro Leu Trp Lys Ile Ala Val Ser Thr Gln Ala Trp Asn Gln His Ser
            195                 200                 205
Gly Val Val Arg Pro Asp Gly His Ser Gln Gly Ala Pro Asn Ser Asp
        210                 215                 220
Pro Ser Leu Glu Pro Glu Asp Arg Asn Ser Thr Ser Val Ser Glu Asp
225                 230                 235                 240
Leu Leu Glu Pro Phe Ile Ala Val Ser Ala Gln Ala Trp Asn Gln His
                245                 250                 255
Ser Gly Val Val Arg Pro Asp Ser His Ser Gln Gly Ser Pro Asn Ser
            260                 265                 270
Asp Pro Gly Leu Glu Pro Glu Asp Ser Asn Ser Thr Ser Ala Leu Glu
        275                 280                 285
Asp Pro Leu Glu Phe Leu Asp Met Ala Glu Ile Lys Glu Lys Ile Cys
    290                 295                 300
Asp Tyr Leu Phe Asn Val Ser Asp Ser Ser Ala Leu Asn Leu Ala Lys
305                 310                 315                 320
Asn Ile Gly Leu Thr Lys Ala Arg Asp Ile Asn Ala Val Leu Ile Asp
                325                 330                 335
Met Glu Arg Gln Gly Asp Val Tyr Arg Gln Gly Thr Thr Pro Pro Ile
            340                 345                 350
Trp His Leu Thr Asp Lys Lys Arg Glu Arg Met Gln Ile Lys Arg Asn
        355                 360                 365
Thr Asn Ser Val Pro Glu Thr Ala Pro Ala Ala Ile Pro Glu Thr Lys
    370                 375                 380
Arg Asn Ala Glu Phe Leu Thr Cys Asn Ile Pro Thr Ser Asn Ala Ser
385                 390                 395                 400
Asn Asn Met Val Thr Thr Glu Lys Val Glu Asn Gly Gln Glu Pro Val
                405                 410                 415
Ile Lys Leu Glu Asn Arg Gln Glu Ala Arg Pro Glu Pro Ala Arg Leu
            420                 425                 430
Lys Pro Pro Val His Tyr Asn Gly Pro Ser Lys Ala Gly Tyr Val Asp
        435                 440                 445
Phe Glu Asn Gly Gln Trp Ala Thr Asp Asp Ile Pro Asp Asp Leu Asn
    450                 455                 460
Ser Ile Arg Ala Ala Pro Gly Glu Phe Arg Ala Ile Met Glu Met Pro
465                 470                 475                 480
Ser Phe Tyr Ser His Gly Leu Pro Arg Cys Ser Pro Tyr Lys Lys Leu
                485                 490                 495
Thr Glu Cys Gln Leu Lys Asn Pro Ile Ser Gly Leu Leu Glu Tyr Ala
            500                 505                 510
Gln Phe Ala Ser Gln Thr Cys Glu Phe Asn Met Ile Glu Gln Ser Gly
        515                 520                 525
Pro Pro His Glu Pro Arg Phe Lys Phe Gln Val Val Ile Asn Gly Arg
    530                 535                 540
Glu Phe Pro Pro Ala Glu Ala Gly Ser Lys Lys Val Ala Lys Gln Asp
545                 550                 555                 560
Ala Ala Met Lys Ala Met Thr Ile Leu Leu Glu Glu Ala Lys Ala Lys
                565                 570                 575
Asp Ser Gly Lys Ser Glu Glu Ser Ser His Tyr Ser Thr Glu Lys Glu
            580                 585                 590
Ser Glu Lys Thr Ala Glu Ser Gln Thr Pro Thr Pro Ser Ala Thr Ser
        595                 600                 605
Phe Phe Ser Gly Lys Ser Pro Val Thr Thr Leu Leu Glu Cys Met His
```

```
            610                 615                 620
Lys Leu Gly Asn Ser Cys Glu Phe Arg Leu Leu Ser Lys Glu Gly Pro
625                 630                 635                 640

Ala His Glu Pro Lys Phe Gln Tyr Cys Val Ala Val Gly Ala Gln Thr
            645                 650                 655

Phe Pro Ser Val Ser Ala Pro Ser Lys Val Ala Lys Gln Met Ala
            660                 665                 670

Ala Glu Ala Met Lys Ala Leu His Gly Glu Ala Thr Asn Ser Met
            675                 680                 685

Ala Ser Asp Asn Gln Pro Glu Gly Met Ile Ser Glu Ser Leu Asp Asn
690                 695                 700

Leu Glu Ser Met Met Pro Asn Lys Val Arg Lys Ile Gly Glu Leu Val
705                 710                 715                 720

Arg Tyr Leu Asn Thr Asn Pro Val Gly Gly Leu Leu Glu Tyr Ala Arg
                725                 730                 735

Ser His Gly Phe Ala Ala Glu Phe Lys Leu Val Asp Gln Ser Gly Pro
            740                 745                 750

Pro His Glu Pro Lys Phe Val Tyr Gln Ala Lys Val Gly Gly Arg Trp
            755                 760                 765

Phe Pro Ala Val Cys Ala His Ser Lys Lys Gln Gly Lys Gln Glu Ala
770                 775                 780

Ala Asp Ala Ala Leu Arg Val Leu Ile Gly Glu Asn Glu Lys Ala Glu
785                 790                 795                 800

Arg Met Gly Phe Thr Glu Val Thr Pro Val Thr Gly Ala Ser Leu Arg
                805                 810                 815

Arg Thr Met Leu Leu Leu Ser Arg Ser Pro Glu Ala Gln Pro Lys Thr
                820                 825                 830

Leu Pro Leu Thr Gly Ser Thr Phe His Asp Gln Ile Ala Met Leu Ser
            835                 840                 845

His Arg Cys Phe Asn Thr Leu Thr Asn Ser Phe Gln Pro Ser Leu Leu
            850                 855                 860

Gly Arg Lys Ile Leu Ala Ala Ile Ile Met Lys Lys Asp Ser Glu Asp
865                 870                 875                 880

Met Gly Val Val Val Ser Leu Gly Thr Gly Asn Arg Cys Val Lys Gly
                    885                 890                 895

Asp Ser Leu Ser Leu Lys Gly Glu Thr Val Asn Asp Cys His Ala Glu
                900                 905                 910

Ile Ile Ser Arg Arg Gly Phe Ile Arg Phe Leu Tyr Ser Glu Leu Met
            915                 920                 925

Lys Tyr Asn Ser Gln Thr Ala Lys Asp Ser Ile Phe Glu Pro Ala Lys
930                 935                 940

Gly Gly Glu Lys Leu Gln Ile Lys Lys Thr Val Ser Phe His Leu Tyr
945                 950                 955                 960

Ile Ser Thr Ala Pro Cys Gly Asp Gly Ala Leu Phe Asp Lys Ser Cys
                965                 970                 975

Ser Asp Arg Ala Met Glu Ser Thr Glu Ser Arg His Tyr Pro Val Phe
            980                 985                 990

Glu Asn Pro Lys Gln Gly Lys Leu Arg Thr Lys Val Glu Asn Gly Gln
            995                 1000                1005

Gly Thr Ile Pro Val Glu Ser Ser Asp Ile Val Pro Thr Trp Asp
            1010                1015                1020

Gly Ile Arg Leu Gly Glu Arg Leu Arg Thr Met Ser Cys Ser Asp
            1025                1030                1035
```

```
Lys Ile Leu Arg Trp Asn Val Leu Gly Leu Gln Gly Ala Leu Leu
    1040                1045                1050

Thr His Phe Leu Gln Pro Ile Tyr Leu Lys Ser Val Thr Leu Gly
    1055                1060                1065

Tyr Leu Phe Ser Gln Gly His Leu Thr Arg Ala Ile Cys Cys Arg
    1070                1075                1080

Val Thr Arg Asp Gly Ser Ala Phe Glu Asp Gly Leu Arg His Pro
    1085                1090                1095

Phe Ile Val Asn His Pro Lys Val Gly Arg Val Ser Ile Tyr Asp
    1100                1105                1110

Ser Lys Arg Gln Ser Gly Lys Thr Lys Glu Thr Ser Val Asn Trp
    1115                1120                1125

Cys Leu Ala Asp Gly Tyr Asp Leu Glu Ile Leu Asp Gly Thr Arg
    1130                1135                1140

Gly Thr Val Asp Gly Pro Arg Asn Glu Leu Ser Arg Val Ser Lys
    1145                1150                1155

Lys Asn Ile Phe Leu Leu Phe Lys Lys Leu Cys Ser Phe Arg Tyr
    1160                1165                1170

Arg Arg Asp Leu Leu Arg Leu Ser Tyr Gly Glu Ala Lys Lys Ala
    1175                1180                1185

Ala Arg Asp Tyr Glu Thr Ala Lys Asn Tyr Phe Lys Lys Gly Leu
    1190                1195                1200

Lys Asp Met Gly Tyr Gly Asn Trp Ile Ser Lys Pro Gln Glu Glu
    1205                1210                1215

Lys Asn Phe Tyr Leu Cys Pro Val
    1220                1225

<210> SEQ ID NO 54
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Asp Ile Glu Asp Glu Glu Asn Met Ser Ser Ser Thr Asp Val
1               5                   10                  15

Lys Glu Asn Arg Asn Leu Asp Asn Val Ser Pro Lys Asp Gly Ser Thr
                20                  25                  30

Pro Gly Pro Gly Glu Gly Ser Gln Leu Ser Asn Gly Gly Gly Gly
            35                  40                  45

Pro Gly Arg Lys Arg Pro Leu Glu Glu Gly Ser Asn Gly His Ser Lys
        50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
```

```
            145                 150                 155                 160

Val Asn Thr Asp Phe Thr Ser Asp Gln Ala Asp Phe Pro Asp Thr Leu
                        165                 170                 175

Phe Asn Gly Phe Glu Thr Pro Asp Lys Ala Glu Pro Pro Phe Tyr Val
                        180                 185                 190

Gly Ser Asn Gly Asp Asp Ser Phe Ser Ser Gly Asp Leu Ser Leu
                        195                 200                 205

Ser Ala Ser Pro Val Pro Ala Ser Leu Ala Gln Pro Pro Leu Pro Val
        210                 215                 220

Leu Pro Pro Phe Pro Pro Ser Gly Lys Asn Pro Val Met Ile Leu
        225                 230                 235                 240

Asn Glu Leu Arg Pro Gly Leu Lys Tyr Asp Phe Leu Ser Glu Ser Gly
                        245                 250                 255

Glu Ser His Ala Lys Ser Phe Val Met Ser Val Val Asp Gly Gln
                        260                 265                 270

Phe Phe Glu Gly Ser Gly Arg Asn Lys Lys Leu Ala Lys Ala Arg Ala
                        275                 280                 285

Ala Gln Ser Ala Leu Ala Ala Ile Phe Asn Leu His Leu Asp Gln Thr
                        290                 295                 300

Pro Ser Arg Gln Pro Ile Pro Ser Glu Gly Leu Gln Leu His Leu Pro
        305                 310                 315                 320

Gln Val Leu Ala Asp Ala Val Ser Arg Leu Val Leu Gly Lys Phe Gly
                        325                 330                 335

Asp Leu Thr Asp Asn Phe Ser Ser Pro His Ala Arg Arg Lys Val Leu
                        340                 345                 350

Ala Gly Val Val Met Thr Thr Gly Thr Asp Val Lys Asp Ala Lys Val
                        355                 360                 365

Ile Ser Val Ser Thr Gly Thr Lys Cys Ile Asn Gly Glu Tyr Met Ser
                        370                 375                 380

Asp Arg Gly Leu Ala Leu Asn Asp Cys His Ala Glu Ile Ile Ser Arg
        385                 390                 395                 400

Arg Ser Leu Leu Arg Phe Leu Tyr Thr Gln Leu Glu Leu Tyr Leu Asn
                        405                 410                 415

Asn Lys Asp Asp Gln Lys Arg Ser Ile Phe Gln Lys Ser Glu Arg Gly
                        420                 425                 430

Gly Phe Arg Leu Lys Glu Asn Val Gln Phe His Leu Tyr Ile Ser Thr
                        435                 440                 445

Ser Pro Cys Gly Asp Ala Arg Ile Phe Ser Pro His Glu Pro Ile Leu
        450                 455                 460

Glu Glu Pro Ala Asp Arg His Pro Asn Arg Lys Ala Arg Gly Gln Leu
        465                 470                 475                 480

Arg Thr Lys Ile Glu Ser Gly Gln Gly Thr Ile Pro Val Arg Ser Asn
                        485                 490                 495

Ala Ser Ile Gln Thr Trp Asp Gly Val Leu Gln Gly Glu Arg Leu Leu
                        500                 505                 510

Thr Met Ser Cys Ser Asp Lys Ile Ala Arg Trp Asn Val Val Gly Ile
                        515                 520                 525

Gln Gly Ser Leu Leu Ser Ile Phe Val Glu Pro Ile Tyr Phe Ser Ser
                        530                 535                 540

Ile Ile Leu Gly Ser Leu Tyr His Gly Asp His Leu Ser Arg Ala Met
        545                 550                 555                 560

Tyr Gln Arg Ile Ser Asn Ile Glu Asp Leu Pro Pro Leu Tyr Thr Leu
                        565                 570                 575
```

-continued

```
Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
        595                 600                 605

Ile Glu Val Ile Asn Ala Thr Thr Gly Lys Asp Glu Leu Gly Arg Ala
    610                 615                 620

Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
            660                 665                 670

Ala Arg Leu Phe Thr Ala Phe Ile Lys Ala Gly Leu Gly Ala Trp Val
        675                 680                 685

Glu Lys Pro Thr Glu Gln Asp Gln Phe Ser Leu Thr Pro
690                 695                 700
```

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 55
gcucgcgaug cuagagggcu cugc                                        24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 56
gcagagcccc ccagcaucgc gagc                                        24

<210> SEQ ID NO 57
<211> LENGTH: 12
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 57
agagggcucu gc                                                     12

<210> SEQ ID NO 58
<211> LENGTH: 12
<212> TYPE: RNA
<213> ORGANISM: Artificial Sequence
<220> FEATURE:
<223> OTHER INFORMATION: Description of Artificial Sequence: Synthetic
    oligonucleotide -continued

```
<400> SEQUENCE: 58
gcucgcgaug cu                                                         12

<210> SEQ ID NO 59
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (488)..(488)
<223> OTHER INFORMATION: Any amino acid

<400> SEQUENCE: 59
```

Met Asp Ile Glu Asp Glu Glu Asn Met Ser Ser Ser Thr Asp Val
1               5                   10                  15

Lys Glu Asn Arg Asn Leu Asp Asn Val Ser Pro Lys Asp Gly Ser Thr
            20                  25                  30

Pro Gly Pro Gly Glu Gly Ser Gln Leu Ser Asn Gly Gly Gly Gly
        35                  40                  45

Pro Gly Arg Lys Arg Pro Leu Glu Glu Gly Ser Asn Gly His Ser Lys
    50                  55                  60

Tyr Arg Leu Lys Lys Arg Arg Lys Thr Pro Gly Pro Val Leu Pro Lys
65              70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Ser Gly Asp Leu Ser Leu
        195                 200                 205

Ser Ala Ser Pro Val Pro Ala Ser Leu Ala Gln Pro Pro Leu Pro Val
    210                 215                 220

Leu Pro Pro Phe Pro Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
    290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
            325                 330                 335

Asp Leu Thr Asp Asn Phe Ser Ser Pro His Ala Arg Arg Lys Val Leu
        340                 345                 350

Ala Gly Val Val Met Thr Thr Gly Thr Asp Val Lys Asp Ala Lys Val
    355                 360                 365

Ile Ser Val Ser Thr Gly Thr Lys Cys Ile Asn Gly Glu Tyr Met Ser
370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
        435                 440                 445

Ser Pro Cys Gly Asp Ala Arg Ile Phe Ser Pro His Glu Pro Ile Leu
    450                 455                 460

Glu Glu Pro Ala Asp Arg His Pro Asn Arg Lys Ala Arg Gly Gln Leu
465                 470                 475                 480

Arg Thr Lys Ile Glu Ser Gly Xaa Gly Thr Ile Pro Val Arg Ser Asn
                485                 490                 495

Ala Ser Ile Gln Thr Trp Asp Gly Val Leu Gln Gly Glu Arg Leu Leu
            500                 505                 510

Thr Met Ser Cys Ser Asp Lys Ile Ala Arg Trp Asn Val Val Gly Ile
        515                 520                 525

Gln Gly Ser Leu Leu Ser Ile Phe Val Glu Pro Ile Tyr Phe Ser Ser
    530                 535                 540

Ile Ile Leu Gly Ser Leu Tyr His Gly Asp His Leu Ser Arg Ala Met
545                 550                 555                 560

Tyr Gln Arg Ile Ser Asn Ile Glu Asp Leu Pro Pro Leu Tyr Thr Leu
                565                 570                 575

Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
        595                 600                 605

Ile Glu Val Ile Asn Ala Thr Thr Gly Lys Asp Glu Leu Gly Arg Ala
    610                 615                 620

Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
            660                 665                 670

Ala Arg Leu Phe Thr Ala Phe Ile Lys Ala Gly Leu Gly Ala Trp Val
        675                 680                 685

Glu Lys Pro Thr Glu Gln Asp Gln Phe Ser Leu Thr Pro
    690                 695                 700

<210> SEQ ID NO 60
<211> LENGTH: 701
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Met Asp Ile Glu Asp Glu Asn Met Ser Ser Ser Thr Asp Val
1               5                   10                  15

Lys Glu Asn Arg Asn Leu Asp Asn Val Ser Pro Lys Asp Gly Ser Thr
            20                  25                  30

Pro Gly Pro Gly Glu Gly Ser Gln Leu Ser Asn Gly Gly Gly Gly
        35                  40                  45

Pro Gly Arg Lys Arg Pro Leu Glu Glu Gly Ser Asn Gly His Ser Lys
    50                  55                  60

Tyr Arg Leu Lys Lys Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Ser Gly Asp Leu Ser Leu
        195                 200                 205

Ser Ala Ser Pro Val Pro Ala Ser Leu Ala Gln Pro Pro Leu Pro Val
    210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
    290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
            340                 345                 350

Ala Gly Val Val Met Thr Thr Gly Thr Asp Val Lys Asp Ala Lys Val
        355                 360                 365

Ile Ser Val Ser Thr Gly Thr Lys Cys Ile Asn Gly Glu Tyr Met Ser
    370                 375                 380

Asp Arg Gly Leu Ala Leu Asn Asp Cys His Ala Glu Ile Ile Ser Arg
385                 390                 395                 400
```

```
Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
        435                 440                 445

Ser Pro Cys Gly Asp Ala Arg Ile Phe Ser Pro His Glu Pro Ile Leu
    450                 455                 460

Glu Glu Pro Ala Asp Arg His Pro Asn Arg Lys Ala Arg Gly Gln Leu
465                 470                 475                 480

Arg Thr Lys Ile Glu Ser Gly His Gly Thr Ile Pro Val Arg Ser Asn
                485                 490                 495

Ala Ser Ile Gln Thr Trp Asp Gly Val Leu Gln Gly Glu Arg Leu Leu
            500                 505                 510

Thr Met Ser Cys Ser Asp Lys Ile Ala Arg Trp Asn Val Val Gly Ile
        515                 520                 525

Gln Gly Ser Leu Leu Ser Ile Phe Val Glu Pro Ile Tyr Phe Ser Ser
    530                 535                 540

Ile Ile Leu Gly Ser Leu Tyr His Gly Asp His Leu Ser Arg Ala Met
545                 550                 555                 560

Tyr Gln Arg Ile Ser Asn Ile Glu Asp Leu Pro Pro Leu Tyr Thr Leu
                565                 570                 575

Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
        595                 600                 605

Ile Glu Val Ile Asn Ala Thr Thr Gly Lys Asp Glu Leu Gly Arg Ala
    610                 615                 620

Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
            660                 665                 670

Ala Arg Leu Phe Thr Ala Phe Ile Lys Ala Gly Leu Gly Ala Trp Val
        675                 680                 685

Glu Lys Pro Thr Glu Gln Asp Gln Phe Ser Leu Thr Pro
            690                 695                 700

<210> SEQ ID NO 61
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Asp Ile Glu Asp Glu Glu Asn Met Ser Ser Ser Ser Thr Asp Val
1               5                   10                  15

Lys Glu Asn Arg Asn Leu Asp Asn Val Ser Pro Lys Asp Gly Ser Thr
            20                  25                  30

Pro Gly Pro Gly Glu Gly Ser Gln Leu Ser Asn Gly Gly Gly Gly Gly
        35                  40                  45

Pro Gly Arg Lys Arg Pro Leu Glu Glu Gly Ser Asn Gly His Ser Lys
    50                  55                  60
```

```
Tyr Arg Leu Lys Lys Arg Arg Lys Thr Pro Gly Pro Val Leu Pro Lys
 65                  70                  75                  80

Asn Ala Leu Met Gln Leu Asn Glu Ile Lys Pro Gly Leu Gln Tyr Thr
                 85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Gly Asp Leu Ser Leu
        195                 200                 205

Ser Ala Ser Pro Val Pro Ala Ser Leu Ala Gln Pro Pro Leu Pro Val
210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Asp Gly Gln
            260                 265                 270

Phe Phe Glu Gly Ser Gly Arg Asn Lys Lys Leu Ala Lys Ala Arg Ala
            275                 280                 285

Ala Gln Ser Ala Leu Ala Ala Ile Phe Asn Leu His Leu Asp Gln Thr
            290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
            340                 345                 350

Ala Gly Val Val Met Thr Thr Gly Thr Asp Val Lys Asp Ala Lys Val
            355                 360                 365

Ile Ser Val Ser Thr Gly Thr Lys Cys Ile Asn Gly Glu Tyr Met Ser
            370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
            435                 440                 445

Ser Pro Cys Gly Asp Ala Arg Ile Phe Ser Pro His Glu Pro Ile Leu
            450                 455                 460

Glu Glu Pro Ala Asp Arg His Pro Asn Arg Lys Ala Arg Gly Gln Leu
465                 470                 475                 480
```

```
Arg Thr Lys Ile Glu Ser Gly Tyr Gly Thr Ile Pro Val Arg Ser Asn
                485                 490                 495

Ala Ser Ile Gln Thr Trp Asp Gly Val Leu Gln Gly Glu Arg Leu Leu
            500                 505                 510

Thr Met Ser Cys Ser Asp Lys Ile Ala Arg Trp Asn Val Val Gly Ile
        515                 520                 525

Gln Gly Ser Leu Leu Ser Ile Phe Val Glu Pro Ile Tyr Phe Ser Ser
    530                 535                 540

Ile Ile Leu Gly Ser Leu Tyr His Gly Asp His Leu Ser Arg Ala Met
545                 550                 555                 560

Tyr Gln Arg Ile Ser Asn Ile Glu Asp Leu Pro Pro Leu Tyr Thr Leu
                565                 570                 575

Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
        595                 600                 605

Ile Glu Val Ile Asn Ala Thr Thr Gly Lys Asp Glu Leu Gly Arg Ala
    610                 615                 620

Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
            660                 665                 670

Ala Arg Leu Phe Thr Ala Phe Ile Lys Ala Gly Leu Gly Ala Trp Val
        675                 680                 685

Glu Lys Pro Thr Glu Gln Asp Gln Phe Ser Leu Thr Pro
    690                 695                 700

<210> SEQ ID NO 62
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Asp Ile Glu Asp Glu Glu Asn Met Ser Ser Ser Thr Asp Val
1               5                   10                  15

Lys Glu Asn Arg Asn Leu Asp Asn Val Ser Pro Lys Asp Gly Ser Thr
                20                  25                  30

Pro Gly Pro Gly Glu Gly Ser Gln Leu Ser Asn Gly Gly Gly Gly
            35                  40                  45

Pro Gly Arg Lys Arg Pro Leu Glu Glu Gly Ser Asn Gly His Ser Lys
        50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140
```

```
Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Gly Asp Leu Ser Leu
        195                 200                 205

Ser Ala Ser Pro Val Pro Ala Ser Leu Ala Gln Pro Pro Leu Pro Val
    210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Asp Gly Gln
            260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
    290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
            340                 345                 350

Ala Gly Val Val Met Thr Thr Gly Thr Asp Val Lys Asp Ala Lys Val
        355                 360                 365

Ile Ser Val Ser Thr Gly Thr Lys Cys Ile Asn Gly Glu Tyr Met Ser
    370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
        435                 440                 445

Ser Pro Cys Gly Asp Ala Arg Ile Phe Ser Pro His Glu Pro Ile Leu
    450                 455                 460

Glu Glu Pro Ala Asp Arg His Pro Asn Arg Lys Ala Arg Gly Gln Leu
465                 470                 475                 480

Arg Thr Lys Ile Glu Ser Gly Trp Gly Thr Ile Pro Val Arg Ser Asn
                485                 490                 495

Ala Ser Ile Gln Thr Trp Asp Gly Val Leu Gln Gly Glu Arg Leu Leu
            500                 505                 510

Thr Met Ser Cys Ser Asp Lys Ile Ala Arg Trp Asn Val Val Gly Ile
        515                 520                 525

Gln Gly Ser Leu Leu Ser Ile Phe Val Glu Pro Ile Tyr Phe Ser Ser
    530                 535                 540

Ile Ile Leu Gly Ser Leu Tyr His Gly Asp His Leu Ser Arg Ala Met
545                 550                 555                 560
```

```
Tyr Gln Arg Ile Ser Asn Ile Glu Asp Leu Pro Pro Leu Tyr Thr Leu
                565                 570                 575

Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
        595                 600                 605

Ile Glu Val Ile Asn Ala Thr Thr Gly Lys Asp Glu Leu Gly Arg Ala
    610                 615                 620

Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
            660                 665                 670

Ala Arg Leu Phe Thr Ala Phe Ile Lys Ala Gly Leu Gly Ala Trp Val
        675                 680                 685

Glu Lys Pro Thr Glu Gln Asp Gln Phe Ser Leu Thr Pro
    690                 695                 700

<210> SEQ ID NO 63
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Asp Ile Glu Asp Glu Glu Asn Met Ser Ser Ser Thr Asp Val
1               5                   10                  15

Lys Glu Asn Arg Asn Leu Asp Asn Val Ser Pro Lys Asp Gly Ser Thr
            20                  25                  30

Pro Gly Pro Gly Glu Gly Ser Gln Leu Ser Asn Gly Gly Gly Gly
        35                  40                  45

Pro Gly Arg Lys Arg Pro Leu Glu Glu Gly Ser Asn Gly His Ser Lys
    50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
            100                 105                 110

Val Glu Val Asn Gly Gln Val Phe Glu Gly Ser Gly Pro Thr Lys Lys
        115                 120                 125

Lys Ala Lys Leu His Ala Ala Glu Lys Ala Leu Arg Ser Phe Val Gln
    130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
            180                 185                 190

Gly Ser Asn Gly Asp Asp Ser Phe Ser Ser Gly Asp Leu Ser Leu
        195                 200                 205

Ser Ala Ser Pro Val Pro Ala Ser Leu Ala Gln Pro Pro Leu Pro Val
    210                 215                 220
```

```
Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
            245                 250                 255

Glu Ser His Ala Lys Ser Phe Val Met Ser Val Val Asp Gly Gln
        260                 265                 270

Phe Phe Glu Gly Ser Gly Arg Asn Lys Lys Leu Ala Lys Ala Arg Ala
        275                 280                 285

Ala Gln Ser Ala Leu Ala Ala Ile Phe Asn Leu His Leu Asp Gln Thr
    290                 295                 300

Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
                340                 345                 350

Ala Gly Val Val Met Thr Thr Gly Thr Asp Val Lys Asp Ala Lys Val
            355                 360                 365

Ile Ser Val Ser Thr Gly Thr Lys Cys Ile Asn Gly Glu Tyr Met Ser
370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
            435                 440                 445

Ser Pro Cys Gly Asp Ala Arg Ile Phe Ser Pro His Glu Pro Ile Leu
    450                 455                 460

Glu Glu Pro Ala Asp Arg His Pro Asn Arg Lys Ala Arg Gly Gln Leu
465                 470                 475                 480

Arg Thr Lys Ile Glu Ser Gly Leu Gly Thr Ile Pro Val Arg Ser Asn
                485                 490                 495

Ala Ser Ile Gln Thr Trp Asp Gly Val Leu Gln Gly Glu Arg Leu Leu
            500                 505                 510

Thr Met Ser Cys Ser Asp Lys Ile Ala Arg Trp Asn Val Val Gly Ile
            515                 520                 525

Gln Gly Ser Leu Leu Ser Ile Phe Val Glu Pro Ile Tyr Phe Ser Ser
    530                 535                 540

Ile Ile Leu Gly Ser Leu Tyr His Gly Asp His Leu Ser Arg Ala Met
545                 550                 555                 560

Tyr Gln Arg Ile Ser Asn Ile Glu Asp Leu Pro Pro Leu Tyr Thr Leu
                565                 570                 575

Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
            595                 600                 605

Ile Glu Val Ile Asn Ala Thr Thr Gly Lys Asp Glu Leu Gly Arg Ala
            610                 615                 620

Ser Arg Leu Cys Lys His Ala Leu Tyr Cys Arg Trp Met Arg Val His
625                 630                 635                 640
```

```
Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
                660                 665                 670

Ala Arg Leu Phe Thr Ala Phe Ile Lys Ala Gly Leu Gly Ala Trp Val
                675                 680                 685

Glu Lys Pro Thr Glu Gln Asp Gln Phe Ser Leu Thr Pro
                690                 695                 700

<210> SEQ ID NO 64
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Asp Ile Glu Asp Glu Glu Asn Met Ser Ser Ser Ser Thr Asp Val
1               5                   10                  15

Lys Glu Asn Arg Asn Leu Asp Asn Val Ser Pro Lys Asp Gly Ser Thr
                20                  25                  30

Pro Gly Pro Gly Glu Gly Ser Gln Leu Ser Asn Gly Gly Gly Gly Gly
            35                  40                  45

Pro Gly Arg Lys Arg Pro Leu Glu Glu Gly Ser Asn Gly His Ser Lys
        50                  55                  60

Tyr Arg Leu Lys Lys Arg Arg Lys Thr Pro Gly Pro Val Leu Pro Lys
65                  70                  75                  80

Asn Ala Leu Met Gln Leu Asn Glu Ile Lys Pro Gly Leu Gln Tyr Thr
                85                  90                  95

Leu Leu Ser Gln Thr Gly Pro Val His Ala Pro Leu Phe Val Met Ser
                100                 105                 110

Val Glu Val Asn Gly Gln Val Phe Glu Gly Ser Gly Pro Thr Lys Lys
            115                 120                 125

Lys Ala Lys Leu His Ala Ala Glu Lys Ala Leu Arg Ser Phe Val Gln
        130                 135                 140

Phe Pro Asn Ala Ser Glu Ala His Leu Ala Met Gly Arg Thr Leu Ser
145                 150                 155                 160

Val Asn Thr Asp Phe Thr Ser Asp Gln Ala Asp Phe Pro Asp Thr Leu
                165                 170                 175

Phe Asn Gly Phe Glu Thr Pro Asp Lys Ala Glu Pro Pro Phe Tyr Val
                180                 185                 190

Gly Ser Asn Gly Asp Asp Ser Phe Ser Ser Ser Gly Asp Leu Ser Leu
            195                 200                 205

Ser Ala Ser Pro Val Pro Ala Ser Leu Ala Gln Pro Pro Leu Pro Val
        210                 215                 220

Leu Pro Pro Phe Pro Pro Ser Gly Lys Asn Pro Val Met Ile Leu
225                 230                 235                 240

Asn Glu Leu Arg Pro Gly Leu Lys Tyr Asp Phe Leu Ser Glu Ser Gly
                245                 250                 255

Glu Ser His Ala Lys Ser Phe Val Met Ser Val Val Val Asp Gly Gln
                260                 265                 270

Phe Phe Glu Gly Ser Gly Arg Asn Lys Lys Leu Ala Lys Ala Arg Ala
            275                 280                 285

Ala Gln Ser Ala Leu Ala Ala Ile Phe Asn Leu His Leu Asp Gln Thr
        290                 295                 300
```

```
Pro Ser Arg Gln Pro Ile Pro Ser Glu Gly Leu Gln Leu His Leu Pro
305                 310                 315                 320

Gln Val Leu Ala Asp Ala Val Ser Arg Leu Val Leu Gly Lys Phe Gly
                325                 330                 335

Asp Leu Thr Asp Asn Phe Ser Ser Pro His Ala Arg Arg Lys Val Leu
            340                 345                 350

Ala Gly Val Val Met Thr Thr Gly Thr Asp Val Lys Asp Ala Lys Val
            355                 360                 365

Ile Ser Val Ser Thr Gly Thr Lys Cys Ile Asn Gly Glu Tyr Met Ser
370                 375                 380

Asp Arg Gly Leu Ala Leu Asn Asp Cys His Ala Glu Ile Ile Ser Arg
385                 390                 395                 400

Arg Ser Leu Leu Arg Phe Leu Tyr Thr Gln Leu Glu Leu Tyr Leu Asn
                405                 410                 415

Asn Lys Asp Asp Gln Lys Arg Ser Ile Phe Gln Lys Ser Glu Arg Gly
            420                 425                 430

Gly Phe Arg Leu Lys Glu Asn Val Gln Phe His Leu Tyr Ile Ser Thr
            435                 440                 445

Ser Pro Cys Gly Asp Ala Arg Ile Phe Ser Pro His Glu Pro Ile Leu
450                 455                 460

Glu Glu Pro Ala Asp Arg His Pro Asn Arg Lys Ala Arg Gly Gln Leu
465                 470                 475                 480

Arg Thr Lys Ile Glu Ser Gly Ile Gly Thr Ile Pro Val Arg Ser Asn
                485                 490                 495

Ala Ser Ile Gln Thr Trp Asp Gly Val Leu Gln Gly Glu Arg Leu Leu
            500                 505                 510

Thr Met Ser Cys Ser Asp Lys Ile Ala Arg Trp Asn Val Val Gly Ile
            515                 520                 525

Gln Gly Ser Leu Leu Ser Ile Phe Val Glu Pro Ile Tyr Phe Ser Ser
530                 535                 540

Ile Ile Leu Gly Ser Leu Tyr His Gly Asp His Leu Ser Arg Ala Met
545                 550                 555                 560

Tyr Gln Arg Ile Ser Asn Ile Glu Asp Leu Pro Pro Leu Tyr Thr Leu
                565                 570                 575

Asn Lys Pro Leu Leu Ser Gly Ile Ser Asn Ala Glu Ala Arg Gln Pro
            580                 585                 590

Gly Lys Ala Pro Asn Phe Ser Val Asn Trp Thr Val Gly Asp Ser Ala
            595                 600                 605

Ile Glu Val Ile Asn Ala Thr Thr Gly Lys Asp Glu Leu Gly Arg Ala
610                 615                 620

Ser Arg Leu Cys Lys His Ala Leu Tyr Cys Arg Trp Met Arg Val His
625                 630                 635                 640

Gly Lys Val Pro Ser His Leu Leu Arg Ser Lys Ile Thr Lys Pro Asn
                645                 650                 655

Val Tyr His Glu Ser Lys Leu Ala Ala Lys Glu Tyr Gln Ala Ala Lys
            660                 665                 670

Ala Arg Leu Phe Thr Ala Phe Ile Lys Ala Gly Leu Gly Ala Trp Val
            675                 680                 685

Glu Lys Pro Thr Glu Gln Asp Gln Phe Ser Leu Thr Pro
            690                 695                 700

<210> SEQ ID NO 65
<211> LENGTH: 42
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gaccaaaata gagtctggtt ttgggacgat tccagtgcgc tc                           42

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gagcgcactg gaatcgtccc aaaaccagac tctattttgg tc                           42

<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gaccaaaata gagtctggtt atgggacgat tccagtgcgc tc                           42

<210> SEQ ID NO 68
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gagcgcactg gaatcgtccc ataaccagac tctattttgg tc                           42

<210> SEQ ID NO 69
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gaccaaaata gagtctggtt gggggacgat tccagtgcgc tc                           42

<210> SEQ ID NO 70
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gagcgcactg gaatcgtccc ccaaccagac tctattttgg tc                           42

<210> SEQ ID NO 71
<211> LENGTH: 23
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: 8-azanebularine

<400> SEQUENCE: 71
gcucgcgaug cungagggcu cug                                            23

<210> SEQ ID NO 72
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: Reduced abasic nucleotide

<400> SEQUENCE: 72
cagagccccc nagcaucgcg agc                                            23

<210> SEQ ID NO 73
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agagggcucu g                                                         11

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cagagccccc cagcatcgcg agc                                            23

<210> SEQ ID NO 75
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
cagagccccc cagcaucgcg agc                                            23

<210> SEQ ID NO 76
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
```
uucgcaccaa guucgacaug cgc 23

<210> SEQ ID NO 77
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
uacgccggua ccaaguaucg cac 23

<210> SEQ ID NO 78
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: Reduced abasic nucleotide

<400> SEQUENCE: 78
uucgcacnaa guucgacaug cgc 23

<210> SEQ ID NO 79
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: Reduced abasic nucleotide

<400> SEQUENCE: 79
uacgccggua cnaaguaucg cac 23

<210> SEQ ID NO 80
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gcgcatgtcg aacttggtgc gaagtgcgat acttggtacc ggcgtacatt ggtatccacc    60
gacgtgacgc gtct    74

<210> SEQ ID NO 81
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcgcatgtcg aacttagagc gaagtgcgat acttagaacc ggcgtacatt agaatccacc    60
gacgtgacgc gtct    74

<210> SEQ ID NO 82
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gtgtgtgtaa gctttcgtgg tccttagact tcgtgcacat acaggcgcat gtcgaactta    60
gagcgaag                                                             68

<210> SEQ ID NO 83
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gtgtgtgtgg atccctgcaa gacgcgtcac gtcggtggat tc                       42

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tgggtacgaa ttccccgtac aagctt                                         26

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
agacgcgtca cgtcggtgga tt                                             22

<210> SEQ ID NO 86
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
atctcagagg aggacctgga attcatggga taccoctacg acgtgcccga ctacgccgga    60
tccgccgaga tcaaggagaa aatctgc                                        87

<210> SEQ ID NO 87
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 87
agggccctct agatgcatgc tcgagcggcc gctcatactg ggcagagata aaagttcttt    60
tcct                                                                64

<210> SEQ ID NO 88
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gaagcaactc ttgagtgtta atatgttgac ccctgtatta gggatgcggg aattgggtac    60
gaattccccg tacatcgctg tccacct                                       87

<210> SEQ ID NO 89
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
agatgataag ctccggcaag caatattgaa caacgcaagg atcggcgata ttccacgtga    60
tatcccgaca cggatccggg gca                                           83

<210> SEQ ID NO 90
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gactcactat agggagaccc agaagcaact cttgagtgtt aatatgttga ccctgtatt    60 agggatgcgg g                                                       71

<210> SEQ ID NO 91
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tagggccctc tagatgcatg ctcgaagatg ataagctccg gcaagcaata ttgaacaacg    60
caaggatcgg cg                                                       72

<210> SEQ ID NO 92
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uugucaagaa aggguguaac gcaaccaagu cauaguccg                          39
```

<210> SEQ ID NO 93
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (26)..(26)
<223> OTHER INFORMATION: Reduced abasic nucleotide

<400> SEQUENCE: 93
uugucaagaa aggguguaac gcaacnaagu cauaguccg                         39

<210> SEQ ID NO 94
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 94
ugucuacugu acagaauacu gccgccagcu ggauuuccc                         39

<210> SEQ ID NO 95
<211> LENGTH: 39
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (26)..(26)
<223> OTHER INFORMATION: Reduced abasic nucleotide

<400> SEQUENCE: 95
ugucuacugu acagaauacu gccgcnagcu ggauuuccc                         39

<210> SEQ ID NO 96
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
agacccagaa gcaactcttg agtgttaata tgttgacccc t                     41

<210> SEQ ID NO 97
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
gcatgctcga agatgataag ctccggcaag ca                               32

<210> SEQ ID NO 98
<211> LENGTH: 45
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 98
gtattaggga tgcgggaatt gggtacgaat tccccgtaca tcgct                    45

<210> SEQ ID NO 99
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
atattgaaca acgcaaggat cggcgatatt ccacgtgata tcccg                    45

<210> SEQ ID NO 100
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cagcagatgt ggatcagcaa gcaggag                                        27

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101 ggaaggggggg gcacgaaggc tcatc                                         25

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tatgacgagt ccggcccctc catcgt                                         26

<210> SEQ ID NO 103
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcaatgctat cacctcccct gtgtggact                                      29

<210> SEQ ID NO 104
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
aacaaataaa gccatgccaa tctcatcttg tt					32

<210> SEQ ID NO 105
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gcaaccaatt aaaatgtata aattagtgta agaaatt					37

<210> SEQ ID NO 106
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gctacaatgc aggggcagat cctaggaag						29

<210> SEQ ID NO 107
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cttggattat gtgtttaagt cctgtaatgc aggcc					35

<210> SEQ ID NO 108
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ggagcagaac tgccagggtt ccaacc						26

<210> SEQ ID NO 109
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ccgctggctc tttgataaga aattcttggc tgagg					35

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
agccagaaga ggcagaggat gggcg                                          25

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cagctattcg gtttgagtgt gtgttcc                                        27

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cggccaccac ctggttcaca gccc                                           24

<210> SEQ ID NO 113
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcctggccaa ccacaacagg atcacccagt gtc                                 33

<210> SEQ ID NO 114
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
taggtcgaag agctcgcgat actcctcgtc tg                                  32

<210> SEQ ID NO 115
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tccaccagca acttgaagtg atcccaggct atga                                34

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
acttctggct gtccagccct gagcccg                                           27

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tcagtatctg gacccgggaa gctggtgc                                          28

<210> SEQ ID NO 118
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tgccgttgaa cttgacgtca atcaggtaaa cgcc                                   34

<210> SEQ ID NO 119
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tggaggcctg gccattgctg tcgaggg                                           27

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
attctcccga gggatgaagc gcacagc                                           27

<210> SEQ ID NO 121
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cagatgcata gatagggcag tgttccaagg a                                      31

<210> SEQ ID NO 122
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
acctttgtca tgaactcctc cagctgttc                                   29

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ttatcacagg aagcattgtc tgcctgcatt cagtc                             35

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tacaaacagc ttggtctgct gctgaat                                      27

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cgagccgagt atccaggata caac                                         24

<210> SEQ ID NO 126
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cccatatccc agagtatcag taggtgg                                      27

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cccaatgcag gggtcacccg gaggg                                        25

<210> SEQ ID NO 128
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gaagtccata tagggggttca gaccactgcc cac          33

<210> SEQ ID NO 129
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Lys Ile Glu Ser Gly Tyr Gly Thr Ile Pro Val Arg
1               5                   10

<210> SEQ ID NO 130
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
gaagcaactc ttgagtgtta atatgttgac ccctgtatta gggatgcggg aattgggtac     60
gaattccccg tacatcgctg tccaccttcc agcagatgtg gatcagcaag caggagtatg    120
acgagtccgg cccctccatc gtccaccgca aatgcttcta gcggactat gacttagttg     180 cgttacaccc tttcttgaca aaacctaact tgcgcagaaa acaagatgag attggcatgg    240
ctttatttgt tttttttgtt ttgttttggt tttttttttt ttttggctt gactcaggat     300 ttaaaaactg gaacggtgaa ggtgacagca gtcggttgga gcgagcatcc cccaaagttc    360
acaatgtggc cgaggacttt gattgcacat tgttgttttt ttaatagtca ttccaaatat    420
gagatgcgtt gttacaggaa gtcccttgcc atcctaaaag ccacccccact tctctctaag   480 gagaatggcc cagtcctctc ccaagtccac acagggagg tgatagcatt gctttcgtgt     540
aaattatgta atgcaaaatt ttttttaatct tcgccttaat acttttttat tttgttttat   600
tttgaatgat gagccttcgt gccccggatc cgtgtcggga tatcacgtgg aatatcgccg   660
atccttgcgt tgttcaatat tgcttgccgg agcttatcat ct                       702

<210> SEQ ID NO 131
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131 gctagag                                                                7

<210> SEQ ID NO 132
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132 gctggag                                                                7

<210> SEQ ID NO 133

<211> LENGTH: 152
<212> TYPE: RNA
<213> ORGANISM: Artificial Sequence
<220> FEATURE:
<223> OTHER INFORMATION: Description of Artificial Sequence: Synthetic
     polynucleotide
<220> FEATURE:
<221> NAME/KEY: modified_base
<222> LOCATION: (1)..(67)
<223> OTHER INFORMATION: a, c, u, g, unknown or other
<220> FEATURE:
<221> NAME/KEY: modified_base
<222> LOCATION: (114)..(152)
<223> OTHER INFORMATION: a, c, u, g, unknown or other

<400> SEQUENCE: 133
nnnnnnnnnn nnnnnnnnnn nnnnnnnnnn nnnnnnnnnn nnnnnnnnnn nnnnnnnnnn       60
nnnnnnngcg caugucgaac uuagagcgaa gugcgauacu agaaccggc guannnnnnn        120 nnnnnnnnnn nnnnnnnnnn nnnnnnnnnn nn                                    152

<210> SEQ ID NO 134
<211> LENGTH: 46
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (12)..(12)
<223> OTHER INFORMATION: c or reduced abasic nucleotide
<220> FEATURE:
<221> NAME/KEY: modified_base
<222> LOCATION: (31)..(31)
<223> OTHER INFORMATION: c or reduced abasic nucleotide

<400> SEQUENCE: 134
uacgccggua cnaaguaucg cacuucgcac naaguucgac augcgc                      46

<210> SEQ ID NO 135
<211> LENGTH: 49
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 135
cuaggcggac uaugacuuag uugcguuaca cccuuucuug acaaaaccu                   49

<210> SEQ ID NO 136
<211> LENGTH: 39
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (26)..(26)
<223> OTHER INFORMATION: c or reduced abasic nucleotide

<400> SEQUENCE: 136
uugucaagaa aggguguaac gcaacnaagu cauaguccg                              39

<210> SEQ ID NO 137
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 137
tgtaacgcaa ctaagtcata gtccgcctag                                          30

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
tgtaacgcaa cyaagtcata gtccgccyag                                          30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tgtaacgcaa cyaagtcata gtccgcctag                                          30

<210> SEQ ID NO 140
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140
```

His His His His His His His His His Glu Asn Leu Tyr Phe Gln
1               5                   10                  15

Gly Met Phe Tyr Ala Val Arg Arg Gly Arg Lys Thr Gly Val Phe Leu
            20                  25                  30

Thr Trp Asn Glu Cys Arg Ala Gln Val Asp Arg Phe Pro Ala Ala Arg
        35                  40                  45

Phe Lys Lys Phe Ala Thr Glu Asp Glu Ala Trp Ala Phe Val Arg Lys
    50                  55                  60

Ser Ala Ser Leu His Leu Asp Gln Thr Pro Ser Arg Gln Pro Ile Pro
65                  70                  75                  80

Ser Glu Gly Leu Gln Leu His Leu Pro Gln Val Leu Ala Asp Ala Val
                85                  90                  95

Ser Arg Leu Val Leu Gly Lys Phe Gly Asp Leu Thr Asp Asn Phe Ser
            100                 105                 110

Ser Pro His Ala Arg Arg Lys Val Leu Ala Gly Val Val Met Thr Thr
        115                 120                 125

Gly Thr Asp Val Lys Asp Ala Lys Val Ile Ser Val Ser Thr Gly Thr
    130                 135                 140

Lys Cys Ile Asn Gly Glu Tyr Met Ser Asp Arg Gly Leu Ala Leu Asn
145                 150                 155                 160

Asp Cys His Ala Glu Ile Ile Ser Arg Arg Ser Leu Leu Arg Phe Leu
                165                 170                 175

Tyr Thr Gln Leu Glu Leu Tyr Leu Asn Asn Lys Asp Asp Gln Lys Arg

```
            180                 185                 190
Ser Ile Phe Gln Lys Ser Glu Arg Gly Gly Phe Arg Leu Lys Glu Asn
            195                 200                 205

Val Gln Phe His Leu Tyr Ile Ser Thr Ser Pro Cys Gly Asp Ala Arg
            210                 215                 220

Ile Phe Ser Pro His Glu Pro Ile Leu Glu Glu Pro Ala Asp Arg His
225                 230                 235                 240

Pro Asn Arg Lys Ala Arg Gly Gln Leu Arg Thr Lys Ile Glu Ser Gly
            245                 250                 255

Glu Gly Thr Ile Pro Val Arg Ser Asn Ala Ser Ile Gln Thr Trp Asp
            260                 265                 270

Gly Val Leu Gln Gly Glu Arg Leu Leu Thr Met Ser Cys Ser Asp Lys
            275                 280                 285

Ile Ala Arg Trp Asn Val Val Gly Ile Gln Gly Ser Leu Leu Ser Ile
            290                 295                 300

Phe Val Glu Pro Ile Tyr Phe Ser Ser Ile Ile Leu Gly Ser Leu Tyr
305                 310                 315                 320

His Gly Asp His Leu Ser Arg Ala Met Tyr Gln Arg Ile Ser Asn Ile
            325                 330                 335

Glu Asp Leu Pro Pro Leu Tyr Thr Leu Asn Lys Pro Leu Leu Ser Gly
            340                 345                 350

Ile Ser Asn Ala Glu Ala Arg Gln Pro Gly Lys Ala Pro Asn Phe Ser
            355                 360                 365

Val Asn Trp Thr Val Gly Asp Ser Ala Ile Glu Val Ile Asn Ala Thr
            370                 375                 380

Thr Gly Lys Asp Glu Leu Gly Arg Ala Ser Arg Leu Cys Lys His Ala
385                 390                 395                 400

Leu Tyr Cys Arg Trp Met Arg Val His Gly Lys Val Pro Ser His Leu
            405                 410                 415

Leu Arg Ser Lys Ile Thr Lys Pro Asn Val Tyr His Glu Ser Lys Leu
            420                 425                 430

Ala Ala Lys Glu Tyr Gln Ala Ala Lys Ala Arg Leu Phe Thr Ala Phe
            435                 440                 445

Ile Lys Ala Gly Leu Gly Ala Trp Val Glu Lys Pro Thr Glu Gln Asp
            450                 455                 460

Gln Phe Ser Leu Thr Pro
465                 470

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Leu His Leu Asp Gln Thr Pro Ser Arg Gln Pro Ile Pro Ser Glu Gly
1               5                   10                  15

Leu Gln Leu His Leu
            20

<210> SEQ ID NO 142
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 142

Glu Asn Leu Tyr Phe Gln Gly
1               5

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 6-10 residues

<400> SEQUENCE: 143

His His His His His His His His His His
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

His His His His His His His His His His
1               5                   10

<210> SEQ ID NO 145
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
gaagagaagc                                                              10

<210> SEQ ID NO 146
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gcttctcttc                                                              10

<210> SEQ ID NO 147
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tcgtaattcc t                                                            11
```